US012767956B2

(12) United States Patent
Daigle et al.

(10) Patent No.: US 12,767,956 B2
(45) Date of Patent: Oct. 20, 2026

(54) ARTIFICIAL EXPRESSION CONSTRUCTS FOR MODULATING GENE EXPRESSION IN CLAUSTRUM NEURONS

(71) Applicant: Allen Institute, Seattle, WA (US)

(72) Inventors: Tanya Daigle, Seattle, WA (US); Lucas T. Graybuck, Seattle, WA (US); Adriana Estela Sedeño Cortés, Seattle, WA (US); Bosiljka Tasic, Seattle, WA (US); Jonathan Ting, Seattle, WA (US)

(73) Assignee: Allen Institute, Seattle, WA (US)

( * ) Notice: Subject to any disclaimer, the term of this patent is extended or adjusted under 35 U.S.C. 154(b) by 381 days.

(21) Appl. No.: 18/285,188

(22) PCT Filed: Mar. 30, 2022

(86) PCT No.: PCT/US2022/022656

§ 371 (c)(1),
(2) Date: Sep. 29, 2023

(87) PCT Pub. No.: WO2022/212585

PCT Pub. Date: Oct. 6, 2022

(65) Prior Publication Data

US 2024/0182923 A1 Jun. 6, 2024

Related U.S. Application Data

(60) Provisional application No. 63/167,995, filed on Mar. 30, 2021.

(51) Int. Cl.

| | |
|---|---|
| ***C12N 15/86*** | (2006.01) |
| ***A61K 48/00*** | (2006.01) |
| ***C07K 14/47*** | (2006.01) |

(52) U.S. Cl.

CPC .......... *C12N 15/86* (2013.01); *A61K 48/0058* (2013.01); *C07K 14/4702* (2013.01); *C12N 2750/14143* (2013.01); *C12N 2830/008* (2013.01)

(58) Field of Classification Search

None

See application file for complete search history.

(56) References Cited

FOREIGN PATENT DOCUMENTS

| | | |
|---|---|---|
| WO | WO2020097121 A1 | 5/2020 |
| WO | WO2020168279 A2 | 8/2020 |

OTHER PUBLICATIONS

Evsikov et al., "Cracking the egg: molecular dynamics and evolutionary aspects of the transition from the fully grwon oocyte to embryo" Genes & Development (Year: 2006).*

Shen et al., "A map of the cis-regulatory sequences in the mouse genome" Nature (Year: 2012).*

Choi, et al., "Optimization of AAV expression cassettes to improve packaging capacity and transgene expression on neurons", Molecular brain, vol. 7, No. 17, 2014, 10 pages.

GenBank Accession No. AC116452, "Mus musculus chromosome 1, clone RP24-287C2, complete sequence", retrieved from <https://www.ncbi.nlm.nih.gov/nuccore/AC116452>, Sep. 15, 2004, 2 pages.

Invitation to Pay Fees Dated Jun. 13, 2022 for International Application No. PCT/US2022/022656, 3 pages.

PCT Search Report and Written Opinion mailed Aug. 18, 2022 for PCT Application No. PCT/ US2022/022656, 14 pages.

Abhyankar, et al., "A novel CpG-free vertebrate insulator silences the testis-specific SP-10 gene in somatic tissues: role for TDP-43 in insulator function," J. Biol. Chem., vol. 282, No. 50, 2007, pp. 36143-36154.

Albright, et al., "Mapping the Structural Determinants Required for AAVrh. 10 Transport across the Blood-Brain Barrier," Molecular Therapy, vol. 26, No. 2, 2018, pp. 510-523.

Burgess-Beusse, et al., "The Insulation of Genes from External Enhancers and Silencing Chromatin,", PNAS USA, vol. 99, No. 4, 2002, pp. 16433-16437.

Chan et al., "Engineered AAVs for efficient noninvasive gene delivery to the central and peripheral nervous systems," Nat. Neurosci., vol. 20, No. 8, 2017, pp. 1172-1179.

Chen, et al., "Molecular signatures of disease brain endothelia provide new sites for CNS-directed enzyme therapy," Nat. Med., vol. 15, No. 10, 2009, pp. 1215-1218.

Daigle, et al., "A Suite of Transgenic Driver and Reporter Mouse Lines with Enhanced Brain-Cell-Type Targeting and Functionality," Cell., vol. 174, No. 2, 2018, pp. 465-480.

Deverman, et al., "Cre-dependent selection yields AAV variants for widespread gene transfer to the adult brain," Nat Biotechnol., vol. 34, No. 2, 2016, pp. 204-209.

Gombash, et al., "Intravenous AAV9 efficiently transduces myenteric neurons in neonate and juvenile mice," Front. Mol. Neurosci., vol. 7, No. 81, 2014, 11 pages.

Gong et al., "Targeting Cre recombinase to specific neuron populations with bacterial artificial chromosome constructs," J. Neurosci., vol. 27, No. 37, 2007, pp. 9817-9823.

Korbelin, et al., "A brain microvasculature endothelial cell-specific viral vector with the potential to treat neurovascular and neurological diseases," EMBO Mol. Med., vol. 8, No. 6, 2016, pp. 609-625.

Marchio, et al., "Brain endothelial cell-targeted gene therapy of neurovascular disorders," EMBO Mol. Med., vol. 8, No. 6, 2016, pp. 592-594.

Selot, et al., "Optimized AAV rh. 10 Vectors That Partially Evade Neutralizing Antibodies during Hepatic Gene Transfer," Front Pharmacol., vol. 8, 2017, 10 pages.

(Continued)

*Primary Examiner* — Tracy Vivlemore
*Assistant Examiner* — John David Moore
(74) *Attorney, Agent, or Firm* — C. Rachal Winger; Shan Liao; Lee & Hayes PC

(57) ABSTRACT

Artificial expression constructs for modulating gene expression in targeted central nervous system cell types are described. The artificial expression constructs can be used to express synthetic genes or modify gene expression in claustrum neurons including L6 IT Car3 neurons.

20 Claims, 47 Drawing Sheets

Specification includes a Sequence Listing.

(56) References Cited

OTHER PUBLICATIONS

Taniguchi, et al., “A resource of Cre driver lines for genetic targeting of GABAergic neurons in cerebral cortex,” Neuron, vol. 71, No. 6, 2011, pp. 995-1013.
Tasic, Bosiljka., “Single cell transcriptomics in neuroscience: cell classification and beyond,” Curr. Opin. Neurobiol., vol. 50, 2018, pp. 242-249.
Yang, et al., “Global CNS transduction of adult mice by intravenously delivered rAAVrh.8 and rAAVrh.10 and nonhuman primates by rAAVrh. 10,” Mol. Ther., vol. 22, No. 7, 2014, pp. 1299-1309.
Zeng and Sanes, “Neuronal cell-type classification: challenges, opportunities and the path forward,” Nat. Rev. Neurosci., vol. 18, No. 9, 2017, pp. 530-546.
Zhan, et al., “Insulator: from chromatin domain boundary to gene regulation,” Hum. Genet., vol. 109, No. 5, 2001, pp. 471-478.
Zufferey, et al., “Woodchuck hepatitis virus posttranscriptional regulatory element enhances expression of transgenes delivered by retroviral vectors,” J. Virol., vol. 73, No. 4, 1999, pp. 2886-2892.

* cited by examiner rAAV-MGT_E51-minBGpromoter-dTomato-WPRE3-BGHpA; wt
1.00E+12 gc rAAV-MGT_E51-minBGprom-SYFP2-WPRE-bGHpA; wt
1.00E+12 gc rAAV-MGT_E51-minBGprom-FlpO-WPRE-hGHpA; Ai193/wt
1.00E+11 gc rAAV-MGT_E51-minBGpromoter-iCre-hGHpA; Ai193/wt
5.00E+10 gc

FIG. 10 core2_eHGT_774m:
ACAGCAAGTGTTCTATGATTTTCAACAGGACACTTGGATCTAGCCAACTCAGTTTTCAAGCC
TGCCCCCGAGTTGTAGATCCTGTCTTCACATTCTAAACTAATCTCACACCACTTTGTGCCAA
CTCCACTCTGGTAAAGACCATGCACTCGAGTTAGTGCAAGACATTTTGTTCTGGCCTCGGG
GTGTGCTGCCGCCTCGTCAGGATGGGAGGTGGAGGCGAGTCCAG (SEQ ID NO: 54)

3xcore2_eHGT_774m:
ACAGCAAGTGTTCTATGATTTTCAACAGGACACTTGGATCTAGCCAACTCAGTTTTCAAGCC
TGCCCCCGAGTTGTAGATCCTGTCTTCACATTCTAAACTAATCTCACACCACTTTGTGCCAA
CTCCACTCTGGTAAAGACCATGCACTCGAGTTAGTGCAAGACATTTTGTTCTGGCCTCGGG
GTGTGCTGCCGCCTCGTCAGGATGGGAGGTGGAGGCGAGTCCAGACAGCAAGTGTTCTA
TGATTTTCAACAGGACACTTGGATCTAGCCAACTCAGTTTTCAAGCCTGCCCCCGAGTTGT
AGATCCTGTCTTCACATTCTAAACTAATCTCACACCACTTTGTGCCAACTCCACTCTGGTAA
AGACCATGCACTCGAGTTAGTGCAAGACATTTTGTTCTGGCCTCGGGGTGTGCTGCCGCC
TCGTCAGGATGGGAGGTGGAGGCGAGTCCAGACAGCAAGTGTTCTATGATTTTCAACAGG
ACACTTGGATCTAGCCAACTCAGTTTTCAAGCCTGCCCCCGAGTTGTAGATCCTGTCTTCA
CATTCTAAACTAATCTCACACCACTTTGTGCCAACTCCACTCTGGTAAAGACCATGCACTCG
AGTTAGTGCAAGACATTTTGTTCTGGCCTCGGGGTGTGCTGCCGCCTCGTCAGGATGGGA
GGTGGAGGCGAGTCCAG (SEQ ID NO: 55)

core2_eHGT_772m:
CCCCACTCCTGCCTCTGCCTATAAGAGTTTGGCACAGTTGGAGATTTGTATACACAAATGC
ATGCGTGGAAATACTGCGCTCTGATGACATTCCTCAGGGGGCGACCTTTGATGATGAATTT
TCTTGCCCTTTTTAGGGGAGGAGAAGAGGAGGCGGGTGGTACTTCACAAGACTAAATTTAC
TCAACTTTTTTGGGTCTAAATTTCTTTAGGAAAAAAAATGTCAAATGATTGTAGATCCCAAAC
TGTCTTTGTTGGCATTTGA (SEQ ID NO: 56)

3xcore2_eHGT_772m:
CCCCACTCCTGCCTCTGCCTATAAGAGTTTGGCACAGTTGGAGATTTGTATACACAAATGC
ATGCGTGGAAATACTGCGCTCTGATGACATTCCTCAGGGGGCGACCTTTGATGATGAATTT
TCTTGCCCTTTTTAGGGGAGGAGAAGAGGAGGCGGGTGGTACTTCACAAGACTAAATTTAC
TCAACTTTTTTGGGTCTAAATTTCTTTAGGAAAAAAAATGTCAAATGATTGTAGATCCCAAAC
TGTCTTTGTTGGCATTTGACCCCACTCCTGCCTCTGCCTATAAGAGTTTGGCACAGTTGGA
GATTTGTATACACAAATGCATGCGTGGAAATACTGCGCTCTGATGACATTCCTCAGGGGGC
GACCTTTGATGATGAATTTTCTTGCCCTTTTTAGGGGAGGAGAAGAGGAGGCGGGTGGTA
CTTCACAAGACTAAATTTACTCAACTTTTTTGGGTCTAAATTTCTTTAGGAAAAAAAATGTCA
AATGATTGTAGATCCCAAACTGTCTTTGTTGGCATTTGACCCCACTCCTGCCTCTGCCTATA
AGAGTTTGGCACAGTTGGAGATTTGTATACACAAATGCATGCGTGGAAATACTGCGCTCTG
ATGACATTCCTCAGGGGGCGACCTTTGATGATGAATTTTCTTGCCCTTTTTAGGGGAGGAG
AAGAGGAGGCGGGTGGTACTTCACAAGACTAAATTTACTCAACTTTTTTGGGTCTAAATTTC
TTTAGGAAAAAAAATGTCAAATGATTGTAGATCCCAAACTGTCTTTGTTGGCATTTGA (SEQ
ID NO: 57)

Core_eHGT486m:
AAAATCAAATCAGTTGCAAAATCCATACAGTCTTCCAGTTTCTCAGCTGTGGAAACTTTGTG
TCTCTTCTTTTCCACCAAAACAGCTATCTCGTCTTTCAAGTCCTTGCTGAAAAAAAAAAGTGT

FIG. 10 cont'd

TAAATTTTTCTCAATTTAGACTTCCAGCAAAACAGATTCTGCTTGTTGAAAGGCATTGGTGTT
CATGAGTAAGTGAGTTTCCATTTTATTTCTTCACAAATAAGTTACATGAAGTACTT (SEQ ID NO: 58)

3xCore_eHGT486m:
AAAATCAAATCAGTTGCAAAATCCATACAGTCTTCCAGTTTCTCAGCTGTGGAAACTTTGTG
TCTCTTCTTTTCCACCAAAACAGCTATCTCGTCTTTCAAGTCCTTGCTGAAAAAAAAAAGTGT
TAAATTTTTCTCAATTTAGACTTCCAGCAAAACAGATTCTGCTTGTTGAAAGGCATTGGTGTT
CATGAGTAAGTGAGTTTCCATTTTATTTCTTCACAAATAAGTTACATGAAGTACTTAAAATCA
AATCAGTTGCAAAATCCATACAGTCTTCCAGTTTCTCAGCTGTGGAAACTTTGTGTCTCTTC
TTTTCCACCAAAACAGCTATCTCGTCTTTCAAGTCCTTGCTGAAAAAAAAAAGTGTTAAATTT
TTCTCAATTTAGACTTCCAGCAAAACAGATTCTGCTTGTTGAAAGGCATTGGTGTTCATGAG
TAAGTGAGTTTCCATTTTATTTCTTCACAAATAAGTTACATGAAGTACTTAAAATCAAATCAG
TTGCAAAATCCATACAGTCTTCCAGTTTCTCAGCTGTGGAAACTTTGTGTCTCTTCTTTTCCA
CCAAAACAGCTATCTCGTCTTTCAAGTCCTTGCTGAAAAAAAAAAGTGTTAAATTTTTCTCAA
TTTAGACTTCCAGCAAAACAGATTCTGCTTGTTGAAAGGCATTGGTGTTCATGAGTAAGTGA
GTTTCCATTTTATTTCTTCACAAATAAGTTACATGAAGTACTT (SEQ ID NO: 59)

MGT_E51:
CCTTTTAGAAACACTCCCTTTACCATCTTCAAACATGTTTTTAGCTGAGAACTCTCTTCCAAC
CCCTGTTTCTTAACTCTGAGTGCCGTATCACTTCATATTCTGTGTCAGGGGAAAAGAAATCA
GCACCTCCCACAACGTCAACTGTGTCCTTTAGAGTAAGCATTCCAAAGTCTATATTCTGAGT
CTAATCTCTCTTGGAAAGGTCAGCCTTTTCTTCCAAATACCAAGTGGACATCTTTATGCACA
GGCCTTCAAGGATATTCAAGTCAGTGTGTCCTACGGAGAAAACTCCTTTTAAAACCCGAAT
CCTGTGGTTTCCCCAAGATGATTATTGGGTGGTCACTGCAGC (SEQ ID NO: 1)

MGT_E52:
ATATGGATGTCTTACCTGCATGAATACTTGTGTACCACATGTATGCCTTTCTCCATGGAGGC
CAGAAGAGGGTATCAGATTCCCTGGAACTGAAGTTACAGATAGTTGTGAGCTGCCATGTGG
GTACTGGAAATACATGTGTCTAATTTTAAGGACCAGCTCCTACTGAGGACATAAATGTTATG
TTTCTTAAAAGTCTATACCATAAGAATCTTCTTCAGATCTTGGTGTGAAGATTCTTACCCCAG
ATTGGTTACAGAAGCGGTACCAGGTGGGTGGATCCCATCAAAAGCTTTAGTGAGAAATCAC
CCTTTTCCTTCACAGCAGCCCAGCTGACTGGTGAACTTTGCCGAACTGTAAAATATCAAAC
CTTTGGGAAGCTTTCTGCAACACGAGAAGTTTTAATCCTTCAATATTAAAAAGAAAAATAAG
AAAAAAAAACTGTGGAGAAGTCACGAACAGGAGAAACAAAAAGGAATTGTGCACAGGGTCA
GTCG (SEQ ID NO: 2)

MGT_E57:
CCCAGGATCTATTGACATCCAACATCGGATGGAGAAACTGAAGTTCACATCATAGCTCATC
TCTCATAGTATCCTATACGGTGTTTCTCTTTCTTGGAGAAACAACCCCACCCCACCCGCCTT
GATGTTAATGCCAGGACACACATGTTTTCTTGACCCCACTTCTCTGATCACTCATCGCTCTG
CTTCCTCAGCCTGTTGTTGGTACCAGTTCTCAGATAGTTGCAGTCTCCAAGTTCAGTTCCTA
CCGATTTATGCCATGCTGTCTTTTTTGAGAAATACCACTCACCATGTGAGTGAATCTGTGAA
TGCCTCCTAAATGCCCGTTGCCAATTTGAGAATAAAAGTTCATGTGATTATGTTCAAGGCAT

FIG. 10 cont'd

TTCAGATTAAATATGACCAAAATCACTCCGTGGTGCCTTCCTGTACGCCTCACCGTGAATC
CAGTTTG (SEQ ID NO: 3)

eHGT_770m:
ATGGGAAAGCAGCACGTGTTCTTAACTGCTAGACTCCTATTTACCATGACAGTAATATCATT
ATTATTTTTAAATCATTTTATAATTTCAGGAGAAAGCAAATGATTGCTAATAACGGTCTCCCT
CTTCAGTACATATGCACTACACGCGCATGTGTCCTTTAAAGATAAATTTGAGTTGGAAGCAT
CGGTATGAGCTGGTGAGTTTTAAGAAGTTCCAGAAAAAAAAAAGAAGTTCCAGTATTTCCTA
GATTTGTCCTCTGCAAAGTCCTAGGCATAAAGGCAGCGCAGTTTGTGGCCTTTAAATACCA
CTTCCCACGAAAGCAACCAAGGCTCCTTGGAGACGTGAGCGATTTGATGTCTATAAATATG
AGCACACAGTGCTGTGCTTCCCCACTGAGGTCAGAAAGACCACTACCCTGAATCCAAACCA
CCTTCATGGCTTAGCAGATGAGGCCAGAGCTGGACAAGAGCAATTAAAGGGAACAATTACA
TTACATGTTGGTGTTTGATTTATCTGCAGATTTTTTTAACCAGTAAAGTTTATTTTGAAATGC
AATTAATTTGTAAGATCAGACCGCCCATTGGTTAGTT (SEQ ID NO: 4)

eHGT_774m:
TCCAGATGCTTGTCTTCTCTCTCTCTCTCTCTCTCTCTCTCTCTCTCTCTCTCTGTATGTGTG
TGTGTGTGTGTGTGTGTATGTGTGTCTTCCCCCNTNTTTTTCACCCCACCCCGACATCTA
CAACAAAAATTTTAACCATATTATGGAGTGGTCATATTGGCAGTTTTTTTACTGCAGCCCTTC
ACATGCACTGACATTCTAGACAGCAAGTGTTCTATGATTTTCAACAGGACACTTGGATCTAG
CCAACTCAGTTTTCAAGCCTGCCCCCGAGTTGTAGATCCTGTCTTCACATTCTAAACTAATC
TCACACCACTTTGTGCCAACTCCACTCTGGTAAAGACCATGCACTCGAGTTAGTGCAAGAC
ATTTTGTTCTGGCCTCGGGGTGTGCTGCCGCCTCGTCAGGATGGGAGGTGGAGGCGAGT
CCAGTGAAGGTCACTGGCATCACAAGAGTGAGGGACAGATATGTTCCCGAGCCTTCAGAT
TCAAGTCCTGCACTTGCAAAAAAGACTTCTGCCTTTTCTATTTGACCCAACTAGCTATTGCA
TTATTGAGCCAGACAGTGGCTCAAATTAAATGTCACAGGAGCACACCCTAACAAAAAGAAG
AGGCCAGCATGCT (SEQ ID NO: 5)

eHGT_772m:
TAGAGAAATGTGCTGTGGTTTAACTTTTGGAATAAAAATAGTGAATTTTTAATGAGCAGGTG
GGAATGTCCTTGGGTTCTGAGTTAGGATGGTGGAGCAAGGAAAGAAAAGGTCTCTCTTCCT
TTTCCCTGTGTGCTGAGTAGAGACAGGATTGCCCAGAACACCAGGAACNTAGGTTGTACTG
ACAAAAGTGGAAAACAGCCGCAAAACCGCTAGGGAAAGCAGCTGTCCCCTTGCCCAGTCT
CCTGCCCCACTCCTGCCTCTGCCTATAAGAGTTTGGCACAGTTGGAGATTTGTATACACAA
ATGCATGCGTGGAAATACTGCGCTCTGATGACATTCCTCAGGGGGCGACCTTTGATGATGA
ATTTTCTTGCCCTTTTTAGGGGAGGAGAAGAGGAGGCGGGTGGTACTTCACAAGACTAAAT
TTACTCAACTTTTTTGGGTCTAAATTTCTTTAGGAAAAAAAATGTCAAATGATTGTAGATCCC
AAACTGTCTTTGTTGGCATTTGAATGGCTCTGTGAGTCCAGTGTGGGGAGCAAGTGAAAAG
AAAAGCCACCTCTCCCCTCGCTGGCGTGGTATTGAAGCTGAAGCCCTGGACCACACAGTG
TCTTGGGGACCTTCATGATTTATATATTGTATGTGATCTTTTCTTAAACATTGTTAACCTGTG
CCCTTTACAGACAATGCCGGGTCAGAAAATGTCAGGGGAACTTCGGACTGCTTTCATAATT
GTGTAAAGAAAATTGTTGTCTTCAGAATCCAGAGCCCA (SEQ ID NO: 6)

FIG. 10 cont'd eHGT_486m:
TTCAGGCCAATACCTCAGCGAAAATCAAATCAGTTGCAAAATCCATACAGTCTTCCAGTTTC
TCAGCTGTGGAAACTTTGTGTCTCTTCTTTTCCACCAAAACAGCTATCTCGTCTTTCAAGTC
CTTGCTGAAAAAAAAAAGTGTTAAATTTTTCTCAATTTAGACTTCCAGCAAAACAGATTCTGC
TTGTTGAAAGGCATTGGTGTTCATGAGTAAGTGAGTTTCCATTTTATTTCTTCACAAATAAGT
TACATGAAGTACTTATCTTATGGTACTAGAGTTAACTGGGATTTCTAAACACAGGT (SEQ ID NO: 7)

eHGT_875m:
ACTGACTGAGGCTGCTCAATGTACCATATTAAAAAGGGAGCTGCGGCTAAGCCAGTTTCTG
CAGGACAGAGCCACAGACTATGGGATACTTCCAAGGAGAAGGAAGGAGTGGCGAGGTGG
CACTGCGTCAGCTGACCGCTAGACTGTGACTTTATCCAGCTCTGTGTTAGCTGAGTGATGA
CAGTAATGCCGTATCTACACACCCACCGCCTACTGGGAACCTCCACATGAGTACATAACAT
AGCATCTGAGGCCAGCAGTGCGCAGAACACATCTGCTCATCTACAGTGCCTTCAAACGGG
AGGGAAGTACCAGTCCTCTCTCAGTGAGAACACCATCCGTCCTGGGTGAGAGCTTTAGGC
ATTGCCATGGCTCCCTGTCACTCGGCCCTGACCCACACATTCACAGCCAT (SEQ ID NO: 60)

eHGT_923m:
GAGTTAACATTTCAAATAAAATAGGTGTGTGTGTGTGTGTGTGTGTGTGTGTGTGTGTGTGT
GTGTGTGTGTGTGTGTTTTAGAAAAAGATCAATTATGGGTTGAATCTGTTGTCACCCCACTT
GCATGTAGCTCTATTTCTTAGTCATATTTTATTATTTTATGCCCAAAGGCATGGCACTGGAA
GACAAGTTTCAATTTTTCTCTTTTGATGTTTCATTCTTATGAAGTGGAAGGTTGAAAGTTTGA
AATCCATATGACTCAGGAATTGAATTTCAGCTCTTCTAAATACAGACTGTGTTAAAGGGCAA
CACTTTTATATATATATATTCACAGCTAAGGCAGCATTTACTTCACATAGTAGTTAAAGAAGT
TAAGAATTAAGTTAGTCACATGTAACAGAATTCTCCCATTTCATAGAAACTCAAATTTTTGTT
TCCTTTTTCCTTTCCTTCTCTCATTCTTTCTCCACAGCTTACAAGAAGTTAGAATGTATACTT
TCATATAATAGATCCCCCTCCTCCCACTAAAAGAGATTTGAGAGATG (SEQ ID NO: 61)

eHGT_924m:
TCAGAGGCCAGTGTGTATTTAGGGTAGGGCAGTACATTAAAGTTCTGGTTTGTGTGCTGTC
ACCCTATCCTAGAAACTGGTTTGAGAGTTTTAGTTCACATGCAAAATGAAGGTCAAAGTCAA
TACCAAGGAGTCTAAAATCAACGTGAAGTGATACAGAGATGTGCACAGTTTGTTTGTTACG
AACATCACTGCCTCCTACAGAATGAACTTATCATCATGTGTCACAATCATCCCATGCATTTT
CCAGCTACTTCCAGTGAGCTCCAAATCTTTACACATTTTGAGGTTGAAGTAAAAGAGCAATG
TGCACAGTGAGATAGTCACAGTTTCTTTACCCAGTCTTGGGTGATTCAGATTCAGTCAGGC
CAACAGGGAGGACTTTCCTGCCAGGAGGGGGGCCCGAGCAAGAACAGGAGCTTAGACCC
TATGATGCTTAGAAAGAACCCAGGAAACTGCCTATGCTGTCTGTTGATTATGCCGTGATTG
CTGCAGGAAATGCAGTAGTTTATGAAACAGTAGAAGCTAAGCATGT (SEQ ID NO: 62)

eHGT_925m:
AGAGCCAACGAACTCGAAGAAAACATACGTAATTAAAGAGAAACTGCTCTTCAACATAGGA
GAGATGGAAGGCATCAGCAAAATATACACATGAAATGAATGGTCAAGTGGAAGGTTTAAGA
TTTGCTCTATACAGATTGAGACGCCAGTTTAAAAATAACATGGGGAAGGGAATGCTAGAAA
TGGTGTAATCAGTAAGAAGGACAATCTAAGGGAATCTAAGGCTTGAAAGGAAACAGAAAAC

FIG. 10 cont'd

CGGGTGTGGTGGTAAATGGATTGTGACTTAGAAGCTGGCCTGAGCTATATACAGAGACCC
TGTCAAGAAAAGAGAGATGGGAGTAGTAGGAGAGGAAAGTGTGAAGGGAAGGGAAAAGAA
AGGGAGGGGGAAAGAAGCAACCAAACAAGCAATCTTGCAGTGGCTTCTGCCAGCATGCTG
GCAAACCCTGCAGTGATATTTTCACATCTATGTAAAAACCCATTTTAGCACCTCCAGAATGA
ACTTTACAAGAATTGAGAAAGTCAAGTGAGAGAGCACCAAAGAAGGAAGGAAAGAAAAAAG
CAAGAACACTTGCCAGAAAGATAGGAAACCAAGAACCAGAAAAATAGGAAACAAAACTAAG
GAAAGCTGCAGAGCAGTATTCATGGCAAACACAGAAAGAGAAATTCTCAAAACAAGGCTAG
CAACCCAAACACAAAAGCACAGAAAAGAGATGTTTCATCACAAGTATGATGTATCTCAAGTA
TGCTCAAATGACTGAAGATACACAAGCCAGCCAAGGTGATACGCTACCACATCAACAGCAC
AACAGGCA (SEQ ID NO: 63)

eHGT_926m:
GTGTGTGTGTGTGTGTGTGTGTGTGTGTGTGTCTCTGTGTGTGTGTGTGTGTGTGTGTGTGTG
TGTATGTGTGTGTATGTGAAATTATCAGGCCTCAGTTTCCTCCTCTACAAAATGGAAATGCT
TACAAATGTCTTGCCATGCTTAGCATACACAAGTTGCTTTGCTAAGATGCTGAATTTAGTAA
AGGTCAGTTACTATTCTAACCGATGGTAGACAGAGACTCCAACAGAGCTCTTAGAAAGCCT
GCATAACAGTAAGTCTAAGCAATGGAGTAGGGCACTAGATTATTTTATTCCTTTGCAAAAGT
TTCTGCCTGAAATTGCAATGTTTTCTAGGTATAATTTTCATAGACTATAAACTCAAGTAGAAC
AAAGATAC (SEQ ID NO: 64)

Beta-Globin Minimal Promoter (pBGmin/minBGlobin/minBGprom):
GGGCTGGGCATAAAAGTCAGGGCAGAGCCATCTATTGCTTACATTTGCTTCTG (SEQ ID NO: 8)

minCMV Promoter:
GAGGTAGGCGTGTACGGTGGGAGGCCTATATAAGCAGAGCTCGTTTAGTGAACCGTCAGA
TCGCCTGG (SEQ ID NO: 9)

Mutated minCMV Promoter (SacI RE site removed):
GAGGTAGGCGTGTACGGTGGGAGGCCTATATAAGCAGAGCTGGTTTAGTGAACCGTCAGA
TCGCCTGG (SEQ ID NO: 10)

minRho Promoter:
GATTCAGCCGGGAGCTTAGGGAGGGGAGGTCACTTCATAAGGGCCTGGGGGGGGAGTTG
GAGCCACGAGTCGTCCAGCCGGAGCCCCGTGTGGCTGAGCTCCGGCCTCAGAAGCATCC
CC (SEQ ID NO: 11)

**minRho* Promoter:**
GATTCAGCCGGGAGCTTAGGGAGGGGAGGTCACTTCATAAGGGCTTGGGGGGGGAGTTG
GAGCCACGAGTCGTCCAGCCGGAGCCCCGTGTGGCTGTGCTCCGGCCTCAGAAGCATCC
CC (SEQ ID NO: 12)

Hsp68 minimal Promoter (proHsp68):
CAGGAACATCCAAACTGAGCAGCCGGGGTCCCCCCCACCCCCCACCCCGCCCCACGCGG
CAACTTTGAGCCTGTGCTGGGACAGAGCCTCTAGTTCCTAAATTAGTCCATGAGGTCAGAG

FIG. 10 cont'd

GCAGCACTGCCATTGTAACGCGATTGGAGAGGATCACGTCACCGGACACGCCCCCAGGC
ATCTCCCTGGGTCTCCTAAACTTGGCGGGGAGAAGTTTTAGCCCTTAAGTTTTAGCCTTTAA
CCCCCATATTCAGAACTGTGCGAGTTGGCGAAACCCCACAAATCACAACAAACTGTACACA
ACACCGAGCTAGAGGTGATCTTTCTTGTCCATTCCACACAGGCCTTAGTAATGCGTCGCCA
TAGCAACAGTGTCACTAGTAGCACCAGCACTTCCCCACACCCTCCCCCTCAGGAATCCGTA
CTCTCCAGTGAACCCCAGAAACCTCTGGAGAGTTCTGGACAAGGGCGGAACCCACAACTC
CGATTACTCAAGGGAGGCGGGGAAGCTCCACCAGACGCGAAACTGCTGGAAGATTCCTG
GCCCCAAGGCCTCCTCCGGCTCGCTGATTGGCCCAGCGGAGAGTGGGCGGGGCCGGTG
AAGACTCCTTAAAGGCGCAGGGCGGCGAGCAGGTCACCAGACGCTGACAGCTACTCAGA
ACCAAATCTGGTTCCATCCAGAGACAAGCGAAGACAAGAGAAGCAGAGCGAGCGGCGCGT
TCCCGATCCTCGGCCAGGACCAGCCTTCCCCAGAGCATCCCTGCCGCGGAGCGCAACCT
TCCCAGGAGCATCCCTGCCGCGGAGCGCAACTTTCCCCGGAGCATCCACGCCGCGGAGC
GCAGCCTTCCAGAAGCAGAGCGCGGCGCC (SEQ ID NO: 13)

SYFP2:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGCTGATCTGCACCACCGGCAAGCTGCCCGTGCCCTGGCCC
ACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAA (SEQ ID NO: 14)

EGFP:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTACGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAA
GAACGGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGTAA (SEQ ID NO: 15)

FIG. 10 cont'd

Optimized Flp recombinase (FlpO):
ATGGCTCCTAAGAAGAAGAGGAAGGTGATGAGCCAGTTCGACATCCTGTGCAAGACCCCC
CCCAAGGTGCTGGTGCGGCAGTTCGTGGAGAGATTCGAGAGGCCCAGCGGCGAGAAGAT
CGCCAGCTGTGCCGCCGAGCTGACCTACCTGTGCTGGATGATCACCCACAACGGCACCG
CCATCAAGAGGGCCACCTTCATGAGCTACAACACCATCATCAGCAACAGCCTGAGCTTCGA
CATCGTGAACAAGAGCCTGCAGTTCAAGTACAAGACCCAGAAGGCCACCATCCTGGAGGC
CAGCCTGAAGAAGCTGATCCCCGCCTGGGAGTTCACCATCATCCCTTACAACGGCCAGAA
GCACCAGAGCGACATCACCGACATCGTGTCCAGCCTGCAGCTGCAGTTCGAGAGCAGCG
AGGAGGCCGACAAGGGCAACAGCCACAGCAAGAAGATGCTGAAGGCCCTGCTGTCCGAG
GGCGAGAGCATCTGGGAGATCACCGAGAAGATCCTGAACAGCTTCGAGTACACCAGCAGG
TTCACCAAGACCAAGACCCTGTACCAGTTCCTGTTCCTGGCCACATTCATCAACTGCGGCA
GGTTCAGCGACATCAAGAACGTGGACCCCAAGAGCTTCAAGCTGGTGCAGAACAAGTACC
TGGGCGTGATCATTCAGTGCCTGGTGACCGAGACCAAGACAAGCGTGTCCAGGCACATCT
ACTTTTTCAGCGCCAGAGGCAGGATCGACCCCCTGGTGTACCTGGACGAGTTCCTGAGGA
ACAGCGAGCCCGTGCTGAAGAGAGTGAACAGGACCGGCAACAGCAGCAGCAACAAGCAG
GAGTACCAGCTGCTGAAGGACAACCTGGTGCGCAGCTACAACAAGGCCCTGAAGAAGAAC
GCCCCCTACCCCATCTTCGCTATCAAGAACGGCCCTAAGAGCCACATCGGCAGGCACCTG
ATGACCAGCTTTCTGAGCATGAAGGGCCTGACCGAGCTGACAAACGTGGTGGGCAACTGG
AGCGACAAGAGGGCCTCCGCCGTGGCCAGGACCACCTACACCCACCAGATCACCGCCAT
CCCCGACCACTACTTCGCCCTGGTGTCCAGGTACTACGCCTACGACCCCATCAGCAAGGA
GATGATCGCCCTGAAGGACGAGACCAACCCCATCGAGGAGTGGCAGCACATCGAGCAGC
TGAAGGGCAGCGCCGAGGGCAGCATCAGATACCCCGCCTGGAACGGCATCATCAGCCAG
GAGGTGCTGGACTACCTGAGCAGCTACATCAACAGGCGGATCTGA (SEQ ID NO: 16)

Improved Cre recombinase (iCre):
ATGGTGCCCAAGAAGAAGAGGAAAGTCTCCAACCTGCTGACTGTGCACCAAAACCTGCCT
GCCCTCCCTGTGGATGCCACCTCTGATGAAGTCAGGAAGAACCTGATGGACATGTTCAGG
GACAGGCAGGCCTTCTCTGAACACACCTGGAAGATGCTCCTGTCTGTGTGCAGATCCTGG
GCTGCCTGGTGCAAGCTGAACAACAGGAAATGGTTCCCTGCTGAACCTGAGGATGTGAGG
GACTACCTCCTGTACCTGCAAGCCAGAGGCCTGGCTGTGAAGACCATCCAACAGCACCTG
GGCCAGCTCAACATGCTGCACAGGAGATCTGGCCTGCCTCGCCCTTCTGACTCCAATGCT
GTGTCCCTGGTGATGAGGAGAATCAGAAAGGAGAATGTGGATGCTGGGGAGAGAGCCAA
GCAGGCCCTGGCCTTTGAACGCACTGACTTTGACCAAGTCAGATCCCTGATGGAGAACTC
TGACAGATGCCAGGACATCAGGAACCTGGCCTTCCTGGGCATTGCCTACAACACCCTGCT
GCGCATTGCCGAAATTGCCAGAATCAGAGTGAAGGACATCTCCCGCACCGATGGTGGGAG
AATGCTGATCCACATTGGCAGGACCAAGACCCTGGTGTCCACAGCTGGTGTGGAGAAGGC
CCTGTCCCTGGGGGTTACCAAGCTGGTGGAGAGATGGATCTCTGTGTCTGGTGTGGCTGA
TGACCCCAACAACTACCTGTTCTGCCGGGTCAGAAAGAATGGTGTGGCTGCCCCTTCTGC
CACCTCCCAACTGTCCACCCGGGCCCTGGAAGGGATCTTTGAGGCCACCCACCGCCTGAT
CTATGGTGCCAAGGATGACTCTGGGCAGAGATACCTGGCCTGGTCTGGCCACTCTGCCAG
AGTGGGTGCTGCCAGGGACATGGCCAGGGCTGGTGTGTCCATCCCTGAAATCATGCAGG
CTGGTGGCTGGACCAATGTGAACATTGTGATGAACTACATCAGAAACCTGGACTCTGAGAC
TGGGGCCATGGTGAGGCTGCTCGAGGATGGGGACTAA (SEQ ID NO: 17)

FIG. 10 cont'd

SP10 insulator (SP10ins):
GAAGCTACCCCTAACACACTATTCTACACACAGAAAATGCTCTTCACTAG (SEQ ID NO: 18)

3xSP10ins:
GAAGCTACCCCTAACACACTATTCTACACACAGAAAATGCTCTTCACTAGGAAGCTACCCC
TAACACACTATTCTACACACAGAAAATGCTCTTCACTAGGAAGCTACCCCTAACACACTATT
CTACACACAGAAAATGCTCTTCACTAG (SEQ ID NO: 19)

3XFLAG:
GACTACAAAGACCATGACGGAGATTATAAAGATCATGACATCGATTACAAGGATGACGATG
ACAAG (SEQ ID NO: 65)

10aa:
TCCGGACTCAGATCTGGAGGCTCCGGAGGC (SEQ ID NO: 66)

H2B:
CCAGAGCCAGCGAAGTCTGCTCCCGCCCCGAAAAAGGGCTCCAAGAAGGCGGTGACTAA
GGCGCAGAAGAAAGGCGGCAAGAAGCGCAAGCGCAGCCGCAAGGAGAGCTATTCCATCT
ATGTGTACAAGGTTCTGAAGCAGGTCCACCCTGACACCGGCATTTCGTCCAAGGCCATGG
GCATCATGAATTCGTTTGTGAACGACATTTTCGAGCGCATCGCAGGAGAGGCTTCCCGCCT
GGCGCATTACAACAAGCGCTCGACCATCACCTCCCGGGAGATCCAGACGGCCGTGCGCC
TGCTGCTGCCTGGGGAGTTGGCCAAGCACGCCGTGTCCGAGGGTACTAAGGCCATCACC
AAGTACACCAGCGCTAAGTAA (SEQ ID NO: 67)

WPRE3:
ATAATCAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCGTATG
GCTTTCATTTTCTCCTCCTTGTATAAATCCTGGTTAGTTCTTGCCACGGCGGAACTCATCGC
CGCCTGCCTTGCCCGCTGCTGGACAGGGGCTCGGCTGTTGGGCACTGACAATTCCGTGG
(SEQ ID NO: 20)

WPRE:
GCTTATCGATAATCAACCTCTGGATTACAAAATTTGTGAAAGATTGACTGGTATTCTTAACTA
TGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTGACGCAACCCCC
ACTGGTTGGGGCATTGCCACCACCTGTCAGCTCCTTTCCGGGACTTTCGCTTTCCCCCTCC
CTATTGCCACGGCGGAACTCATCGCCGCCTGCCTTGCCCGCTGCTGGACAGGGGCTCGG
CTGTTGGGCACTGACAATTCCGTGGTGTTGTCGGGGAAATCATCGTCCTTTCCTTGGCTGC
TCGCCTATGTTGCCACCTGGATTCTGCGCGGGACGTCCTTCTGCTACGTCCCTTCGGCCC
TCAATCCAGCGGACCTTCCTTCCCGCGGCCTGCTGCCGGCTCTGCGGCCTCTTCCGCGTC
TTCGCCTTCGCCCTCAGACGAGTCGGATCTCCCTTTGGGCCGCCTCCCCGCATCGATACC
G (SEQ ID NO: 21)

FIG. 10 cont'd

BGHpA:
CGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGAGGA
TTGGGAAGACAATAGCAGGCATG (SEQ ID NO: 22)

HGHpA:
ACGGGTGGCATCCCTGTGACCCCTCCCCAGTGCCTCTCCTGGCCCTGGAAGTTGCCACTC
CAGTGCCCACCAGCCTTGTCCTAATAAAATTAAGTTGCATCATTTTGTCTGACTAGGTGTCC
TTCTATAATATTATGGGGTGGAGGGGGGTGGTATGGAGCAAGGGGCAAGTTGGGAAGACA
ACCTGTAGGGCCTGCGGGGTCTATTGGGAACCAAGCTGGAGTGCAGTGGCACAATCTTGG
CTCACTGCAATCTCCGCCTCCTGGGTTCAAGCGATTCTCCTGCCTCAGCCTCCCGAGTTGT
TGGGATTCCAGGCATGCATGACCAGGCTCAGCTAATTTTTGTTTTTTTGGTAGAGACGGGG
TTTCACCATATTGGCCAGGCTGGTCTCCAACTCCTAATCTCAGGTGATCTACCCACCTTGG
CCTCCCAAATTGCTGGGATTACAGGCGTGAACCACTGCTCCCTTCCCTGTCCTT (SEQ ID
NO: 23)

P2A:
GGCAGCGGCGCCACCAACTTCAGCCTGCTGAAGCAGGCCGGCGACGTGGAGGAGAACCC
CGGCCCCGGAGCTAGCGGA (SEQ ID NO: 24)

T2A:
(GSG)EGRGSLLTCGDVEENPGP (SEQ ID NO: 25)

E2A:
(GSG)QCTNYALLKLAGDVESNPGPP (SEQ ID NO: 26)

F2A:
(GSG)VKQTLNFDLLKLAGDVESNPGP (SEQ ID NO: 27)

Exemplary Plasmid Backbone 1 – Left ITR:
CCTGCAGGCAGCTGCGCGCTCGCTCGCTCACTGAGGCCGCCCGGGCGTCGGGCGACCTT
TGGTCGCCCGGCCTCAGTGAGCGAGCGAGCGCGCAGAGAGGGAGTGGCCAACTCCATCA
CTAGGGGTTCCT (SEQ ID NO: 28)

Exemplary Plasmid Backbone 1 – Right ITR:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCT (SEQ ID NO: 29)

Exemplary Plasmid Backbone 2 – Left ITR:
CATGTCCTGCAGGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCGCAGAGAGGG
AGTGGCCAACTCCATCACTAGGGGTTCCT (SEQ ID NO: 30)

FIG. 10 cont'd

Exemplary Plasmid Backbone 2 – Right ITR:
AGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGCTGCCTGCAGGGGCGCCTG (SEQ ID NO: 31)

PHP.eB capsid:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSDGTLAVPFKAQAQTGWVQNQGILPGMVWQDRDV
YLQGPIWAKIPHTDGNFHPSPLMGGFGMKHPPPQILIKNTPVPADPPTAFNKDKLNSFITQYST
GQVSVEIEWELQKENSKRWNPEIQYTSNYYKSNNVEFAVNTEGVYSEPRPIGTRYLTRNL
(SEQ ID NO: 32)

AAV9 VP1 capsid protein:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSAQAQAQTGWVQNQGILPGMVWQDRDVYLQGPIW
AKIPHTDGNFHPSPLMGGFGMKHPPPQILIKNTPVPADPPTAFNKDKLNSFITQYSTGQVSVEIE
WELQKENSKRWNPEIQYTSNYYKSNNVEFAVNTEGVYSEPRPIGTRYLTRNL (SEQ ID NO:
33)

tet-Transactivator version 2 (tTA2):
ATGTCTAGACTGGACAAGAGCAAAGTCATAAACTCTGCTCTGGAATTACTCAATGAAGTCG
GTATCGAAGGCCTGACGACAAGGAAACTCGCTCAAAAGCTGGGAGTTGAGCAGCCTACCC
TGTACTGGCACGTGAAGAACAAGCGGGCCCTGCTCGATGCCCTGGCAATCGAGATGCTGG
ACAGGCATCATACCCACTTCTGCCCCCTGGAAGGCGAGTCATGGCAAGACTTTCTGCGGA
ACAACGCCAAGTCATTCCGCTGTGCTCTCCTCTCACATCGCGACGGGGCTAAAGTGCATCT
CGGCACCCGCCCAACAGAGAAACAGTACGAAACCCTGGAAAATCAGCTCGCGTTCCTGTG
TCAGCAAGGCTTCTCCCTGGAGAACGCACTGTACGCTCTGTCCGCCGTGGGCCACTTTAC
ACTGGGCTGCGTATTGGAGGATCAGGAGCATCAAGTAGCAAAAGAGGAAAGAGAGACACC
TACCACCGATTCTATGCCCCCACTTCTGAGACAAGCAATTGAGCTGTTCGACCATCAGGGA

FIG. 10 cont'd

GCCGAACCTGCCTTCCTTTTCGGCCTGGAACTAATCATATGTGGCCTGGAGAAACAGCTAA
AGTGCGAAAGCGGCGGGCCGGCCGACGCCCTTGACGATTTTGACTTAGACATGCTCCCAG
CCGATGCCCTTGACGACTTTGACCTTGATATGCTGCCTGCTGACGCTCTTGACGATTTTGA
CCTTGACATGCTCCCCGGGTAA (SEQ ID NO: 34)

GTPase HRas [Homo sapiens]:
MTEYKLVVVGAGGVGKSALTIQLIQNHFVDEYDPTIEDSYRKQVVIDGETCLLDILDTAGQEEYS
AMRDQYMRTGEGFLCVFAINNTKSFEDIHQYREQIKRVKDSDDVPMVLVGNKCDLAARTVESR
QAQDLARSYGIPYIETSAKTRQGVEDAFYTLVREIRQHKLRKLNPPDESGPGCMSCKCVLS
(SEQ ID NO: 35)

Substance P is position 58-68 of Protachykinin-1 [Homo sapiens]:
RPKPQQFFGLM (SEQ ID NO: 36)

Oxytocin is position 20-28 of Oxytocin-neurophysin 1 [Homo sapiens]:
CYIQNCPLG (SEQ ID NO: 37)

GCaMP6m:
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAGGGA
GCTACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 38)

GCaMP6s:
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC

FIG. 10 cont'd

GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCCACATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 39)

GCaMP6f:
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGAATTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA

FIG. 10 cont'd

CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 40)

AiP1211 (length between ITRs: 2901):
GCGGCCGCACGCGTCCTTTTAGAAACACTCCCTTTACCATCTTCAAACATGTTTTTAGCTGA
GAACTCTCTTCCAACCCCTGTTTCTTAACTCTGAGTGCCGTATCACTTCATATTCTGTGTCA
GGGGAAAAGAAATCAGCACCTCCCACAACGTCAACTGTGTCCTTTAGAGTAAGCATTCCAA
AGTCTATATTCTGAGTCTAATCTCTCTTGGAAAGGTCAGCCTTTTCTTCCAAATACCAAGTG
GACATCTTTATGCACAGGCCTTCAAGGATATTCAAGTCAGTGTGTCCTACGGAGAAAACTC
CTTTTAAAACCCGAATCCTGTGGTTTCCCCAAGATGATTATTGGGTGGTCACTGCAGCCTTA
AGGAGCTCGGGCTGGGCATAAAAGTCAGGGCAGAGCCATCTATTGCTTACATTTGCTTCTG
GCGTGGCCACCATGGCTCCTAAGAAGAAGAGGAAGGTGATGAGCCAGTTCGACATCCTGT
GCAAGACCCCCCCCAAGGTGCTGGTGCGGCAGTTCGTGGAGAGATTCGAGAGGCCCAGC
GGCGAGAAGATCGCCAGCTGTGCCGCCGAGCTGACCTACCTGTGCTGGATGATCACCCA
CAACGGCACCGCCATCAAGAGGGCCACCTTCATGAGCTACAACACCATCATCAGCAACAG
CCTGAGCTTCGACATCGTGAACAAGAGCCTGCAGTTCAAGTACAAGACCCAGAAGGCCAC
CATCCTGGAGGCCAGCCTGAAGAAGCTGATCCCCGCCTGGGAGTTCACCATCATCCCTTA
CAACGGCCAGAAGCACCAGAGCGACATCACCGACATCGTGTCCAGCCTGCAGCTGCAGTT
CGAGAGCAGCGAGGAGGCCGACAAGGGCAACAGCCACAGCAAGAAGATGCTGAAGGCCC
TGCTGTCCGAGGGCGAGAGCATCTGGGAGATCACCGAGAAGATCCTGAACAGCTTCGAGT
ACACCAGCAGGTTCACCAAGACCAAGACCCTGTACCAGTTCCTGTTCCTGGCCACATTCAT
CAACTGCGGCAGGTTCAGCGACATCAAGAACGTGGACCCCAAGAGCTTCAAGCTGGTGCA
GAACAAGTACCTGGGCGTGATCATTCAGTGCCTGGTGACCGAGACCAAGACAAGCGTGTC
CAGGCACATCTACTTTTTCAGCGCCAGAGGCAGGATCGACCCCCTGGTGTACCTGGACGA
GTTCCTGAGGAACAGCGAGCCCGTGCTGAAGAGAGTGAACAGGACCGGCAACAGCAGCA
GCAACAAGCAGGAGTACCAGCTGCTGAAGGACAACCTGGTGCGCAGCTACAACAAGGCC
CTGAAGAAGAACGCCCCCTACCCCATCTTCGCTATCAAGAACGGCCCTAAGAGCCACATC
GGCAGGCACCTGATGACCAGCTTTCTGAGCATGAAGGGCCTGACCGAGCTGACAAACGTG
GTGGGCAACTGGAGCGACAAGAGGGCCTCCGCCGTGGCCAGGACCACCTACACCCACCA
GATCACCGCCATCCCCGACCACTACTTCGCCCTGGTGTCCAGGTACTACGCCTACGACCC
CATCAGCAAGGAGATGATCGCCCTGAAGGACGAGACCAACCCCATCGAGGAGTGGCAGC
ACATCGAGCAGCTGAAGGGCAGCGCCGAGGGCAGCATCAGATACCCCGCCTGGAACGGC
ATCATCAGCCAGGAGGTGCTGGACTACCTGAGCAGCTACATCAACAGGCGGATCTGAGAA
TTCGATATCAAGCTTATCGATAATCAACCTCTGGATTACAAAATTTGTGAAAGATTGACTGG
TATTCTTAACTATGTTGCTCCTTTTACGCTATGTGGATACGCTGCTTTAATGCCTTTGTATCA
TGCTATTGCTTCCCGTATGGCTTTCATTTTCTCCTCCTTGTATAAATCCTGGTTGCTGTCTCT
TTATGAGGAGTTGTGGCCCGTTGTCAGGCAACGTGGCGTGGTGTGCACTGTGTTTGCTGA
CGCAACCCCCACTGGTTGGGGCATTGCCACCACCTGTCAGCTCCTTTCCGGGACTTTCGC
TTTCCCCCTCCCTATTGCCACGGCGGAACTCATCGCCGCCTGCCTTGCCCGCTGCTGGAC
AGGGGCTCGGCTGTTGGGCACTGACAATTCCGTGGTGTTGTCGGGGAAATCATCGTCCTT
TCCTTGGCTGCTCGCCTATGTTGCCACCTGGATTCTGCGCGGGACGTCCTTCTGCTACGT
CCCTTCGGCCCTCAATCCAGCGGACCTTCCTTCCCGCGGCCTGCTGCCGGCTCTGCGGC
CTCTTCCGCGTCTTCGCCTTCGCCCTCAGACGAGTCGGATCTCCCTTTGGGCCGCCTCCC
CGCATCGATACCGAGCGCTGCTCGAGAGATCTACGGGTGGCATCCCTGTGACCCCTCCCC
AGTGCCTCTCCTGGCCCTGGAAGTTGCCACTCCAGTGCCCACCAGCCTTGTCCTAATAAAA

FIG. 10 cont'd

TTAAGTTGCATCATTTTGTCTGACTAGGTGTCCTTCTATAATATTATGGGTGGAGGGGGGT
GGTATGGAGCAAGGGGCAAGTTGGGAAGACAACCTGTAGGGCCTGCGGGGTCTATTGGG
AACCAAGCTGGAGTGCAGTGGCACAATCTTGGCTCACTGCAATCTCCGCCTCCTGGGTTC
AAGCGATTCTCCTGCCTCAGCCTCCCGAGTTGTTGGGATTCCAGGCATGCATGACCAGGC
TCAGCTAATTTTTGTTTTTTTGGTAGAGACGGGGTTTCACCATATTGGCCAGGCTGGTCTCC
AACTCCTAATCTCAGGTGATCTACCCACCTTGGCCTCCCAAATTGCTGGGATTACAGGCGT
GAACCACTGCTCCCTTCCCTGTCCTTCTGATTTTGTAGGTAACCACGTGCGGACCGAGCG
GCCGC (SEQ ID NO: 41)

AiP1212 (length between ITRs: 3046):
GCGGCCGCACGCGTATATGGATGTCTTACCTGCATGAATACTTGTGTACCACATGTATGCC
TTTCTCCATGGAGGCCAGAAGAGGGTATCAGATTCCCTGGAACTGAAGTTACAGATAGTTG
TGAGCTGCCATGTGGGTACTGGAAATACATGTGTCTAATTTTAAGGACCAGCTCCTACTGA
GGACATAAATGTTATGTTTCTTAAAAGTCTATACCATAAGAATCTTCTTCAGATCTTGGTGTG
AAGATTCTTACCCCAGATTGGTTACAGAAGCGGTACCAGGTGGGTGGATCCCATCAAAAGC
TTTAGTGAGAAATCACCCTTTTCCTTCACAGCAGCCCAGCTGACTGGTGAACTTTGCCGAA
CTGTAAAATATCAAACCTTTGGGAAGCTTTCTGCAACACGAGAAGTTTTAATCCTTCAATATT
AAAAAGAAAAATAAGAAAAAAAAACTGTGGAGAAGTCACGAACAGGAGAAACAAAAAGGAA
TTGTGCACAGGGTCAGTCGCTTAAGGAGCTCGGGCTGGGCATAAAAGTCAGGGCAGAGC
CATCTATTGCTTACATTTGCTTCTGGCGTGGCCACCATGGCTCCTAAGAAGAAGAGGAAGG
TGATGAGCCAGTTCGACATCCTGTGCAAGACCCCCCCCAAGGTGCTGGTGCGGCAGTTCG
TGGAGAGATTCGAGAGGCCCAGCGGCGAGAAGATCGCCAGCTGTGCCGCCGAGCTGACC
TACCTGTGCTGGATGATCACCCACAACGGCACCGCCATCAAGAGGGCCACCTTCATGAGC
TACAACACCATCATCAGCAACAGCCTGAGCTTCGACATCGTGAACAAGAGCCTGCAGTTCA
AGTACAAGACCCAGAAGGCCACCATCCTGGAGGCCAGCCTGAAGAAGCTGATCCCCGCCT
GGGAGTTCACCATCATCCCTTACAACGGCCAGAAGCACCAGAGCGACATCACCGACATCG
TGTCCAGCCTGCAGCTGCAGTTCGAGAGCAGCGAGGAGGCCGACAAGGGCAACAGCCAC
AGCAAGAAGATGCTGAAGGCCCTGCTGTCCGAGGGCGAGAGCATCTGGGAGATCACCGA
GAAGATCCTGAACAGCTTCGAGTACACCAGCAGGTTCACCAAGACCAAGACCCTGTACCA
GTTCCTGTTCCTGGCCACATTCATCAACTGCGGCAGGTTCAGCGACATCAAGAACGTGGA
CCCCAAGAGCTTCAAGCTGGTGCAGAACAAGTACCTGGGCGTGATCATTCAGTGCCTGGT
GACCGAGACCAAGACAAGCGTGTCCAGGCACATCTACTTTTTCAGCGCCAGAGGCAGGAT
CGACCCCCTGGTGTACCTGGACGAGTTCCTGAGGAACAGCGAGCCCGTGCTGAAGAGAG
TGAACAGGACCGGCAACAGCAGCAGCAACAAGCAGGAGTACCAGCTGCTGAAGGACAAC
CTGGTGCGCAGCTACAACAAGGCCCTGAAGAAGAACGCCCCCTACCCCATCTTCGCTATC
AAGAACGGCCCTAAGAGCCACATCGGCAGGCACCTGATGACCAGCTTTCTGAGCATGAAG
GGCCTGACCGAGCTGACAAACGTGGTGGGCAACTGGAGCGACAAGAGGGCCTCCGCCGT
GGCCAGGACCACCTACACCCACCAGATCACCGCCATCCCCGACCACTACTTCGCCCTGGT
GTCCAGGTACTACGCCTACGACCCCATCAGCAAGGAGATGATCGCCCTGAAGGACGAGAC
CAACCCCATCGAGGAGTGGCAGCACATCGAGCAGCTGAAGGGCAGCGCCGAGGGCAGCA
TCAGATACCCCGCCTGGAACGGCATCATCAGCCAGGAGGTGCTGGACTACCTGAGCAGCT
ACATCAACAGGCGGATCTGAGAATTCGATATCAAGCTTATCGATAATCAACCTCTGGATTAC
AAAATTTGTGAAAGATTGACTGGTATTCTTAACTATGTTGCTCCTTTTACGCTATGTGGATAC
GCTGCTTTAATGCCTTTGTATCATGCTATTGCTTCCCGTATGGCTTTCATTTTCTCCTCCTTG
TATAAATCCTGGTTGCTGTCTCTTTATGAGGAGTTGTGGCCCGTTGTCAGGCAACGTGGCG

FIG. 10 cont'd

TGGTGTGCACTGTGTTTGCTGACGCAACCCCCACTGGTTGGGGCATTGCCACCACCTGTC
AGCTCCTTTCCGGGACTTTCGCTTTCCCCCTCCCTATTGCCACGGCGGAACTCATCGCCG
CCTGCCTTGCCCGCTGCTGGACAGGGGCTCGGCTGTTGGGCACTGACAATTCCGTGGTGT
TGTCGGGGAAATCATCGTCCTTTCCTTGGCTGCTCGCCTATGTTGCCACCTGGATTCTGCG
CGGGACGTCCTTCTGCTACGTCCCTTCGGCCCTCAATCCAGCGGACCTTCCTTCCCGCGG
CCTGCTGCCGGCTCTGCGGCCTCTTCCGCGTCTTCGCCTTCGCCCTCAGACGAGTCGGAT
CTCCCTTTGGGCCGCCTCCCCGCATCGATACCGAGCGCTGCTCGAGAGATCTACGGGTG
GCATCCCTGTGACCCCTCCCCAGTGCCTCTCCTGGCCCTGGAAGTTGCCACTCCAGTGCC
CACCAGCCTTGTCCTAATAAAATTAAGTTGCATCATTTTGTCTGACTAGGTGTCCTTCTATAA
TATTATGGGGTGGAGGGGGGTGGTATGGAGCAAGGGGCAAGTTGGGAAGACAACCTGTA
GGGCCTGCGGGGTCTATTGGGAACCAAGCTGGAGTGCAGTGGCACAATCTTGGCTCACTG
CAATCTCCGCCTCCTGGGTTCAAGCGATTCTCCTGCCTCAGCCTCCCGAGTTGTTGGGATT
CCAGGCATGCATGACCAGGCTCAGCTAATTTTTGTTTTTTTGGTAGAGACGGGGTTTCACC
ATATTGGCCAGGCTGGTCTCCAACTCCTAATCTCAGGTGATCTACCCACCTTGGCCTCCCA
AATTGCTGGGATTACAGGCGTGAACCACTGCTCCCTTCCCTGTCCTTCTGATTTTGTAGGT
AACCACGTGCGGACCGAGCGGCCGC (SEQ ID NO: 42)

AiP1218 (length between ITRs: 2988):
GCGGCCGCACGCGTCCCAGGATCTATTGACATCCAACATCGGATGGAGAAACTGAAGTTC
ACATCATAGCTCATCTCTCATAGTATCCTATACGGTGTTTCTCTTTCTTGGAGAAACAACCC
CACCCCACCCGCCTTGATGTTAATGCCAGGACACACATGTTTTCTTGACCCCACTTCTCTG
ATCACTCATCGCTCTGCTTCCTCAGCCTGTTGTTGGTACCAGTTCTCAGATAGTTGCAGTCT
CCAAGTTCAGTTCCTACCGATTTATGCCATGCTGTCTTTTTTGAGAAATACCACTCACCATG
TGAGTGAATCTGTGAATGCCTCCTAAATGCCCGTTGCCAATTTGAGAATAAAAGTTCATGTG
ATTATGTTCAAGGCATTTCAGATTAAATATGACCAAAATCACTCCGTGGTGCCTTCCTGTAC
GCCTCACCGTGAATCCAGTTTGCTTAAGGAGCTCGGGCTGGGCATAAAAGTCAGGGCAGA
GCCATCTATTGCTTACATTTGCTTCTGGCGTGGCCACCATGGCTCCTAAGAAGAAGAGGAA
GGTGATGAGCCAGTTCGACATCCTGTGCAAGACCCCCCCCAAGGTGCTGGTGCGGCAGTT
CGTGGAGAGATTCGAGAGGCCCAGCGGCGAGAAGATCGCCAGCTGTGCCGCCGAGCTGA
CCTACCTGTGCTGGATGATCACCCACAACGGCACCGCCATCAAGAGGGCCACCTTCATGA
GCTACAACACCATCATCAGCAACAGCCTGAGCTTCGACATCGTGAACAAGAGCCTGCAGTT
CAAGTACAAGACCCAGAAGGCCACCATCCTGGAGGCCAGCCTGAAGAAGCTGATCCCCGC
CTGGGAGTTCACCATCATCCCTTACAACGGCCAGAAGCACCAGAGCGACATCACCGACAT
CGTGTCCAGCCTGCAGCTGCAGTTCGAGAGCAGCGAGGAGGCCGACAAGGGCAACAGCC
ACAGCAAGAAGATGCTGAAGGCCCTGCTGTCCGAGGGCGAGAGCATCTGGGAGATCACC
GAGAAGATCCTGAACAGCTTCGAGTACACCAGCAGGTTCACCAAGACCAAGACCCTGTAC
CAGTTCCTGTTCCTGGCCACATTCATCAACTGCGGCAGGTTCAGCGACATCAAGAACGTG
GACCCCAAGAGCTTCAAGCTGGTGCAGAACAAGTACCTGGGCGTGATCATTCAGTGCCTG
GTGACCGAGACCAAGACAAGCGTGTCCAGGCACATCTACTTTTTCAGCGCCAGAGGCAGG
ATCGACCCCCTGGTGTACCTGGACGAGTTCCTGAGGAACAGCGAGCCCGTGCTGAAGAGA
GTGAACAGGACCGGCAACAGCAGCAGCAACAAGCAGGAGTACCAGCTGCTGAAGGACAA
CCTGGTGCGCAGCTACAACAAGGCCCTGAAGAAGAACGCCCCCTACCCCATCTTCGCTAT
CAAGAACGGCCCTAAGAGCCACATCGGCAGGCACCTGATGACCAGCTTTCTGAGCATGAA
GGGCCTGACCGAGCTGACAAACGTGGTGGGCAACTGGAGCGACAAGAGGGCCTCCGCCG
TGGCCAGGACCACCTACACCCACCAGATCACCGCCATCCCCGACCACTACTTCGCCCTGG

FIG. 10 cont'd

TGTCCAGGTACTACGCCTACGACCCCATCAGCAAGGAGATGATCGCCCTGAAGGACGAGA
CCAACCCCATCGAGGAGTGGCAGCACATCGAGCAGCTGAAGGGCAGCGCCGAGGGCAGC
ATCAGATACCCCGCCTGGAACGGCATCATCAGCCAGGAGGTGCTGGACTACCTGAGCAGC
TACATCAACAGGCGGATCTGAGAATTCGATATCAAGCTTATCGATAATCAACCTCTGGATTA
CAAAATTTGTGAAAGATTGACTGGTATTCTTAACTATGTTGCTCCTTTTACGCTATGTGGATA
CGCTGCTTTAATGCCTTTGTATCATGCTATTGCTTCCCGTATGGCTTTCATTTTCTCCTCCTT
GTATAAATCCTGGTTGCTGTCTCTTTATGAGGAGTTGTGGCCCGTTGTCAGGCAACGTGGC
GTGGTGTGCACTGTGTTTGCTGACGCAACCCCCACTGGTTGGGGCATTGCCACCACCTGT
CAGCTCCTTTCCGGGACTTTCGCTTTCCCCCTCCCTATTGCCACGGCGGAACTCATCGCC
GCCTGCCTTGCCCGCTGCTGGACAGGGGCTCGGCTGTTGGGCACTGACAATTCCGTGGT
GTTGTCGGGGAAATCATCGTCCTTTCCTTGGCTGCTCGCCTATGTTGCCACCTGGATTCTG
CGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCG
GATCTCCCTTTGGGCCGCCTCCCCGCATCGATACCGAGCGCTGCTCGAGAGATCTACGGG
TGGCATCCCTGTGACCCCTCCCCAGTGCCTCTCCTGGCCCTGGAAGTTGCCACTCCAGTG
CCCACCAGCCTTGTCCTAATAAAATTAAGTTGCATCATTTTGTCTGACTAGGTGTCCTTCTA
TAATATTATGGGGTGGAGGGGGGTGGTATGGAGCAAGGGGCAAGTTGGGAAGACAACCT
GTAGGGCCTGCGGGGTCTATTGGGAACCAAGCTGGAGTGCAGTGGCACAATCTTGGCTCA
CTGCAATCTCCGCCTCCTGGGTTCAAGCGATTCTCCTGCCTCAGCCTCCCGAGTTGTTGG
GATTCCAGGCATGCATGACCAGGCTCAGCTAATTTTTGTTTTTTTGGTAGAGACGGGGTTT
CACCATATTGGCCAGGCTGGTCTCCAACTCCTAATCTCAGGTGATCTACCCACCTTGGCCT
CCCAAATTGCTGGGATTACAGGCGTGAACCACTGCTCCCTTCCCTGTCCTTCTGATTTTGT
AGGTAACCACGTGCGGACCGAGCGGCCGC (SEQ ID NO: 43)

CN2603 (length between ITRs: 1951):
GCGGCCGCACGCGTATGGGAAAGCAGCACGTGTTCTTAACTGCTAGACTCCTATTTACCAT
GACAGTAATATCATTATTATTTTTAAATCATTTTATAATTTCAGGAGAAAGCAAATGATTGCTA
ATAACGGTCTCCCTCTTCAGTACATATGCACTACACGCGCATGTGTCCTTTAAAGATAAATT
TGAGTTGGAAGCATCGGTATGAGCTGGTGAGTTTTAAGAAGTTCCAGAAAAAAAAAAGAAG
TTCCAGTATTTCCTAGATTTGTCCTCTGCAAAGTCCTAGGCATAAAGGCAGCGCAGTTTGT
GGCCTTTAAATACCACTTCCCACGAAAGCAACCAAGGCTCCTTGGAGACGTGAGCGATTTG
ATGTCTATAAATATGAGCACACAGTGCTGTGCTTCCCCACTGAGGTCAGAAAGACCACTAC
CCTGAATCCAAACCACCTTCATGGCTTAGCAGATGAGGCCAGAGCTGGACAAGAGCAATTA
AAGGGAACAATTACATTACATGTTGGTGTTTGATTTATCTGCAGATTTTTTTAACCAGTAAAG
TTTATTTTGAAATGCAATTAATTTGTAAGATCAGACCGCCCATTGGTTAGTTGAGCTCGGGC
TGGGCATAAAAGTCAGGGCAGAGCCATCTATTGCTTACATTTGCTTCTGGGATCCAGATCT
TTCGAAGCTAGCGCTACCGGTCGCCACCATGGTGAGCAAGGGCGAGGAGCTGTTCACCG
GGGTGGTGCCCATCCTGGTCGAGCTGGACGGCGACGTAAACGGCCACAAGTTCAGCGTG
TCCGGCGAGGGCGAGGGCGATGCCACCTACGGCAAGCTGACCCTGAAGCTGATCTGCAC
CACCGGCAAGCTGCCCGTGCCCTGGCCCACCCTCGTGACCACCCTGGGCTACGGCGTGC
AGTGCTTCGCCCGCTACCCCGACCACATGAAGCAGCACGACTTCTTCAAGTCCGCCATGC
CCGAAGGCTACGTCCAGGAGCGCACCATCTTCTTCAAGGACGACGGCAACTACAAGACCC
GCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCAC
AACGTCTATATCACCGCCGACAAGCAGAAGAACGGCATCAAGGCCAACTTCAAGATCCGC

FIG. 10 cont'd

CACAACATCGAGGACGGCGGCGTGCAGCTCGCCGACCACTACCAGCAGAACACCCCCAT
CGGCGACGGCCCCGTGCTGCTGCCCGACAACCACTACCTGAGCTACCAGTCCAAGCTGA
GCAAAGACCCCAACGAGAAGCGCGATCACATGGTCCTGCTGGAGTTCGTGACCGCCGCC
GGGATCACTCTCGGCATGGACGAGCTGTACAAGTAAGTCGACGGCGCGCCGCGGCCGCG
AATTCGATATCATAATCAACCTCTGGATTACAAAATTTGTGAAAGATTGACTGGTATTCTTAA
CTATGTTGCTCCTTTTACGCTATGTGGATACGCTGCTTTAATGCCTTTGTATCATGCTATTG
CTTCCCGTATGGCTTTCATTTTCTCCTCCTTGTATAAATCCTGGTTAGTTCTTGCCACGGCG
GAACTCATCGCCGCCTGCCTTGCCCGCTGCTGGACAGGGGCTCGGCTGTTGGGCACTGA
CAATTCCGTGGCTCGAGAGATCTTCGACTGTGCCTTCTAGTTGCCAGCCATCTGTTGTTTG
CCCCTCCCCCGTGCCTTCCTTGACCCTGGAAGGTGCCACTCCCACTGTCCTTTCCTAATAA
AATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGAGATCTCACGTGC
GGACCGAGCGGCCGC (SEQ ID NO: 44)

CN2606 (length between ITRs: 1985):
GCGGCCGCACGCGTTCCAGATGCTTGTCTTCTCTCTCTCTCTCTCTCTCTCTCTCTCTCT
CTCTCTGTATGTGTGTGTGTGTGTGTGTGTGTATGTGTGTCTTCCCCCNTNTTTTCACCC
CACCCCGACATCTACAACAAAAATTTTAACCATATTATGGAGTGGTCATATTGGCAGTTTTT
TTACTGCAGCCCTTCACATGCACTGACATTCTAGACAGCAAGTGTTCTATGATTTTCAACAG
GACACTTGGATCTAGCCAACTCAGTTTTCAAGCCTGCCCCCGAGTTGTAGATCCTGTCTTC
ACATTCTAAACTAATCTCACACCACTTTGTGCCAACTCCACTCTGGTAAAGACCATGCACTC
GAGTTAGTGCAAGACATTTTGTTCTGGCCTCGGGGTGTGCTGCCGCCTCGTCAGGATGGG
AGGTGGAGGCGAGTCCAGTGAAGGTCACTGGCATCACAAGAGTGAGGGACAGATATGTTC
CCGAGCCTTCAGATTCAAGTCCTGCACTTGCAAAAAAGACTTCTGCCTTTTCTATTTGACCC
AACTAGCTATTGCATTATTGAGCCAGACAGTGGCTCAAATTAAATGTCACAGGAGCACACC
CTAACAAAAAGAAGAGGCCAGCATGCTGAGCTCGGGCTGGGCATAAAAGTCAGGGCAGAG
CCATCTATTGCTTACATTTGCTTCTGGGATCCAGATCTTTCGAAGCTAGCGCTACCGGTCG
CCACCATGGTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAGGGCGATGC
CACCTACGGCAAGCTGACCCTGAAGCTGATCTGCACCACCGGCAAGCTGCCCGTGCCCTG
GCCCACCCTCGTGACCACCCTGGGCTACGGCGTGCAGTGCTTCGCCCGCTACCCCGACC
ACATGAAGCAGCACGACTTCTTCAAGTCCGCCATGCCCGAAGGCTACGTCCAGGAGCGCA
CCATCTTCTTCAAGGACGACGGCAACTACAAGACCCGCGCCGAGGTGAAGTTCGAGGGCG
ACACCCTGGTGAACCGCATCGAGCTGAAGGGCATCGACTTCAAGGAGGACGGCAACATCC
TGGGGCACAAGCTGGAGTACAACTACAACAGCCACAACGTCTATATCACCGCCGACAAGC
AGAAGAACGGCATCAAGGCCAACTTCAAGATCCGCCACAACATCGAGGACGGCGGCGTG
CAGCTCGCCGACCACTACCAGCAGAACACCCCCATCGGCGACGGCCCCGTGCTGCTGCC
CGACAACCACTACCTGAGCTACCAGTCCAAGCTGAGCAAAGACCCCAACGAGAAGCGCGA
TCACATGGTCCTGCTGGAGTTCGTGACCGCCGCCGGGATCACTCTCGGCATGGACGAGCT
GTACAAGTAAGTCGACGGCGCGCCGCGGCCGCGAATTCGATATCATAATCAACCTCTGGA
TTACAAAATTTGTGAAAGATTGACTGGTATTCTTAACTATGTTGCTCCTTTTACGCTATGTGG
ATACGCTGCTTTAATGCCTTTGTATCATGCTATTGCTTCCCGTATGGCTTTCATTTTCTCCTC
CTTGTATAAATCCTGGTTAGTTCTTGCCACGGCGGAACTCATCGCCGCCTGCCTTGCCCGC
TGCTGGACAGGGGCTCGGCTGTTGGGCACTGACAATTCCGTGGCTCGAGAGATCTTCGAC
TGTGCCTTCTAGTTGCCAGCCATCTGTTGTTTGCCCCTCCCCCGTGCCTTCCTTGACCCTG

FIG. 10 cont'd

GAAGGTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGATTGG
GAAGACAATAGCAGGCATGAGATCTCACGTGCGGACCGAGCGGCCGC (SEQ ID NO: 45)

CN2612 (length between ITRs: 2131):
GCGGCCGCACGCGTTAGAGAAATGTGCTGTGGTTTAACTTTTGGAATAAAAATAGTGAATT
TTTAATGAGCAGGTGGGAATGTCCTTGGGTTCTGAGTTAGGATGGTGGAGCAAGGAAAGA
AAAGGTCTCTCTTCCTTTTCCCTGTGTGCTGAGTAGAGACAGGATTGCCCAGAACACCAGG
AACNTAGGTTGTACTGACAAAAGTGGAAAACAGCCGCAAAACCGCTAGGGAAAGCAGCTG
TCCCCTTGCCCAGTCTCCTGCCCCACTCCTGCCTCTGCCTATAAGAGTTTGGCACAGTTGG
AGATTTGTATACACAAATGCATGCGTGGAAATACTGCGCTCTGATGACATTCCTCAGGGGG
CGACCTTTGATGATGAATTTTCTTGCCCTTTTTAGGGGAGGAGAAGAGGAGGCGGGTGGT
ACTTCACAAGACTAAATTTACTCAACTTTTTTGGGTCTAAATTTCTTTAGGAAAAAAAATGTC
AAATGATTGTAGATCCCAAACTGTCTTTGTTGGCATTTGAATGGCTCTGTGAGTCCAGTGTG
GGGAGCAAGTGAAAAGAAAAGCCACCTCTCCCCTCGCTGGCGTGGTATTGAAGCTGAAGC
CCTGGACCACACAGTGTCTTGGGGACCTTCATGATTTATATATTGTATGTGATCTTTTCTTA
AACATTGTTAACCTGTGCCCTTTACAGACAATGCCGGGTCAGAAAATGTCAGGGGAACTTC
GGACTGCTTTCATAATTGTGTAAAGAAAATTGTTGTCTTCAGAATCCAGAGCCCAGAGCTC
GGGCTGGGCATAAAAGTCAGGGCAGAGCCATCTATTGCTTACATTTGCTTCTGGGATCCAG
ATCTTTCGAAGCTAGCGCTACCGGTCGCCACCATGGTGAGCAAGGGCGAGGAGCTGTTCA
CCGGGGTGGTGCCCATCCTGGTCGAGCTGGACGGCGACGTAAACGGCCACAAGTTCAGC
GTGTCCGGCGAGGGCGAGGGCGATGCCACCTACGGCAAGCTGACCCTGAAGCTGATCTG
CACCACCGGCAAGCTGCCCGTGCCCTGGCCCACCCTCGTGACCACCCTGGGCTACGGCG
TGCAGTGCTTCGCCCGCTACCCCGACCACATGAAGCAGCACGACTTCTTCAAGTCCGCCA
TGCCCGAAGGCTACGTCCAGGAGCGCACCATCTTCTTCAAGGACGACGGCAACTACAAGA
CCCGCGCCGAGGTGAAGTTCGAGGGCGACACCCTGGTGAACCGCATCGAGCTGAAGGGC
ATCGACTTCAAGGAGGACGGCAACATCCTGGGGCACAAGCTGGAGTACAACTACAACAGC
CACAACGTCTATATCACCGCCGACAAGCAGAAGAACGGCATCAAGGCCAACTTCAAGATC
CGCCACAACATCGAGGACGGCGGCGTGCAGCTCGCCGACCACTACCAGCAGAACACCCC
CATCGGCGACGGCCCCGTGCTGCTGCCCGACAACCACTACCTGAGCTACCAGTCCAAGCT
GAGCAAAGACCCCAACGAGAAGCGCGATCACATGGTCCTGCTGGAGTTCGTGACCGCCG
CCGGGATCACTCTCGGCATGGACGAGCTGTACAAGTAAGTCGACGGCGCGCCGCGGCCG
CGAATTCGATATCATAATCAACCTCTGGATTACAAAATTTGTGAAAGATTGACTGGTATTCTT
AACTATGTTGCTCCTTTTACGCTATGTGGATACGCTGCTTTAATGCCTTTGTATCATGCTATT
GCTTCCCGTATGGCTTTCATTTTCTCCTCCTTGTATAAATCCTGGTTAGTTCTTGCCACGGC
GGAACTCATCGCCGCCTGCCTTGCCCGCTGCTGGACAGGGGCTCGGCTGTTGGGCACTG
ACAATTCCGTGGCTCGAGAGATCTTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGAGATCTCACGTGC
GGACCGAGCGGCCGC (SEQ ID NO: 46)

CN2261 (length between ITRs: 1664):
GCGGCCGCACGCGTTTCAGGCCAATACCTCAGCGAAAATCAAATCAGTTGCAAAATCCATA
CAGTCTTCCAGTTTCTCAGCTGTGGAAACTTTGTGTCTCTTCTTTTCCACCAAAACAGCTAT

FIG. 10 cont'd

CTCGTCTTTCAAGTCCTTGCTGAAAAAAAAAAGTGTTAAATTTTTCTCAATTTAGACTTCCAG
CAAAACAGATTCTGCTTGTTGAAAGGCATTGGTGTTCATGAGTAAGTGAGTTTCCATTTTAT
TTCTTCACAAATAAGTTACATGAAGTACTTATCTTATGGTACTAGAGTTAACTGGGATTTCTA
AACACAGGTGAGCTCGGGCTGGGCATAAAAGTCAGGGCAGAGCCATCTATTGCTTACATTT
GCTTCTGGGATCCAGATCTTTCGAAGCTAGCGCTACCGGTCGCCACCATGGTGAGCAAGG
GCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGAC
CCTGAAGCTGATCTGCACCACCGGCAAGCTGCCCGTGCCCTGGCCCACCCTCGTGACCA
CCCTGGGCTACGGCGTGCAGTGCTTCGCCCGCTACCCCGACCACATGAAGCAGCACGAC
TTCTTCAAGTCCGCCATGCCCGAAGGCTACGTCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAGTAAGTCGAC
GGCGCGCCGCGGCCGCGAATTCGATATCATAATCAACCTCTGGATTACAAAATTTGTGAAA
GATTGACTGGTATTCTTAACTATGTTGCTCCTTTTACGCTATGTGGATACGCTGCTTTAATG
CCTTTGTATCATGCTATTGCTTCCCGTATGGCTTTCATTTTCTCCTCCTTGTATAAATCCTGG
TTAGTTCTTGCCACGGCGGAACTCATCGCCGCCTGCCTTGCCCGCTGCTGGACAGGGGCT
CGGCTGTTGGGCACTGACAATTCCGTGGCTCGAGAGATCTTCGACTGTGCCTTCTAGTTG
CCAGCCATCTGTTGTTTGCCCCTCCCCCGTGCCTTCCTTGACCCTGGAAGGTGCCACTCC
CACTGTCCTTTCCTAATAAAATGAGGAAATTGCATCGCATTGTCTGAGTAGGTGTCATTCTA
TTCTGGGGGGTGGGGTGGGGCAGGACAGCAAGGGGGAGGATTGGGAAGACAATAGCAG
GCATGAGATCTCACGTGCGGACCGAGCGGCCGC (SEQ ID NO: 47)

AiP1279 (length between ITRs: 2988):
GCGGCCGCACGCGTCCCAGGATCTATTGACATCCAACATCGGATGGAGAAACTGAAGTTC
ACATCATAGCTCATCTCTCATAGTATCCTATACGGTGTTTCTCTTTCTTGGAGAAACAACCC
CACCCCACCCGCCTTGATGTTAATGCCAGGACACACATGTTTTCTTGACCCCACTTCTCTG
ATCACTCATCGCTCTGCTTCCTCAGCCTGTTGTTGGTACCAGTTCTCAGATAGTTGCAGTCT
CCAAGTTCAGTTCCTACCGATTTATGCCATGCTGTCTTTTTTGAGAAATACCACTCACCATG
TGAGTGAATCTGTGAATGCCTCCTAAATGCCCGTTGCCAATTTGAGAATAAAAGTTCATGTG
ATTATGTTCAAGGCATTTCAGATTAAATATGACCAAAATCACTCCGTGGTGCCTTCCTGTAC
GCCTCACCGTGAATCCAGTTTGCTTAAGGAGCTCGGGCTGGGCATAAAAGTCAGGGCAGA
GCCATCTATTGCTTACATTTGCTTCTGGCGTGGCCACCATGGCTCCTAAGAAGAAGAGGAA
GGTGATGAGCCAGTTCGACATCCTGTGCAAGACCCCCCCCAAGGTGCTGGTGCGGCAGTT
CGTGGAGAGATTCGAGAGGCCCAGCGGCGAGAAGATCGCCAGCTGTGCCGCCGAGCTGA
CCTACCTGTGCTGGATGATCACCCACAACGGCACCGCCATCAAGAGGGCCACCTTCATGA
GCTACAACACCATCATCAGCAACAGCCTGAGCTTCGACATCGTGAACAAGAGCCTGCAGTT
CAAGTACAAGACCCAGAAGGCCACCATCCTGGAGGCCAGCCTGAAGAAGCTGATCCCCGC
CTGGGAGTTCACCATCATCCCTTACAACGGCCAGAAGCACCAGAGCGACATCACCGACAT
CGTGTCCAGCCTGCAGCTGCAGTTCGAGAGCAGCGAGGAGGCCGACAAGGGCAACAGCC
ACAGCAAGAAGATGCTGAAGGCCCTGCTGTCCGAGGGCGAGAGCATCTGGGAGATCACC

FIG. 10 cont'd

GAGAAGATCCTGAACAGCTTCGAGTACACCAGCAGGTTCACCAAGACCAAGACCCTGTAC
CAGTTCCTGTTCCTGGCCACATTCATCAACTGCGGCAGGTTCAGCGACATCAAGAACGTG
GACCCCAAGAGCTTCAAGCTGGTGCAGAACAAGTACCTGGGCGTGATCATTCAGTGCCTG
GTGACCGAGACCAAGACAAGCGTGTCCAGGCACATCTACTTTTTCAGCGCCAGAGGCAGG
ATCGACCCCCTGGTGTACCTGGACGAGTTCCTGAGGAACAGCGAGCCCGTGCTGAAGAGA
GTGAACAGGACCGGCAACAGCAGCAGCAACAAGCAGGAGTACCAGCTGCTGAAGGACAA
CCTGGTGCGCAGCTACAACAAGGCCCTGAAGAAGAACGCCCCCTACCCCATCTTCGCTAT
CAAGAACGGCCCTAAGAGCCACATCGGCAGGCACCTGATGACCAGCTTTCTGAGCATGAA
GGGCCTGACCGAGCTGACAAACGTGGTGGGCAACTGGAGCGACAAGAGGGCCTCCGCCG
TGGCCAGGACCACCTACACCCACCAGATCACCGCCATCCCCGACCACTACTTCGCCCTGG
TGTCCAGGTACTACGCCTACGACCCCATCAGCAAGGAGATGATCGCCCTGAAGGACGAGA
CCAACCCCATCGAGGAGTGGCAGCACATCGAGCAGCTGAAGGGCAGCGCCGAGGGCAGC
ATCAGATACCCCGCCTGGAACGGCATCATCAGCCAGGAGGTGCTGGACTACCTGAGCAGC
TACATCAACAGGCGGATCTGAGAATTCGATATCAAGCTTATCGATAATCAACCTCTGGATTA
CAAAATTTGTGAAAGATTGACTGGTATTCTTAACTATGTTGCTCCTTTTACGCTATGTGGATA
CGCTGCTTTAATGCCTTTGTATCATGCTATTGCTTCCCGTATGGCTTTCATTTTCTCCTCCTT
GTATAAATCCTGGTTGCTGTCTCTTTATGAGGAGTTGTGGCCCGTTGTCAGGCAACGTGGC
GTGGTGTGCACTGTGTTTGCTGACGCAACCCCCACTGGTTGGGGCATTGCCACCACCTGT
CAGCTCCTTTCCGGGACTTTCGCTTTCCCCCTCCCTATTGCCACGGCGGAACTCATCGCC
GCCTGCCTTGCCCGCTGCTGGACAGGGGCTCGGCTGTTGGGCACTGACAATTCCGTGGT
GTTGTCGGGGAAATCATCGTCCTTTCCTTGGCTGCTCGCCTATGTTGCCACCTGGATTCTG
CGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCG
GATCTCCCTTTGGGCCGCCTCCCCGCATCGATACCGAGCGCTGCTCGAGAGATCTACGGG
TGGCATCCCTGTGACCCCTCCCCAGTGCCTCTCCTGGCCCTGGAAGTTGCCACTCCAGTG
CCCACCAGCCTTGTCCTAATAAAATTAAGTTGCATCATTTTGTCTGACTAGGTGTCCTTCTA
TAATATTATGGGGTGGAGGGGGGTGGTATGGAGCAAGGGGCAAGTTGGGAAGACAACCT
GTAGGGCCTGCGGGGTCTATTGGGAACCAAGCTGGAGTGCAGTGGCACAATCTTGGCTCA
CTGCAATCTCCGCCTCCTGGGTTCAAGCGATTCTCCTGCCTCAGCCTCCCGAGTTGTTGG
GATTCCAGGCATGCATGACCAGGCTCAGCTAATTTTTGTTTTTTTGGTAGAGACGGGGTTT
CACCATATTGGCCAGGCTGGTCTCCAACTCCTAATCTCAGGTGATCTACCCACCTTGGCCT
CCCAAATTGCTGGGATTACAGGCGTGAACCACTGCTCCCTTCCCTGTCCTTCTGATTTTGT
AGGTAACCACGTGCGGACCGAGCGGCCGC (SEQ ID NO: 68)

AiP1277 (length between ITRs: 2901):

GCGGCCGCACGCGTCCTTTTAGAAACACTCCCTTTACCATCTTCAAACATGTTTTTAGCTGA
GAACTCTCTTCCAACCCCTGTTTCTTAACTCTGAGTGCCGTATCACTTCATATTCTGTGTCA
GGGGAAAAGAAATCAGCACCTCCCACAACGTCAACTGTGTCCTTTAGAGTAAGCATTCCAA
AGTCTATATTCTGAGTCTAATCTCTCTTGGAAAGGTCAGCCTTTTCTTCCAAATACCAAGTG
GACATCTTTATGCACAGGCCTTCAAGGATATTCAAGTCAGTGTGTCCTACGGAGAAAACTC
CTTTTAAAACCCGAATCCTGTGGTTTCCCCAAGATGATTATTGGGTGGTCACTGCAGCCTTA
AGGAGCTCGGGCTGGGCATAAAAGTCAGGGCAGAGCCATCTATTGCTTACATTTGCTTCTG
GCGTGGCCACCATGGCTCCTAAGAAGAAGAGGAAGGTGATGAGCCAGTTCGACATCCTGT
GCAAGACCCCCCCCAAGGTGCTGGTGCGGCAGTTCGTGGAGAGATTCGAGAGGCCCAGC
GGCGAGAAGATCGCCAGCTGTGCCGCCGAGCTGACCTACCTGTGCTGGATGATCACCCA

FIG. 10 cont'd

CAACGGCACCGCCATCAAGAGGGCCACCTTCATGAGCTACAACACCATCATCAGCAACAG
CCTGAGCTTCGACATCGTGAACAAGAGCCTGCAGTTCAAGTACAAGACCCAGAAGGCCAC
CATCCTGGAGGCCAGCCTGAAGAAGCTGATCCCCGCCTGGGAGTTCACCATCATCCCTTA
CAACGGCCAGAAGCACCAGAGCGACATCACCGACATCGTGTCCAGCCTGCAGCTGCAGTT
CGAGAGCAGCGAGGAGGCCGACAAGGGCAACAGCCACAGCAAGAAGATGCTGAAGGCCC
TGCTGTCCGAGGGCGAGAGCATCTGGGAGATCACCGAGAAGATCCTGAACAGCTTCGAGT
ACACCAGCAGGTTCACCAAGACCAAGACCCTGTACCAGTTCCTGTTCCTGGCCACATTCAT
CAACTGCGGCAGGTTCAGCGACATCAAGAACGTGGACCCCAAGAGCTTCAAGCTGGTGCA
GAACAAGTACCTGGGCGTGATCATTCAGTGCCTGGTGACCGAGACCAAGACAAGCGTGTC
CAGGCACATCTACTTTTTCAGCGCCAGAGGCAGGATCGACCCCCTGGTGTACCTGGACGA
GTTCCTGAGGAACAGCGAGCCCGTGCTGAAGAGAGTGAACAGGACCGGCAACAGCAGCA
GCAACAAGCAGGAGTACCAGCTGCTGAAGGACAACCTGGTGCGCAGCTACAACAAGGCC
CTGAAGAAGAACGCCCCCTACCCCATCTTCGCTATCAAGAACGGCCCTAAGAGCCACATC
GGCAGGCACCTGATGACCAGCTTTCTGAGCATGAAGGGCCTGACCGAGCTGACAAACGTG
GTGGGCAACTGGAGCGACAAGAGGGCCTCCGCCGTGGCCAGGACCACCTACACCCACCA
GATCACCGCCATCCCCGACCACTACTTCGCCCTGGTGTCCAGGTACTACGCCTACGACCC
CATCAGCAAGGAGATGATCGCCCTGAAGGACGAGACCAACCCCATCGAGGAGTGGCAGC
ACATCGAGCAGCTGAAGGGCAGCGCCGAGGGCAGCATCAGATACCCCGCCTGGAACGGC
ATCATCAGCCAGGAGGTGCTGGACTACCTGAGCAGCTACATCAACAGGCGGATCTGAGAA
TTCGATATCAAGCTTATCGATAATCAACCTCTGGATTACAAAATTTGTGAAAGATTGACTGG
TATTCTTAACTATGTTGCTCCTTTTACGCTATGTGGATACGCTGCTTTAATGCCTTTGTATCA
TGCTATTGCTTCCCGTATGGCTTTCATTTTCTCCTCCTTGTATAAATCCTGGTTGCTGTCTCT
TTATGAGGAGTTGTGGCCCGTTGTCAGGCAACGTGGCGTGGTGTGCACTGTGTTTGCTGA
CGCAACCCCCACTGGTTGGGGCATTGCCACCACCTGTCAGCTCCTTTCCGGGACTTTCGC
TTTCCCCCTCCCTATTGCCACGGCGGAACTCATCGCCGCCTGCCTTGCCCGCTGCTGGAC
AGGGGCTCGGCTGTTGGGCACTGACAATTCCGTGGTGTTGTCGGGGAAATCATCGTCCTT
TCCTTGGCTGCTCGCCTATGTTGCCACCTGGATTCTGCGCGGGACGTCCTTCTGCTACGT
CCCTTCGGCCCTCAATCCAGCGGACCTTCCTTCCCGCGGCCTGCTGCCGGCTCTGCGGC
CTCTTCCGCGTCTTCGCCTTCGCCCTCAGACGAGTCGGATCTCCCTTTGGGCCGCCTCCC
CGCATCGATACCGAGCGCTGCTCGAGAGATCTACGGGTGGCATCCCTGTGACCCCTCCCC
AGTGCCTCTCCTGGCCCTGGAAGTTGCCACTCCAGTGCCCACCAGCCTTGTCCTAATAAAA
TTAAGTTGCATCATTTTGTCTGACTAGGTGTCCTTCTATAATATTATGGGGTGGAGGGGGGT
GGTATGGAGCAAGGGGCAAGTTGGGAAGACAACCTGTAGGGCCTGCGGGGTCTATTGGG
AACCAAGCTGGAGTGCAGTGGCACAATCTTGGCTCACTGCAATCTCCGCCTCCTGGGTTC
AAGCGATTCTCCTGCCTCAGCCTCCCGAGTTGTTGGGATTCCAGGCATGCATGACCAGGC
TCAGCTAATTTTTGTTTTTTTGGTAGAGACGGGGTTTCACCATATTGGCCAGGCTGGTCTCC
AACTCCTAATCTCAGGTGATCTACCCACCTTGGCCTCCCAAATTGCTGGGATTACAGGCGT
GAACCACTGCTCCCTTCCCTGTCCTTCTGATTTTGTAGGTAACCACGTGCGGACCGAGCG
GCCGC (SEQ ID NO: 69)

AiP1278 (length between ITRs: 3046):
GCGGCCGCACGCGTATATGGATGTCTTACCTGCATGAATACTTGTGTACCACATGTATGCC
TTTCTCCATGGAGGCCAGAAGAGGGTATCAGATTCCCTGGAACTGAAGTTACAGATAGTTG
TGAGCTGCCATGTGGGTACTGGAAATACATGTGTCTAATTTTAAGGACCAGCTCCTACTGA
GGACATAAATGTTATGTTTCTTAAAAGTCTATACCATAAGAATCTTCTTCAGATCTTGGTGTG

FIG. 10 cont'd

AAGATTCTTACCCCAGATTGGTTACAGAAGCGGTACCAGGTGGGTGGATCCCATCAAAAGC
TTTAGTGAGAAATCACCCTTTTCCTTCACAGCAGCCCAGCTGACTGGTGAACTTTGCCGAA
CTGTAAAATATCAAACCTTTGGGAAGCTTTCTGCAACACGAGAAGTTTTAATCCTTCAATATT
AAAAAGAAAAATAAGAAAAAAAAACTGTGGAGAAGTCACGAACAGGAGAAACAAAAAGGAA
TTGTGCACAGGGTCAGTCGCTTAAGGAGCTCGGGCTGGGCATAAAAGTCAGGGCAGAGC
CATCTATTGCTTACATTTGCTTCTGGCGTGGCCACCATGGCTCCTAAGAAGAAGAGGAAGG
TGATGAGCCAGTTCGACATCCTGTGCAAGACCCCCCCCAAGGTGCTGGTGCGGCAGTTCG
TGGAGAGATTCGAGAGGCCCAGCGGCGAGAAGATCGCCAGCTGTGCCGCCGAGCTGACC
TACCTGTGCTGGATGATCACCCACAACGGCACCGCCATCAAGAGGGCCACCTTCATGAGC
TACAACACCATCATCAGCAACAGCCTGAGCTTCGACATCGTGAACAAGAGCCTGCAGTTCA
AGTACAAGACCCAGAAGGCCACCATCCTGGAGGCCAGCCTGAAGAAGCTGATCCCCGCCT
GGGAGTTCACCATCATCCCTTACAACGGCCAGAAGCACCAGAGCGACATCACCGACATCG
TGTCCAGCCTGCAGCTGCAGTTCGAGAGCAGCGAGGAGGCCGACAAGGGCAACAGCCAC
AGCAAGAAGATGCTGAAGGCCCTGCTGTCCGAGGGCGAGAGCATCTGGGAGATCACCGA
GAAGATCCTGAACAGCTTCGAGTACACCAGCAGGTTCACCAAGACCAAGACCCTGTACCA
GTTCCTGTTCCTGGCCACATTCATCAACTGCGGCAGGTTCAGCGACATCAAGAACGTGGA
CCCCAAGAGCTTCAAGCTGGTGCAGAACAAGTACCTGGGCGTGATCATTCAGTGCCTGGT
GACCGAGACCAAGACAAGCGTGTCCAGGCACATCTACTTTTTCAGCGCCAGAGGCAGGAT
CGACCCCCTGGTGTACCTGGACGAGTTCCTGAGGAACAGCGAGCCCGTGCTGAAGAGAG
TGAACAGGACCGGCAACAGCAGCAGCAACAAGCAGGAGTACCAGCTGCTGAAGGACAAC
CTGGTGCGCAGCTACAACAAGGCCCTGAAGAAGAACGCCCCCTACCCCATCTTCGCTATC
AAGAACGGCCCTAAGAGCCACATCGGCAGGCACCTGATGACCAGCTTTCTGAGCATGAAG
GGCCTGACCGAGCTGACAAACGTGGTGGGCAACTGGAGCGACAAGAGGGCCTCCGCCGT
GGCCAGGACCACCTACACCCACCAGATCACCGCCATCCCCGACCACTACTTCGCCCTGGT
GTCCAGGTACTACGCCTACGACCCCATCAGCAAGGAGATGATCGCCCTGAAGGACGAGAC
CAACCCCATCGAGGAGTGGCAGCACATCGAGCAGCTGAAGGGCAGCGCCGAGGGCAGCA
TCAGATACCCCGCCTGGAACGGCATCATCAGCCAGGAGGTGCTGGACTACCTGAGCAGCT
ACATCAACAGGCGGATCTGAGAATTCGATATCAAGCTTATCGATAATCAACCTCTGGATTAC
AAAATTTGTGAAAGATTGACTGGTATTCTTAACTATGTTGCTCCTTTTACGCTATGTGGATAC
GCTGCTTTAATGCCTTTGTATCATGCTATTGCTTCCCGTATGGCTTTCATTTTCTCCTCCTTG
TATAAATCCTGGTTGCTGTCTCTTTATGAGGAGTTGTGGCCCGTTGTCAGGCAACGTGGCG
TGGTGTGCACTGTGTTTGCTGACGCAACCCCCACTGGTTGGGGCATTGCCACCACCTGTC
AGCTCCTTTCCGGGACTTTCGCTTTCCCCCTCCCTATTGCCACGGCGGAACTCATCGCCG
CCTGCCTTGCCCGCTGCTGGACAGGGGCTCGGCTGTTGGGCACTGACAATTCCGTGGTGT
TGTCGGGGAAATCATCGTCCTTTCCTTGGCTGCTCGCCTATGTTGCCACCTGGATTCTGCG
CGGGACGTCCTTCTGCTACGTCCCTTCGGCCCTCAATCCAGCGGACCTTCCTTCCCGCGG
CCTGCTGCCGGCTCTGCGGCCTCTTCCGCGTCTTCGCCTTCGCCCTCAGACGAGTCGGAT
CTCCCTTTGGGCCGCCTCCCCGCATCGATACCGAGCGCTGCTCGAGAGATCTACGGGTG
GCATCCCTGTGACCCCTCCCCAGTGCCTCTCCTGGCCCTGGAAGTTGCCACTCCAGTGCC
CACCAGCCTTGTCCTAATAAAATTAAGTTGCATCATTTTGTCTGACTAGGTGTCCTTCTATAA
TATTATGGGGTGGAGGGGGGTGGTATGGAGCAAGGGGCAAGTTGGGAAGACAACCTGTA
GGGCCTGCGGGGTCTATTGGGAACCAAGCTGGAGTGCAGTGGCACAATCTTGGCTCACTG
CAATCTCCGCCTCCTGGGTTCAAGCGATTCTCCTGCCTCAGCCTCCCGAGTTGTTGGGATT
CCAGGCATGCATGACCAGGCTCAGCTAATTTTTGTTTTTTTGGTAGAGACGGGGTTTCACC
ATATTGGCCAGGCTGGTCTCCAACTCCTAATCTCAGGTGATCTACCCACCTTGGCCTCCCA

FIG. 10 cont'd

AATTGCTGGGATTACAGGCGTGAACCACTGCTCCCTTCCCTGTCCTTCTGATTTTGTAGGT
AACCACGTGCGGACCGAGCGGCCGC (SEQ ID NO: 70)

AiP1344 (length between ITRs: 2178):
CGGCCGCACGCGTATATGGATGTCTTACCTGCATGAATACTTGTGTACCACATGTATGCCT
TTCTCCATGGAGGCCAGAAGAGGGTATCAGATTCCCTGGAACTGAAGTTACAGATAGTTGT
GAGCTGCCATGTGGGTACTGGAAATACATGTGTCTAATTTTAAGGACCAGCTCCTACTGAG
GACATAAATGTTATGTTTCTTAAAAGTCTATACCATAAGAATCTTCTTCAGATCTTGGTGTGA
AGATTCTTACCCCAGATTGGTTACAGAAGCGGTACCAGGTGGGTGGATCCCATCAAAAGCT
TTAGTGAGAAATCACCCTTTTCCTTCACAGCAGCCCAGCTGACTGGTGAACTTTGCCGAAC
TGTAAAATATCAAACCTTTGGGAAGCTTTCTGCAACACGAGAAGTTTTAATCCTTCAATATTA
AAAAGAAAAATAAGAAAAAAAAACTGTGGAGAAGTCACGAACAGGAGAAACAAAAAGGAAT
TGTGCACAGGGTCAGTCGCTTAAGGAGCTCGGGCTGGGCATAAAAGTCAGGGCAGAGCC
ATCTATTGCTTACATTTGCTTCTGGGATCCGCCACCATGGTGCCCAAGAAGAAGAGGAAAG
TCTCCAACCTGCTGACTGTGCACCAAAACCTGCCTGCCCTCCCTGTGGATGCCACCTCTGA
TGAAGTCAGGAAGAACCTGATGGACATGTTCAGGGACAGGCAGGCCTTCTCTGAACACAC
CTGGAAGATGCTCCTGTCTGTGTGCAGATCCTGGGCTGCCTGGTGCAAGCTGAACAACAG
GAAATGGTTCCCTGCTGAACCTGAGGATGTGAGGGACTACCTCCTGTACCTGCAAGCCAG
AGGCCTGGCTGTGAAGACCATCCAACAGCACCTGGGCCAGCTCAACATGCTGCACAGGAG
ATCTGGCCTGCCTCGCCCTTCTGACTCCAATGCTGTGTCCCTGGTGATGAGGAGAATCAG
AAAGGAGAATGTGGATGCTGGGGAGAGAGCCAAGCAGGCCCTGGCCTTTGAACGCACTG
ACTTTGACCAAGTCAGATCCCTGATGGAGAACTCTGACAGATGCCAGGACATCAGGAACCT
GGCCTTCCTGGGCATTGCCTACAACACCCTGCTGCGCATTGCCGAAATTGCCAGAATCAG
AGTGAAGGACATCTCCCGCACCGATGGTGGGAGAATGCTGATCCACATTGGCAGGACCAA
GACCCTGGTGTCCACAGCTGGTGTGGAGAAGGCCCTGTCCCTGGGGGTTACCAAGCTGG
TGGAGAGATGGATCTCTGTGTCTGGTGTGGCTGATGACCCCAACAACTACCTGTTCTGCC
GGGTCAGAAAGAATGGTGTGGCTGCCCCTTCTGCCACCTCCCAACTGTCCACCCGGGCCC
TGGAAGGGATCTTTGAGGCCACCCACCGCCTGATCTATGGTGCCAAGGATGACTCTGGGC
AGAGATACCTGGCCTGGTCTGGCCACTCTGCCAGAGTGGGTGCTGCCAGGGACATGGCC
AGGGCTGGTGTGTCCATCCCTGAAATCATGCAGGCTGGTGGCTGGACCAATGTGAACATT
GTGATGAACTACATCAGAAACCTGGACTCTGAGACTGGGGCCATGGTGAGGCTGCTCGAG
GATGGGGACTAAGGCTGCTCGAGAGATCTACGGGTGGCATCCCTGTGACCCCTCCCCAGT
GCCTCTCCTGGCCCTGGAAGTTGCCACTCCAGTGCCCACCAGCCTTGTCCTAATAAAATTA
AGTTGCATCATTTTGTCTGACTAGGTGTCCTTCTATAATATTATGGGGTGGAGGGGGGTGG
TATGGAGCAAGGGGCAAGTTGGGAAGACAACCTGTAGGGCCTGCGGGGTCTATTGGGAA
CCAAGCTGGAGTGCAGTGGCACAATCTTGGCTCACTGCAATCTCCGCCTCCTGGGTTCAA
GCGATTCTCCTGCCTCAGCCTCCCGAGTTGTTGGGATTCCAGGCATGCATGACCAGGCTC
AGCTAATTTTTGTTTTTTTGGTAGAGACGGGGTTTCACCATATTGGCCAGGCTGGTCTCCAA
CTCCTAATCTCAGGTGATCTACCCACCTTGGCCTCCCAAATTGCTGGGATTACAGGCGTGA
ACCACTGCTCCCTTCCCTGTCCTTCTGATTTTGTAGGTAACCACGTGCGGACCGAGCGGC
CGC (SEQ ID NO: 71)

CN3041 (length between ITRs: 2039):
GCGGCCGCACGCGTACAGCAAGTGTTCTATGATTTTCAACAGGACACTTGGATCTAGCCAA
CTCAGTTTTCAAGCCTGCCCCCGAGTTGTAGATCCTGTCTTCACATTCTAAACTAATCTCAC

FIG. 10 cont'd

ACCACTTTGTGCCAACTCCACTCTGGTAAAGACCATGCACTCGAGTTAGTGCAAGACATTT
TGTTCTGGCCTCGGGGTGTGCTGCCGCCTCGTCAGGATGGGAGGTGGAGGCGAGTCCAG
ACAGCAAGTGTTCTATGATTTTCAACAGGACACTTGGATCTAGCCAACTCAGTTTTCAAGCC
TGCCCCCGAGTTGTAGATCCTGTCTTCACATTCTAAACTAATCTCACACCACTTTGTGCCAA
CTCCACTCTGGTAAAGACCATGCACTCGAGTTAGTGCAAGACATTTTGTTCTGGCCTCGGG
GTGTGCTGCCGCCTCGTCAGGATGGGAGGTGGAGGCGAGTCCAGACAGCAAGTGTTCTA
TGATTTTCAACAGGACACTTGGATCTAGCCAACTCAGTTTTCAAGCCTGCCCCCGAGTTGT
AGATCCTGTCTTCACATTCTAAACTAATCTCACACCACTTTGTGCCAACTCCACTCTGGTAA
AGACCATGCACTCGAGTTAGTGCAAGACATTTTGTTCTGGCCTCGGGGTGTGCTGCCGCC
TCGTCAGGATGGGAGGTGGAGGCGAGTCCAGGAGCTCGGGCTGGGCATAAAAGTCAGGG
CAGAGCCATCTATTGCTTACATTTGCTTCTGGGATCCAGATCTTTCGAAGCTAGCGCTACC
GGTCGCCACCATGGTGAGCAAGGGCGAGGAGCTGTTCACCGGGGTGGTGCCCATCCTGG
TCGAGCTGGACGGCGACGTAAACGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC
CGACCACATGAAGCAGCACGACTTCTTCAAGTCCGCCATGCCCGAAGGCTACGTCCAGGA
GCGCACCATCTTCTTCAAGGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG
CGCGATCACATGGTCCTGCTGGAGTTCGTGACCGCCGCCGGGATCACTCTCGGCATGGA
CGAGCTGTACAAGTAAGTCGACGGCGCGCCGCGGCCGCGAATTCGATATCATAATCAACC
TCTGGATTACAAAATTTGTGAAAGATTGACTGGTATTCTTAACTATGTTGCTCCTTTTACGCT
ATGTGGATACGCTGCTTTAATGCCTTTGTATCATGCTATTGCTTCCCGTATGGCTTTCATTTT
CTCCTCCTTGTATAAATCCTGGTTAGTTCTTGCCACGGCGGAACTCATCGCCGCCTGCCTT
GCCCGCTGCTGGACAGGGGCTCGGCTGTTGGGCACTGACAATTCCGTGGCTCGAGAGAT
CTTCGACTGTGCCTTCTAGTTGCCAGCCATCTGTTGTTTGCCCCTCCCCCGTGCCTTCCTT
GACCCTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGGGGA
GGATTGGGAAGACAATAGCAGGCATGCACGTGCGGACCGAGCGGCCGC (SEQ ID NO: 72)

CN3608 (length between ITRs: 2153):
GCGGCCGCACGCGTCCCCACTCCTGCCTCTGCCTATAAGAGTTTGGCACAGTTGGAGATT
TGTATACACAAATGCATGCGTGGAAATACTGCGCTCTGATGACATTCCTCAGGGGGCGACC
TTTGATGATGAATTTTCTTGCCCTTTTTAGGGGAGGAGAAGAGGAGGCGGGTGGTACTTCA
CAAGACTAAATTTACTCAACTTTTTTGGGTCTAAATTTCTTTAGGAAAAAAAATGTCAAATGA
TTGTAGATCCCAAACTGTCTTTGTTGGCATTTGACCCCACTCCTGCCTCTGCCTATAAGAGT
TTGGCACAGTTGGAGATTTGTATACACAAATGCATGCGTGGAAATACTGCGCTCTGATGAC
ATTCCTCAGGGGGCGACCTTTGATGATGAATTTTCTTGCCCTTTTTAGGGGAGGAGAAGAG
GAGGCGGGTGGTACTTCACAAGACTAAATTTACTCAACTTTTTTGGGTCTAAATTTCTTTAG
GAAAAAAAATGTCAAATGATTGTAGATCCCAAACTGTCTTTGTTGGCATTTGACCCCACTCC
TGCCTCTGCCTATAAGAGTTTGGCACAGTTGGAGATTTGTATACACAAATGCATGCGTGGA
AATACTGCGCTCTGATGACATTCCTCAGGGGGCGACCTTTGATGATGAATTTTCTTGCCCT

FIG. 10 cont'd

TTTTAGGGGAGGAGAAGAGGAGGCGGGTGGTACTTCACAAGACTAAATTTACTCAACTTTT
TTGGGTCTAAATTTCTTTAGGAAAAAAAATGTCAAATGATTGTAGATCCCAAACTGTCTTTGT
TGGCATTTGAGAGCTCGGGCTGGGCATAAAAGTCAGGGCAGAGCCATCTATTGCTTACATT
TGCTTCTGGGATCCAGATCTTTCGAAGCTAGCGCTACCGGTCGCCACCATGGTGAGCAAG
GGCGAGGAGCTGTTCACCGGGGTGGTGCCCATCCTGGTCGAGCTGGACGGCGACGTAAA
CGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA
CTTCTTCAAGTCCGCCATGCCCGAAGGCTACGTCCAGGAGCGCACCATCTTCTTCAAGGA
CGACGGCAACTACAAGACCCGCGCCGAGGTGAAGTTCGAGGGCGACACCCTGGTGAACC
GCATCGAGCTGAAGGGCATCGACTTCAAGGAGGACGGCAACATCCTGGGGCACAAGCTG
GAGTACAACTACAACAGCCACAACGTCTATATCACCGCCGACAAGCAGAAGAACGGCATC
AAGGCCAACTTCAAGATCCGCCACAACATCGAGGACGGCGGCGTGCAGCTCGCCGACCA
CTACCAGCAGAACACCCCCATCGGCGACGGCCCCGTGCTGCTGCCCGACAACCACTACCT
GAGCTACCAGTCCAAGCTGAGCAAAGACCCCAACGAGAAGCGCGATCACATGGTCCTGCT
GGAGTTCGTGACCGCCGCCGGGATCACTCTCGGCATGGACGAGCTGTACAAGTAAGTCGA
CGGCGCGCCGCGGCCGCGAATTCGATATCATAATCAACCTCTGGATTACAAAATTTGTGAA
AGATTGACTGGTATTCTTAACTATGTTGCTCCTTTTACGCTATGTGGATACGCTGCTTTAAT
GCCTTTGTATCATGCTATTGCTTCCCGTATGGCTTTCATTTTCTCCTCCTTGTATAAATCCTG
GTTAGTTCTTGCCACGGCGGAACTCATCGCCGCCTGCCTTGCCCGCTGCTGGACAGGGG
CTCGGCTGTTGGGCACTGACAATTCCGTGGCTCGAGAGATCTTCGACTGTGCCTTCTAGTT
GCCAGCCATCTGTTGTTTGCCCCTCCCCCGTGCCTTCCTTGACCCTGGAAGGTGCCACTC
CCACTGTCCTTTCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGACAATAGCA
GGCATGAGATCTCACGTGCGGACCGAGCGGCCGC (SEQ ID NO: 73)

CN2582 (length between ITRs: 2090):
GCGGCCGCACGCGTAAAATCAAATCAGTTGCAAAATCCATACAGTCTTCCAGTTTCTCAGC
TGTGGAAACTTTGTGTCTCTTCTTTTCCACCAAAACAGCTATCTCGTCTTTCAAGTCCTTGC
TGAAAAAAAAAAGTGTTAAATTTTTCTCAATTTAGACTTCCAGCAAAACAGATTCTGCTTGTT
GAAAGGCATTGGTGTTCATGAGTAAGTGAGTTTCCATTTTATTTCTTCACAAATAAGTTACAT
GAAGTACTTAAAATCAAATCAGTTGCAAAATCCATACAGTCTTCCAGTTTCTCAGCTGTGGA
AACTTTGTGTCTCTTCTTTTCCACCAAAACAGCTATCTCGTCTTTCAAGTCCTTGCTGAAAAA
AAAAAGTGTTAAATTTTTCTCAATTTAGACTTCCAGCAAAACAGATTCTGCTTGTTGAAAGGC
ATTGGTGTTCATGAGTAAGTGAGTTTCCATTTTATTTCTTCACAAATAAGTTACATGAAGTAC
TTAAAATCAAATCAGTTGCAAAATCCATACAGTCTTCCAGTTTCTCAGCTGTGGAAACTTTG
TGTCTCTTCTTTTCCACCAAAACAGCTATCTCGTCTTTCAAGTCCTTGCTGAAAAAAAAAAGT
GTTAAATTTTTCTCAATTTAGACTTCCAGCAAAACAGATTCTGCTTGTTGAAAGGCATTGGT
GTTCATGAGTAAGTGAGTTTCCATTTTATTTCTTCACAAATAAGTTACATGAAGTACTTGAGC
TCGGGCTGGGCATAAAAGTCAGGGCAGAGCCATCTATTGCTTACATTTGCTTCTGGGATCC
AGATCTTTCGAAGCTAGCGCTACCGGTCGCCACCATGGTGAGCAAGGGCGAGGAGCTGTT
CACCGGGGTGGTGCCCATCCTGGTCGAGCTGGACGGCGACGTAAACGGCCACAAGTTCA
GCGTGTCCGGCGAGGGCGAGGGCGATGCCACCTACGGCAAGCTGACCCTGAAGCTGATC
TGCACCACCGGCAAGCTGCCCGTGCCCTGGCCCACCCTCGTGACCACCCTGGGCTACGG
CGTGCAGTGCTTCGCCCGCTACCCCGACCACATGAAGCAGCACGACTTCTTCAAGTCCGC

FIG. 10 cont'd

CATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGG
GCATCGACTTCAAGGAGGACGGCAACATCCTGGGGCACAAGCTGGAGTACAACTACAACA
GCCACAACGTCTATATCACCGCCGACAAGCAGAAGAACGGCATCAAGGCCAACTTCAAGA
TCCGCCACAACATCGAGGACGGCGGCGTGCAGCTCGCCGACCACTACCAGCAGAACACC
CCCATCGGCGACGGCCCCGTGCTGCTGCCCGACAACCACTACCTGAGCTACCAGTCCAA
GCTGAGCAAAGACCCCAACGAGAAGCGCGATCACATGGTCCTGCTGGAGTTCGTGACCGC
CGCCGGGATCACTCTCGGCATGGACGAGCTGTACAAGTAAGTCGACGGCGCGCCGCGGC
CGCGAATTCGATATCATAATCAACCTCTGGATTACAAAATTTGTGAAAGATTGACTGGTATT
CTTAACTATGTTGCTCCTTTTACGCTATGTGGATACGCTGCTTTAATGCCTTTGTATCATGCT
ATTGCTTCCCGTATGGCTTTCATTTTCTCCTCCTTGTATAAATCCTGGTTAGTTCTTGCCAC
GGCGGAACTCATCGCCGCCTGCCTTGCCCGCTGCTGGACAGGGGCTCGGCTGTTGGGCA
CTGACAATTCCGTGGCTCGAGAGATCTTCGACTGTGCCTTCTAGTTGCCAGCCATCTGTTG
TTTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGAGATCTCACG
TGCGGACCGAGCGGCCGC (SEQ ID NO: 74)

CN3367 (length between ITRs: 2316):
GCGGCCGCACGCGTACTGACTGAGGCTGCTCAATGTACCATATTAAAAAGGGAGCTGCGG
CTAAGCCAGTTTCTGCAGGACAGAGCCACAGACTATGGGATACTTCCAAGGAGAAGGAAG
GAGTGGCGAGGTGGCACTGCGTCAGCTGACCGCTAGACTGTGACTTTATCCAGCTCTGTG
TTAGCTGAGTGATGACAGTAATGCCGTATCTACACACCCACCGCCTACTGGGAACCTCCAC
ATGAGTACATAACATAGCATCTGAGGCCAGCAGTGCGCAGAACACATCTGCTCATCTACAG
TGCCTTCAAACGGGAGGGAAGTACCAGTCCTCTCTCAGTGAGAACACCATCCGTCCTGGG
TGAGAGCTTTAGGCATTGCCATGGCTCCCTGTCACTCGGCCCTGACCCACACATTCACAG
CCATGAGCTCGGGCTGGGCATAAAAGTCAGGGCAGAGCCATCTATTGCTTACATTTGCTTC
TGGGATCCAGATCTTTCGAAGCTAGCGCTACCGGTCGCCACCATGGTCTCCAAGGGCGAG
GAGCTGTTCACCGGGGTGGTGCCCATCCTGGTCGAGCTGGACGGCGATGTCAACGGCCA
CAAGTTCAGCGTGTCCGGCGAGGGCGAGGGCGATGCCACCTACGGCAAGCTGACCCTGA
AGCTGATCTGCACCACCGGCAAGCTGCCCGTGCCCTGGCCCACCCTCGTGACCACCCTG
GGCTACGGCGTGCAGTGCTTCGCCCGCTACCCCGACCACATGAAGCAGCACGACTTCTTC
AAGTCCGCCATGCCCGAAGGCTACGTCCAGGAGCGCACCATCTTCTTCAAAGACGACGGC
AACTACAAGACCCGCGCCGAGGTGAAGTTCGAGGGCGACACCCTGGTGAACCGCATCGA
GCTGAAGGGCATCGACTTCAAGGAGGACGGCAACATCCTGGGGCACAAGCTGGAGTACA
ACTACAACAGCCACAACGTCTATATCACCGCCGACAAGCAGAAGAACGGCATCAAGGCCA
ACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGGGCTCTGGTGCTA
CCAACTTCTCACTGTTGAAACAGGCAGGGGATGTAGAGGAGAATCCAGGGCCTGGTGCTA
GTGGAGACTACAAAGACCATGACGGAGATTATAAAGATCATGACATCGATTACAAGGATGA
CGATGACAAGTCCGGACTCAGATCTGGAGGCTCCGGAGGCCCAGAGCCAGCGAAGTCTG
CTCCCGCCCCGAAAAAGGCTCCAAGAAGGCGGTGACTAAGGCGCAGAAGAAAGGCGGC
AAGAAGCGCAAGCGCAGCCGCAAGGAGAGCTATTCCATCTATGTGTACAAGGTTCTGAAG

FIG. 10 cont'd

CAGGTCCACCCTGACACCGGCATTTCGTCCAAGGCCATGGGCATCATGAATTCGTTTGTGA
ACGACATTTTCGAGCGCATCGCAGGAGAGGCTTCCCGCCTGGCGCATTACAACAAGCGCT
CGACCATCACCTCCCGGGAGATCCAGACGGCCGTGCGCCTGCTGCTGCCTGGGGAGTTG
GCCAAGCACGCCGTGTCCGAGGGTACTAAGGCCATCACCAAGTACACCAGCGCTAAGTAA
TGAGGCGCGCCGCGGCCGCGAATTCGATATCATAATCAACCTCTGGATTACAAAATTTGTG
AAAGATTGACTGGTATTCTTAACTATGTTGCTCCTTTTACGCTATGTGGATACGCTGCTTTA
ATGCCTTTGTATCATGCTATTGCTTCCCGTATGGCTTTCATTTTCTCCTCCTTGTATAAATCC
TGGTTAGTTCTTGCCACGGCGGAACTCATCGCCGCCTGCCTTGCCCGCTGCTGGACAGGG
GCTCGGCTGTTGGGCACTGACAATTCCGTGGCTCGAGAGATCTTCGACTGTGCCTTCTAG
TTGCCAGCCATCTGTTGTTTGCCCCTCCCCCGTGCCTTCCTTGACCCTGGAAGGTGCCACT
CCCACTGTCCTTTCCTAATAAAATGAGGAAATTGCATCGCATTGTCTGAGTAGGTGTCATTC
TATTCTGGGGGGTGGGGTGGGGCAGGACAGCAAGGGGGAGGATTGGGAAGACAATAGCA
GGCATGAGATCTCACGTGCGGACCGAGCGGCCGC (SEQ ID NO: 75)

CN4095 (length between ITRs: 2451):
GCGGCCGCACGCGTGAGTTAACATTTCAAATAAAATAGGTGTGTGTGTGTGTGTGTGTG
TGTGTGTGTGTGTGTGTGTGTGTGTGTGTGTTTAGAAAAAGATCAATTATGGGTTGAATCT
GTTGTCACCCCACTTGCATGTAGCTCTATTTCTTAGTCATATTTTATTATTTTATGCCCAAAG
GCATGGCACTGGAAGACAAGTTTCAATTTTTCTCTTTTGATGTTTCATTCTTATGAAGTGGA
AGGTTGAAAGTTTGAAATCCATATGACTCAGGAATTGAATTTCAGCTCTTCTAAATACAGAC
TGTGTTAAAGGGCAACACTTTTATATATATATATTCACAGCTAAGGCAGCATTTACTTCACAT
AGTAGTTAAAGAAGTTAAGAATTAAGTTAGTCACATGTAACAGAATTCTCCCATTTCATAGAA
ACTCAAATTTTTGTTTCCTTTTTCCTTTCCTTCTCTCATTCTTTCTCCACAGCTTACAAGAAGT
TAGAATGTATACTTTCATATAATAGATCCCCCTCCTCCCACTAAAAGAGATTTGAGAGATGG
AGCTCGGGCTGGGCATAAAAGTCAGGGCAGAGCCATCTATTGCTTACATTTGCTTCTGGGA
TCCAGATCTTTCGAAGCTAGCGCTACCGGTCGCCACCATGGTCTCCAAGGGCGAGGAGCT
GTTCACCGGGGTGGTGCCCATCCTGGTCGAGCTGGACGGCGATGTCAACGGCCACAAGT
TCAGCGTGTCCGGCGAGGGCGAGGGCGATGCCACCTACGGCAAGCTGACCCTGAAGCTG
ATCTGCACCACCGGCAAGCTGCCCGTGCCCTGGCCCACCCTCGTGACCACCCTGGGCTA
CGGCGTGCAGTGCTTCGCCCGCTACCCCGACCACATGAAGCAGCACGACTTCTTCAAGTC
CGCCATGCCCGAAGGCTACGTCCAGGAGCGCACCATCTTCTTCAAAGACGACGGCAACTA
CAAGACCCGCGCCGAGGTGAAGTTCGAGGGCGACACCCTGGTGAACCGCATCGAGCTGA
AGGGCATCGACTTCAAGGAGGACGGCAACATCCTGGGGCACAAGCTGGAGTACAACTACA
ACAGCCACAACGTCTATATCACCGCCGACAAGCAGAAGAACGGCATCAAGGCCAACTTCA
AGATCCGCCACAACATCGAGGACGGCGGCGTGCAGCTCGCCGACCACTACCAGCAGAAC
ACCCCCATCGGCGACGGCCCCGTGCTGCTGCCCGACAACCACTACCTGAGCTACCAGTC
CAAGCTGAGCAAAGACCCCAACGAGAAGCGCGATCACATGGTCCTGCTGGAGTTCGTGAC
CGCCGCCGGGATCACTCTCGGCATGGACGAGCTGTACAAGGGCTCTGGTGCTACCAACTT
CTCACTGTTGAAACAGGCAGGGGATGTAGAGGAGAATCCAGGGCCTGGTGCTAGTGGAGA
CTACAAAGACCATGACGGAGATTATAAAGATCATGACATCGATTACAAGGATGACGATGAC
AAGTCCGGACTCAGATCTGGAGGCTCCGGAGGCCCAGAGCCAGCGAAGTCTGCTCCCGC
CCCGAAAAAGGGCTCCAAGAAGGCGGTGACTAAGGCGCAGAAGAAAGGCGGCAAGAAGC
GCAAGCGCAGCCGCAAGGAGAGCTATTCCATCTATGTGTATAAGGTTCTGAAGCAGGTCC
ACCCTGACACCGGCATTTCGTCCAAGGCCATGGGCATCATGAACTCGTTTGTGAACGACAT
TTTCGAGCGCATCGCAGGTGAGGCTTCCCGCCTGGCGCATTACAACAAGCGCTCGACCAT

FIG. 10 cont'd

CACCTCCAGGGAGATCCAGACGGCCGTGCGCCTGCTGCTGCCTGGGGAGTTGGCCAAGC
ACGCCGTGTCCGAGGGTACTAAGGCCATCACCAAGTACACCAGCGCTAAGTAATGAGGCG
CGCCGCGGCCGCGAATTCGATATCATAATCAACCTCTGGATTACAAAATTTGTGAAAGATT
GACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTAG
TTCTTGCCACGGCGGAACTCATCGCCGCCTGCCTTGCCCGCTGCTGGACAGGGGCTCGG
CTGTTGGGCACTGACAATTCCGTGGCTCGAGAGATCTTCGACTGTGCCTTCTAGTTGCCAG
CCATCTGTTGTTTGCCCCTCCCCCGTGCCTTCCTTGACCCTGGAAGGTGCCACTCCCACTG
TCCTTTCCTAATAAAATGAGGAAATTGCATCGCATTGTCTGAGTAGGTGTCATTCTATTCTG
GGGGGTGGGGTGGGGCAGGACAGCAAGGGGGAGGATTGGGAAGACAATAGCAGGCATG
AGATCTCACGTGCGGACCGAGCGGCCGC (SEQ ID NO: 76)

CN4096 (length between ITRs: 2439):
GCGGCCGCACGCGTTCAGAGGCCAGTGTGTATTTAGGGTAGGGCAGTACATTAAAGTTCT
GGTTTGTGTGCTGTCACCCTATCCTAGAAACTGGTTTGAGAGTTTTAGTTCACATGCAAAAT
GAAGGTCAAAGTCAATACCAAGGAGTCTAAAATCAACGTGAAGTGATACAGAGATGTGCAC
AGTTTGTTTGTTACGAACATCACTGCCTCCTACAGAATGAACTTATCATCATGTGTCACAAT
CATCCCATGCATTTTCCAGCTACTTCCAGTGAGCTCCAAATCTTTACACATTTTGAGGTTGA
AGTAAAAGAGCAATGTGCACAGTGAGATAGTCACAGTTTCTTTACCCAGTCTTGGGTGATT
CAGATTCAGTCAGGCCAACAGGGAGGACTTTCCTGCCAGGAGGGGGGCCCGAGCAAGAA
CAGGAGCTTAGACCCTATGATGCTTAGAAAGAACCCAGGAAACTGCCTATGCTGTCTGTTG
ATTATGCCGTGATTGCTGCAGGAAATGCAGTAGTTTATGAAACAGTAGAAGCTAAGCATGT
GAGCTCGGGCTGGGCATAAAAGTCAGGGCAGAGCCATCTATTGCTTACATTTGCTTCTGG
GATCCAGATCTTTCGAAGCTAGCGCTACCGGTCGCCACCATGGTCTCCAAGGGCGAGGAG
CTGTTCACCGGGGTGGTGCCCATCCTGGTCGAGCTGGACGGCGATGTCAACGGCCACAA
GTTCAGCGTGTCCGGCGAGGGCGAGGGCGATGCCACCTACGGCAAGCTGACCCTGAAGC
TGATCTGCACCACCGGCAAGCTGCCCGTGCCCTGGCCCACCCTCGTGACCACCCTGGGC
TACGGCGTGCAGTGCTTCGCCCGCTACCCCGACCACATGAAGCAGCACGACTTCTTCAAG
TCCGCCATGCCCGAAGGCTACGTCCAGGAGCGCACCATCTTCTTCAAAGACGACGGCAAC
TACAAGACCCGCGCCGAGGTGAAGTTCGAGGGCGACACCCTGGTGAACCGCATCGAGCT
GAAGGGCATCGACTTCAAGGAGGACGGCAACATCCTGGGGCACAAGCTGGAGTACAACTA
CAACAGCCACAACGTCTATATCACCGCCGACAAGCAGAAGAACGGCATCAAGGCCAACTT
CAAGATCCGCCACAACATCGAGGACGGCGGCGTGCAGCTCGCCGACCACTACCAGCAGA
ACACCCCCATCGGCGACGGCCCCGTGCTGCTGCCCGACAACCACTACCTGAGCTACCAGT
CCAAGCTGAGCAAAGACCCCAACGAGAAGCGCGATCACATGGTCCTGCTGGAGTTCGTGA
CCGCCGCCGGGATCACTCTCGGCATGGACGAGCTGTACAAGGGCTCTGGTGCTACCAACT
TCTCACTGTTGAAACAGGCAGGGGATGTAGAGGAGAATCCAGGGCCTGGTGCTAGTGGAG
ACTACAAAGACCATGACGGAGATTATAAAGATCATGACATCGATTACAAGGATGACGATGA
CAAGTCCGGACTCAGATCTGGAGGCTCCGGAGGCCCAGAGCCAGCGAAGTCTGCTCCCG
CCCCGAAAAAGGGCTCCAAGAAGGCGGTGACTAAGGCGCAGAAGAAGGCGGCAAGAAG
CGCAAGCGCAGCCGCAAGGAGAGCTATTCCATCTATGTGTATAAGGTTCTGAAGCAGGTC
CACCCTGACACCGGCATTTCGTCCAAGGCCATGGGCATCATGAACTCGTTTGTGAACGAC
ATTTTCGAGCGCATCGCAGGTGAGGCTTCCCGCCTGGCGCATTACAACAAGCGCTCGACC
ATCACCTCCAGGGAGATCCAGACGGCCGTGCGCCTGCTGCTGCCTGGGGAGTTGGCCAA
GCACGCCGTGTCCGAGGGTACTAAGGCCATCACCAAGTACACCAGCGCTAAGTAATGAGG

FIG. 10 cont'd

CGCGCCGCGGCCGCGAATTCGATATCATAATCAACCTCTGGATTACAAAATTTGTGAAAGA
TTGACTGGTATTCTTAACTATGTTGCTCCTTTTACGCTATGTGGATACGCTGCTTTAATGCC
TTTGTATCATGCTATTGCTTCCCGTATGGCTTTCATTTTCTCCTCCTTGTATAAATCCTGGTT
AGTTCTTGCCACGGCGGAACTCATCGCCGCCTGCCTTGCCCGCTGCTGGACAGGGGCTC
GGCTGTTGGGCACTGACAATTCCGTGGCTCGAGAGATCTTCGACTGTGCCTTCTAGTTGC
CAGCCATCTGTTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGG
CATGAGATCTCACGTGCGGACCGAGCGGCCGC (SEQ ID NO: 77)

CN3430 (length between ITRs: 2704):
GCGGCCGCACGCGTAGAGCCAACGAACTCGAAGAAAACATACGTAATTAAAGAGAAACTG
CTCTTCAACATAGGAGAGATGGAAGGCATCAGCAAAATATACACATGAAATGAATGGTCAA
GTGGAAGGTTTAAGATTTGCTCTATACAGATTGAGACGCCAGTTTAAAAATAACATGGGGA
AGGGAATGCTAGAAATGGTGTAATCAGTAAGAAGGACAATCTAAGGGAATCTAAGGCTTGA
AAGGAAACAGAAAACCGGGTGTGGTGGTAAATGGATTGTGACTTAGAAGCTGGCCTGAGC
TATATACAGAGACCCTGTCAAGAAAAGAGAGATGGGAGTAGTAGGAGAGGAAAGTGTGAA
GGGAAGGGAAAAGAAAGGGAGGGGGAAAGAAGCAACCAAACAAGCAATCTTGCAGTGGC
TTCTGCCAGCATGCTGGCAAACCCTGCAGTGATATTTTCACATCTATGTAAAAACCCATTTT
AGCACCTCCAGAATGAACTTTACAAGAATTGAGAAAGTCAAGTGAGAGAGCACCAAAGAAG
GAAGGAAAGAAAAAAGCAAGAACACTTGCCAGAAAGATAGGAAACCAAGAACCAGAAAAAT
AGGAAACAAAACTAAGGAAAGCTGCAGAGCAGTATTCATGGCAAACACAGAAAGAGAAATT
CTCAAAACAAGGCTAGCAACCCAAACACAAAAGCACAGAAAAGAGATGTTTCATCACAAGT
ATGATGTATCTCAAGTATGCTCAAATGACTGAAGATACACAAGCCAGCCAAGGTGATACGC
TACCACATCAACAGCACAACAGGCAGAGCTCGGGCTGGGCATAAAAGTCAGGGCAGAGCC
ATCTATTGCTTACATTTGCTTCTGGGATCCAGATCTTTCGAAGCTAGCGCTACCGGTCGCC
ACCATGGTCTCCAAGGGCGAGGAGCTGTTCACCGGGGTGGTGCCCATCCTGGTCGAGCT
GGACGGCGATGTCAACGGCCACAAGTTCAGCGTGTCCGGCGAGGGCGAGGGCGATGCCA
CCTACGGCAAGCTGACCCTGAAGCTGATCTGCACCACCGGCAAGCTGCCCGTGCCCTGG
CCCACCCTCGTGACCACCCTGGGCTACGGCGTGCAGTGCTTCGCCCGCTACCCCGACCA
CATGAAGCAGCACGACTTCTTCAAGTCCGCCATGCCCGAAGGCTACGTCCAGGAGCGCAC
CATCTTCTTCAAAGACGACGGCAACTACAAGACCCGCGCCGAGGTGAAGTTCGAGGGCGA
CACCCTGGTGAACCGCATCGAGCTGAAGGGCATCGACTTCAAGGAGGACGGCAACATCCT
GGGGCACAAGCTGGAGTACAACTACAACAGCCACAACGTCTATATCACCGCCGACAAGCA
GAAGAACGGCATCAAGGCCAACTTCAAGATCCGCCACAACATCGAGGACGGCGGCGTGC
AGCTCGCCGACCACTACCAGCAGAACACCCCCATCGGCGACGGCCCCGTGCTGCTGCCC
GACAACCACTACCTGAGCTACCAGTCCAAGCTGAGCAAAGACCCCAACGAGAAGCGCGAT
CACATGGTCCTGCTGGAGTTCGTGACCGCCGCCGGGATCACTCTCGGCATGGACGAGCT
GTACAAGGGCTCTGGTGCTACCAACTTCTCACTGTTGAAACAGGCAGGGGATGTAGAGGA
GAATCCAGGGCCTGGTGCTAGTGGAGACTACAAAGACCATGACGGAGATTATAAAGATCAT
GACATCGATTACAAGGATGACGATGACAAGTCCGGACTCAGATCTGGAGGCTCCGGAGGC
CCAGAGCCAGCGAAGTCTGCTCCCGCCCCGAAAAAGGGCTCCAAGAAGGCGGTGACTAA
GGCGCAGAAGAAAGGCGGCAAGAAGCGCAAGCGCAGCCGCAAGGAGAGCTATTCCATCT
ATGTGTACAAGGTTCTGAAGCAGGTCCACCCTGACACCGGCATTTCGTCCAAGGCCATGG
GCATCATGAATTCGTTTGTGAACGACATTTTCGAGCGCATCGCAGGAGAGGCTTCCCGCCT

FIG. 10 cont'd

GGCGCATTACAACAAGCGCTCGACCATCACCTCCCGGGAGATCCAGACGGCCGTGCGCC
TGCTGCTGCCTGGGGAGTTGGCCAAGCACGCCGTGTCCGAGGGTACTAAGGCCATCACC
AAGTACACCAGCGCTAAGTAATGAGGCGCGCCGCGGCCGCGAATTCGATATCATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTAGTTCTTGCCACGGCGGAACTCATCGCCGCCTGC
CTTGCCCGCTGCTGGACAGGGGCTCGGCTGTTGGGCACTGACAATTCCGTGGCTCGAGA
GATCTTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGACAGCAAGGG
GGAGGATTGGGAAGACAATAGCAGGCATGAGATCTCACGTGCGGACCGAGCGGCCGC
(SEQ ID NO: 78)

CN3431 (length between ITRs: 2283):
GCGGCCGCACGCGTGTGTGTGTGTGTGTGTGTGTGTGTGTGTGTCTCTGTGTGTGTGTGT
GTGTGTGTGTGTGTGTGTATGTGTGTGTATGTGAAATTATCAGGCCTCAGTTTCCTCCTCTA
CAAAATGGAAATGCTTACAAATGTCTTGCCATGCTTAGCATACACAAGTTGCTTTGCTAAGA
TGCTGAATTTAGTAAAGGTCAGTTACTATTCTAACCGATGGTAGACAGAGACTCCAACAGA
GCTCTTAGAAAGCCTGCATAACAGTAAGTCTAAGCAATGGAGTAGGGCACTAGATTATTTTA
TTCCTTTGCAAAAGTTTCTGCCTGAAATTGCAATGTTTTCTAGGTATAATTTTCATAGACTAT
AAACTCAAGTAGAACAAAGATACGAGCTCGGGCTGGGCATAAAAGTCAGGGCAGAGCCAT
CTATTGCTTACATTTGCTTCTGGATCCAGATCTTTCGAAGCTAGCGCTACCGGTCGCCAC
CATGGTCTCCAAGGGCGAGGAGCTGTTCACCGGGGTGGTGCCCATCCTGGTCGAGCTGG
ACGGCGATGTCAACGGCCACAAGTTCAGCGTGTCCGGCGAGGGCGAGGGCGATGCCACC
TACGGCAAGCTGACCCTGAAGCTGATCTGCACCACCGGCAAGCTGCCCGTGCCCTGGCC
CACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAAGACGACGGCAACTACAAGACCCGCGCCGAGGTGAAGTTCGAGGGCGACAC
CCTGGTGAACCGCATCGAGCTGAAGGGCATCGACTTCAAGGAGGACGGCAACATCCTGG
GGCACAAGCTGGAGTACAACTACAACAGCCACAACGTCTATATCACCGCCGACAAGCAGA
AGAACGGCATCAAGGCCAACTTCAAGATCCGCCACAACATCGAGGACGGCGGCGTGCAG
CTCGCCGACCACTACCAGCAGAACACCCCCATCGGCGACGGCCCCGTGCTGCTGCCCGA
CAACCACTACCTGAGCTACCAGTCCAAGCTGAGCAAAGACCCCAACGAGAAGCGCGATCA
CATGGTCCTGCTGGAGTTCGTGACCGCCGCCGGGATCACTCTCGGCATGGACGAGCTGTA
CAAGGGCTCTGGTGCTACCAACTTCTCACTGTTGAAACAGGCAGGGGATGTAGAGGAGAA
TCCAGGGCCTGGTGCTAGTGGAGACTACAAAGACCATGACGGAGATTATAAAGATCATGA
CATCGATTACAAGGATGACGATGACAAGTCCGGACTCAGATCTGGAGGCTCCGGAGGCCC
AGAGCCAGCGAAGTCTGCTCCCGCCCCGAAAAAGGGCTCCAAGAAGGCGGTGACTAAGG
CGCAGAAGAAAGGCGGCAAGAAGCGCAAGCGCAGCCGCAAGGAGAGCTATTCCATCTAT
GTGTACAAGGTTCTGAAGCAGGTCCACCCTGACACCGGCATTTCGTCCAAGGCCATGGGC
ATCATGAATTCGTTTGTGAACGACATTTTCGAGCGCATCGCAGGAGAGGCTTCCCGCCTGG
CGCATTACAACAAGCGCTCGACCATCACCTCCCGGGAGATCCAGACGGCCGTGCGCCTG
CTGCTGCCTGGGGAGTTGGCCAAGCACGCCGTGTCCGAGGGTACTAAGGCCATCACCAA
GTACACCAGCGCTAAGTAATGAGGCGCGCCGCGGCCGCGAATTCGATATCATAATCAACC
TCTGGATTACAAAATTTGTGAAAGATTGACTGGTATTCTTAACTATGTTGCTCCTTTTACGCT

FIG. 10 cont'd

ATGTGGATACGCTGCTTTAATGCCTTTGTATCATGCTATTGCTTCCCGTATGGCTTTCATTTT
CTCCTCCTTGTATAAATCCTGGTTAGTTCTTGCCACGGCGGAACTCATCGCCGCCTGCCTT
GCCCGCTGCTGGACAGGGGCTCGGCTGTTGGGCACTGACAATTCCGTGGCTCGAGAGAT
CTTCGACTGTGCCTTCTAGTTGCCAGCCATCTGTTGTTTGCCCCTCCCCCGTGCCTTCCTT
GACCCTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGGGGA
GGATTGGGAAGACAATAGCAGGCATGAGATCTCACGTGCGGACCGAGCGGCCGC (SEQ
ID NO: 79)

SEQUENCE LISTING

```
<160> NUMBER OF SEQ ID NOS: 91

<210> SEQ ID NO 1
<211> LENGTH: 352
<212> TYPE: DNA
<213> ORGANISM: Mus musculus

<400> SEQUENCE: 1

ccttttagaa acactccctt taccatcttc aaacatgttt ttagctgaga actctcttcc     60

aacccctgtt tcttaactct gagtgccgta tcacttcata ttctgtgtca ggggaaaaga    120

aatcagcacc tcccacaacg tcaactgtgt cctttagagt aagcattcca aagtctatat    180

tctgagtcta atctctcttg gaaaggtcag ccttttcttc caaataccaa gtggacatct    240

ttatgcacag gccttcaagg atattcaagt cagtgtgtcc tacggagaaa actcctttta    300

aaacccgaat cctgtggttt ccccaagatg attattgggt ggtcactgca gc            352


<210> SEQ ID NO 2
<211> LENGTH: 497
<212> TYPE: DNA
<213> ORGANISM: Mus musculus

<400> SEQUENCE: 2

atatggatgt cttacctgca tgaatacttg tgtaccacat gtatgccttt ctccatggag     60

gccagaagag ggtatcagat tccctggaac tgaagttaca gatagttgtg agctgccatg    120

tgggtactgg aaatacatgt gtctaatttt aaggaccagc tcctactgag gacataaatg    180

ttatgtttct taaaagtcta taccataaga atcttcttca gatcttggtg tgaagattct    240

taccccagat tggttacaga agcggtacca ggtgggtgga tcccatcaaa agctttagtg    300

agaaatcacc cttttccttc acagcagccc agctgactgg tgaactttgc cgaactgtaa    360

aatatcaaac ctttgggaag ctttctgcaa cacgagaagt tttaatcctt caatattaaa    420

aagaaaaata agaaaaaaaa actgtggaga agtcacgaac aggagaaaca aaaaggaatt    480

gtgcacaggg tcagtcg                                                   497


<210> SEQ ID NO 3
<211> LENGTH: 439
<212> TYPE: DNA
<213> ORGANISM: Mus musculus

<400> SEQUENCE: 3

cccaggatct attgacatcc aacatcggat ggagaaactg aagttcacat catagctcat     60

ctctcatagt atcctatacg gtgtttctct ttcttggaga aacaacccca ccccacccgc    120
```

```
cttgatgtta atgccaggac acacatgttt tcttgacccc acttctctga tcactcatcg    180

ctctgcttcc tcagcctgtt gttggtacca gttctcagat agttgcagtc tccaagttca    240

gttcctaccg atttatgcca tgctgtcttt tttgagaaat accactcacc atgtgagtga    300

atctgtgaat gcctcctaaa tgcccgttgc caatttgaga ataaaagttc atgtgattat    360

gttcaaggca tttcagatta aatatgacca aaatcactcc gtggtgcctt cctgtacgcc    420

tcaccgtgaa tccagtttg                                                 439


<210> SEQ ID NO 4
<211> LENGTH: 593
<212> TYPE: DNA
<213> ORGANISM: Mus musculus

<400> SEQUENCE: 4

atgggaaagc agcacgtgtt cttaactgct agactcctat ttaccatgac agtaatatca     60

ttattatttt taaatcattt tataatttca ggagaaagca aatgattgct aataacggtc    120

tccctcttca gtacatatgc actacacgcg catgtgtcct ttaaagataa atttgagttg    180

gaagcatcgg tatgagctgg tgagttttaa gaagttccag aaaaaaaaaa gaagttccag    240

tatttcctag atttgtcctc tgcaaagtcc taggcataaa ggcagcgcag tttgtggcct    300

ttaaatacca cttcccacga aagcaaccaa ggctccttgg agacgtgagc gatttgatgt    360

ctataaatat gagcacacag tgctgtgctt ccccactgag gtcagaaaga ccactaccct    420

gaatccaaac caccttcatg gcttagcaga tgaggccaga gctggacaag agcaattaaa    480

gggaacaatt acattacatg ttggtgtttg atttatctgc agattttttt aaccagtaaa    540

gtttattttg aaatgcaatt aatttgtaag atcagaccgc ccattggtta gtt           593


<210> SEQ ID NO 5
<211> LENGTH: 627
<212> TYPE: DNA
<213> ORGANISM: Mus musculus
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t

<400> SEQUENCE: 5

tccagatgct tgtcttctct ctctctctct ctctctctct ctctctctct ctctgtatgt     60

gtgtgtgtgt gtgtgtgtgt atgtgtgtct tccccccntn tttttcaccc caccccgaca    120

tctacaacaa aaattttaac catattatgg agtggtcata ttggcagttt ttttactgca    180

gcccttcaca tgcactgaca ttctagacag caagtgttct atgattttca acaggacact    240

tggatctagc caactcagtt ttcaagcctg cccccgagtt gtagatcctg tcttcacatt    300

ctaaactaat ctcacaccac tttgtgccaa ctccactctg gtaaagacca tgcactcgag    360

ttagtgcaag acattttgtt ctggcctcgg ggtgtgctgc cgcctcgtca ggatgggagg    420

tggaggcgag tccagtgaag gtcactggca tcacaagagt gagggacaga tatgttcccg    480

agccttcaga ttcaagtcct gcacttgcaa aaaagacttc tgccttttct atttgaccca    540

actagctatt gcattattga gccagacagt ggctcaaatt aaatgtcaca ggagcacacc    600

ctaacaaaaa gaagaggcca gcatgct                                        627
```

<210> SEQ ID NO 6
<211> LENGTH: 773
<212> TYPE: DNA
<213> ORGANISM: Mus musculus
<220> FEATURE:
<221> NAME/KEY: misc_feature
<222> LOCATION: (172)..(172)
<223> OTHER INFORMATION: n is a, c, g, or t

<400> SEQUENCE: 6
tagagaaatg tgctgtggtt taacttttgg aataaaaata gtgaattttt aatgagcagg 60
tgggaatgtc cttgggttct gagttaggat ggtggagcaa ggaaagaaaa ggtctctctt 120
ccttttccct gtgtgctgag tagagacagg attgcccaga acaccaggaa cntaggttgt 180
actgacaaaa gtggaaaaca gccgcaaaac cgctagggaa agcagctgtc cccttgccca 240
gtctcctgcc ccactcctgc ctctgcctat aagagtttgg cacagttgga gatttgtata 300
cacaaatgca tgcgtggaaa tactgcgctc tgatgacatt cctcaggggg cgacctttga 360
tgatgaattt tcttgccctt tttaggggag gagaagagga ggcgggtggt acttcacaag 420
actaaattta ctcaactttt ttgggtctaa atttctttag gaaaaaaaat gtcaaatgat 480
tgtagatccc aaactgtctt tgttggcatt tgaatggctc tgtgagtcca gtgtggggag 540
caagtgaaaa gaaaagccac ctctcccctc gctggcgtgg tattgaagct gaagccctgg 600
accacacagt gtcttgggga ccttcatgat ttatatattg tatgtgatct tttcttaaac 660
attgttaacc tgtgcccttt acagacaatg ccgggtcaga aaatgtcagg ggaacttcgg 720
actgctttca taattgtgta aagaaaattg ttgtcttcag aatccagagc cca 773

<210> SEQ ID NO 7
<211> LENGTH: 306
<212> TYPE: DNA
<213> ORGANISM: Mus musculus

<400> SEQUENCE: 7
ttcaggccaa tacctcagcg aaaatcaaat cagttgcaaa atccatacag tcttccagtt 60
tctcagctgt ggaaactttg tgtctcttct tttccaccaa aacagctatc tcgtctttca 120
agtccttgct gaaaaaaaaa agtgttaaat ttttctcaat ttagacttcc agcaaaacag 180
attctgcttg ttgaaaggca ttggtgttca tgagtaagtg agtttccatt ttatttcttc 240
acaaataagt tacatgaagt acttatctta tggtactaga gttaactggg atttctaaac 300
acaggt 306

<210> SEQ ID NO 8
<211> LENGTH: 53
<212> TYPE: DNA
<213> ORGANISM: Artificial Sequence
<220> FEATURE:
<223> OTHER INFORMATION: Beta-Globin Minimal Promoter
(pBGmin/minBGlobin/minBGprom)

<400> SEQUENCE: 8
gggctgggca taaaagtcag ggcagagcca tctattgctt acatttgctt ctg 53

<210> SEQ ID NO 9
<211> LENGTH: 68
<212> TYPE: DNA
<213> ORGANISM: Artificial Sequence
<220> FEATURE:
<223> OTHER INFORMATION: minCMV Promoter

<400> SEQUENCE: 9
gaggtaggcg tgtacggtgg gaggcctata taagcagagc tcgtttagtg aaccgtcaga 60
tcgcctgg 68

<210> SEQ ID NO 10
<211> LENGTH: 68
<212> TYPE: DNA
<213> ORGANISM: Artificial Sequence
<220> FEATURE:
<223> OTHER INFORMATION: Mutated minCMV Promoter (SacI RE site removed)

<400> SEQUENCE: 10
gaggtaggcg tgtacggtgg gaggcctata taagcagagc tggtttagtg aaccgtcaga 60
tcgcctgg 68

<210> SEQ ID NO 11
<211> LENGTH: 120
<212> TYPE: DNA
<213> ORGANISM: Artificial Sequence
<220> FEATURE:
<223> OTHER INFORMATION: minRho Promoter

<400> SEQUENCE: 11
gattcagccg ggagcttagg gaggggaggt cacttcataa gggcctgggg ggggagttgg 60
agccacgagt cgtccagccg gagccccgtg tggctgagct ccggcctcag aagcatcccc 120

<210> SEQ ID NO 12
<211> LENGTH: 120
<212> TYPE: DNA
<213> ORGANISM: Artificial Sequence
<220> FEATURE:
<223> OTHER INFORMATION: minRho* Promoter

<400> SEQUENCE: 12
gattcagccg ggagcttagg gaggggaggt cacttcataa gggcttgggg ggggagttgg 60
agccacgagt cgtccagccg gagccccgtg tggctgtgct ccggcctcag aagcatcccc 120

<210> SEQ ID NO 13
<211> LENGTH: 867
<212> TYPE: DNA
<213> ORGANISM: Artificial Sequence
<220> FEATURE:
<223> OTHER INFORMATION: Hsp68 minimal Promoter (proHsp68)

<400> SEQUENCE: 13
caggaacatc caaactgagc agccggggtc ccccccaccc cccaccccgc cccacgcggc 60
aactttgagc ctgtgctggg acagagcctc tagttcctaa attagtccat gaggtcagag 120
gcagcactgc cattgtaacg cgattggaga ggatcacgtc accggacacg cccccaggca 180
tctccctggg tctcctaaac ttggcgggga gaagttttag cccttaagtt ttagccttta 240
acccccatat tcagaactgt gcgagttggc gaaaccccac aaatcacaac aaactgtaca 300
caacaccgag ctagaggtga tctttcttgt ccattccaca caggccttag taatgcgtcg 360
ccatagcaac agtgtcacta gtagcaccag cacttcccca caccctcccc ctcaggaatc 420
cgtactctcc agtgaacccc agaaacctct ggagagttct ggacaagggc ggaacccaca 480
actccgatta ctcaagggag gcggggaagc tccaccagac gcgaaactgc tggaagattc 540
ctggccccaa ggcctcctcc ggctcgctga ttggcccagc ggagagtggg cggggccggt 600
gaagactcct taaaggcgca gggcggcgag caggtcacca gacgctgaca gctactcaga 660
accaaatctg gttccatcca gagacaagcg aagacaagag aagcagagcg agcggcgcgt 720
tcccgatcct cggccaggac cagccttccc cagagcatcc ctgccgcgga gcgcaacctt 780
cccaggagca tccctgccgc ggagcgcaac tttccccgga gcatccacgc cgcggagcgc 840
agccttccag aagcagagcg cggcgcc 867

<210> SEQ ID NO 14
<211> LENGTH: 720
<212> TYPE: DNA
<213> ORGANISM: Artificial Sequence
<220> FEATURE:
<223> OTHER INFORMATION: SYFP2

<400> SEQUENCE: 14
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagct gatctgcacc accggcaagc tgcccgtgcc ctggcccacc 180
ctcgtgacca ccctgggcta cggcgtgcag tgcttcgccc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca ccgccgacaa gcagaagaac 480
ggcatcaagg ccaacttcaa gatccgccac aacatcgagg acggcggcgt gcagctcgcc 540
gaccactacc agcagaacac ccccatcggc gacggccccg tgctgctgcc cgacaaccac 600
tacctgagct accagtccaa gctgagcaaa gaccccaacg agaagcgcga tcacatggtc 660
ctgctggagt tcgtgaccgc cgccgggatc actctcggca tggacgagct gtacaagtaa 720

<210> SEQ ID NO 15
<211> LENGTH: 720
<212> TYPE: DNA
<213> ORGANISM: Artificial Sequence
<220> FEATURE:
<223> OTHER INFORMATION: EGFP

<400> SEQUENCE: 15
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 16

<211> LENGTH: 1299
<212> TYPE: DNA
<213> ORGANISM: Artificial Sequence
<220> FEATURE:
<223> OTHER INFORMATION: Optimized Flp recombinase (FlpO)

<400> SEQUENCE: 16
atggctccta agaagaagag gaaggtgatg agccagttcg acatcctgtg caagaccccc 60
cccaaggtgc tggtgcggca gttcgtggag agattcgaga ggcccagcgg cgagaagatc 120
gccagctgtg ccgccgagct gacctacctg tgctggatga tcacccacaa cggcaccgcc 180
atcaagaggg ccaccttcat gagctacaac accatcatca gcaacagcct gagcttcgac 240
atcgtgaaca agagcctgca gttcaagtac aagacccaga aggccaccat cctggaggcc 300
agcctgaaga agctgatccc cgcctgggag ttcaccatca tcccttacaa cggccagaag 360
caccagagcg acatcaccga catcgtgtcc agcctgcagc tgcagttcga gagcagcgag 420
gaggccgaca agggcaacag ccacagcaag aagatgctga aggccctgct gtccgagggc 480
gagagcatct gggagatcac cgagaagatc ctgaacagct tcgagtacac cagcaggttc 540
accaagacca agaccctgta ccagttcctg ttcctggcca cattcatcaa ctgcggcagg 600
ttcagcgaca tcaagaacgt ggaccccaag agcttcaagc tggtgcagaa caagtacctg 660
ggcgtgatca ttcagtgcct ggtgaccgag accaagacaa gcgtgtccag gcacatctac 720
tttttcagcg ccagaggcag gatcgacccc ctggtgtacc tggacgagtt cctgaggaac 780
agcgagcccg tgctgaagag agtgaacagg accggcaaca gcagcagcaa caagcaggag 840
taccagctgc tgaaggacaa cctggtgcgc agctacaaca aggccctgaa gaagaacgcc 900
ccctacccca tcttcgctat caagaacggc cctaagagcc acatcggcag gcacctgatg 960
accagctttc tgagcatgaa gggcctgacc gagctgacaa acgtggtggg caactggagc 1020
gacaagaggg cctccgccgt ggccaggacc acctacaccc accagatcac cgccatcccc 1080
gaccactact tcgccctggt gtccaggtac tacgcctacg accccatcag caaggagatg 1140
atcgccctga aggacgagac caaccccatc gaggagtggc agcacatcga gcagctgaag 1200
ggcagcgccg agggcagcat cagatacccc gcctggaacg gcatcatcag ccaggaggtg 1260
ctggactacc tgagcagcta catcaacagg cggatctga 1299

<210> SEQ ID NO 17
<211> LENGTH: 1056
<212> TYPE: DNA
<213> ORGANISM: Artificial Sequence
<220> FEATURE:
<223> OTHER INFORMATION: Improved Cre recombinase (iCre)

<400> SEQUENCE: 17
atggtgccca agaagaagag gaaagtctcc aacctgctga ctgtgcacca aaacctgcct 60
gccctccctg tggatgccac ctctgatgaa gtcaggaaga acctgatgga catgttcagg 120
gacaggcagg ccttctctga acacacctgg aagatgctcc tgtctgtgtg cagatcctgg 180
gctgcctggt gcaagctgaa caacaggaaa tggttccctg ctgaacctga ggatgtgagg 240
gactacctcc tgtacctgca agccagaggc ctggctgtga agaccatcca acagcacctg 300
ggccagctca acatgctgca caggagatct ggcctgcctc gcccttctga ctccaatgct 360
gtgtccctgg tgatgaggag aatcagaaag gagaatgtgg atgctgggga gagagccaag 420
caggccctgg cctttgaacg cactgacttt gaccaagtca gatccctgat ggagaactct 480
gacagatgcc aggacatcag gaacctggcc ttcctgggca ttgcctacaa caccctgctg 540

```
cgcattgccg aaattgccag aatcagagtg aaggacatct cccgcaccga tggtgggaga    600

atgctgatcc acattggcag gaccaagacc ctggtgtcca cagctggtgt ggagaaggcc    660

ctgtccctgg gggttaccaa gctggtggag agatggatct ctgtgtctgg tgtggctgat    720

gaccccaaca actacctgtt ctgccgggtc agaaagaatg gtgtggctgc cccttctgcc    780

acctcccaac tgtccacccg ggccctggaa gggatctttg aggccaccca ccgcctgatc    840

tatggtgcca aggatgactc tgggcagaga tacctggcct ggtctggcca ctctgccaga    900

gtgggtgctg ccagggacat ggccagggct ggtgtgtcca tccctgaaat catgcaggct    960

ggtggctgga ccaatgtgaa cattgtgatg aactacatca gaaacctgga ctctgagact   1020

ggggccatgg tgaggctgct cgaggatggg gactaa                             1056


<210> SEQ ID NO 18
<211> LENGTH: 50
<212> TYPE: DNA
<213> ORGANISM: Artificial Sequence
<220> FEATURE:
<223> OTHER INFORMATION: SP10 insulator (SP10ins)

<400> SEQUENCE: 18

gaagctaccc ctaacacact attctacaca cagaaaatgc tcttcactag                50


<210> SEQ ID NO 19
<211> LENGTH: 150
<212> TYPE: DNA
<213> ORGANISM: Artificial Sequence
<220> FEATURE:
<223> OTHER INFORMATION: 3xSP10ins

<400> SEQUENCE: 19

gaagctaccc ctaacacact attctacaca cagaaaatgc tcttcactag gaagctaccc     60

ctaacacact attctacaca cagaaaatgc tcttcactag gaagctaccc ctaacacact    120

attctacaca cagaaaatgc tcttcactag                                     150


<210> SEQ ID NO 20
<211> LENGTH: 246
<212> TYPE: DNA
<213> ORGANISM: Artificial Sequence
<220> FEATURE:
<223> OTHER INFORMATION: WPRE3

<400> SEQUENCE: 20

ataatcaacc tctggattac aaaatttgtg aaagattgac tggtattctt aactatgttg     60

ctccttttac gctatgtgga tacgctgctt taatgccttt gtatcatgct attgcttccc    120

gtatggcttt cattttctcc tccttgtata aatcctggtt agttcttgcc acggcggaac    180

tcatcgccgc ctgccttgcc cgctgctgga caggggctcg gctgttgggc actgacaatt    240

ccgtgg                                                               246


<210> SEQ ID NO 21
<211> LENGTH: 609
<212> TYPE: DNA
<213> ORGANISM: Artificial Sequence
<220> FEATURE:
<223> OTHER INFORMATION: WPRE

<400> SEQUENCE: 21

gcttatcgat aatcaacctc tggattacaa aatttgtgaa agattgactg gtattcttaa     60
```

```
ctatgttgct ccttttacgc tatgtggata cgctgcttta atgcctttgt atcatgctat    120

tgcttcccgt atggctttca ttttctcctc cttgtataaa tcctggttgc tgtctcttta    180

tgaggagttg tggcccgttg tcaggcaacg tggcgtggtg tgcactgtgt ttgctgacgc    240

aacccccact ggttggggca ttgccaccac ctgtcagctc ctttccggga ctttcgcttt    300

ccccctccct attgccacgg cggaactcat cgccgcctgc cttgcccgct gctggacagg    360

ggctcggctg ttgggcactg acaattccgt ggtgttgtcg gggaaatcat cgtcctttcc    420

ttggctgctc gcctatgttg ccacctggat tctgcgcggg acgtccttct gctacgtccc    480

ttcggccctc aatccagcgg accttccttc ccgcggcctg ctgccggctc tgcggcctct    540

tccgcgtctt cgccttcgcc ctcagacgag tcggatctcc ctttgggccg cctccccgca    600

tcgataccg                                                            609


<210> SEQ ID NO 22
<211> LENGTH: 204
<212> TYPE: DNA
<213> ORGANISM: Artificial Sequence
<220> FEATURE:
<223> OTHER INFORMATION: BGHpA

<400> SEQUENCE: 22

cgactgtgcc ttctagttgc cagccatctg ttgtttgccc ctcccccgtg ccttccttga     60

ccctggaagg tgccactccc actgtccttt cctaataaaa tgaggaaatt gcatcgcatt    120

gtctgagtag gtgtcattct attctggggg gtggggtggg gcaggacagc aagggggagg    180

attgggaaga caatagcagg catg                                           204


<210> SEQ ID NO 23
<211> LENGTH: 479
<212> TYPE: DNA
<213> ORGANISM: Artificial Sequence
<220> FEATURE:
<223> OTHER INFORMATION: HGHpA

<400> SEQUENCE: 23

acgggtggca tccctgtgac ccctccccag tgcctctcct ggccctggaa gttgccactc     60

cagtgcccac cagccttgtc ctaataaaat taagttgcat cattttgtct gactaggtgt    120

ccttctataa tattatgggg tggagggggg tggtatggag caaggggcaa gttgggaaga    180

caacctgtag ggcctgcggg gtctattggg aaccaagctg gagtgcagtg gcacaatctt    240

ggctcactgc aatctccgcc tcctgggttc aagcgattct cctgcctcag cctcccgagt    300

tgttgggatt ccaggcatgc atgaccaggc tcagctaatt tttgtttttt tggtagagac    360

ggggtttcac catattggcc aggctggtct ccaactccta atctcaggtg atctacccac    420

cttggcctcc caaattgctg ggattacagg cgtgaaccac tgctcccttc cctgtcctt     479


<210> SEQ ID NO 24
<211> LENGTH: 78
<212> TYPE: DNA
<213> ORGANISM: Artificial Sequence
<220> FEATURE:
<223> OTHER INFORMATION: P2A

<400> SEQUENCE: 24

ggcagcggcg ccaccaactt cagcctgctg aagcaggccg gcgacgtgga ggagaacccc     60

ggccccggag ctagcgga                                                   78
```

```
<210> SEQ ID NO 25
<211> LENGTH: 21
<212> TYPE: PRT
<213> ORGANISM: Artificial Sequence
<220> FEATURE:
<223> OTHER INFORMATION: T2A

<400> SEQUENCE: 25

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 26
<211> LENGTH: 24
<212> TYPE: PRT
<213> ORGANISM: Artificial Sequence
<220> FEATURE:
<223> OTHER INFORMATION: E2A

<400> SEQUENCE: 26

Gly Ser Gly Gln Cys Thr Asn Tyr Ala Leu Leu Lys Leu Ala Gly Asp
1               5                   10                  15

Val Glu Ser Asn Pro Gly Pro Pro
            20


<210> SEQ ID NO 27
<211> LENGTH: 25
<212> TYPE: PRT
<213> ORGANISM: Artificial Sequence
<220> FEATURE:
<223> OTHER INFORMATION: F2A

<400> SEQUENCE: 27

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25


<210> SEQ ID NO 28
<211> LENGTH: 130
<212> TYPE: DNA
<213> ORGANISM: Artificial Sequence
<220> FEATURE:
<223> OTHER INFORMATION: Exemplary Plasmid Backbone 1, Left ITR

<400> SEQUENCE: 28

cctgcaggca gctgcgcgct cgctcgctca ctgaggccgc ccgggcgtcg ggcgaccttt      60

ggtcgcccgg cctcagtgag cgagcgagcg cgcagagagg gagtggccaa ctccatcact     120

aggggttcct                                                            130


<210> SEQ ID NO 29
<211> LENGTH: 141
<212> TYPE: DNA
<213> ORGANISM: Artificial Sequence
<220> FEATURE:
<223> OTHER INFORMATION: Exemplary Plasmid Backbone 1, Right ITR

<400> SEQUENCE: 29

cctgcaggca gctgcgcgct cgctcgctca ctgaggccgc ccgggcaaag cccgggcgtc      60

gggcgacctt tggtcgcccg gcctcagtga gcgagcgagc gcgcagagag ggagtggcca     120

actccatcac taggggttcc t                                               141
```

<210> SEQ ID NO 30
<211> LENGTH: 146
<212> TYPE: DNA
<213> ORGANISM: Artificial Sequence
<220> FEATURE:
<223> OTHER INFORMATION: Exemplary Plasmid Backbone 2, Left ITR

<400> SEQUENCE: 30
catgtcctgc aggcagctgc gcgctcgctc gctcactgag gccgcccggg caaagcccgg 60
gcgtcgggcg acctttggtc gcccggcctc agtgagcgag cgagcgcgca gagagggagt 120
ggccaactcc atcactaggg gttcct 146

<210> SEQ ID NO 31
<211> LENGTH: 149
<212> TYPE: DNA
<213> ORGANISM: Artificial Sequence
<220> FEATURE:
<223> OTHER INFORMATION: Exemplary Plasmid Backbone 2, Right ITR

<400> SEQUENCE: 31
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctgcctgcag gggcgcctg 149

<210> SEQ ID NO 32
<211> LENGTH: 743
<212> TYPE: PRT
<213> ORGANISM: Artificial Sequence
<220> FEATURE:
<223> OTHER INFORMATION: PHP.eB capsid

<400> SEQUENCE: 32

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly

```
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Asp Gly Thr Leu Ala Val
            580                 585                 590

Pro Phe Lys Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620
```

Ile Trp Ala Lys Ile Pro His Thr Asp Gly Asn Phe His Pro Ser Pro
625 630 635 640

Leu Met Gly Gly Phe Gly Met Lys His Pro Pro Pro Gln Ile Leu Ile
645 650 655

Lys Asn Thr Pro Val Pro Ala Asp Pro Pro Thr Ala Phe Asn Lys Asp
660 665 670

Lys Leu Asn Ser Phe Ile Thr Gln Tyr Ser Thr Gly Gln Val Ser Val
675 680 685

Glu Ile Glu Trp Glu Leu Gln Lys Glu Asn Ser Lys Arg Trp Asn Pro
690 695 700

Glu Ile Gln Tyr Thr Ser Asn Tyr Tyr Lys Ser Asn Asn Val Glu Phe
705 710 715 720

Ala Val Asn Thr Glu Gly Val Tyr Ser Glu Pro Arg Pro Ile Gly Thr
725 730 735

Arg Tyr Leu Thr Arg Asn Leu
740

<210> SEQ ID NO 33
<211> LENGTH: 736
<212> TYPE: PRT
<213> ORGANISM: Artificial Sequence
<220> FEATURE:
<223> OTHER INFORMATION: AAV9 VP1 capsid protein

<400> SEQUENCE: 33

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile
225 230 235 240

-continued

Thr Thr Ser Thr Arg Thr Trp Ala Leu Pro Thr Tyr Asn Asn His Leu
245 250 255

Tyr Lys Gln Ile Ser Asn Ser Thr Ser Gly Gly Ser Ser Asn Asp Asn
260 265 270

Ala Tyr Phe Gly Tyr Ser Thr Pro Trp Gly Tyr Phe Asp Phe Asn Arg
275 280 285

Phe His Cys His Phe Ser Pro Arg Asp Trp Gln Arg Leu Ile Asn Asn
290 295 300

Asn Trp Gly Phe Arg Pro Lys Arg Leu Asn Phe Lys Leu Phe Asn Ile
305 310 315 320

Gln Val Lys Glu Val Thr Asp Asn Asn Gly Val Lys Thr Ile Ala Asn
325 330 335

Asn Leu Thr Ser Thr Val Gln Val Phe Thr Asp Ser Asp Tyr Gln Leu
340 345 350

Pro Tyr Val Leu Gly Ser Ala His Glu Gly Cys Leu Pro Pro Phe Pro
355 360 365

Ala Asp Val Phe Met Ile Pro Gln Tyr Gly Tyr Leu Thr Leu Asn Asp
370 375 380

Gly Ser Gln Ala Val Gly Arg Ser Ser Phe Tyr Cys Leu Glu Tyr Phe
385 390 395 400

Pro Ser Gln Met Leu Arg Thr Gly Asn Asn Phe Gln Phe Ser Tyr Glu
405 410 415

Phe Glu Asn Val Pro Phe His Ser Ser Tyr Ala His Ser Gln Ser Leu
420 425 430

Asp Arg Leu Met Asn Pro Leu Ile Asp Gln Tyr Leu Tyr Tyr Leu Ser
435 440 445

Lys Thr Ile Asn Gly Ser Gly Gln Asn Gln Gln Thr Leu Lys Phe Ser
450 455 460

Val Ala Gly Pro Ser Asn Met Ala Val Gln Gly Arg Asn Tyr Ile Pro
465 470 475 480

Gly Pro Ser Tyr Arg Gln Gln Arg Val Ser Thr Thr Val Thr Gln Asn
485 490 495

Asn Asn Ser Glu Phe Ala Trp Pro Gly Ala Ser Ser Trp Ala Leu Asn
500 505 510

Gly Arg Asn Ser Leu Met Asn Pro Gly Pro Ala Met Ala Ser His Lys
515 520 525

Glu Gly Glu Asp Arg Phe Phe Pro Leu Ser Gly Ser Leu Ile Phe Gly
530 535 540

Lys Gln Gly Thr Gly Arg Asp Asn Val Asp Ala Asp Lys Val Met Ile
545 550 555 560

Thr Asn Glu Glu Glu Ile Lys Thr Thr Asn Pro Val Ala Thr Glu Ser
565 570 575

Tyr Gly Gln Val Ala Thr Asn His Gln Ser Ala Gln Ala Gln Ala Gln
580 585 590

Thr Gly Trp Val Gln Asn Gln Gly Ile Leu Pro Gly Met Val Trp Gln
595 600 605

Asp Arg Asp Val Tyr Leu Gln Gly Pro Ile Trp Ala Lys Ile Pro His
610 615 620

Thr Asp Gly Asn Phe His Pro Ser Pro Leu Met Gly Gly Phe Gly Met
625 630 635 640

Lys His Pro Pro Pro Gln Ile Leu Ile Lys Asn Thr Pro Val Pro Ala
645 650 655

```
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 34
<211> LENGTH: 747
<212> TYPE: PRT
<213> ORGANISM: Artificial Sequence
<220> FEATURE:
<223> OTHER INFORMATION: tet-Transactivator version 2 (tTA2)

<400> SEQUENCE: 34

Ala Thr Gly Thr Cys Thr Ala Gly Ala Cys Thr Gly Gly Ala Cys Ala
1               5                   10                  15

Ala Gly Ala Gly Cys Ala Ala Ala Gly Thr Cys Ala Thr Ala Ala Ala
            20                  25                  30

Cys Thr Cys Thr Gly Cys Thr Cys Thr Gly Gly Ala Ala Thr Thr Ala
        35                  40                  45

Cys Thr Cys Ala Ala Thr Gly Ala Ala Gly Thr Cys Gly Gly Thr Ala
    50                  55                  60

Thr Cys Gly Ala Ala Gly Gly Cys Cys Thr Gly Ala Cys Gly Ala Cys
65                  70                  75                  80

Ala Ala Gly Gly Ala Ala Ala Cys Thr Cys Gly Cys Thr Cys Ala Ala
                85                  90                  95

Ala Ala Gly Cys Thr Gly Gly Gly Ala Gly Thr Thr Gly Ala Gly Cys
            100                 105                 110

Ala Gly Cys Cys Thr Ala Cys Cys Cys Thr Gly Thr Ala Cys Thr Gly
        115                 120                 125

Gly Cys Ala Cys Gly Thr Gly Ala Ala Gly Ala Ala Cys Ala Ala Gly
    130                 135                 140

Cys Gly Gly Gly Cys Cys Cys Thr Gly Cys Thr Cys Gly Ala Thr Gly
145                 150                 155                 160

Cys Cys Cys Thr Gly Gly Cys Ala Ala Thr Cys Gly Ala Gly Ala Thr
                165                 170                 175

Gly Cys Thr Gly Gly Ala Cys Ala Gly Gly Cys Ala Thr Cys Ala Thr
            180                 185                 190

Ala Cys Cys Cys Ala Cys Thr Thr Cys Thr Gly Cys Cys Cys Cys Cys
        195                 200                 205

Thr Gly Gly Ala Ala Gly Gly Cys Gly Ala Gly Thr Cys Ala Thr Gly
    210                 215                 220

Gly Cys Ala Ala Gly Ala Cys Thr Thr Thr Cys Thr Gly Cys Gly Gly
225                 230                 235                 240

Ala Ala Cys Ala Ala Cys Gly Cys Cys Ala Ala Gly Thr Cys Ala Thr
                245                 250                 255

Thr Cys Cys Gly Cys Thr Gly Thr Gly Cys Thr Cys Thr Cys Cys Thr
            260                 265                 270

Cys Thr Cys Ala Cys Ala Thr Cys Gly Cys Gly Ala Cys Gly Gly Gly
        275                 280                 285
```

Gly Cys Thr Ala Ala Ala Gly Thr Gly Cys Ala Thr Cys Thr Cys Gly
    290                 295                 300

Gly Cys Ala Cys Cys Cys Gly Cys Cys Cys Ala Ala Cys Ala Gly Ala
305                 310                 315                 320

Gly Ala Ala Ala Cys Ala Gly Thr Ala Cys Gly Ala Ala Ala Cys Cys
                325                 330                 335

Cys Thr Gly Gly Ala Ala Ala Ala Thr Cys Ala Gly Cys Thr Cys Gly
            340                 345                 350

Cys Gly Thr Thr Cys Cys Thr Gly Thr Gly Thr Cys Ala Gly Cys Ala
        355                 360                 365

Ala Gly Gly Cys Thr Thr Cys Thr Cys Cys Cys Thr Gly Gly Ala Gly
    370                 375                 380

Ala Ala Cys Gly Cys Ala Cys Thr Gly Thr Ala Cys Gly Cys Thr Cys
385                 390                 395                 400

Thr Gly Thr Cys Cys Gly Cys Cys Gly Thr Gly Gly Gly Cys Cys Ala
                405                 410                 415

Cys Thr Thr Thr Ala Cys Ala Cys Thr Gly Gly Gly Cys Thr Gly Cys
            420                 425                 430

Gly Thr Ala Thr Thr Gly Gly Ala Gly Gly Ala Thr Cys Ala Gly Gly
        435                 440                 445

Ala Gly Cys Ala Thr Cys Ala Ala Gly Thr Ala Gly Cys Ala Ala Ala
    450                 455                 460

Ala Gly Ala Gly Gly Ala Ala Ala Gly Ala Gly Ala Gly Ala Cys Ala
465                 470                 475                 480

Cys Cys Thr Ala Cys Cys Ala Cys Cys Gly Ala Thr Thr Cys Thr Ala
                485                 490                 495

Thr Gly Cys Cys Cys Cys Ala Cys Thr Thr Cys Thr Gly Ala Gly
            500                 505                 510

Ala Cys Ala Ala Gly Cys Ala Ala Thr Thr Gly Ala Gly Cys Thr Gly
        515                 520                 525

Thr Thr Cys Gly Ala Cys Cys Ala Thr Cys Ala Gly Gly Gly Ala Gly
    530                 535                 540

Cys Cys Gly Ala Ala Cys Cys Thr Gly Cys Cys Thr Thr Cys Cys Thr
545                 550                 555                 560

Thr Thr Thr Cys Gly Gly Cys Cys Thr Gly Gly Ala Ala Cys Thr Ala
                565                 570                 575

Ala Thr Cys Ala Thr Ala Thr Gly Thr Gly Gly Cys Cys Thr Gly Gly
            580                 585                 590

Ala Gly Ala Ala Ala Cys Ala Gly Cys Thr Ala Ala Ala Gly Thr Gly
        595                 600                 605

Cys Gly Ala Ala Ala Gly Cys Gly Gly Cys Gly Gly Gly Cys Cys Gly
    610                 615                 620

Gly Cys Cys Gly Ala Cys Gly Cys Cys Cys Thr Thr Gly Ala Cys Gly
625                 630                 635                 640

Ala Thr Thr Thr Thr Gly Ala Cys Thr Thr Ala Gly Ala Cys Ala Thr
                645                 650                 655

Gly Cys Thr Cys Cys Cys Ala Gly Cys Cys Gly Ala Thr Gly Cys Cys
            660                 665                 670

Cys Thr Thr Gly Ala Cys Gly Ala Cys Thr Thr Thr Gly Ala Cys Cys
        675                 680                 685

Thr Thr Gly Ala Thr Ala Thr Gly Cys Thr Gly Cys Cys Thr Gly Cys
    690                 695                 700

Thr Gly Ala Cys Gly Cys Thr Cys Thr Thr Gly Ala Cys Gly Ala Thr

```
705                 710                 715                 720

Thr Thr Thr Gly Ala Cys Cys Thr Thr Gly Ala Cys Ala Thr Gly Cys
                725                 730                 735

Thr Cys Cys Cys Cys Gly Gly Gly Thr Ala Ala
            740                 745


<210> SEQ ID NO 35
<211> LENGTH: 189
<212> TYPE: PRT
<213> ORGANISM: Homo sapiens

<400> SEQUENCE: 35

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185


<210> SEQ ID NO 36
<211> LENGTH: 11
<212> TYPE: PRT
<213> ORGANISM: Homo sapiens

<400> SEQUENCE: 36

Arg Pro Lys Pro Gln Gln Phe Phe Gly Leu Met
1               5                   10


<210> SEQ ID NO 37
<211> LENGTH: 9
<212> TYPE: PRT
<213> ORGANISM: Homo sapiens

<400> SEQUENCE: 37

Cys Tyr Ile Gln Asn Cys Pro Leu Gly
1               5


<210> SEQ ID NO 38
<211> LENGTH: 1353
<212> TYPE: DNA
<213> ORGANISM: Artificial Sequence
```

<220> FEATURE:
<223> OTHER INFORMATION: GCaMP6m

<400> SEQUENCE: 38
atgggttctc atcatcatca tcatcatggt atggctagca tgactggtgg acagcaaatg 60
ggtcgggatc tgtacgacga tgacgataag gatctcgcca ccatggtcga ctcatcacgt 120
cgtaagtgga ataagacagg tcacgcagtc agagctatag gtcggctgag ctcactcgag 180
aacgtctata tcaaggccga caagcagaag aacggcatca aggcgaactt caagatccgc 240
cacaacatcg aggacggcgg cgtgcagctc gcctaccact accagcagaa cacccccatc 300
ggcgacggcc ccgtgctgct gcccgacaac cactacctga gcgtgcagtc caaactttcg 360
aaagacccca acgagaagcg cgatcacatg gtcctgctgg agttcgtgac cgccgccggg 420
atcactctcg gcatggacga gctgtacaag ggcggtaccg gagggagcat ggtgagcaag 480
ggcgaggagc tgttcaccgg ggtggtgccc atcctggtcg agctggacgg cgacgtaaac 540
ggccacaagt tcagcgtgtc cggcgagggt gagggcgatg ccacctacgg caagctgacc 600
ctgaagttca tctgcaccac cggcaagctg cccgtgccct ggcccaccct cgtgaccacc 660
ctgacctacg gcgtgcagtg cttcagccgc taccccgacc acatgaagca gcacgacttc 720
ttcaagtccg ccatgcccga aggctacatc caggagcgca ccatcttctt caaggacgac 780
ggcaactaca agacccgcgc cgaggtgaag ttcgagggcg acaccctggt gaaccgcatc 840
gagctgaagg gcatcgactt caaggaggac ggcaacatcc tggggcacaa gctggagtac 900
aacctgccgg accaactgac tgaagagcag atcgcagaat ttaaagaggc tttctcccta 960
tttgacaagg acggggatgg gacaataaca accaaggagc tggggacggt gatgcggtct 1020
ctggggcaga accccacaga agcagagctg caggacatga tcaatgaagt agatgccgac 1080
ggtgacggca caatcgactt ccctgagttc ctgacaatga tggcaagaaa agggagctac 1140
agggacacgg aagaagaaat tagagaagcg ttcggtgtgt ttgataagga tggcaatggc 1200
tacatcagtg cagcagagct tcgccacgtg atgacaaacc ttggagagaa gttaacagat 1260
gaagaggttg atgaaatgat cagggaagca gacatcgatg gggatggtca ggtaaactac 1320
gaagagtttg tacaaatgat gacagcgaag tga 1353

<210> SEQ ID NO 39
<211> LENGTH: 1353
<212> TYPE: DNA
<213> ORGANISM: Artificial Sequence
<220> FEATURE:
<223> OTHER INFORMATION: GCaMP6s

<400> SEQUENCE: 39
atgggttctc atcatcatca tcatcatggt atggctagca tgactggtgg acagcaaatg 60
ggtcgggatc tgtacgacga tgacgataag gatctcgcca ccatggtcga ctcatcacgt 120
cgtaagtgga ataagacagg tcacgcagtc agagctatag gtcggctgag ctcactcgag 180
aacgtctata tcaaggccga caagcagaag aacggcatca aggcgaactt ccacatccgc 240
cacaacatcg aggacggcgg cgtgcagctc gcctaccact accagcagaa cacccccatc 300
ggcgacggcc ccgtgctgct gcccgacaac cactacctga gcgtgcagtc caaactttcg 360
aaagacccca acgagaagcg cgatcacatg gtcctgctgg agttcgtgac cgccgccggg 420
atcactctcg gcatggacga gctgtacaag ggcggtaccg gagggagcat ggtgagcaag 480
ggcgaggagc tgttcaccgg ggtggtgccc atcctggtcg agctggacgg cgacgtaaac 540

```
ggccacaagt tcagcgtgtc cggcgagggt gagggcgatg ccacctacgg caagctgacc    600

ctgaagttca tctgcaccac cggcaagctg cccgtgccct ggcccaccct cgtgaccacc    660

ctgacctacg gcgtgcagtg cttcagccgc taccccgacc acatgaagca gcacgacttc    720

ttcaagtccg ccatgcccga aggctacatc caggagcgca ccatcttctt caaggacgac    780

ggcaactaca agacccgcgc cgaggtgaag ttcgagggcg acaccctggt gaaccgcatc    840

gagctgaagg gcatcgactt caaggaggac ggcaacatcc tggggcacaa gctggagtac    900

aacctgccgg accaactgac tgaagagcag atcgcagaat ttaaagaggc tttctcccta    960

tttgacaagg acggggatgg gacaataaca accaaggagc tggggacggt gatgcggtct   1020

ctggggcaga accccacaga agcagagctg caggacatga tcaatgaagt agatgccgac   1080

ggtgacggca caatcgactt ccctgagttc ctgacaatga tggcaagaaa aatgaaatac   1140

agggacacgg aagaagaaat tagagaagcg ttcggtgtgt ttgataagga tggcaatggc   1200

tacatcagtg cagcagagct tcgccacgtg atgacaaacc ttggagagaa gttaacagat   1260

gaagaggttg atgaaatgat cagggaagca gacatcgatg gggatggtca ggtaaactac   1320

gaagagtttg tacaaatgat gacagcgaag tga                                1353
```

```
<210> SEQ ID NO 40
<211> LENGTH: 1353
<212> TYPE: DNA
<213> ORGANISM: Artificial Sequence
<220> FEATURE:
<223> OTHER INFORMATION: GCaMP6f

<400> SEQUENCE: 40

atgggttctc atcatcatca tcatcatggt atggctagca tgactggtgg acagcaaatg     60

ggtcgggatc tgtacgacga tgacgataag gatctcgcca ccatggtcga ctcatcacgt    120

cgtaagtgga ataagacagg tcacgcagtc agagctatag gtcggctgag ctcactcgag    180

aacgtctata tcaaggccga caagcagaag aacggcatca aggcgaactt caagatccgc    240

cacaacatcg aggacggcgg cgtgcagctc gcctaccact accagcagaa cacccccatc    300

ggcgacggcc ccgtgctgct gcccgacaac cactacctga gcgtgcagtc caaactttcg    360

aaagacccca acgagaagcg cgatcacatg gtcctgctgg agttcgtgac cgccgccggg    420

atcactctcg gcatggacga gctgtacaag ggcggtaccg gagggagcat ggtgagcaag    480

ggcgaggagc tgttcaccgg ggtggtgccc atcctggtcg agctggacgg cgacgtaaac    540

ggccacaagt tcagcgtgtc cggcgagggt gagggcgatg ccacctacgg caagctgacc    600

ctgaagttca tctgcaccac cggcaagctg cccgtgccct ggcccaccct cgtgaccacc    660

ctgacctacg gcgtgcagtg cttcagccgc taccccgacc acatgaagca gcacgacttc    720

ttcaagtccg ccatgcccga aggctacatc caggagcgca ccatcttctt caaggacgac    780

ggcaactaca agacccgcgc cgaggtgaag ttcgagggcg acaccctggt gaaccgcatc    840

gagctgaagg gcatcgactt caaggaggac ggcaacatcc tggggcacaa gctggagtac    900

aacctgccgg accaactgac tgaagagcag atcgcagaat ttaaagagga attctcccta    960

tttgacaagg acggggatgg gacaataaca accaaggagc tggggacggt gatgcggtct   1020

ctggggcaga accccacaga agcagagctg caggacatga tcaatgaagt agatgccgac   1080

ggtgacggca caatcgactt ccctgagttc ctgacaatga tggcaagaaa aatgaaatac   1140

agggacacgg aagaagaaat tagagaagcg ttcggtgtgt ttgataagga tggcaatggc   1200

tacatcagtg cagcagagct tcgccacgtg atgacaaacc ttggagagaa gttaacagat   1260
```

```
gaagaggttg atgaaatgat cagggaagca gacatcgatg gggatggtca ggtaaactac   1320

gaagagtttg tacaaatgat gacagcgaag tga                                1353


<210> SEQ ID NO 41
<211> LENGTH: 2901
<212> TYPE: DNA
<213> ORGANISM: Artificial Sequence
<220> FEATURE:
<223> OTHER INFORMATION: AiP1211

<400> SEQUENCE: 41

gcggccgcac gcgtcctttt agaaacactc cctttaccat cttcaaacat gtttttagct     60

gagaactctc ttccaacccc tgtttcttaa ctctgagtgc cgtatcactt catattctgt    120

gtcaggggaa aagaaatcag cacctcccac aacgtcaact gtgtccttta gagtaagcat    180

tccaaagtct atattctgag tctaatctct cttggaaagg tcagcctttt cttccaaata    240

ccaagtggac atctttatgc acaggccttc aaggatattc aagtcagtgt gtcctacgga    300

gaaaactcct tttaaaaccc gaatcctgtg gtttccccaa gatgattatt gggtggtcac    360

tgcagcctta aggagctcgg gctgggcata aaagtcaggg cagagccatc tattgcttac    420

atttgcttct ggcgtggcca ccatggctcc taagaagaag aggaaggtga tgagccagtt    480

cgacatcctg tgcaagaccc cccccaaggt gctggtgcgg cagttcgtgg agagattcga    540

gaggcccagc ggcgagaaga tcgccagctg tgccgccgag ctgacctacc tgtgctggat    600

gatcacccac aacggcaccg ccatcaagag ggccaccttc atgagctaca acaccatcat    660

cagcaacagc ctgagcttcg acatcgtgaa caagagcctg cagttcaagt acaagaccca    720

gaaggccacc atcctggagg ccagcctgaa gaagctgatc cccgcctggg agttcaccat    780

catcccttac aacggccaga agcaccagag cgacatcacc gacatcgtgt ccagcctgca    840

gctgcagttc gagagcagcg aggaggccga caagggcaac agccacagca agaagatgct    900

gaaggccctg ctgtccgagg gcgagagcat ctgggagatc accgagaaga tcctgaacag    960

cttcgagtac accagcaggt tcaccaagac caagaccctg taccagttcc tgttcctggc   1020

cacattcatc aactgcggca ggttcagcga catcaagaac gtggaccccca agagcttcaa   1080

gctggtgcag aacaagtacc tgggcgtgat cattcagtgc ctggtgaccg agaccaagac   1140

aagcgtgtcc aggcacatct actttttcag cgccagaggc aggatcgacc ccctggtgta   1200

cctggacgag ttcctgagga acagcgagcc cgtgctgaag agagtgaaca ggaccggcaa   1260

cagcagcagc aacaagcagg agtaccagct gctgaaggac aacctggtgc gcagctacaa   1320

caaggccctg aagaagaacg ccccctaccc catcttcgct atcaagaacg gccctaagag   1380

ccacatcggc aggcacctga tgaccagctt tctgagcatg aagggcctga ccgagctgac   1440

aaacgtggtg ggcaactgga gcgacaagag ggcctccgcc gtggccagga ccacctacac   1500

ccaccagatc accgccatcc ccgaccacta cttcgccctg gtgtccaggt actacgccta   1560

cgaccccatc agcaaggaga tgatcgccct gaaggacgag accaacccca tcgaggagtg   1620

gcagcacatc gagcagctga agggcagcgc cgagggcagc atcagatacc ccgcctggaa   1680

cggcatcatc agccaggagg tgctggacta cctgagcagc tacatcaaca ggcggatctg   1740

agaattcgat atcaagctta tcgataatca acctctggat tacaaaattt gtgaaagatt   1800

gactggtatt cttaactatg ttgctccttt tacgctatgt ggatacgctg ctttaatgcc   1860

tttgtatcat gctattgctt cccgtatggc tttcattttc tcctccttgt ataaatcctg   1920
```

```
gttgctgtct ctttatgagg agttgtggcc cgttgtcagg caacgtggcg tggtgtgcac   1980
tgtgtttgct gacgcaaccc ccactggttg gggcattgcc accacctgtc agctcctttc   2040
cgggactttc gctttccccc tccctattgc cacggcggaa ctcatcgccg cctgccttgc   2100
ccgctgctgg acaggggctc ggctgttggg cactgacaat tccgtggtgt tgtcggggaa   2160
atcatcgtcc tttccttggc tgctcgccta tgttgccacc tggattctgc gcgggacgtc   2220
cttctgctac gtcccttcgg ccctcaatcc agcggacctt ccttcccgcg gcctgctgcc   2280
ggctctgcgg cctcttccgc gtcttcgcct tcgccctcag acgagtcgga tctccctttg   2340
ggccgcctcc ccgcatcgat accgagcgct gctcgagaga tctacgggtg gcatccctgt   2400
gacccctccc cagtgcctct cctggccctg gaagttgcca ctccagtgcc caccagcctt   2460
gtcctaataa aattaagttg catcattttg tctgactagg tgtccttcta taatattatg   2520
gggtggaggg gggtggtatg gagcaagggg caagttggga agacaacctg tagggcctgc   2580
ggggtctatt gggaaccaag ctggagtgca gtggcacaat cttggctcac tgcaatctcc   2640
gcctcctggg ttcaagcgat tctcctgcct cagcctcccg agttgttggg attccaggca   2700
tgcatgacca ggctcagcta atttttgttt ttttggtaga gacggggttt caccatattg   2760
gccaggctgg tctccaactc ctaatctcag gtgatctacc caccttggcc tcccaaattg   2820
ctgggattac aggcgtgaac cactgctccc ttccctgtcc ttctgatttt gtaggtaacc   2880
acgtgcggac cgagcggccg c                                             2901
```

```
<210> SEQ ID NO 42
<211> LENGTH: 3046
<212> TYPE: DNA
<213> ORGANISM: Artificial Sequence
<220> FEATURE:
<223> OTHER INFORMATION: AiP1212

<400> SEQUENCE: 42
```

```
gcggccgcac gcgtatatgg atgtcttacc tgcatgaata cttgtgtacc acatgtatgc     60
ctttctccat ggaggccaga agagggtatc agattccctg gaactgaagt tacagatagt    120
tgtgagctgc catgtgggta ctggaaatac atgtgtctaa ttttaaggac cagctcctac    180
tgaggacata aatgttatgt ttcttaaaag tctataccat aagaatcttc ttcagatctt    240
ggtgtgaaga ttcttacccc agattggtta cagaagcggt accaggtggg tggatcccat    300
caaaagcttt agtgagaaat caccctttc cttcacagca gcccagctga ctggtgaact    360
ttgccgaact gtaaaatatc aaacctttgg gaagctttct gcaacacgag aagttttaat    420
ccttcaatat taaaaagaaa aataagaaaa aaaaactgtg gagaagtcac gaacaggaga    480
aacaaaaagg aattgtgcac agggtcagtc gcttaaggag ctcgggctgg gcataaaagt    540
cagggcagag ccatctattg cttacatttg cttctggcgt ggccaccatg gctcctaaga    600
agaagaggaa ggtgatgagc cagttcgaca tcctgtgcaa gacccccccc aaggtgctgg    660
tgcggcagtt cgtggagaga ttcgagaggc ccagcggcga gaagatcgcc agctgtgccg    720
ccgagctgac ctacctgtgc tggatgatca cccacaacgg caccgccatc aagagggcca    780
ccttcatgag ctacaacacc atcatcagca acagcctgag cttcgacatc gtgaacaaga    840
gcctgcagtt caagtacaag acccagaagg ccaccatcct ggaggccagc ctgaagaagc    900
tgatccccgc ctgggagttc accatcatcc cttacaacgg ccagaagcac cagagcgaca    960
tcaccgacat cgtgtccagc ctgcagctgc agttcgagag cagcgaggag gccgacaagg   1020
gcaacagcca cagcaagaag atgctgaagg ccctgctgtc cgagggcgag agcatctggg   1080
```

```
agatcaccga gaagatcctg aacagcttcg agtacaccag caggttcacc aagaccaaga   1140
ccctgtacca gttcctgttc ctggccacat tcatcaactg cggcaggttc agcgacatca   1200
agaacgtgga ccccaagagc ttcaagctgg tgcagaacaa gtacctgggc gtgatcattc   1260
agtgcctggt gaccgagacc aagacaagcg tgtccaggca catctacttt ttcagcgcca   1320
gaggcaggat cgaccccctg gtgtacctgg acgagttcct gaggaacagc gagcccgtgc   1380
tgaagagagt gaacaggacc ggcaacagca gcagcaacaa gcaggagtac cagctgctga   1440
aggacaacct ggtgcgcagc tacaacaagg ccctgaagaa gaacgccccc taccccatct   1500
tcgctatcaa gaacggccct aagagccaca tcggcaggca cctgatgacc agctttctga   1560
gcatgaaggg cctgaccgag ctgacaaacg tggtgggcaa ctggagcgac aagagggcct   1620
ccgccgtggc caggaccacc tacacccacc agatcaccgc catccccgac cactacttcg   1680
ccctggtgtc caggtactac gcctacgacc ccatcagcaa ggagatgatc gccctgaagg   1740
acgagaccaa ccccatcgag gagtggcagc acatcgagca gctgaagggc agcgccgagg   1800
gcagcatcag ataccccgcc tggaacggca tcatcagcca ggaggtgctg gactacctga   1860
gcagctacat caacaggcgg atctgagaat tcgatatcaa gcttatcgat aatcaacctc   1920
tggattacaa aatttgtgaa agattgactg gtattcttaa ctatgttgct ccttttacgc   1980
tatgtggata cgctgcttta atgcctttgt atcatgctat tgcttcccgt atggctttca   2040
ttttctcctc cttgtataaa tcctggttgc tgtctcttta tgaggagttg tggcccgttg   2100
tcaggcaacg tggcgtggtg tgcactgtgt ttgctgacgc aacccccact ggttggggca   2160
ttgccaccac ctgtcagctc ctttccggga ctttcgcttt ccccctccct attgccacgg   2220
cggaactcat cgccgcctgc cttgcccgct gctggacagg ggctcggctg ttgggcactg   2280
acaattccgt ggtgttgtcg gggaaatcat cgtcctttcc ttggctgctc gcctatgttg   2340
ccacctggat tctgcgcggg acgtccttct gctacgtccc ttcggccctc aatccagcgg   2400
accttccttc ccgcggcctg ctgccggctc tgcggcctct tccgcgtctt cgccttcgcc   2460
ctcagacgag tcggatctcc ctttgggccg cctccccgca tcgataccga gcgctgctcg   2520
agagatctac gggtggcatc cctgtgaccc ctccccagtg cctctcctgg ccctggaagt   2580
tgccactcca gtgcccacca gccttgtcct aataaaatta agttgcatca ttttgtctga   2640
ctaggtgtcc ttctataata ttatggggtg gaggggggtg gtatggagca aggggcaagt   2700
tgggaagaca acctgtaggg cctgcggggt ctattgggaa ccaagctgga gtgcagtggc   2760
acaatcttgg ctcactgcaa tctccgcctc ctgggttcaa gcgattctcc tgcctcagcc   2820
tcccgagttg ttgggattcc aggcatgcat gaccaggctc agctaatttt tgttttttttg   2880
gtagagacgg ggtttcacca tattggccag gctggtctcc aactcctaat ctcaggtgat   2940
ctacccacct tggcctccca aattgctggg attacaggcg tgaaccactg ctcccttccc   3000
tgtccttctg attttgtagg taaccacgtg cggaccgagc ggccgc                  3046
```

<210> SEQ ID NO 43
<211> LENGTH: 2988
<212> TYPE: DNA
<213> ORGANISM: Artificial Sequence
<220> FEATURE:
<223> OTHER INFORMATION: AiP1218

<400> SEQUENCE: 43

```
gcggccgcac gcgtcccagg atctattgac atccaacatc ggatggagaa actgaagttc     60
```

```
acatcatagc tcatctctca tagtatccta tacggtgttt ctctttcttg gagaaacaac    120
cccaccccac ccgccttgat gttaatgcca ggacacacat gttttcttga ccccacttct    180
ctgatcactc atcgctctgc ttcctcagcc tgttgttggt accagttctc agatagttgc    240
agtctccaag ttcagttcct accgatttat gccatgctgt ctttttgag aaataccact     300
caccatgtga gtgaatctgt gaatgcctcc taaatgcccg ttgccaattt gagaataaaa    360
gttcatgtga ttatgttcaa ggcatttcag attaaatatg accaaaatca ctccgtggtg    420
ccttcctgta cgcctcaccg tgaatccagt ttgcttaagg agctcgggct gggcataaaa    480
gtcagggcag agccatctat tgcttacatt tgcttctggc gtggccacca tggctcctaa    540
gaagaagagg aaggtgatga gccagttcga catcctgtgc aagacccccc ccaaggtgct    600
ggtgcggcag ttcgtggaga gattcgagag gcccagcggc gagaagatcg ccagctgtgc    660
cgccgagctg acctacctgt gctggatgat cacccacaac ggcaccgcca tcaagagggc    720
caccttcatg agctacaaca ccatcatcag caacagcctg agcttcgaca tcgtgaacaa    780
gagcctgcag ttcaagtaca agacccagaa ggccaccatc ctggaggcca gcctgaagaa    840
gctgatcccc gcctgggagt tcaccatcat cccttacaac ggccagaagc accagagcga    900
catcaccgac atcgtgtcca gcctgcagct gcagttcgag agcagcgagg aggccgacaa    960
gggcaacagc cacagcaaga agatgctgaa ggccctgctg tccgagggcg agagcatctg   1020
ggagatcacc gagaagatcc tgaacagctt cgagtacacc agcaggttca ccaagaccaa   1080
gaccctgtac cagttcctgt tcctggccac attcatcaac tgcggcaggt tcagcgacat   1140
caagaacgtg gaccccaaga gcttcaagct ggtgcagaac aagtacctgg gcgtgatcat   1200
tcagtgcctg gtgaccgaga ccaagacaag cgtgtccagg cacatctact tttcagcgc    1260
cagaggcagg atcgaccccc tggtgtacct ggacgagttc ctgaggaaca gcgagcccgt   1320
gctgaagaga gtgaacagga ccggcaacag cagcagcaac aagcaggagt accagctgct   1380
gaaggacaac ctggtgcgca gctacaacaa ggccctgaag aagaacgccc cctaccccat   1440
cttcgctatc aagaacggcc ctaagagcca catcggcagg cacctgatga ccagctttct   1500
gagcatgaag ggcctgaccg agctgacaaa cgtggtgggc aactggagcg acaagagggc   1560
ctccgccgtg gccaggacca cctacaccca ccagatcacc gccatccccg accactactt   1620
cgccctggtg tccaggtact acgcctacga ccccatcagc aaggagatga tcgccctgaa   1680
ggacgagacc aaccccatcg aggagtggca gcacatcgag cagctgaagg gcagcgccga   1740
gggcagcatc agataccccg cctggaacgg catcatcagc caggaggtgc tggactacct   1800
gagcagctac atcaacaggc ggatctgaga attcgatatc aagcttatcg ataatcaacc   1860
tctggattac aaaatttgtg aaagattgac tggtattctt aactatgttg ctccttttac   1920
gctatgtgga tacgctgctt taatgccttt gtatcatgct attgcttccc gtatggcttt   1980
cattttctcc tccttgtata aatcctggtt gctgtctctt tatgaggagt tgtggcccgt   2040
tgtcaggcaa cgtggcgtgg tgtgcactgt gtttgctgac gcaaccccca ctggttgggg   2100
cattgccacc acctgtcagc tcctttccgg gactttcgct ttccccctcc ctattgccac   2160
ggcggaactc atcgccgcct gccttgcccg ctgctggaca ggggctcggc tgttgggcac   2220
tgacaattcc gtggtgttgt cggggaaatc atcgtccttt ccttggctgc tcgcctatgt   2280
tgccacctgg attctgcgcg ggacgtcctt ctgctacgtc ccttcggccc tcaatccagc   2340
ggaccttcct tcccgcggcc tgctgccggc tctgcggcct cttccgcgtc ttcgccttcg   2400
ccctcagacg agtcggatct ccctttgggc cgcctccccg catcgatacc gagcgctgct   2460
```

```
cgagagatct acgggtggca tccctgtgac ccctccccag tgcctctcct ggccctggaa   2520

gttgccactc cagtgcccac cagccttgtc ctaataaaat taagttgcat cattttgtct   2580

gactaggtgt ccttctataa tattatgggg tggagggggg tggtatggag caaggggcaa   2640

gttgggaaga caacctgtag ggcctgcggg gtctattggg aaccaagctg gagtgcagtg   2700

gcacaatctt ggctcactgc aatctccgcc tcctgggttc aagcgattct cctgcctcag   2760

cctcccgagt tgttgggatt ccaggcatgc atgaccaggc tcagctaatt tttgtttttt   2820

tggtagagac ggggtttcac catattggcc aggctggtct ccaactccta atctcaggtg   2880

atctacccac cttggcctcc caaattgctg ggattacagg cgtgaaccac tgctcccttc   2940

cctgtccttc tgattttgta ggtaaccacg tgcggaccga gcggccgc                2988
```

<210> SEQ ID NO 44
<211> LENGTH: 1951
<212> TYPE: DNA
<213> ORGANISM: Artificial Sequence
<220> FEATURE:
<223> OTHER INFORMATION: CN2603

<400> SEQUENCE: 44

```
gcggccgcac gcgtatggga aagcagcacg tgttcttaac tgctagactc ctatttacca     60

tgacagtaat atcattatta tttttaaatc attttataat ttcaggagaa agcaaatgat    120

tgctaataac ggtctccctc ttcagtacat atgcactaca cgcgcatgtg tcctttaaag    180

ataaatttga gttggaagca tcggtatgag ctggtgagtt ttaagaagtt ccagaaaaaa    240

aaaagaagtt ccagtatttc ctagatttgt cctctgcaaa gtcctaggca taaaggcagc    300

gcagtttgtg gcctttaaat accacttccc acgaaagcaa ccaaggctcc ttggagacgt    360

gagcgatttg atgtctataa atatgagcac acagtgctgt gcttccccac tgaggtcaga    420

aagaccacta ccctgaatcc aaaccacctt catggcttag cagatgaggc cagagctgga    480

caagagcaat taaagggaac aattacatta catgttggtg tttgatttat ctgcagattt    540

ttttaaccag taaagtttat tttgaaatgc aattaatttg taagatcaga ccgcccattg    600

gttagttgag ctcgggctgg gcataaaagt cagggcagag ccatctattg cttacatttg    660

cttctgggat ccagatcttt cgaagctagc gctaccggtc gccaccatgg tgagcaaggg    720

cgaggagctg ttcaccgggg tggtgcccat cctggtcgag ctggacggcg acgtaaacgg    780

ccacaagttc agcgtgtccg gcgagggcga gggcgatgcc acctacggca agctgaccct    840

gaagctgatc tgcaccaccg gcaagctgcc cgtgccctgg cccaccctcg tgaccaccct    900

gggctacggc gtgcagtgct tcgcccgcta ccccgaccac atgaagcagc acgacttctt    960

caagtccgcc atgcccgaag gctacgtcca ggagcgcacc atcttcttca aggacgacgg   1020

caactacaag acccgcgccg aggtgaagtt cgagggcgac accctggtga accgcatcga   1080

gctgaagggc atcgacttca aggaggacgg caacatcctg gggcacaagc tggagtacaa   1140

ctacaacagc cacaacgtct atatcaccgc cgacaagcag aagaacggca tcaaggccaa   1200

cttcaagatc cgccacaaca tcgaggacgg cggcgtgcag ctcgccgacc actaccagca   1260

gaacaccccc atcggcgacg gccccgtgct gctgcccgac aaccactacc tgagctacca   1320

gtccaagctg agcaaagacc ccaacgagaa gcgcgatcac atggtcctgc tggagttcgt   1380

gaccgccgcc gggatcactc tcggcatgga cgagctgtac aagtaagtcg acggcgcgcc   1440

gcggccgcga attcgatatc ataatcaacc tctggattac aaaatttgtg aaagattgac   1500
```

```
tggtattctt aactatgttg ctccttttac gctatgtgga tacgctgctt taatgccttt   1560

gtatcatgct attgcttccc gtatggcttt cattttctcc tccttgtata aatcctggtt   1620

agttcttgcc acggcggaac tcatcgccgc ctgccttgcc cgctgctgga caggggctcg   1680

gctgttgggc actgacaatt ccgtggctcg agagatcttc gactgtgcct tctagttgcc   1740

agccatctgt tgtttgcccc tcccccgtgc cttccttgac cctggaaggt gccactccca   1800

ctgtcctttc ctaataaaat gaggaaattg catcgcattg tctgagtagg tgtcattcta   1860

ttctgggggg tggggtgggg caggacagca agggggagga ttgggaagac aatagcaggc   1920

atgagatctc acgtgcggac cgagcggccg c                                  1951
```

<210> SEQ ID NO 45
<211> LENGTH: 1985
<212> TYPE: DNA
<213> ORGANISM: Artificial Sequence
<220> FEATURE:
<223> OTHER INFORMATION: CN2606
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t

<400> SEQUENCE: 45

```
gcggccgcac gcgttccaga tgcttgtctt ctctctctct ctctctctct ctctctctct     60

ctctctctgt atgtgtgtgt gtgtgtgtgt gtgtatgtgt gtcttccccc cntntttttc    120

accccacccc gacatctaca acaaaaattt taaccatatt atggagtggt catattggca    180

gtttttttac tgcagccctt cacatgcact gacattctag acagcaagtg ttctatgatt    240

ttcaacagga cacttggatc tagccaactc agttttcaag cctgccccccg agttgtagat    300

cctgtcttca cattctaaac taatctcaca ccactttgtg ccaactccac tctggtaaag    360

accatgcact cgagttagtg caagacattt tgttctggcc tcggggtgtg ctgccgcctc    420

gtcaggatgg gaggtggagg cgagtccagt gaaggtcact ggcatcacaa gagtgaggga    480

cagatatgtt cccgagcctt cagattcaag tcctgcactt gcaaaaaaga cttctgcctt    540

ttctatttga cccaactagc tattgcatta ttgagccaga cagtggctca aattaaatgt    600

cacaggagca caccctaaca aaaagaagag gccagcatgc tgagctcggg ctgggcataa    660

aagtcagggc agagccatct attgcttaca tttgcttctg ggatccagat ctttcgaagc    720

tagcgctacc ggtcgccacc atggtgagca agggcgagga gctgttcacc ggggtggtgc    780

ccatcctggt cgagctggac ggcgacgtaa acggccacaa gttcagcgtg tccggcgagg    840

gcgagggcga tgccacctac ggcaagctga ccctgaagct gatctgcacc accggcaagc    900

tgcccgtgcc ctggcccacc ctcgtgacca ccctgggcta cggcgtgcag tgcttcgccc    960

gctaccccga ccacatgaag cagcacgact tcttcaagtc cgccatgccc gaaggctacg   1020

tccaggagcg caccatcttc ttcaaggacg acggcaacta caagacccgc gccgaggtga   1080

agttcgaggg cgacaccctg gtgaaccgca tcgagctgaa gggcatcgac ttcaaggagg   1140

acggcaacat cctggggcac aagctggagt acaactacaa cagccacaac gtctatatca   1200

ccgccgacaa gcagaagaac ggcatcaagg ccaacttcaa gatccgccac aacatcgagg   1260

acggcggcgt gcagctcgcc gaccactacc agcagaacac ccccatcggc gacggccccg   1320

tgctgctgcc cgacaaccac tacctgagct accagtccaa gctgagcaaa gaccccaacg   1380
```

```
agaagcgcga tcacatggtc ctgctggagt tcgtgaccgc cgccgggatc actctcggca   1440

tggacgagct gtacaagtaa gtcgacggcg cgccgcggcc gcgaattcga tatcataatc   1500

aacctctgga ttacaaaatt tgtgaaagat tgactggtat tcttaactat gttgctcctt   1560

ttacgctatg tggatacgct gctttaatgc ctttgtatca tgctattgct tcccgtatgg   1620

ctttcatttt ctcctccttg tataaatcct ggttagttct tgccacggcg gaactcatcg   1680

ccgcctgcct tgcccgctgc tggacagggg ctcggctgtt gggcactgac aattccgtgg   1740

ctcgagagat cttcgactgt gccttctagt tgccagccat ctgttgtttg cccctccccc   1800

gtgccttcct tgaccctgga aggtgccact cccactgtcc tttcctaata aaatgaggaa   1860

attgcatcgc attgtctgag taggtgtcat tctattctgg ggggtggggt ggggcaggac   1920

agcaaggggg aggattggga agacaatagc aggcatgaga tctcacgtgc ggaccgagcg   1980

gccgc                                                               1985


<210> SEQ ID NO 46
<211> LENGTH: 2131
<212> TYPE: DNA
<213> ORGANISM: Artificial Sequence
<220> FEATURE:
<223> OTHER INFORMATION: CN2612
<220> FEATURE:
<221> NAME/KEY: misc_feature
<222> LOCATION: (186)..(186)
<223> OTHER INFORMATION: n is a, c, g, or t

<400> SEQUENCE: 46

gcggccgcac gcgttagaga aatgtgctgt ggtttaactt ttggaataaa aatagtgaat     60

ttttaatgag caggtgggaa tgtccttggg ttctgagtta ggatggtgga gcaaggaaag    120

aaaaggtctc tcttcctttt ccctgtgtgc tgagtagaga caggattgcc cagaacacca    180

ggaacntagg ttgtactgac aaaagtggaa aacagccgca aaaccgctag ggaaagcagc    240

tgtccccttg cccagtctcc tgccccactc ctgcctctgc ctataagagt ttggcacagt    300

tggagatttg tatacacaaa tgcatgcgtg gaaatactgc gctctgatga cattcctcag    360

ggggcgacct ttgatgatga attttcttgc cctttttagg ggaggagaag aggaggcggg    420

tggtacttca caagactaaa tttactcaac ttttttgggt ctaaatttct ttaggaaaaa    480

aaatgtcaaa tgattgtaga tcccaaactg tctttgttgg catttgaatg gctctgtgag    540

tccagtgtgg ggagcaagtg aaaagaaaag ccacctctcc cctcgctggc gtggtattga    600

agctgaagcc ctggaccaca cagtgtcttg gggaccttca tgatttatat attgtatgtg    660

atcttttctt aaacattgtt aacctgtgcc ctttacagac aatgccgggt cagaaaatgt    720

caggggaact tcggactgct ttcataattg tgtaaagaaa attgttgtct tcagaatcca    780

gagcccagag ctcgggctgg gcataaaagt cagggcagag ccatctattg cttacatttg    840

cttctgggat ccagatcttt cgaagctagc gctaccggtc gccaccatgg tgagcaaggg    900

cgaggagctg ttcaccgggg tggtgcccat cctggtcgag ctggacggcg acgtaaacgg    960

ccacaagttc agcgtgtccg gcgagggcga gggcgatgcc acctacggca agctgaccct   1020

gaagctgatc tgcaccaccg gcaagctgcc cgtgccctgg cccaccctcg tgaccaccct   1080

gggctacggc gtgcagtgct tcgcccgcta ccccgaccac atgaagcagc acgacttctt   1140

caagtccgcc atgcccgaag gctacgtcca ggagcgcacc atcttcttca aggacgacgg   1200

caactacaag acccgcgccg aggtgaagtt cgagggcgac accctggtga accgcatcga   1260
```

```
gctgaagggc atcgacttca aggaggacgg caacatcctg gggcacaagc tggagtacaa   1320
ctacaacagc cacaacgtct atatcaccgc cgacaagcag aagaacggca tcaaggccaa   1380
cttcaagatc cgccacaaca tcgaggacgg cggcgtgcag ctcgccgacc actaccagca   1440
gaacaccccc atcggcgacg gccccgtgct gctgcccgac aaccactacc tgagctacca   1500
gtccaagctg agcaaagacc ccaacgagaa gcgcgatcac atggtcctgc tggagttcgt   1560
gaccgccgcc gggatcactc tcggcatgga cgagctgtac aagtaagtcg acggcgcgcc   1620
gcggccgcga attcgatatc ataatcaacc tctggattac aaaatttgtg aaagattgac   1680
tggtattctt aactatgttg ctccttttac gctatgtgga tacgctgctt taatgccttt   1740
gtatcatgct attgcttccc gtatggcttt cattttctcc tccttgtata aatcctggtt   1800
agttcttgcc acggcggaac tcatcgccgc ctgccttgcc cgctgctgga caggggctcg   1860
gctgttgggc actgacaatt ccgtggctcg agagatcttc gactgtgcct tctagttgcc   1920
agccatctgt tgtttgcccc tcccccgtgc cttccttgac cctggaaggt gccactccca   1980
ctgtcctttc ctaataaaat gaggaaattg catcgcattg tctgagtagg tgtcattcta   2040
ttctgggggg tggggtgggg caggacagca agggggagga ttgggaagac aatagcaggc   2100
atgagatctc acgtgcggac cgagcggccg c                                  2131
```

```
<210> SEQ ID NO 47
<211> LENGTH: 1664
<212> TYPE: DNA
<213> ORGANISM: Artificial Sequence
<220> FEATURE:
<223> OTHER INFORMATION: CN2261

<400> SEQUENCE: 47
```

```
gcggccgcac gcgtttcagg ccaatacctc agcgaaaatc aaatcagttg caaaatccat     60
acagtcttcc agtttctcag ctgtggaaac tttgtgtctc ttcttttcca ccaaaacagc    120
tatctcgtct ttcaagtcct tgctgaaaaa aaaaagtgtt aaatttttct caatttagac    180
ttccagcaaa acagattctg cttgttgaaa ggcattggtg ttcatgagta agtgagtttc    240
cattttattt cttcacaaat aagttacatg aagtacttat cttatggtac tagagttaac    300
tgggatttct aaacacaggt gagctcgggc tgggcataaa agtcagggca gagccatcta    360
ttgcttacat ttgcttctgg gatccagatc tttcgaagct agcgctaccg gtcgccacca    420
tggtgagcaa gggcgaggag ctgttcaccg gggtggtgcc catcctggtc gagctggacg    480
gcgacgtaaa cggccacaag ttcagcgtgt ccggcgaggg cgagggcgat gccacctacg    540
gcaagctgac cctgaagctg atctgcacca ccggcaagct gcccgtgccc tggcccaccc    600
tcgtgaccac cctgggctac ggcgtgcagt gcttcgcccg ctaccccgac cacatgaagc    660
agcacgactt cttcaagtcc gccatgcccg aaggctacgt ccaggagcgc accatcttct    720
tcaaggacga cggcaactac aagacccgcg ccgaggtgaa gttcgagggc gacaccctgg    780
tgaaccgcat cgagctgaag ggcatcgact tcaaggagga cggcaacatc ctggggcaca    840
agctggagta caactacaac agccacaacg tctatatcac cgccgacaag cagaagaacg    900
gcatcaaggc caacttcaag atccgccaca acatcgagga cggcggcgtg cagctcgccg    960
accactacca gcagaacacc cccatcggcg acggccccgt gctgctgccc gacaaccact   1020
acctgagcta ccagtccaag ctgagcaaag accccaacga gaagcgcgat cacatggtcc   1080
tgctggagtt cgtgaccgcc gccgggatca ctctcggcat ggacgagctg tacaagtaag   1140
tcgacggcgc gccgcggccg cgaattcgat atcataatca acctctggat tacaaaattt   1200
```

```
gtgaaagatt gactggtatt cttaactatg ttgctccttt tacgctatgt ggatacgctg   1260

ctttaatgcc tttgtatcat gctattgctt cccgtatggc tttcattttc tcctccttgt   1320

ataaatcctg gttagttctt gccacggcgg aactcatcgc cgcctgcctt gcccgctgct   1380

ggacaggggc tcggctgttg ggcactgaca attccgtggc tcgagagatc ttcgactgtg   1440

ccttctagtt gccagccatc tgttgtttgc ccctcccccg tgccttcctt gaccctggaa   1500

ggtgccactc ccactgtcct ttcctaataa aatgaggaaa ttgcatcgca ttgtctgagt   1560

aggtgtcatt ctattctggg gggtggggtg gggcaggaca gcaaggggga ggattgggaa   1620

gacaatagca ggcatgagat ctcacgtgcg gaccgagcgg ccgc                    1664
```

<210> SEQ ID NO 48
<211> LENGTH: 4
<212> TYPE: PRT
<213> ORGANISM: Artificial Sequence
<220> FEATURE:
<223> OTHER INFORMATION: synthetic construct

<400> SEQUENCE: 48

```
Ser Ala Gln Ala
1
```

<210> SEQ ID NO 49
<211> LENGTH: 11
<212> TYPE: PRT
<213> ORGANISM: Artificial Sequence
<220> FEATURE:
<223> OTHER INFORMATION: synthetic construct

<400> SEQUENCE: 49

```
Ser Asp Gly Thr Leu Ala Val Pro Phe Lys Ala
1               5                   10
```

<210> SEQ ID NO 50
<211> LENGTH: 7
<212> TYPE: PRT
<213> ORGANISM: Artificial Sequence
<220> FEATURE:
<223> OTHER INFORMATION: AAV-BR1

<400> SEQUENCE: 50

```
Asn Arg Gly Thr Glu Trp Asp
1               5
```

<210> SEQ ID NO 51
<211> LENGTH: 7
<212> TYPE: PRT
<213> ORGANISM: Artificial Sequence
<220> FEATURE:
<223> OTHER INFORMATION: AAV-PHP.S

<400> SEQUENCE: 51

```
Gln Ala Val Arg Thr Ser Leu
1               5
```

<210> SEQ ID NO 52
<211> LENGTH: 7
<212> TYPE: PRT
<213> ORGANISM: Artificial Sequence
<220> FEATURE:
<223> OTHER INFORMATION: AAV-PHP.B

<400> SEQUENCE: 52

```
Thr Leu Ala Val Pro Phe Lys
1               5


<210> SEQ ID NO 53
<211> LENGTH: 7
<212> TYPE: PRT
<213> ORGANISM: Artificial Sequence
<220> FEATURE:
<223> OTHER INFORMATION: AAV-PPS

<400> SEQUENCE: 53

Asp Ser Pro Ala His Pro Ser
1               5


<210> SEQ ID NO 54
<211> LENGTH: 229
<212> TYPE: DNA
<213> ORGANISM: Mus musculus

<400> SEQUENCE: 54

acagcaagtg ttctatgatt ttcaacagga cacttggatc tagccaactc agttttcaag     60

cctgcccccg agttgtagat cctgtcttca cattctaaac taatctcaca ccactttgtg    120

ccaactccac tctggtaaag accatgcact cgagttagtg caagacattt tgttctggcc    180

tcggggtgtg ctgccgcctc gtcaggatgg gaggtggagg cgagtccag                229


<210> SEQ ID NO 55
<211> LENGTH: 687
<212> TYPE: DNA
<213> ORGANISM: Artificial Sequence
<220> FEATURE:
<223> OTHER INFORMATION: 3xcore2_eHGT_774m

<400> SEQUENCE: 55

acagcaagtg ttctatgatt ttcaacagga cacttggatc tagccaactc agttttcaag     60

cctgcccccg agttgtagat cctgtcttca cattctaaac taatctcaca ccactttgtg    120

ccaactccac tctggtaaag accatgcact cgagttagtg caagacattt tgttctggcc    180

tcggggtgtg ctgccgcctc gtcaggatgg gaggtggagg cgagtccaga cagcaagtgt    240

tctatgattt tcaacaggac acttggatct agccaactca gttttcaagc ctgcccccga    300

gttgtagatc ctgtcttcac attctaaact aatctcacac cactttgtgc caactccact    360

ctggtaaaga ccatgcactc gagttagtgc aagacatttt gttctggcct cggggtgtgc    420

tgccgcctcg tcaggatggg aggtggaggc gagtccagac agcaagtgtt ctatgatttt    480

caacaggaca cttggatcta gccaactcag ttttcaagcc tgcccccgag ttgtagatcc    540

tgtcttcaca ttctaaacta atctcacacc actttgtgcc aactccactc tggtaaagac    600

catgcactcg agttagtgca agacattttg ttctggcctc ggggtgtgct gccgcctcgt    660

caggatggga ggtggaggcg agtccag                                        687


<210> SEQ ID NO 56
<211> LENGTH: 265
<212> TYPE: DNA
<213> ORGANISM: Mus musculus

<400> SEQUENCE: 56

ccccactcct gcctctgcct ataagagttt ggcacagttg gagatttgta tacacaaatg     60

catgcgtgga aatactgcgc tctgatgaca ttcctcaggg ggcgaccttt gatgatgaat    120

tttcttgccc tttttagggg aggagaagag gaggcgggtg gtacttcaca agactaaatt    180
```

tactcaactt ttttgggtct aaatttcttt aggaaaaaaa atgtcaaatg attgtagatc 240
ccaaactgtc tttgttggca tttga 265

<210> SEQ ID NO 57
<211> LENGTH: 795
<212> TYPE: DNA
<213> ORGANISM: Artificial Sequence
<220> FEATURE:
<223> OTHER INFORMATION: 3xcore2_eHGT_772m

<400> SEQUENCE: 57
ccccactcct gcctctgcct ataagagttt ggcacagttg gagatttgta tacacaaatg 60
catgcgtgga aatactgcgc tctgatgaca ttcctcaggg ggcgaccttt gatgatgaat 120
tttcttgccc tttttagggg aggagaagag gaggcgggtg gtacttcaca agactaaatt 180
tactcaactt ttttgggtct aaatttcttt aggaaaaaaa atgtcaaatg attgtagatc 240
ccaaactgtc tttgttggca tttgacccca ctcctgcctc tgcctataag agtttggcac 300
agttggagat ttgtatacac aaatgcatgc gtggaaatac tgcgctctga tgacattcct 360
cagggggcga cctttgatga tgaattttct tgcccttttt aggggaggag aagaggaggc 420
gggtggtact tcacaagact aaatttactc aacttttttg ggtctaaatt tctttaggaa 480
aaaaaatgtc aaatgattgt agatcccaaa ctgtctttgt tggcatttga ccccactcct 540
gcctctgcct ataagagttt ggcacagttg gagatttgta tacacaaatg catgcgtgga 600
aatactgcgc tctgatgaca ttcctcaggg ggcgaccttt gatgatgaat tttcttgccc 660
tttttagggg aggagaagag gaggcgggtg gtacttcaca agactaaatt tactcaactt 720
ttttgggtct aaatttcttt aggaaaaaaa atgtcaaatg attgtagatc ccaaactgtc 780
tttgttggca tttga 795

<210> SEQ ID NO 58
<211> LENGTH: 244
<212> TYPE: DNA
<213> ORGANISM: Mus musculus

<400> SEQUENCE: 58
aaaatcaaat cagttgcaaa atccatacag tcttccagtt tctcagctgt ggaaactttg 60
tgtctcttct tttccaccaa aacagctatc tcgtctttca agtccttgct gaaaaaaaaa 120
agtgttaaat ttttctcaat ttagacttcc agcaaaacag attctgcttg ttgaaaggca 180
ttggtgttca tgagtaagtg agtttccatt ttatttcttc acaaataagt tacatgaagt 240
actt 244

<210> SEQ ID NO 59
<211> LENGTH: 732
<212> TYPE: DNA
<213> ORGANISM: Artificial Sequence
<220> FEATURE:
<223> OTHER INFORMATION: 3xCore_eHGT486m

<400> SEQUENCE: 59
aaaatcaaat cagttgcaaa atccatacag tcttccagtt tctcagctgt ggaaactttg 60
tgtctcttct tttccaccaa aacagctatc tcgtctttca agtccttgct gaaaaaaaaa 120
agtgttaaat ttttctcaat ttagacttcc agcaaaacag attctgcttg ttgaaaggca 180
ttggtgttca tgagtaagtg agtttccatt ttatttcttc acaaataagt tacatgaagt 240

-continued

```
acttaaaatc aaatcagttg caaaatccat acagtcttcc agtttctcag ctgtggaaac    300

tttgtgtctc ttcttttcca ccaaaacagc tatctcgtct ttcaagtcct tgctgaaaaa    360

aaaaagtgtt aaatttttct caatttagac ttccagcaaa acagattctg cttgttgaaa    420

ggcattggtg ttcatgagta agtgagtttc cattttattt cttcacaaat aagttacatg    480

aagtacttaa aatcaaatca gttgcaaaat ccatacagtc ttccagtttc tcagctgtgg    540

aaactttgtg tctcttcttt tccaccaaaa cagctatctc gtctttcaag tccttgctga    600

aaaaaaaaag tgttaaattt ttctcaattt agacttccag caaaacagat tctgcttgtt    660

gaaaggcatt ggtgttcatg agtaagtgag tttccatttt atttcttcac aaataagtta    720

catgaagtac tt                                                         732


<210> SEQ ID NO 60
<211> LENGTH: 412
<212> TYPE: DNA
<213> ORGANISM: Mus musculus

<400> SEQUENCE: 60

actgactgag gctgctcaat gtaccatatt aaaaagggag ctgcggctaa gccagtttct     60

gcaggacaga gccacagact atgggatact tccaaggaga aggaaggagt ggcgaggtgg    120

cactgcgtca gctgaccgct agactgtgac tttatccagc tctgtgttag ctgagtgatg    180

acagtaatgc cgtatctaca cacccaccgc ctactgggaa cctccacatg agtacataac    240

atagcatctg aggccagcag tgcgcagaac acatctgctc atctacagtg ccttcaaacg    300

ggagggaagt accagtcctc tctcagtgag aacaccatcc gtcctgggtg agagctttag    360

gcattgccat ggctccctgt cactcggccc tgacccacac attcacagcc at            412


<210> SEQ ID NO 61
<211> LENGTH: 547
<212> TYPE: DNA
<213> ORGANISM: Mus musculus

<400> SEQUENCE: 61

gagttaacat ttcaaataaa ataggtgtgt gtgtgtgtgt gtgtgtgtgt gtgtgtgtgt     60

gtgtgtgtgt gtgtgtgttt tagaaaaaga tcaattatgg gttgaatctg ttgtcacccc    120

acttgcatgt agctctattt cttagtcata ttttattatt ttatgcccaa aggcatggca    180

ctggaagaca agtttcaatt tttctctttt gatgtttcat tcttatgaag tggaaggttg    240

aaagtttgaa atccatatga ctcaggaatt gaatttcagc tcttctaaat acagactgtg    300

ttaaagggca acacttttat atatatatat tcacagctaa ggcagcattt acttcacata    360

gtagttaaag aagttaagaa ttaagttagt cacatgtaac agaattctcc catttcatag    420

aaactcaaat ttttgtttcc tttttccttt ccttctctca ttctttctcc acagcttaca    480

agaagttaga atgtatactt tcatataata gatccccctc ctcccactaa aagagatttg    540

agagatg                                                               547


<210> SEQ ID NO 62
<211> LENGTH: 535
<212> TYPE: DNA
<213> ORGANISM: Mus musculus

<400> SEQUENCE: 62

tcagaggcca gtgtgtattt agggtagggc agtacattaa agttctggtt tgtgtgctgt     60

caccctatcc tagaaactgg tttgagagtt ttagttcaca tgcaaaatga aggtcaaagt    120
```

caataccaag gagtctaaaa tcaacgtgaa gtgatacaga gatgtgcaca gtttgtttgt 180
tacgaacatc actgcctcct acagaatgaa cttatcatca tgtgtcacaa tcatcccatg 240
cattttccag ctacttccag tgagctccaa atctttacac attttgaggt tgaagtaaaa 300
gagcaatgtg cacagtgaga tagtcacagt ttctttaccc agtcttgggt gattcagatt 360
cagtcaggcc aacagggagg actttcctgc caggaggggg gcccgagcaa gaacaggagc 420
ttagacccta tgatgcttag aaagaaccca ggaaactgcc tatgctgtct gttgattatg 480
ccgtgattgc tgcaggaaat gcagtagttt atgaaacagt agaagctaag catgt 535

<210> SEQ ID NO 63
<211> LENGTH: 800
<212> TYPE: DNA
<213> ORGANISM: Mus musculus

<400> SEQUENCE: 63
agagccaacg aactcgaaga aaacatacgt aattaaagag aaactgctct tcaacatagg 60
agagatggaa ggcatcagca aaatatacac atgaaatgaa tggtcaagtg gaaggtttaa 120
gatttgctct atacagattg agacgccagt ttaaaaataa catggggaag ggaatgctag 180
aaatggtgta atcagtaaga aggacaatct aagggaatct aaggcttgaa aggaaacaga 240
aaaccgggtg tggtggtaaa tggattgtga cttagaagct ggcctgagct atatacagag 300
accctgtcaa gaaaagagag atgggagtag taggagagga aagtgtgaag ggaagggaaa 360
agaaagggag ggggaaagaa gcaaccaaac aagcaatctt gcagtggctt ctgccagcat 420
gctggcaaac cctgcagtga tattttcaca tctatgtaaa aacccatttt agcacctcca 480
gaatgaactt tacaagaatt gagaaagtca agtgagagag caccaaagaa ggaaggaaag 540
aaaaaagcaa gaacacttgc cagaaagata ggaaaccaag aaccagaaaa ataggaaaca 600
aaactaagga aagctgcaga gcagtattca tggcaaacac agaaagagaa attctcaaaa 660
caaggctagc aacccaaaca caaaagcaca gaaaagagat gtttcatcac aagtatgatg 720
tatctcaagt atgctcaaat gactgaagat acacaagcca gccaaggtga tacgctacca 780
catcaacagc acaacaggca 800

<210> SEQ ID NO 64
<211> LENGTH: 379
<212> TYPE: DNA
<213> ORGANISM: Mus musculus

<400> SEQUENCE: 64
gtgtgtgtgt gtgtgtgtgt gtgtgtgtgt ctctgtgtgt gtgtgtgtgt gtgtgtgtgt 60
gtgtatgtgt gtgtatgtga aattatcagg cctcagtttc ctcctctaca aaatggaaat 120
gcttacaaat gtcttgccat gcttagcata cacaagttgc tttgctaaga tgctgaattt 180
agtaaaggtc agttactatt ctaaccgatg gtagacagag actccaacag agctcttaga 240
aagcctgcat aacagtaagt ctaagcaatg gagtagggca ctagattatt ttattccttt 300
gcaaaagttt ctgcctgaaa ttgcaatgtt ttctaggtat aattttcata gactataaac 360
tcaagtagaa caaagatac 379

<210> SEQ ID NO 65
<211> LENGTH: 66
<212> TYPE: DNA
<213> ORGANISM: Artificial Sequence
<220> FEATURE:

<223> OTHER INFORMATION: 3XFLAG

<400> SEQUENCE: 65
gactacaaag accatgacgg agattataaa gatcatgaca tcgattacaa ggatgacgat 60
gacaag 66

<210> SEQ ID NO 66
<211> LENGTH: 30
<212> TYPE: DNA
<213> ORGANISM: Artificial Sequence
<220> FEATURE:
<223> OTHER INFORMATION: 10aa

<400> SEQUENCE: 66
tccggactca gatctggagg ctccggaggc 30

<210> SEQ ID NO 67
<211> LENGTH: 378
<212> TYPE: DNA
<213> ORGANISM: Artificial Sequence
<220> FEATURE:
<223> OTHER INFORMATION: H2B

<400> SEQUENCE: 67
ccagagccag cgaagtctgc tcccgccccg aaaaagggct ccaagaaggc ggtgactaag 60
gcgcagaaga aaggcggcaa gaagcgcaag cgcagccgca aggagagcta ttccatctat 120
gtgtacaagg ttctgaagca ggtccaccct gacaccggca tttcgtccaa ggccatgggc 180
atcatgaatt cgtttgtgaa cgacattttc gagcgcatcg caggagaggc ttcccgcctg 240
gcgcattaca acaagcgctc gaccatcacc tcccgggaga tccagacggc cgtgcgcctg 300
ctgctgcctg gggagttggc caagcacgcc gtgtccgagg gtactaaggc catcaccaag 360
tacaccagcg ctaagtaa 378

<210> SEQ ID NO 68
<211> LENGTH: 2988
<212> TYPE: DNA
<213> ORGANISM: Artificial Sequence
<220> FEATURE:
<223> OTHER INFORMATION: AiP1279

<400> SEQUENCE: 68
gcggccgcac gcgtcccagg atctattgac atccaacatc ggatggagaa actgaagttc 60
acatcatagc tcatctctca tagtatccta tacggtgttt ctctttcttg gagaaacaac 120
cccaccccac ccgccttgat gttaatgcca ggacacacat gttttcttga ccccacttct 180
ctgatcactc atcgctctgc ttcctcagcc tgttgttggt accagttctc agatagttgc 240
agtctccaag ttcagttcct accgatttat gccatgctgt ctttttgag aaataccact 300 caccatgtga gtgaatctgt gaatgcctcc taaatgcccg ttgccaattt gagaataaaa 360
gttcatgtga ttatgttcaa ggcatttcag attaaatatg accaaaatca ctccgtggtg 420
ccttcctgta cgcctcaccg tgaatccagt ttgcttaagg agctcgggct gggcataaaa 480
gtcagggcag agccatctat tgcttacatt tgcttctggc gtggccacca tggctcctaa 540
gaagaagagg aaggtgatga gccagttcga catcctgtgc aagacccccc ccaaggtgct 600
ggtgcggcag ttcgtggaga gattcgagag gcccagcggc gagaagatcg ccagctgtgc 660
cgccgagctg acctacctgt gctggatgat cacccacaac ggcaccgcca tcaagagggc 720
caccttcatg agctacaaca ccatcatcag caacagcctg agcttcgaca tcgtgaacaa 780

```
gagcctgcag ttcaagtaca agacccagaa ggccaccatc ctggaggcca gcctgaagaa    840
gctgatcccc gcctgggagt tcaccatcat cccttacaac ggccagaagc accagagcga    900
catcaccgac atcgtgtcca gcctgcagct gcagttcgag agcagcgagg aggccgacaa    960
gggcaacagc cacagcaaga agatgctgaa ggccctgctg tccgagggcg agagcatctg   1020
ggagatcacc gagaagatcc tgaacagctt cgagtacacc agcaggttca ccaagaccaa   1080
gaccctgtac cagttcctgt tcctggccac attcatcaac tgcggcaggt tcagcgacat   1140
caagaacgtg gaccccaaga gcttcaagct ggtgcagaac aagtacctgg gcgtgatcat   1200
tcagtgcctg gtgaccgaga ccaagacaag cgtgtccagg cacatctact tttcagcgc   1260
cagaggcagg atcgaccccc tggtgtacct ggacgagttc ctgaggaaca gcgagcccgt   1320
gctgaagaga gtgaacagga ccggcaacag cagcagcaac aagcaggagt accagctgct   1380
gaaggacaac ctggtgcgca gctacaacaa ggccctgaag aagaacgccc cctaccccat   1440
cttcgctatc aagaacggcc ctaagagcca catcggcagg cacctgatga ccagctttct   1500
gagcatgaag ggcctgaccg agctgacaaa cgtggtgggc aactggagcg acaagagggc   1560
ctccgccgtg gccaggacca cctacaccca ccagatcacc gccatccccg accactactt   1620
cgccctggtg tccaggtact acgcctacga ccccatcagc aaggagatga tcgccctgaa   1680
ggacgagacc aaccccatcg aggagtggca gcacatcgag cagctgaagg gcagcgccga   1740
gggcagcatc agatacccccg cctggaacgg catcatcagc caggaggtgc tggactacct   1800
gagcagctac atcaacaggc ggatctgaga attcgatatc aagcttatcg ataatcaacc   1860
tctggattac aaaatttgtg aaagattgac tggtattctt aactatgttg ctccttttac   1920
gctatgtgga tacgctgctt taatgccttt gtatcatgct attgcttccc gtatggcttt   1980
cattttctcc tccttgtata aatcctggtt gctgtctctt tatgaggagt tgtggcccgt   2040
tgtcaggcaa cgtggcgtgg tgtgcactgt gtttgctgac gcaaccccca ctggttgggg   2100
cattgccacc acctgtcagc tcctttccgg gactttcgct ttccccctcc ctattgccac   2160
ggcggaactc atcgccgcct gccttgcccg ctgctggaca ggggctcggc tgttgggcac   2220
tgacaattcc gtggtgttgt cggggaaatc atcgtccttt ccttggctgc tcgcctatgt   2280
tgccacctgg attctgcgcg ggacgtcctt ctgctacgtc ccttcggccc tcaatccagc   2340
ggaccttcct tcccgcggcc tgctgccggc tctgcggcct cttccgcgtc ttcgccttcg   2400
ccctcagacg agtcggatct ccctttgggc cgcctccccg catcgatacc gagcgctgct   2460
cgagagatct acgggtggca tccctgtgac ccctccccag tgcctctcct ggccctggaa   2520
gttgccactc cagtgcccac cagccttgtc ctaataaaat taagttgcat cattttgtct   2580
gactaggtgt ccttctataa tattatgggg tggagggggg tggtatggag caaggggcaa   2640
gttgggaaga caacctgtag ggcctgcggg gtctattggg aaccaagctg gagtgcagtg   2700
gcacaatctt ggctcactgc aatctccgcc tcctgggttc aagcgattct cctgcctcag   2760
cctcccgagt tgttgggatt ccaggcatgc atgaccaggc tcagctaatt tttgtttttt   2820
tggtagagac ggggtttcac catattggcc aggctggtct ccaactccta atctcaggtg   2880
atctacccac cttggcctcc caaattgctg ggattacagg cgtgaaccac tgctcccttc   2940
cctgtccttc tgattttgta ggtaaccacg tgcggaccga gcggccgc                2988
```

<210> SEQ ID NO 69
<211> LENGTH: 2901
<212> TYPE: DNA

<213> ORGANISM: Artificial Sequence
<220> FEATURE:
<223> OTHER INFORMATION: AiP1277

<400> SEQUENCE: 69
gcggccgcac gcgtcctttt agaaacactc cctttaccat cttcaaacat gtttttagct 60
gagaactctc ttccaacccc tgtttcttaa ctctgagtgc cgtatcactt catattctgt 120
gtcaggggaa aagaaatcag cacctcccac aacgtcaact gtgtccttta gagtaagcat 180
tccaaagtct atattctgag tctaatctct cttggaaagg tcagcctttt cttccaaata 240
ccaagtggac atctttatgc acaggccttc aaggatattc aagtcagtgt gtcctacgga 300
gaaaactcct tttaaaaccc gaatcctgtg gtttccccaa gatgattatt gggtggtcac 360
tgcagcctta aggagctcgg gctgggcata aaagtcaggg cagagccatc tattgcttac 420
atttgcttct ggcgtggcca ccatggctcc taagaagaag aggaaggtga tgagccagtt 480
cgacatcctg tgcaagaccc cccccaaggt gctggtgcgg cagttcgtgg agagattcga 540
gaggcccagc ggcgagaaga tcgccagctg tgccgccgag ctgacctacc tgtgctggat 600
gatcacccac aacggcaccg ccatcaagag ggccaccttc atgagctaca acaccatcat 660
cagcaacagc ctgagcttcg acatcgtgaa caagagcctg cagttcaagt acaagaccca 720
gaaggccacc atcctggagg ccagcctgaa gaagctgatc cccgcctggg agttcaccat 780
catcccttac aacggccaga agcaccagag cgacatcacc gacatcgtgt ccagcctgca 840
gctgcagttc gagagcagcg aggaggccga caagggcaac agccacagca agaagatgct 900
gaaggccctg ctgtccgagg gcgagagcat ctgggagatc accgagaaga tcctgaacag 960
cttcgagtac accagcaggt tcaccaagac caagaccctg taccagttcc tgttcctggc 1020
cacattcatc aactgcggca ggttcagcga catcaagaac gtggaccccca agagcttcaa 1080 gctggtgcag aacaagtacc tgggcgtgat cattcagtgc ctggtgaccg agaccaagac 1140
aagcgtgtcc aggcacatct actttttcag cgccagaggc aggatcgacc ccctggtgta 1200
cctggacgag ttcctgagga acagcgagcc cgtgctgaag agagtgaaca ggaccggcaa 1260
cagcagcagc aacaagcagg agtaccagct gctgaaggac aacctggtgc gcagctacaa 1320
caaggccctg aagaagaacg cccccctaccc catcttcgct atcaagaacg gccctaagag 1380
ccacatcggc aggcacctga tgaccagctt tctgagcatg aagggcctga ccgagctgac 1440
aaacgtggtg ggcaactgga gcgacaagag ggcctccgcc gtggccagga ccacctacac 1500
ccaccagatc accgccatcc ccgaccacta cttcgccctg gtgtccaggt actacgccta 1560
cgaccccatc agcaaggaga tgatcgccct gaaggacgag accaaccccca tcgaggagtg 1620 gcagcacatc gagcagctga agggcagcgc cgagggcagc atcagatacc ccgcctggaa 1680
cggcatcatc agccaggagg tgctggacta cctgagcagc tacatcaaca ggcggatctg 1740
agaattcgat atcaagctta tcgataatca acctctggat tacaaaattt gtgaaagatt 1800
gactggtatt cttaactatg ttgctccttt tacgctatgt ggatacgctg ctttaatgcc 1860
tttgtatcat gctattgctt cccgtatggc tttcattttc tcctccttgt ataaatcctg 1920
gttgctgtct ctttatgagg agttgtggcc cgttgtcagg caacgtggcg tggtgtgcac 1980
tgtgtttgct gacgcaaccc ccactggttg gggcattgcc accacctgtc agctcctttc 2040
cgggactttc gctttccccc tccctattgc cacggcggaa ctcatcgccg cctgccttgc 2100
ccgctgctgg acaggggctc ggctgttggg cactgacaat tccgtggtgt tgtcggggaa 2160
atcatcgtcc tttccttggc tgctcgccta tgttgccacc tggattctgc gcgggacgtc 2220

```
cttctgctac gtcccttcgg ccctcaatcc agcggacctt ccttcccgcg gcctgctgcc   2280

ggctctgcgg cctcttccgc gtcttcgcct tcgccctcag acgagtcgga tctccctttg   2340

ggccgcctcc ccgcatcgat accgagcgct gctcgagaga tctacgggtg gcatccctgt   2400

gacccctccc cagtgcctct cctggccctg gaagttgcca ctccagtgcc caccagcctt   2460

gtcctaataa aattaagttg catcattttg tctgactagg tgtccttcta taatattatg   2520

gggtggaggg gggtggtatg gagcaagggg caagttggga agacaacctg tagggcctgc   2580

ggggtctatt gggaaccaag ctggagtgca gtggcacaat cttggctcac tgcaatctcc   2640

gcctcctggg ttcaagcgat tctcctgcct cagcctcccg agttgttggg attccaggca   2700

tgcatgacca ggctcagcta atttttgttt ttttggtaga gacggggttt caccatattg   2760

gccaggctgg tctccaactc ctaatctcag gtgatctacc caccttggcc tcccaaattg   2820

ctgggattac aggcgtgaac cactgctccc ttccctgtcc ttctgatttt gtaggtaacc   2880

acgtgcggac cgagcggccg c                                             2901
```

```
<210> SEQ ID NO 70
<211> LENGTH: 3046
<212> TYPE: DNA
<213> ORGANISM: Artificial Sequence
<220> FEATURE:
<223> OTHER INFORMATION: AiP1278

<400> SEQUENCE: 70
```

```
gcggccgcac gcgtatatgg atgtcttacc tgcatgaata cttgtgtacc acatgtatgc     60

ctttctccat ggaggccaga agagggtatc agattccctg gaactgaagt tacagatagt    120

tgtgagctgc catgtgggta ctggaaatac atgtgtctaa ttttaaggac cagctcctac    180

tgaggacata aatgttatgt ttcttaaaag tctataccat aagaatcttc ttcagatctt    240

ggtgtgaaga ttcttacccc agattggtta cagaagcggt accaggtggg tggatcccat    300

caaaagcttt agtgagaaat caccctttc cttcacagca gcccagctga ctggtgaact     360

ttgccgaact gtaaaatatc aaacctttgg gaagcttttct gcaacacgag aagttttaat   420

ccttcaatat taaaaagaaa aataagaaaa aaaaactgtg gagaagtcac gaacaggaga    480

aacaaaaagg aattgtgcac agggtcagtc gcttaaggag ctcgggctgg gcataaaagt    540

cagggcagag ccatctattg cttacatttg cttctggcgt ggccaccatg gctcctaaga    600

agaagaggaa ggtgatgagc cagttcgaca tcctgtgcaa gacccccccc aaggtgctgg    660

tgcggcagtt cgtggagaga ttcgagaggc ccagcggcga gaagatcgcc agctgtgccg    720

ccgagctgac ctacctgtgc tggatgatca cccacaacgg caccgccatc aagagggcca    780

ccttcatgag ctacaacacc atcatcagca acagcctgag cttcgacatc gtgaacaaga    840

gcctgcagtt caagtacaag acccagaagg ccaccatcct ggaggccagc ctgaagaagc    900

tgatccccgc ctgggagttc accatcatcc cttacaacgg ccagaagcac cagagcgaca    960

tcaccgacat cgtgtccagc ctgcagctgc agttcgagag cagcgaggag gccgacaagg   1020

gcaacagcca cagcaagaag atgctgaagg ccctgctgtc cgagggcgag agcatctggg   1080

agatcaccga gaagatcctg aacagcttcg agtacaccag caggttcacc aagaccaaga   1140

ccctgtacca gttcctgttc ctggccacat tcatcaactg cggcaggttc agcgacatca   1200

agaacgtgga ccccaagagc ttcaagctgg tgcagaacaa gtacctgggc gtgatcattc   1260

agtgcctggt gaccgagacc aagacaagcg tgtccaggca catctacttt ttcagcgcca   1320
```

```
gaggcaggat cgaccccctg gtgtacctgg acgagttcct gaggaacagc gagcccgtgc   1380

tgaagagagt gaacaggacc ggcaacagca gcagcaacaa gcaggagtac cagctgctga   1440

aggacaacct ggtgcgcagc tacaacaagg ccctgaagaa gaacgccccc taccccatct   1500

tcgctatcaa gaacggccct aagagccaca tcggcaggca cctgatgacc agctttctga   1560

gcatgaaggg cctgaccgag ctgacaaacg tggtgggcaa ctggagcgac aagagggcct   1620

ccgccgtggc caggaccacc tacacccacc agatcaccgc catccccgac cactacttcg   1680

ccctggtgtc caggtactac gcctacgacc ccatcagcaa ggagatgatc gccctgaagg   1740

acgagaccaa ccccatcgag gagtggcagc acatcgagca gctgaagggc agcgccgagg   1800

gcagcatcag ataccccgcc tggaacggca tcatcagcca ggaggtgctg gactacctga   1860

gcagctacat caacaggcgg atctgagaat tcgatatcaa gcttatcgat aatcaacctc   1920

tggattacaa aatttgtgaa agattgactg gtattcttaa ctatgttgct ccttttacgc   1980

tatgtggata cgctgcttta atgcctttgt atcatgctat tgcttcccgt atggctttca   2040

ttttctcctc cttgtataaa tcctggttgc tgtctcttta tgaggagttg tggcccgttg   2100

tcaggcaacg tggcgtggtg tgcactgtgt ttgctgacgc aacccccact ggttggggca   2160

ttgccaccac ctgtcagctc ctttccggga ctttcgcttt ccccctccct attgccacgg   2220

cggaactcat cgccgcctgc cttgcccgct gctggacagg ggctcggctg ttgggcactg   2280

acaattccgt ggtgttgtcg gggaaatcat cgtcctttcc ttggctgctc gcctatgttg   2340

ccacctggat tctgcgcggg acgtccttct gctacgtccc ttcggccctc aatccagcgg   2400

accttccttc ccgcggcctg ctgccggctc tgcggcctct tccgcgtctt cgccttcgcc   2460

ctcagacgag tcggatctcc ctttgggccg cctccccgca tcgataccga gcgctgctcg   2520

agagatctac gggtggcatc cctgtgaccc ctccccagtg cctctcctgg ccctggaagt   2580

tgccactcca gtgcccacca gccttgtcct aataaaatta agttgcatca ttttgtctga   2640

ctaggtgtcc ttctataata ttatggggtg gaggggggtg gtatggagca aggggcaagt   2700

tgggaagaca acctgtaggg cctgcggggt ctattgggaa ccaagctgga gtgcagtggc   2760

acaatcttgg ctcactgcaa tctccgcctc ctgggttcaa gcgattctcc tgcctcagcc   2820

tcccgagttg ttgggattcc aggcatgcat gaccaggctc agctaatttt tgtttttttg   2880

gtagagacgg ggtttcacca tattggccag gctggtctcc aactcctaat ctcaggtgat   2940

ctacccacct tggcctccca aattgctggg attacaggcg tgaaccactg ctcccttccc   3000

tgtccttctg attttgtagg taaccacgtg cggaccgagc ggccgc                  3046
```

```
<210> SEQ ID NO 71
<211> LENGTH: 2178
<212> TYPE: DNA
<213> ORGANISM: Artificial Sequence
<220> FEATURE:
<223> OTHER INFORMATION: AiP1344

<400> SEQUENCE: 71

cggccgcacg cgtatatgga tgtcttacct gcatgaatac ttgtgtacca catgtatgcc     60

tttctccatg gaggccagaa gagggtatca gattccctgg aactgaagtt acagatagtt    120

gtgagctgcc atgtgggtac tggaaataca tgtgtctaat tttaaggacc agctcctact    180

gaggacataa atgttatgtt tcttaaaagt ctataccata agaatcttct tcagatcttg    240

gtgtgaagat tcttacccca gattggttac agaagcggta ccaggtgggt ggatcccatc    300

aaaagcttta gtgagaaatc accctttcc ttcacagcag cccagctgac tggtgaactt     360
```

```
tgccgaactg taaaatatca aacctttggg aagctttctg caacacgaga agttttaatc    420

cttcaatatt aaaaagaaaa ataagaaaaa aaaactgtgg agaagtcacg aacaggagaa    480

acaaaaagga attgtgcaca gggtcagtcg cttaaggagc tcgggctggg cataaaagtc    540

agggcagagc catctattgc ttacatttgc ttctgggatc cgccaccatg gtgcccaaga    600

agaagaggaa agtctccaac ctgctgactg tgcaccaaaa cctgcctgcc ctccctgtgg    660

atgccacctc tgatgaagtc aggaagaacc tgatggacat gttcagggac aggcaggcct    720

tctctgaaca cacctggaag atgctcctgt ctgtgtgcag atcctgggct gcctggtgca    780

agctgaacaa caggaaatgg ttccctgctg aacctgagga tgtgagggac tacctcctgt    840

acctgcaagc cagaggcctg gctgtgaaga ccatccaaca gcacctgggc cagctcaaca    900

tgctgcacag gagatctggc ctgcctcgcc cttctgactc caatgctgtg tccctggtga    960

tgaggagaat cagaaaggag aatgtggatg ctggggagag agccaagcag gccctggcct   1020

ttgaacgcac tgactttgac caagtcagat ccctgatgga gaactctgac agatgccagg   1080

acatcaggaa cctggccttc ctgggcattg cctacaacac cctgctgcgc attgccgaaa   1140

ttgccagaat cagagtgaag gacatctccc gcaccgatgg tgggagaatg ctgatccaca   1200

ttggcaggac caagaccctg gtgtccacag ctggtgtgga gaaggccctg tccctggggg   1260

ttaccaagct ggtggagaga tggatctctg tgtctggtgt ggctgatgac cccaacaact   1320

acctgttctg ccgggtcaga aagaatggtg tggctgcccc ttctgccacc tcccaactgt   1380

ccacccgggc cctggaaggg atctttgagg ccacccaccg cctgatctat ggtgccaagg   1440

atgactctgg gcagagatac ctggcctggt ctggccactc tgccagagtg ggtgctgcca   1500

gggacatggc cagggctggt gtgtccatcc ctgaaatcat gcaggctggt ggctggacca   1560

atgtgaacat tgtgatgaac tacatcagaa acctggactc tgagactggg gccatggtga   1620

ggctgctcga ggatggggac taaggctgct cgagagatct acgggtggca tccctgtgac   1680

ccctccccag tgcctctcct ggccctggaa gttgccactc cagtgcccac cagccttgtc   1740

ctaataaaat taagttgcat cattttgtct gactaggtgt ccttctataa tattatgggg   1800

tggagggggg tggtatggag caaggggcaa gttgggaaga caacctgtag ggcctgcggg   1860

gtctattggg aaccaagctg gagtgcagtg gcacaatctt ggctcactgc aatctccgcc   1920

tcctgggttc aagcgattct cctgcctcag cctcccgagt tgttgggatt ccaggcatgc   1980

atgaccaggc tcagctaatt tttgtttttt tggtagagac ggggtttcac catattggcc   2040

aggctggtct ccaactccta atctcaggtg atctacccac cttggcctcc caaattgctg   2100

ggattacagg cgtgaaccac tgctcccttc cctgtccttc tgattttgta ggtaaccacg   2160

tgcggaccga gcggccgc                                                 2178
```

<210> SEQ ID NO 72
<211> LENGTH: 2039
<212> TYPE: DNA
<213> ORGANISM: Artificial Sequence
<220> FEATURE:
<223> OTHER INFORMATION: CN3041

<400> SEQUENCE: 72

```
gcggccgcac gcgtacagca agtgttctat gattttcaac aggacacttg gatctagcca     60

actcagtttt caagcctgcc cccgagttgt agatcctgtc ttcacattct aaactaatct    120

cacaccactt tgtgccaact ccactctggt aaagaccatg cactcgagtt agtgcaagac    180
```

```
atttgttct ggcctcgggg tgtgctgccg cctcgtcagg atgggaggtg gaggcgagtc    240
cagacagcaa gtgttctatg attttcaaca ggacacttgg atctagccaa ctcagttttc    300
aagcctgccc ccgagttgta gatcctgtct tcacattcta aactaatctc acaccacttt    360
gtgccaactc cactctggta aagaccatgc actcgagtta gtgcaagaca ttttgttctg    420
gcctcggggt gtgctgccgc ctcgtcagga tgggaggtgg aggcgagtcc agacagcaag    480
tgttctatga ttttcaacag gacacttgga tctagccaac tcagttttca agcctgcccc    540
cgagttgtag atcctgtctt cacattctaa actaatctca caccactttg tgccaactcc    600
actctggtaa agaccatgca ctcgagttag tgcaagacat tttgttctgg cctcggggtg    660
tgctgccgcc tcgtcaggat gggaggtgga ggcgagtcca ggagctcggg ctgggcataa    720
aagtcagggc agagccatct attgcttaca tttgcttctg ggatccagat ctttcgaagc    780
tagcgctacc ggtcgccacc atggtgagca agggcgagga gctgttcacc ggggtggtgc    840
ccatcctggt cgagctggac ggcgacgtaa acggccacaa gttcagcgtg tccggcgagg    900
gcgagggcga tgccacctac ggcaagctga ccctgaagct gatctgcacc accggcaagc    960
tgcccgtgcc ctggcccacc ctcgtgacca ccctgggcta cggcgtgcag tgcttcgccc   1020
gctaccccga ccacatgaag cagcacgact tcttcaagtc cgccatgccc gaaggctacg   1080
tccaggagcg caccatcttc ttcaaggacg acggcaacta caagacccgc gccgaggtga   1140
agttcgaggg cgacaccctg gtgaaccgca tcgagctgaa gggcatcgac ttcaaggagg   1200
acggcaacat cctggggcac aagctggagt acaactacaa cagccacaac gtctatatca   1260
ccgccgacaa gcagaagaac ggcatcaagg ccaacttcaa gatccgccac aacatcgagg   1320
acggcggcgt gcagctcgcc gaccactacc agcagaacac ccccatcggc gacggccccg   1380
tgctgctgcc cgacaaccac tacctgagct accagtccaa gctgagcaaa gaccccaacg   1440
agaagcgcga tcacatggtc ctgctggagt tcgtgaccgc cgccgggatc actctcggca   1500
tggacgagct gtacaagtaa gtcgacggcg cgccgcggcc gcgaattcga tatcataatc   1560
aacctctgga ttacaaaatt tgtgaaagat tgactggtat tcttaactat gttgctcctt   1620
ttacgctatg tggatacgct gctttaatgc ctttgtatca tgctattgct tcccgtatgg   1680
ctttcatttt ctcctccttg tataaatcct ggttagttct tgccacggcg gaactcatcg   1740
ccgcctgcct tgcccgctgc tggacagggg ctcggctgtt gggcactgac aattccgtgg   1800
ctcgagagat cttcgactgt gccttctagt tgccagccat ctgttgtttg cccctccccc   1860
gtgccttcct tgaccctgga aggtgccact cccactgtcc tttcctaata aaatgaggaa   1920
attgcatcgc attgtctgag taggtgtcat tctattctgg ggggtggggt ggggcaggac   1980
agcaaggggg aggattggga agacaatagc aggcatgcac gtgcggaccg agcggccgc    2039
```

<210> SEQ ID NO 73
<211> LENGTH: 2153
<212> TYPE: DNA
<213> ORGANISM: Artificial Sequence
<220> FEATURE:
<223> OTHER INFORMATION: CN3608

<400> SEQUENCE: 73

```
gcggccgcac gcgtccccac tcctgcctct gcctataaga gtttggcaca gttggagatt     60
tgtatacaca aatgcatgcg tggaaatact gcgctctgat gacattcctc agggggcgac    120
ctttgatgat gaattttctt gccctttttta ggggaggaga agaggaggcg ggtggtactt    180
cacaagacta aatttactca actttttgg gtctaaattt ctttaggaaa aaaaatgtca    240
```

aatgattgta gatcccaaac tgtctttgtt ggcatttgac cccactcctg cctctgccta 300
taagagtttg gcacagttgg agatttgtat acacaaatgc atgcgtggaa atactgcgct 360
ctgatgacat tcctcagggg gcgacctttg atgatgaatt ttcttgccct ttttagggga 420
ggagaagagg aggcgggtgg tacttcacaa gactaaattt actcaacttt tttgggtcta 480
aatttcttta ggaaaaaaaa tgtcaaatga ttgtagatcc caaactgtct ttgttggcat 540
ttgaccccac tcctgcctct gcctataaga gtttggcaca gttggagatt tgtatacaca 600
aatgcatgcg tggaaatact gcgctctgat gacattcctc aggggggcgac ctttgatgat 660 gaattttctt gccctttta ggggaggaga agaggaggcg ggtggtactt cacaagacta 720
aatttactca actttttttgg gtctaaattt ctttaggaaa aaaaatgtca aatgattgta 780
gatcccaaac tgtctttgtt ggcatttgag agctcgggct gggcataaaa gtcagggcag 840
agccatctat tgcttacatt tgcttctggg atccagatct ttcgaagcta gcgctaccgg 900
tcgccaccat ggtgagcaag ggcgaggagc tgttcaccgg ggtggtgccc atcctggtcg 960
agctggacgg cgacgtaaac ggccacaagt tcagcgtgtc cggcgagggc gagggcgatg 1020
ccacctacgg caagctgacc ctgaagctga tctgcaccac cggcaagctg cccgtgccct 1080
ggcccaccct cgtgaccacc ctgggctacg gcgtgcagtg cttcgcccgc taccccgacc 1140
acatgaagca gcacgacttc ttcaagtccg ccatgcccga aggctacgtc caggagcgca 1200
ccatcttctt caaggacgac ggcaactaca agacccgcgc cgaggtgaag ttcgagggcg 1260
acaccctggt gaaccgcatc gagctgaagg gcatcgactt caaggaggac ggcaacatcc 1320
tggggcacaa gctggagtac aactacaaca gccacaacgt ctatatcacc gccgacaagc 1380
agaagaacgg catcaaggcc aacttcaaga tccgccacaa catcgaggac ggcggcgtgc 1440
agctcgccga ccactaccag cagaacaccc ccatcggcga cggccccgtg ctgctgcccg 1500
acaaccacta cctgagctac cagtccaagc tgagcaaaga ccccaacgag aagcgcgatc 1560
acatggtcct gctggagttc gtgaccgccg ccgggatcac tctcggcatg gacgagctgt 1620
acaagtaagt cgacggcgcg ccgcggccgc gaattcgata tcataatcaa cctctggatt 1680
acaaaatttg tgaaagattg actggtattc ttaactatgt tgctcctttt acgctatgtg 1740
gatacgctgc tttaatgcct ttgtatcatg ctattgcttc ccgtatggct ttcattttct 1800
cctccttgta taaatcctgg ttagttcttg ccacggcgga actcatcgcc gcctgccttg 1860
cccgctgctg gacaggggct cggctgttgg gcactgacaa ttccgtggct cgagagatct 1920
tcgactgtgc cttctagttg ccagccatct gttgtttgcc cctcccccgt gccttccttg 1980
accctggaag gtgccactcc cactgtcctt tcctaataaa atgaggaaat tgcatcgcat 2040
tgtctgagta ggtgtcattc tattctgggg ggtggggtgg ggcaggacag caaggggggag 2100 gattgggaag acaatagcag gcatgagatc tcacgtgcgg accgagcggc cgc 2153

<210> SEQ ID NO 74
<211> LENGTH: 2090
<212> TYPE: DNA
<213> ORGANISM: Artificial Sequence
<220> FEATURE:
<223> OTHER INFORMATION: CN2582

<400> SEQUENCE: 74
gcggccgcac gcgtaaaatc aaatcagttg caaaatccat acagtcttcc agtttctcag 60
ctgtggaaac tttgtgtctc ttcttttcca ccaaaacagc tatctcgtct ttcaagtcct 120

```
tgctgaaaaa aaaaagtgtt aaatttttct caatttagac ttccagcaaa acagattctg    180
cttgttgaaa ggcattggtg ttcatgagta agtgagtttc cattttattt cttcacaaat    240
aagttacatg aagtacttaa aatcaaatca gttgcaaaat ccatacagtc ttccagtttc    300
tcagctgtgg aaactttgtg tctcttcttt tccaccaaaa cagctatctc gtctttcaag    360
tccttgctga aaaaaaaaag tgttaaattt ttctcaattt agacttccag caaaacagat    420
tctgcttgtt gaaaggcatt ggtgttcatg agtaagtgag tttccatttt atttcttcac    480
aaataagtta catgaagtac ttaaaatcaa atcagttgca aaatccatac agtcttccag    540
tttctcagct gtggaaactt tgtgtctctt cttttccacc aaaacagcta tctcgtcttt    600
caagtccttg ctgaaaaaaa aaagtgttaa atttttctca atttagactt ccagcaaaac    660
agattctgct tgttgaaagg cattggtgtt catgagtaag tgagtttcca ttttatttct    720
tcacaaataa gttacatgaa gtacttgagc tcgggctggg cataaaagtc agggcagagc    780
catctattgc ttacatttgc ttctgggatc cagatctttc gaagctagcg ctaccggtcg    840
ccaccatggt gagcaagggc gaggagctgt tcaccggggt ggtgcccatc ctggtcgagc    900
tggacggcga cgtaaacggc cacaagttca gcgtgtccgg cgagggcgag ggcgatgcca    960
cctacggcaa gctgaccctg aagctgatct gcaccaccgg caagctgccc gtgccctggc   1020
ccaccctcgt gaccaccctg ggctacggcg tgcagtgctt cgcccgctac cccgaccaca   1080
tgaagcagca cgacttcttc aagtccgcca tgcccgaagg ctacgtccag gagcgcacca   1140
tcttcttcaa ggacgacggc aactacaaga cccgcgccga ggtgaagttc gagggcgaca   1200
ccctggtgaa ccgcatcgag ctgaagggca tcgacttcaa ggaggacggc aacatcctgg   1260
ggcacaagct ggagtacaac tacaacagcc acaacgtcta tatcaccgcc gacaagcaga   1320
agaacggcat caaggccaac ttcaagatcc gccacaacat cgaggacggc ggcgtgcagc   1380
tcgccgacca ctaccagcag aacaccccca tcggcgacgg ccccgtgctg ctgcccgaca   1440
accactacct gagctaccag tccaagctga gcaaagaccc caacgagaag cgcgatcaca   1500
tggtcctgct ggagttcgtg accgccgccg ggatcactct cggcatggac gagctgtaca   1560
agtaagtcga cggcgcgccg cggccgcgaa ttcgatatca taatcaacct ctggattaca   1620
aaatttgtga aagattgact ggtattctta actatgttgc tccttttacg ctatgtggat   1680
acgctgcttt aatgcctttg tatcatgcta ttgcttcccg tatggctttc attttctcct   1740
ccttgtataa atcctggtta gttcttgcca cggcggaact catcgccgcc tgccttgccc   1800
gctgctggac aggggctcgg ctgttgggca ctgacaattc cgtggctcga gagatcttcg   1860
actgtgcctt ctagttgcca gccatctgtt gtttgcccct cccccgtgcc ttccttgacc   1920
ctggaaggtg ccactcccac tgtcctttcc taataaaatg aggaaattgc atcgcattgt   1980
ctgagtaggt gtcattctat tctggggggt ggggtggggc aggacagcaa gggggaggat   2040
tgggaagaca atagcaggca tgagatctca cgtgcggacc gagcggccgc              2090
```

<210> SEQ ID NO 75
<211> LENGTH: 2316
<212> TYPE: DNA
<213> ORGANISM: Artificial Sequence
<220> FEATURE:
<223> OTHER INFORMATION: CN3367

<400> SEQUENCE: 75

```
gcggccgcac gcgtactgac tgaggctgct caatgtacca tattaaaaag ggagctgcgg     60
ctaagccagt ttctgcagga cagagccaca gactatggga tacttccaag gagaaggaag    120
```

```
gagtggcgag gtggcactgc gtcagctgac cgctagactg tgactttatc cagctctgtg    180
ttagctgagt gatgacagta atgccgtatc tacacaccca ccgcctactg ggaacctcca    240
catgagtaca taacatagca tctgaggcca gcagtgcgca gaacacatct gctcatctac    300
agtgccttca aacgggaggg aagtaccagt cctctctcag tgagaacacc atccgtcctg    360
ggtgagagct ttaggcattg ccatggctcc ctgtcactcg gccctgaccc acacattcac    420
agccatgagc tcgggctggg cataaaagtc agggcagagc catctattgc ttacatttgc    480
ttctgggatc cagatctttc gaagctagcg ctaccggtcg ccaccatggt ctccaagggc    540
gaggagctgt tcaccggggt ggtgcccatc ctggtcgagc tggacggcga tgtcaacggc    600
cacaagttca gcgtgtccgg cgagggcgag ggcgatgcca cctacggcaa gctgaccctg    660
aagctgatct gcaccaccgg caagctgccc gtgccctggc ccaccctcgt gaccaccctg    720
ggctacggcg tgcagtgctt cgcccgctac cccgaccaca tgaagcagca cgacttcttc    780
aagtccgcca tgcccgaagg ctacgtccag gagcgcacca tcttcttcaa agacgacggc    840
aactacaaga cccgcgccga ggtgaagttc gagggcgaca ccctggtgaa ccgcatcgag    900
ctgaagggca tcgacttcaa ggaggacggc aacatcctgg ggcacaagct ggagtacaac    960
tacaacagcc acaacgtcta tatcaccgcc gacaagcaga agaacggcat caaggccaac   1020
ttcaagatcc gccacaacat cgaggacggc ggcgtgcagc tcgccgacca ctaccagcag   1080
aacaccccca tcggcgacgg ccccgtgctg ctgcccgaca accactacct gagctaccag   1140
tccaagctga gcaaagaccc caacgagaag cgcgatcaca tggtcctgct ggagttcgtg   1200
accgccgccg ggatcactct cggcatggac gagctgtaca agggctctgg tgctaccaac   1260
ttctcactgt tgaaacaggc aggggatgta gaggagaatc cagggcctgg tgctagtgga   1320
gactacaaag accatgacgg agattataaa gatcatgaca tcgattacaa ggatgacgat   1380
gacaagtccg gactcagatc tggaggctcc ggaggcccag agccagcgaa gtctgctccc   1440
gccccgaaaa agggctccaa gaaggcggtg actaaggcgc agaagaaagg cggcaagaag   1500
cgcaagcgca gccgcaagga gagctattcc atctatgtgt acaaggttct gaagcaggtc   1560
caccctgaca ccggcatttc gtccaaggcc atgggcatca tgaattcgtt tgtgaacgac   1620
attttcgagc gcatcgcagg agaggcttcc cgcctggcgc attacaacaa gcgctcgacc   1680
atcacctccc gggagatcca gacggccgtg cgcctgctgc tgcctgggga gttggccaag   1740
cacgccgtgt ccgagggtac taaggccatc accaagtaca ccagcgctaa gtaatgaggc   1800
gcgccgcggc cgcgaattcg atatcataat caacctctgg attacaaaat ttgtgaaaga   1860
ttgactggta ttcttaacta tgttgctcct tttacgctat gtggatacgc tgctttaatg   1920
cctttgtatc atgctattgc ttcccgtatg gctttcattt tctcctcctt gtataaatcc   1980
tggttagttc ttgccacggc ggaactcatc gccgcctgcc ttgcccgctg ctggacaggg   2040
gctcggctgt tgggcactga caattccgtg gctcgagaga tcttcgactg tgccttctag   2100
ttgccagcca tctgttgttt gcccctcccc cgtgccttcc ttgaccctgg aaggtgccac   2160
tcccactgtc ctttcctaat aaaatgagga aattgcatcg cattgtctga gtaggtgtca   2220
ttctattctg gggggtgggg tggggcagga cagcaagggg gaggattggg aagacaatag   2280
caggcatgag atctcacgtg cggaccgagc ggccgc                             2316
```

<210> SEQ ID NO 76
<211> LENGTH: 2451
<212> TYPE: DNA

<213> ORGANISM: Artificial Sequence
<220> FEATURE:
<223> OTHER INFORMATION: CN4095

<400> SEQUENCE: 76

```
gcggccgcac gcgtgagtta acatttcaaa taaaataggt gtgtgtgtgt gtgtgtgtgt     60
gtgtgtgtgt gtgtgtgtgt gtgtgtgtgt gttttagaaa aagatcaatt atgggttgaa    120
tctgttgtca ccccacttgc atgtagctct atttcttagt catattttat tattttatgc    180
ccaaaggcat ggcactggaa gacaagtttc aatttttctc ttttgatgtt tcattcttat    240
gaagtggaag gttgaaagtt tgaaatccat atgactcagg aattgaattt cagctcttct    300
aaatacagac tgtgttaaag ggcaacactt ttatatatat atattcacag ctaaggcagc    360
atttacttca catagtagtt aaagaagtta agaattaagt tagtcacatg taacagaatt    420
ctcccatttc atagaaactc aaatttttgt ttcctttttc ctttccttct ctcattcttt    480
ctccacagct tacaagaagt tagaatgtat actttcatat aatagatccc cctcctccca    540
ctaaaagaga tttgagagat ggagctcggg ctgggcataa aagtcagggc agagccatct    600
attgcttaca tttgcttctg ggatccagat ctttcgaagc tagcgctacc ggtcgccacc    660
atggtctcca agggcgagga gctgttcacc ggggtggtgc ccatcctggt cgagctggac    720
ggcgatgtca acggccacaa gttcagcgtg tccggcgagg gcgagggcga tgccacctac    780
ggcaagctga ccctgaagct gatctgcacc accggcaagc tgcccgtgcc ctggcccacc    840
ctcgtgacca ccctgggcta cggcgtgcag tgcttcgccc gctaccccga ccacatgaag    900
cagcacgact tcttcaagtc cgccatgccc gaaggctacg tccaggagcg caccatcttc    960
ttcaaagacg acggcaacta caagacccgc gccgaggtga agttcgaggg cgacaccctg   1020
gtgaaccgca tcgagctgaa gggcatcgac ttcaaggagg acggcaacat cctggggcac   1080
aagctggagt acaactacaa cagccacaac gtctatatca ccgccgacaa gcagaagaac   1140
ggcatcaagg ccaacttcaa gatccgccac aacatcgagg acggcggcgt gcagctcgcc   1200
gaccactacc agcagaacac ccccatcggc gacggccccg tgctgctgcc cgacaaccac   1260
tacctgagct accagtccaa gctgagcaaa gaccccaacg agaagcgcga tcacatggtc   1320
ctgctggagt tcgtgaccgc cgccgggatc actctcggca tggacgagct gtacaagggc   1380
tctggtgcta ccaacttctc actgttgaaa caggcagggg atgtagagga gaatccaggg   1440
cctggtgcta gtggagacta caaagaccat gacggagatt ataaagatca tgacatcgat   1500
tacaaggatg acgatgacaa gtccggactc agatctggag gctccggagg cccagagcca   1560
gcgaagtctg ctcccgcccc gaaaaagggc tccaagaagg cggtgactaa ggcgcagaag   1620
aaaggcggca agaagcgcaa gcgcagccgc aaggagagct attccatcta tgtgtataag   1680
gttctgaagc aggtccaccc tgacaccggc atttcgtcca aggccatggg catcatgaac   1740
tcgtttgtga acgacatttt cgagcgcatc gcaggtgagg cttcccgcct ggcgcattac   1800
aacaagcgct cgaccatcac ctccagggag atccagacgg ccgtgcgcct gctgctgcct   1860
ggggagttgg ccaagcacgc cgtgtccgag ggtactaagg ccatcaccaa gtacaccagc   1920
gctaagtaat gaggcgcgcc gcggccgcga attcgatatc ataatcaacc tctggattac   1980
aaaatttgtg aaagattgac tggtattctt aactatgttg ctccttttac gctatgtgga   2040
tacgctgctt taatgccttt gtatcatgct attgcttccc gtatggcttt cattttctcc   2100
tccttgtata aatcctggtt agttcttgcc acggcggaac tcatcgccgc ctgccttgcc   2160
cgctgctgga caggggctcg gctgttgggc actgacaatt ccgtggctcg agagatcttc   2220
```

gactgtgcct tctagttgcc agccatctgt tgtttgcccc tcccccgtgc cttccttgac 2280
cctggaaggt gccactccca ctgtcctttc ctaataaaat gaggaaattg catcgcattg 2340
tctgagtagg tgtcattcta ttctgggggg tggggtgggg caggacagca agggggagga 2400
ttgggaagac aatagcaggc atgagatctc acgtgcggac cgagcggccg c 2451

<210> SEQ ID NO 77
<211> LENGTH: 2439
<212> TYPE: DNA
<213> ORGANISM: Artificial Sequence
<220> FEATURE:
<223> OTHER INFORMATION: CN4096

<400> SEQUENCE: 77
gcggccgcac gcgttcagag gccagtgtgt atttagggta gggcagtaca ttaaagttct 60
ggtttgtgtg ctgtcaccct atcctagaaa ctggtttgag agttttagtt cacatgcaaa 120
atgaaggtca aagtcaatac caaggagtct aaaatcaacg tgaagtgata cagagatgtg 180
cacagtttgt ttgttacgaa catcactgcc tcctacagaa tgaacttatc atcatgtgtc 240
acaatcatcc catgcatttt ccagctactt ccagtgagct ccaaatcttt acacattttg 300
aggttgaagt aaaagagcaa tgtgcacagt gagatagtca cagtttcttt acccagtctt 360
gggtgattca gattcagtca ggccaacagg gaggactttc ctgccaggag gggggcccga 420
gcaagaacag gagcttagac cctatgatgc ttagaaagaa cccaggaaac tgcctatgct 480
gtctgttgat tatgccgtga ttgctgcagg aaatgcagta gtttatgaaa cagtagaagc 540
taagcatgtg agctcgggct gggcataaaa gtcagggcag agccatctat tgcttacatt 600
tgcttctggg atccagatct ttcgaagcta gcgctaccgg tcgccaccat ggtctccaag 660
ggcgaggagc tgttcaccgg ggtggtgccc atcctggtcg agctggacgg cgatgtcaac 720
ggccacaagt tcagcgtgtc cggcgagggc gagggcgatg ccacctacgg caagctgacc 780
ctgaagctga tctgcaccac cggcaagctg cccgtgccct ggcccaccct cgtgaccacc 840
ctgggctacg gcgtgcagtg cttcgcccgc taccccgacc acatgaagca gcacgacttc 900
ttcaagtccg ccatgcccga aggctacgtc caggagcgca ccatcttctt caaagacgac 960
ggcaactaca agacccgcgc cgaggtgaag ttcgagggcg acaccctggt gaaccgcatc 1020
gagctgaagg gcatcgactt caaggaggac ggcaacatcc tggggcacaa gctggagtac 1080
aactacaaca gccacaacgt ctatatcacc gccgacaagc agaagaacgg catcaaggcc 1140
aacttcaaga tccgccacaa catcgaggac ggcggcgtgc agctcgccga ccactaccag 1200
cagaacaccc ccatcggcga cggccccgtg ctgctgcccg acaaccacta cctgagctac 1260
cagtccaagc tgagcaaaga ccccaacgag aagcgcgatc acatggtcct gctggagttc 1320
gtgaccgccg ccgggatcac tctcggcatg gacgagctgt acaagggctc tggtgctacc 1380
aacttctcac tgttgaaaca ggcaggggat gtagaggaga atccagggcc tggtgctagt 1440
ggagactaca aagaccatga cggagattat aaagatcatg acatcgatta caaggatgac 1500
gatgacaagt ccggactcag atctggaggc tccggaggcc cagagccagc gaagtctgct 1560
cccgccccga aaaagggctc caagaaggcg gtgactaagg cgcagaagaa aggcggcaag 1620
aagcgcaagc gcagccgcaa ggagagctat tccatctatg tgtataaggt tctgaagcag 1680
gtccaccctg acaccggcat ttcgtccaag gccatgggca tcatgaactc gtttgtgaac 1740
gacattttcg agcgcatcgc aggtgaggct tcccgcctgg cgcattacaa caagcgctcg 1800

```
accatcacct ccagggagat ccagacggcc gtgcgcctgc tgctgcctgg ggagttggcc   1860

aagcacgccg tgtccgaggg tactaaggcc atcaccaagt acaccagcgc taagtaatga   1920

ggcgcgccgc ggccgcgaat tcgatatcat aatcaacctc tggattacaa aatttgtgaa   1980

agattgactg gtattcttaa ctatgttgct ccttttacgc tatgtggata cgctgcttta   2040

atgcctttgt atcatgctat tgcttcccgt atggctttca ttttctcctc cttgtataaa   2100

tcctggttag ttcttgccac ggcggaactc atcgccgcct gccttgcccg ctgctggaca   2160

ggggctcggc tgttgggcac tgacaattcc gtggctcgag agatcttcga ctgtgccttc   2220

tagttgccag ccatctgttg tttgcccctc ccccgtgcct tccttgaccc tggaaggtgc   2280

cactcccact gtcctttcct aataaaatga ggaaattgca tcgcattgtc tgagtaggtg   2340

tcattctatt ctggggggtg gggtggggca ggacagcaag ggggaggatt gggaagacaa   2400

tagcaggcat gagatctcac gtgcggaccg agcggccgc                          2439
```

```
<210> SEQ ID NO 78
<211> LENGTH: 2704
<212> TYPE: DNA
<213> ORGANISM: Artificial Sequence
<220> FEATURE:
<223> OTHER INFORMATION: CN3430

<400> SEQUENCE: 78
```

```
gcggccgcac gcgtagagcc aacgaactcg aagaaaacat acgtaattaa agagaaactg     60

ctcttcaaca taggagagat ggaaggcatc agcaaaatat acacatgaaa tgaatggtca    120

agtggaaggt ttaagatttg ctctatacag attgagacgc cagtttaaaa ataacatggg    180

gaagggaatg ctagaaatgg tgtaatcagt aagaaggaca atctaaggga atctaaggct    240

tgaaaggaaa cagaaaaccg ggtgtggtgg taaatggatt gtgacttaga agctggcctg    300

agctatatac agagaccctg tcaagaaaag agagatggga gtagtaggag aggaaagtgt    360

gaagggaagg gaaaagaaag ggagggggaa agaagcaacc aaacaagcaa tcttgcagtg    420

gcttctgcca gcatgctggc aaaccctgca gtgatatttt cacatctatg taaaaaccca    480

ttttagcacc tccagaatga actttacaag aattgagaaa gtcaagtgag agagcaccaa    540

agaaggaagg aaagaaaaaa gcaagaacac ttgccagaaa gataggaaac caagaaccag    600

aaaaatagga aacaaaacta aggaaagctg cagagcagta ttcatggcaa acacagaaag    660

agaaattctc aaaacaaggc tagcaaccca aacacaaaag cacagaaaag agatgtttca    720

tcacaagtat gatgtatctc aagtatgctc aaatgactga agatacacaa gccagccaag    780

gtgatacgct accacatcaa cagcacaaca ggcagagctc gggctgggca taaaagtcag    840

ggcagagcca tctattgctt acatttgctt ctgggatcca gatctttcga agctagcgct    900

accggtcgcc accatggtct ccaagggcga ggagctgttc accggggtgg tgcccatcct    960

ggtcgagctg gacggcgatg tcaacggcca caagttcagc gtgtccggcg agggcgaggg   1020

cgatgccacc tacggcaagc tgaccctgaa gctgatctgc accaccggca agctgcccgt   1080

gccctggccc accctcgtga ccaccctggg ctacggcgtg cagtgcttcg cccgctaccc   1140

cgaccacatg aagcagcacg acttcttcaa gtccgccatg cccgaaggct acgtccagga   1200

gcgcaccatc ttcttcaaag acgacggcaa ctacaagacc cgcgccgagg tgaagttcga   1260

gggcgacacc ctggtgaacc gcatcgagct gaagggcatc gacttcaagg aggacggcaa   1320

catcctgggg cacaagctgg agtacaacta caacagccac aacgtctata tcaccgccga   1380

caagcagaag aacggcatca aggccaactt caagatccgc cacaacatcg aggacggcgg   1440
```

cgtgcagctc gccgaccact accagcagaa cacccccatc ggcgacggcc ccgtgctgct 1500
gcccgacaac cactacctga gctaccagtc caagctgagc aaagacccca acgagaagcg 1560
cgatcacatg gtcctgctgg agttcgtgac cgccgccggg atcactctcg gcatggacga 1620
gctgtacaag ggctctggtg ctaccaactt ctcactgttg aaacaggcag gggatgtaga 1680
ggagaatcca gggcctggtg ctagtggaga ctacaaagac catgacggag attataaaga 1740
tcatgacatc gattacaagg atgacgatga caagtccgga ctcagatctg gaggctccgg 1800
aggcccagag ccagcgaagt ctgctcccgc cccgaaaaag ggctccaaga aggcggtgac 1860
taaggcgcag aagaaaggcg gcaagaagcg caagcgcagc cgcaaggaga gctattccat 1920
ctatgtgtac aaggttctga agcaggtcca ccctgacacc ggcatttcgt ccaaggccat 1980
gggcatcatg aattcgtttg tgaacgacat tttcgagcgc atcgcaggag aggcttcccg 2040
cctggcgcat tacaacaagc gctcgaccat cacctcccgg gagatccaga cggccgtgcg 2100
cctgctgctg cctggggagt tggccaagca cgccgtgtcc gagggtacta aggccatcac 2160
caagtacacc agcgctaagt aatgaggcgc gccgcggccg cgaattcgat atcataatca 2220
acctctggat tacaaaattt gtgaaagatt gactggtatt cttaactatg ttgctccttt 2280
tacgctatgt ggatacgctg ctttaatgcc tttgtatcat gctattgctt cccgtatggc 2340
tttcattttc tcctccttgt ataaatcctg gttagttctt gccacggcgg aactcatcgc 2400
cgcctgcctt gcccgctgct ggacaggggc tcggctgttg ggcactgaca attccgtggc 2460
tcgagagatc ttcgactgtg ccttctagtt gccagccatc tgttgtttgc ccctcccccg 2520
tgccttcctt gaccctggaa ggtgccactc ccactgtcct ttcctaataa aatgaggaaa 2580
ttgcatcgca ttgtctgagt aggtgtcatt ctattctggg gggtggggtg gggcaggaca 2640
gcaaggggga ggattgggaa gacaatagca ggcatgagat ctcacgtgcg gaccgagcgg 2700
ccgc 2704

<210> SEQ ID NO 79
<211> LENGTH: 2283
<212> TYPE: DNA
<213> ORGANISM: Artificial Sequence
<220> FEATURE:
<223> OTHER INFORMATION: CN3431

<400> SEQUENCE: 79
gcggccgcac gcgtgtgtgt gtgtgtgtgt gtgtgtgtgt gtgtctctgt gtgtgtgtgt 60
gtgtgtgtgt gtgtgtgtat gtgtgtgtat gtgaaattat caggcctcag tttcctcctc 120
tacaaaatgg aaatgcttac aaatgtcttg ccatgcttag catacacaag ttgctttgct 180
aagatgctga atttagtaaa ggtcagttac tattctaacc gatggtagac agagactcca 240
acagagctct tagaaagcct gcataacagt aagtctaagc aatggagtag ggcactagat 300
tattttattc ctttgcaaaa gtttctgcct gaaattgcaa tgttttctag gtataatttt 360
catagactat aaactcaagt agaacaaaga tacgagctcg ggctgggcat aaaagtcagg 420
gcagagccat ctattgctta catttgcttc tgggatccag atctttcgaa gctagcgcta 480
ccggtcgcca ccatggtctc caagggcgag gagctgttca ccggggtggt gcccatcctg 540
gtcgagctgg acggcgatgt caacggccac aagttcagcg tgtccggcga gggcgagggc 600
gatgccacct acggcaagct gaccctgaag ctgatctgca ccaccggcaa gctgcccgtg 660
ccctggccca ccctcgtgac caccctgggc tacggcgtgc agtgcttcgc ccgctacccc 720

```
gaccacatga agcagcacga cttcttcaag tccgccatgc ccgaaggcta cgtccaggag    780

cgcaccatct tcttcaaaga cgacggcaac tacaagaccc gcgccgaggt gaagttcgag    840

ggcgacaccc tggtgaaccg catcgagctg aagggcatcg acttcaagga ggacggcaac    900

atcctggggc acaagctgga gtacaactac aacagccaca acgtctatat caccgccgac    960

aagcagaaga acggcatcaa ggccaacttc aagatccgcc acaacatcga ggacggcggc   1020

gtgcagctcg ccgaccacta ccagcagaac acccccatcg gcgacggccc cgtgctgctg   1080

cccgacaacc actacctgag ctaccagtcc aagctgagca aagaccccaa cgagaagcgc   1140

gatcacatgg tcctgctgga gttcgtgacc gccgccggga tcactctcgg catggacgag   1200

ctgtacaagg gctctggtgc taccaacttc tcactgttga aacaggcagg ggatgtagag   1260

gagaatccag ggcctggtgc tagtggagac tacaaagacc atgacggaga ttataaagat   1320

catgacatcg attacaagga tgacgatgac aagtccggac tcagatctgg aggctccgga   1380

ggcccagagc cagcgaagtc tgctcccgcc ccgaaaaagg gctccaagaa ggcggtgact   1440

aaggcgcaga agaaaggcgg caagaagcgc aagcgcagcc gcaaggagag ctattccatc   1500

tatgtgtaca aggttctgaa gcaggtccac cctgacaccg gcatttcgtc caaggccatg   1560

ggcatcatga attcgtttgt gaacgacatt ttcgagcgca tcgcaggaga ggcttcccgc   1620

ctggcgcatt acaacaagcg ctcgaccatc acctcccggg agatccagac ggccgtgcgc   1680

ctgctgctgc ctggggagtt ggccaagcac gccgtgtccg agggtactaa ggccatcacc   1740

aagtacacca gcgctaagta atgaggcgcg ccgcggccgc gaattcgata tcataatcaa   1800

cctctggatt acaaaatttg tgaaagattg actggtattc ttaactatgt tgctcctttt   1860

acgctatgtg gatacgctgc tttaatgcct ttgtatcatg ctattgcttc ccgtatggct   1920

ttcattttct cctccttgta taaatcctgg ttagttcttg ccacggcgga actcatcgcc   1980

gcctgccttg cccgctgctg gacaggggct cggctgttgg gcactgacaa ttccgtggct   2040

cgagagatct tcgactgtgc cttctagttg ccagccatct gttgtttgcc cctcccccgt   2100

gccttccttg accctggaag gtgccactcc cactgtcctt tcctaataaa atgaggaaat   2160

tgcatcgcat tgtctgagta ggtgtcattc tattctgggg ggtggggtgg ggcaggacag   2220

caagggggag gattgggaag acaatagcag gcatgagatc tcacgtgcgg accgagcggc   2280

cgc                                                                 2283
```

<210> SEQ ID NO 80
<211> LENGTH: 6
<212> TYPE: PRT
<213> ORGANISM: Artificial Sequence
<220> FEATURE:
<223> OTHER INFORMATION: His tag

<400> SEQUENCE: 80

```
His His His His His His
1               5
```

<210> SEQ ID NO 81
<211> LENGTH: 8
<212> TYPE: PRT
<213> ORGANISM: Artificial Sequence
<220> FEATURE:
<223> OTHER INFORMATION: Flag tag

<400> SEQUENCE: 81

```
Asp Tyr Lys Asp Asp Asp Asp Lys
1               5
```

<210> SEQ ID NO 82
<211> LENGTH: 8
<212> TYPE: PRT
<213> ORGANISM: Artificial Sequence
<220> FEATURE:
<223> OTHER INFORMATION: Xpress tag

<400> SEQUENCE: 82

```
Asp Leu Tyr Asp Asp Asp Asp Lys
1               5
```

<210> SEQ ID NO 83
<211> LENGTH: 15
<212> TYPE: PRT
<213> ORGANISM: Artificial Sequence
<220> FEATURE:
<223> OTHER INFORMATION: Avi tag

<400> SEQUENCE: 83

```
Gly Leu Asn Asp Ile Phe Glu Ala Gln Lys Ile Glu Trp His Glu
1               5                   10                  15
```

<210> SEQ ID NO 84
<211> LENGTH: 26
<212> TYPE: PRT
<213> ORGANISM: Artificial Sequence
<220> FEATURE:
<223> OTHER INFORMATION: Calmodulin tag

<400> SEQUENCE: 84

```
Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

<210> SEQ ID NO 85
<211> LENGTH: 9
<212> TYPE: PRT
<213> ORGANISM: Artificial Sequence
<220> FEATURE:
<223> OTHER INFORMATION: HA tag

<400> SEQUENCE: 85

```
Tyr Pro Tyr Asp Val Pro Asp Tyr Ala
1               5
```

<210> SEQ ID NO 86
<211> LENGTH: 10
<212> TYPE: PRT
<213> ORGANISM: Artificial Sequence
<220> FEATURE:
<223> OTHER INFORMATION: Myc tag

<400> SEQUENCE: 86

```
Glu Gln Lys Leu Ile Ser Glu Glu Asp Leu
1               5                   10
```

<210> SEQ ID NO 87
<211> LENGTH: 8
<212> TYPE: PRT
<213> ORGANISM: Artificial Sequence
<220> FEATURE:
<223> OTHER INFORMATION: Strep tag

<400> SEQUENCE: 87

-continued

```
Trp Arg His Pro Gln Phe Gly Gly
1               5


<210> SEQ ID NO 88
<211> LENGTH: 8
<212> TYPE: PRT
<213> ORGANISM: Artificial Sequence
<220> FEATURE:
<223> OTHER INFORMATION: Strep tag II

<400> SEQUENCE: 88

Trp Ser His Pro Gln Phe Glu Lys
1               5


<210> SEQ ID NO 89
<211> LENGTH: 13
<212> TYPE: PRT
<213> ORGANISM: Artificial Sequence
<220> FEATURE:
<223> OTHER INFORMATION: Softag 1

<400> SEQUENCE: 89

Ser Leu Ala Glu Leu Leu Asn Ala Gly Leu Gly Gly Ser
1               5                   10


<210> SEQ ID NO 90
<211> LENGTH: 8
<212> TYPE: PRT
<213> ORGANISM: Artificial Sequence
<220> FEATURE:
<223> OTHER INFORMATION: Softag 3

<400> SEQUENCE: 90

Thr Gln Asp Pro Ser Arg Val Gly
1               5


<210> SEQ ID NO 91
<211> LENGTH: 14
<212> TYPE: PRT
<213> ORGANISM: Artificial Sequence
<220> FEATURE:
<223> OTHER INFORMATION: V5 tag

<400> SEQUENCE: 91

Gly Lys Pro Ile Pro Asn Pro Leu Leu Gly Leu Asp Ser Thr
1               5                   10
```

ARTIFICIAL EXPRESSION CONSTRUCTS FOR MODULATING GENE EXPRESSION IN CLAUSTRUM NEURONS

CROSS-REFERENCE TO RELATED APPLICATIONS

This application is a U.S. National Phase Patent Application based on International Patent Application No. PCT/US2022/022656, filed on Mar. 30, 2022, which claims priority to U.S. Provisional Patent Application No. 63/167,995 filed on Mar. 30, 2021, the contents of both of which are incorporated herein by reference in their entirety as if fully set forth herein.

STATEMENT REGARDING FEDERALLY SPONSORED RESEARCH OR DEVELOPMENT

This invention was made with government support under MH121274 awarded by the National Institutes of Health. The government has certain rights in the invention.

REFERENCE TO SEQUENCE LISTING

The Sequence Listing associated with this application is provided in text format in lieu of a paper copy and is hereby incorporated by reference into the specification. The name of the text file containing the Sequence Listing is 2YZ0627_ST25.txt. The text file is 122,946 bytes, was created on Sep. 25, 2023, and is being submitted electronically via EFS Web or Patent Center.

FIELD OF THE DISCLOSURE

The current disclosure provides artificial expression constructs for modulating gene expression in targeted central nervous system cell types. The artificial expression constructs can be used to express synthetic genes or modify gene expression in claustrum neurons including L6 IT Car3 neurons.

BACKGROUND OF THE DISCLOSURE

To fully understand the biology of the brain, different cell types need to be distinguished and defined and, to further study them, artificial expression constructs that can label and perturb them need to be identified. In mouse, recombinase driver lines have been used to great effect to label cell populations that share marker gene expression. However, the creation, maintenance, and use of such lines that label cell types with high specificity can be costly, frequently requiring triple transgenic crosses, which yield a low frequency of experimental animals. Furthermore, those tools require germline transgenic animals and thus are not applicable to humans.

Serotonergic psychedelic drugs such as psilocybin have been purported to have broad therapeutic potential for a range of human disorders including anxiety, depression, obsessive compulsive disorder (OCD), addiction, etc., yet the cellular mechanisms of action in the mammalian brain remain poorly understood. In order to better understand the cellular mechanism of drug action it will be helpful to directly assay the effects of these drugs on living brain cells. A promising approach in this context is to use mature brain slices of the mammalian brain and assay drug effects on intrinsic and synaptic responses measured from neurons using electrophysiology and/or activity imaging.

One major target for evaluating effects of serotonergic psychedelic drugs is the claustrum, a small brain region rich in expression of the gene HTR2a, which is believed to be the main brain receptor through which these drugs act. The claustrum is a thin, sheet-like structure between the insular cortex and the putamen. Although its function is not well understood, it has been implicated in various mechanisms involved in directing attention, cross-modal transfer, salience detection, multisensory integration, perceptual binding, cognition, and consciousness. Thus, tools for providing targeted gene expression in the claustrum can be used to facilitate targeted analysis of serotonergic psychedelic drug action, or for screening the efficacy of new related compounds with therapeutic potential but that do not elicit a psychedelic experience. Additionally, tools for providing targeted gene expression in the claustrum may be leveraged to deliver various transgenes into neurons that could be helpful in dissecting the signaling pathways activated by these drugs.

SUMMARY OF THE DISCLOSURE

The current disclosure provides artificial expression constructs that drive gene expression in claustrum neurons. Particular embodiments of the artificial expression constructs utilize the following enhancers to drive gene expression within claustrum neurons: MGT_E51, MGT_E52, MGT_E57, eHGT_770m, eHGT_774m, eHGT_772m, eHGT_486m, eHGT_875m, eHGT_923m, eHGT_924m, eHGT_925m, and eHGT_926m.

In particular embodiments, the artificial enhancer elements include a concatenated core of an enhancer. Examples include a core or concatenated core of eHGT_774m, eHGT_772m, and/or eHGT486m. These artificial enhancer elements can provide higher levels and more rapid onset of transgene expression compared to a single full length original (native) enhancer.

In particular embodiments, the enhancer core includes the sequence as set forth in any one of SEQ ID NO: 54, SEQ ID NO: 56, and SEQ ID NO: 58. In particular embodiments, these cores are concatenated and have 2, 3, 4, 5, 6, 7, 8, 9, or 10 copies of the core sequence. In particular embodiments, a three-copy concatemer of the selected enhancer cores include the sequence as set forth in any one of SEQ ID NO: 55, SEQ ID NO: 57, and SEQ ID NO: 59.

Particular embodiments of the artificial expression constructs utilize 3xcore2_eHGT_774m, 3xcore2_eHGT_772m, and/or 3xCore_eHGT486m to drive gene expression within claustrum neurons.

Particular embodiments provide artificial expression constructs including the features of vectors described herein including vectors: AiP1211, AiP1212, AiP1218, ON2603, CN2606, CN2612, CN2261, AiP1279, AiP1277, AiP1278, AiP1344, CN3041, CN3608, CN2582, CN3367, CN4095, CN4096, CN3430, and CN3431.

BRIEF DESCRIPTION OF THE FIGURES

Some of the drawings submitted herein may be better understood in color. Applicant considers the color versions of the drawings as part of the original submission and reserves the right to present color images of the drawings in later proceedings.

FIG. 10. Sequences supporting the disclosure. Sequences include: core2_eHGT_774m (SEQ ID NO: 54); 3xcore2_eHGT_774m (SEQ ID NO: 55); core2_eHGT_772m (SEQ ID NO: 56); 3xcore2_eHGT_772m (SEQ ID NO: 57); Core_eHGT486m (SEQ ID NO: 58); 3xCore_eHGT486m (SEQ ID NO: 59); MGT_E51 (SEQ ID NO: 1); MGT_E52 (SEQ ID NO: 2); MGT_E57 (SEQ ID NO: 3); eHGT_770m (SEQ ID NO: 4); eHGT_774m (SEQ ID NO: 5); eHGT_772m (SEQ ID NO: 6); eHGT_486m (SEQ ID NO: 7); eHGT_875m (SEQ ID NO: 60); eHGT_923m (SEQ ID NO: 61); eHGT_924m (SEQ ID NO: 62); eHGT_925m (SEQ ID NO: 63); eHGT_926m (SEQ ID NO: 64); Beta-Globin Minimal Promoter (pBGmin/minBGlobin/minBGprom) (SEQ ID NO: 8); minCMV Promoter (SEQ ID NO: 9); Mutated minCMV Promoter (SacI R E site removed) (SEQ ID NO: 10); minRho Promoter (SEQ ID NO: 11); minRho* Promoter (SEQ ID NO: 12); Hsp68 minimal Promoter (proHsp68) (SEQ ID NO: 13); SYFP2 (SEQ ID NO: 14); EGFP (SEQ ID NO: 15); Optimized Flp recombinase (FlpO) (SEQ ID NO: 16); Improved Cre recombinase (iCre) (SEQ ID NO: 17); SP10 insulator (SP10ins) (SEQ ID NO: 18); 3xSP10ins (SEQ ID NO: 19); 3XFLAG (SEQ ID NO: 65); 10aa (SEQ ID NO: 66); H2B (SEQ ID NO: 67); WPRE3 (SEQ ID NO: 20); WPRE (SEQ ID NO: 21); BGHpA (SEQ ID NO: 22); HGHpA (SEQ ID NO: 23); P2A (SEQ ID NO: 24); T2A (SEQ ID NO: 25); E2A (SEQ ID NO: 26); F2A (SEQ ID NO: 27); Exemplary Plasmid Backbone 1—Left ITR (SEQ ID NO: 28); Exemplary Plasmid Backbone 1—Right ITR: (SEQ ID NO: 29); Exemplary Plasmid Backbone 2—Left ITR (SEQ ID NO: 30); Exemplary Plasmid Backbone 2—Right ITR (SEQ ID NO: 31); PHP.eB capsid (SEQ ID NO: 32); AAV9 VP1 capsid protein (SEQ ID NO: 33); tet-Transactivator version 2 (tTA2) (SEQ ID NO: 34); GTPase HRas [*Homo sapiens*](SEQ ID NO: 35); Substance P is position 58-68 of Protachykinin-1 [*Homo sapiens*](SEQ ID NO: 36); Oxytocin is position 20-28 of Oxytocin-neurophysin 1 [*Homo sapiens*](SEQ ID NO: 37); GCaMP6m (SEQ ID NO: 38); GCaMP6s (SEQ ID NO: 39); GCaMP6f (SEQ ID NO: 40); AiP1211 (length between ITRs: 2901) (SEQ ID NO: 41); AiP1212 (length between ITRs: 3046) (SEQ ID NO: 42); AiP1218 (length between ITRs: 2988) (SEQ ID NO: 43); CN2603 (length between ITRs: 1951) (SEQ ID NO: 44); CN2606 (length between ITRs: 1985) (SEQ ID NO: 45); CN2612 (length between ITRs: 2131) (SEQ ID NO: 46); CN2261 (length between ITRs: 1664) (SEQ ID NO: 47); AiP1211 (length between ITRs: 2901) (SEQ ID NO: 41); AiP1212 (length between ITRs: 3046) (SEQ ID NO: 42); AiP1218 (length between ITRs: 2988) (SEQ ID NO: 43); CN2603 (length between ITRs: 1951) (SEQ ID NO: 44); CN2606 (length between ITRs: 1985) (SEQ ID NO: 45); CN2612 (length between ITRs: 2131) (SEQ ID NO: 46); CN2261 (length between ITRs: 1664) (SEQ ID NO: 47); AiP1279 (length between ITRs: 2988) (SEQ ID NO: 68); AiP1277 (length between ITRs: 2901) (SEQ ID NO: 69); AiP1278 (length between ITRs: 3046) (SEQ ID NO: 70); AiP1344 (length between ITRs: 2178) (SEQ ID NO: 71); CN3041 (length between ITRs: 2039) (SEQ ID NO: 72); CN3608 (length between ITRs: 2153) (SEQ ID NO: 73); CN2582 (length between ITRs: 2090) (SEQ ID NO: 74); CN3367 (length between ITRs: 2316) (SEQ ID NO: 75); CN4095 (length between ITRs: 2451) (SEQ ID NO: 76); CN4096 (length between ITRs: 2439) (SEQ ID NO: 77); CN3430 (length between ITRs: 2704) (SEQ ID NO: 78); and CN3431 (length between ITRs: 2283) (SEQ ID NO: 79).

DETAILED DESCRIPTION

Figure 1A:
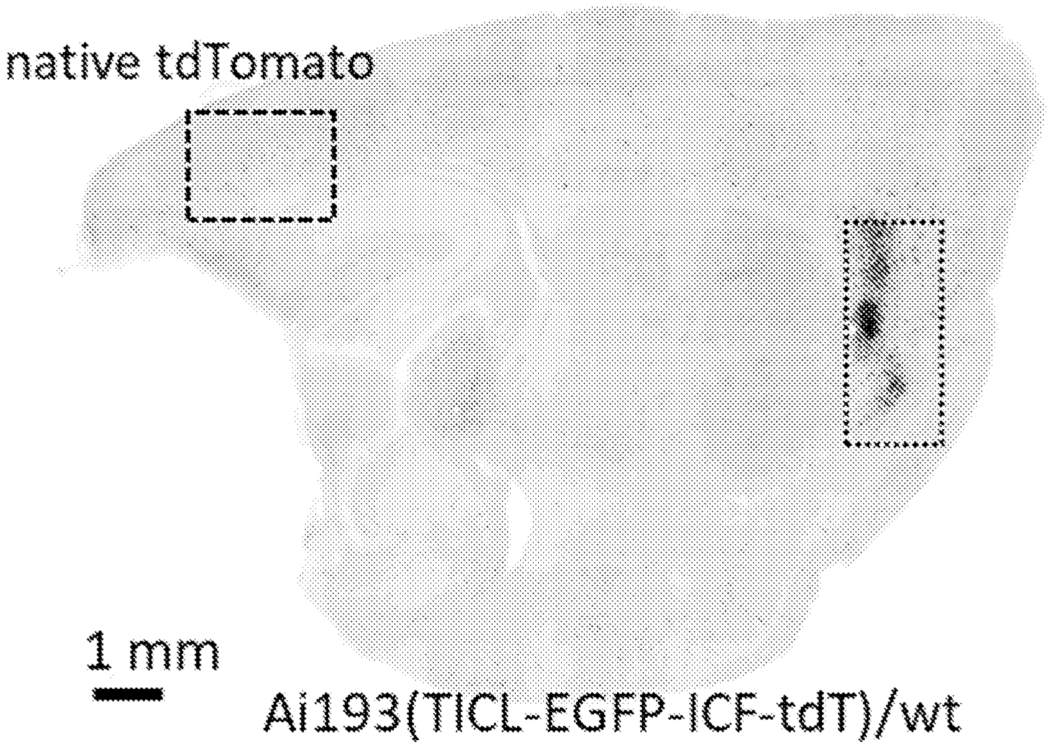
FIGS. 1A-1C. AiV1211.1 (VT1130c) rAAV-MGT_E51-minBGprom-FlpO-WPRE-hGHpA, 1E+11 genome copies (gc) delivered via retro-orbital (RO) injection. (1A) Representative images of tdTomato fluorescent reporter expression in a mouse brain sagittal section following retro-orbital injection of AiV1211.1 virus into an Ai193 reporter animal. (1B, 1C) Higher magnification images of native tdTomato signal in the primary visual cortex (V1) and claustrum (CLA) are shown. Scale bars are indicated.
Figure 1B:
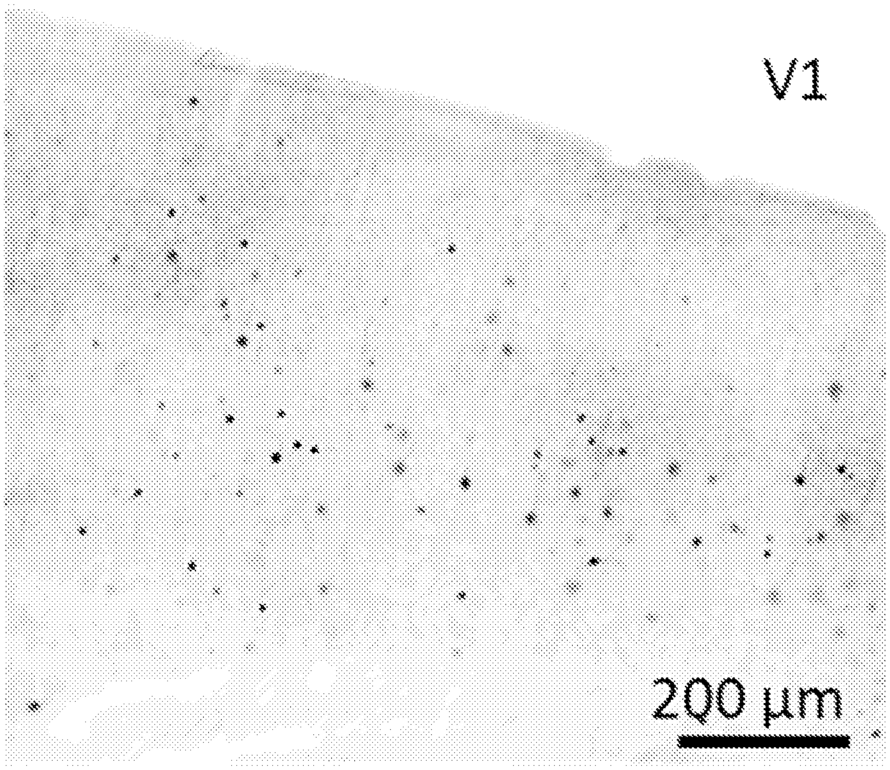
Figure 1C:
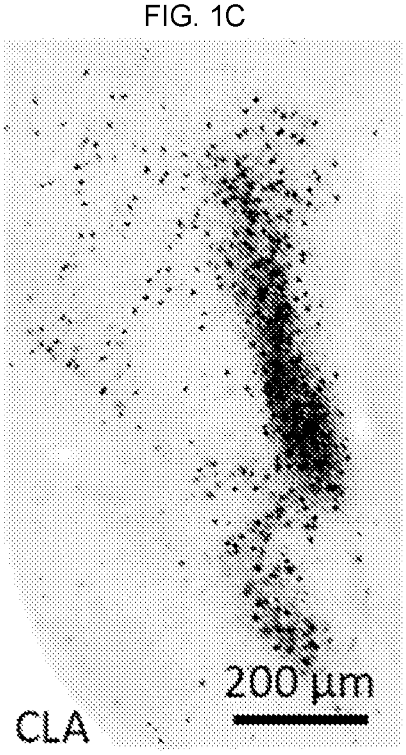
Figure 2A:
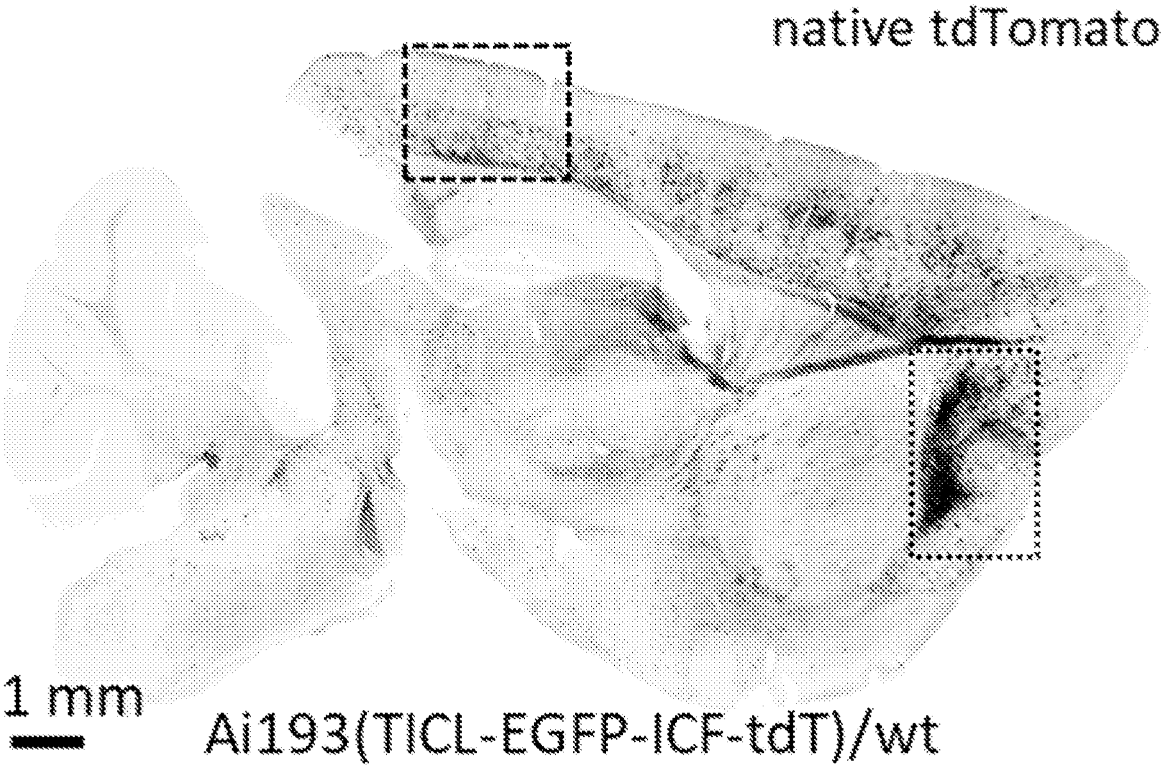
FIGS. 2A-2C: AiV1212.1 (VT1131c) rAAV-MGT_E52-minBGprom-FlpO-WPRE-hGHpA, 1E+11 gc delivered via RO injection. (2A) Representative images of tdTomato fluorescent reporter expression in a mouse brain sagittal section following retro-orbital injection of AiV1212.1 virus into an Ai193 reporter animal. (2B, 2C) Higher magnification images of native tdTomato signal in the primary visual cortex (V1) and claustrum (CLA) are shown. Scale bars are indicated.
Figure 2B:
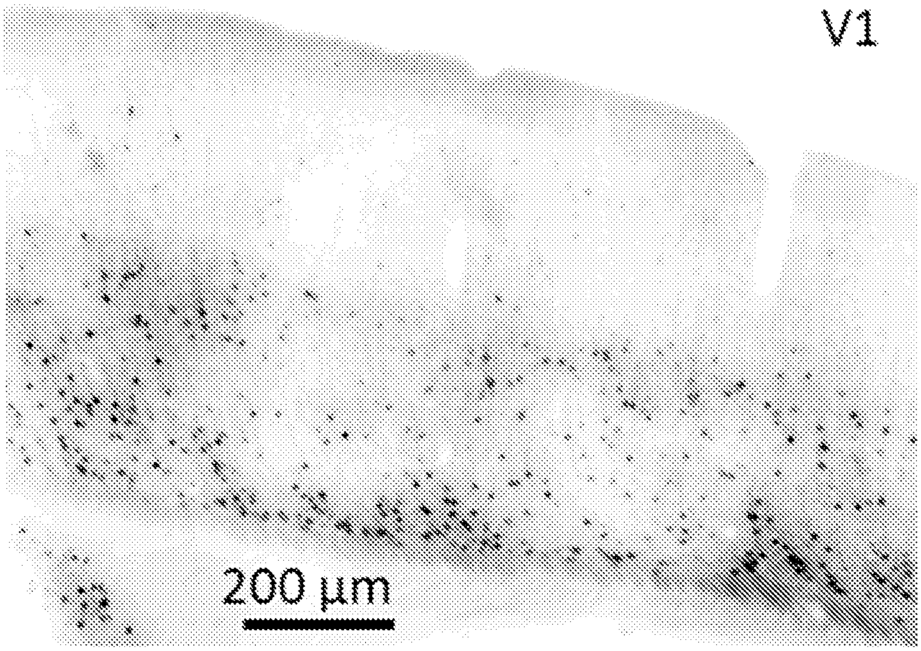
Figure 2C:
Figure 3A:
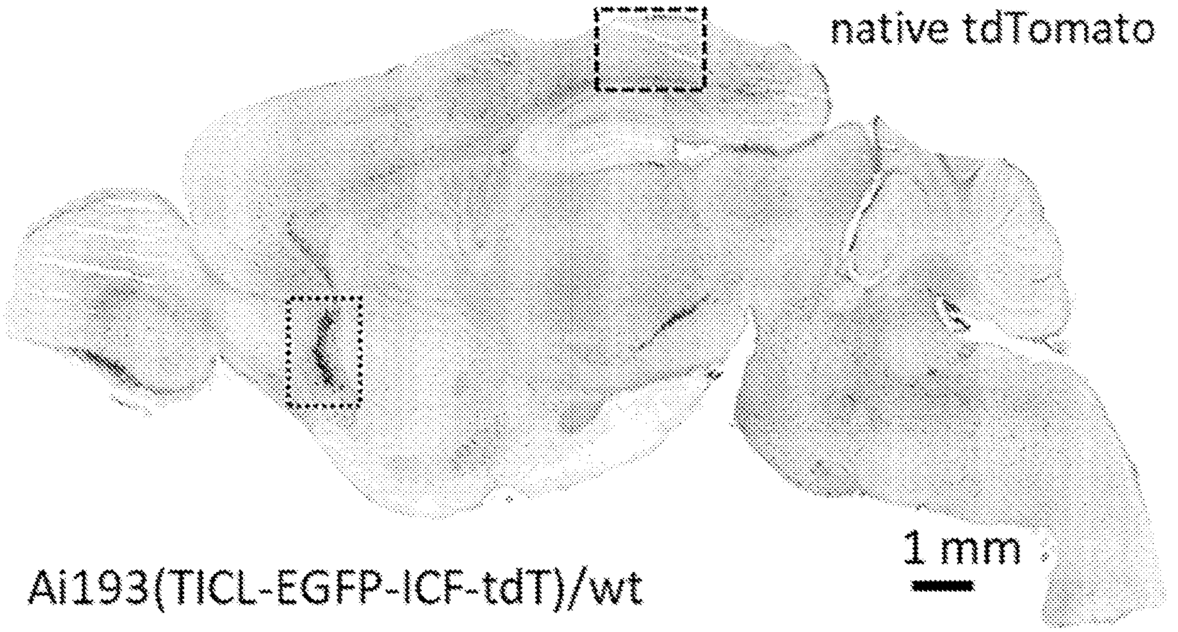
FIGS. 3A-3C: AiV1218.1 (VT1135c) rAAV-MGT_E57-minBGprom-FlpO-WPRE-hGHpA, 1E+11 gc delivered via RO injection (3A) Representative images of tdTomato fluorescent reporter expression in a mouse brain sagittal section following retro-orbital injection of AiV218.1 virus into an Ai193 reporter animal. (3B, 3C) Higher magnification images of native tdTomato signal in the primary visual cortex (V1) and claustrum (CLA) are shown. Scale bars are indicated.
Figure 3B:
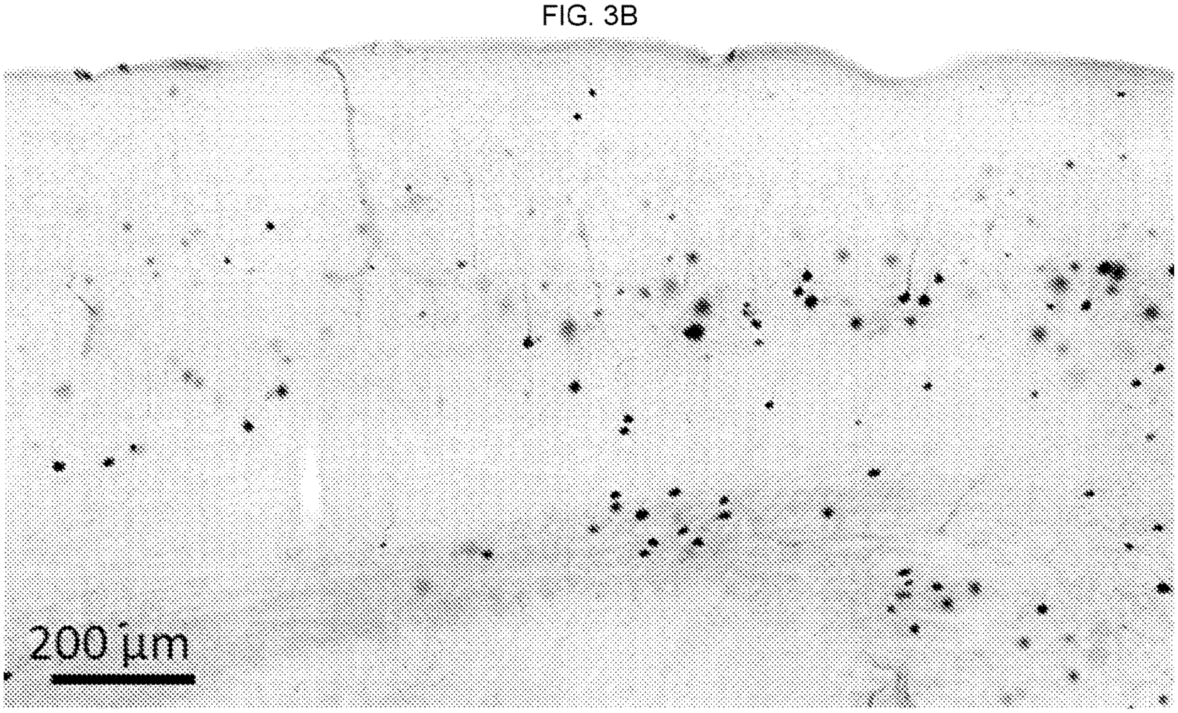
Figure 3C:
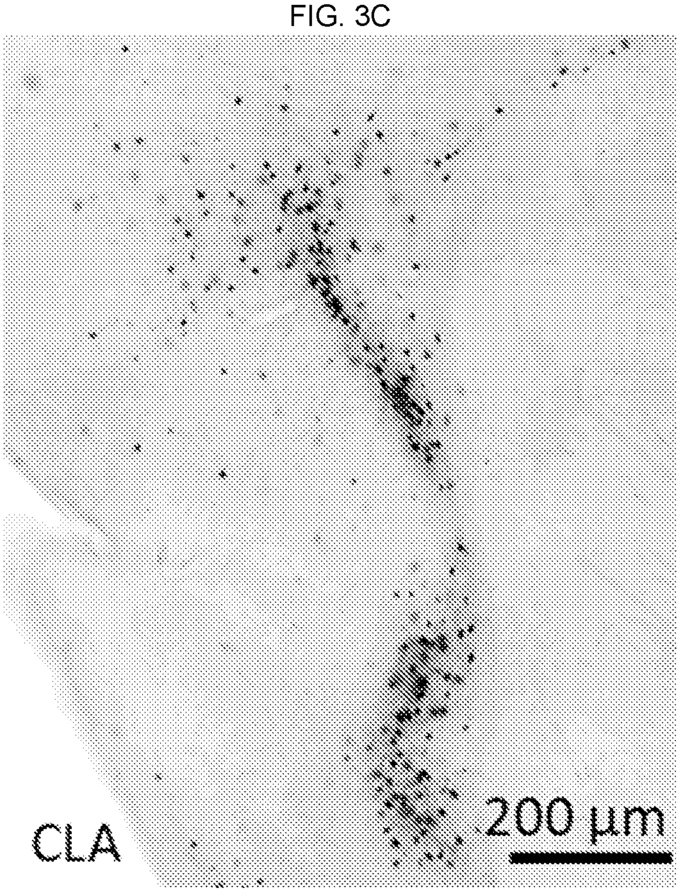
Figures 4A, 4B:
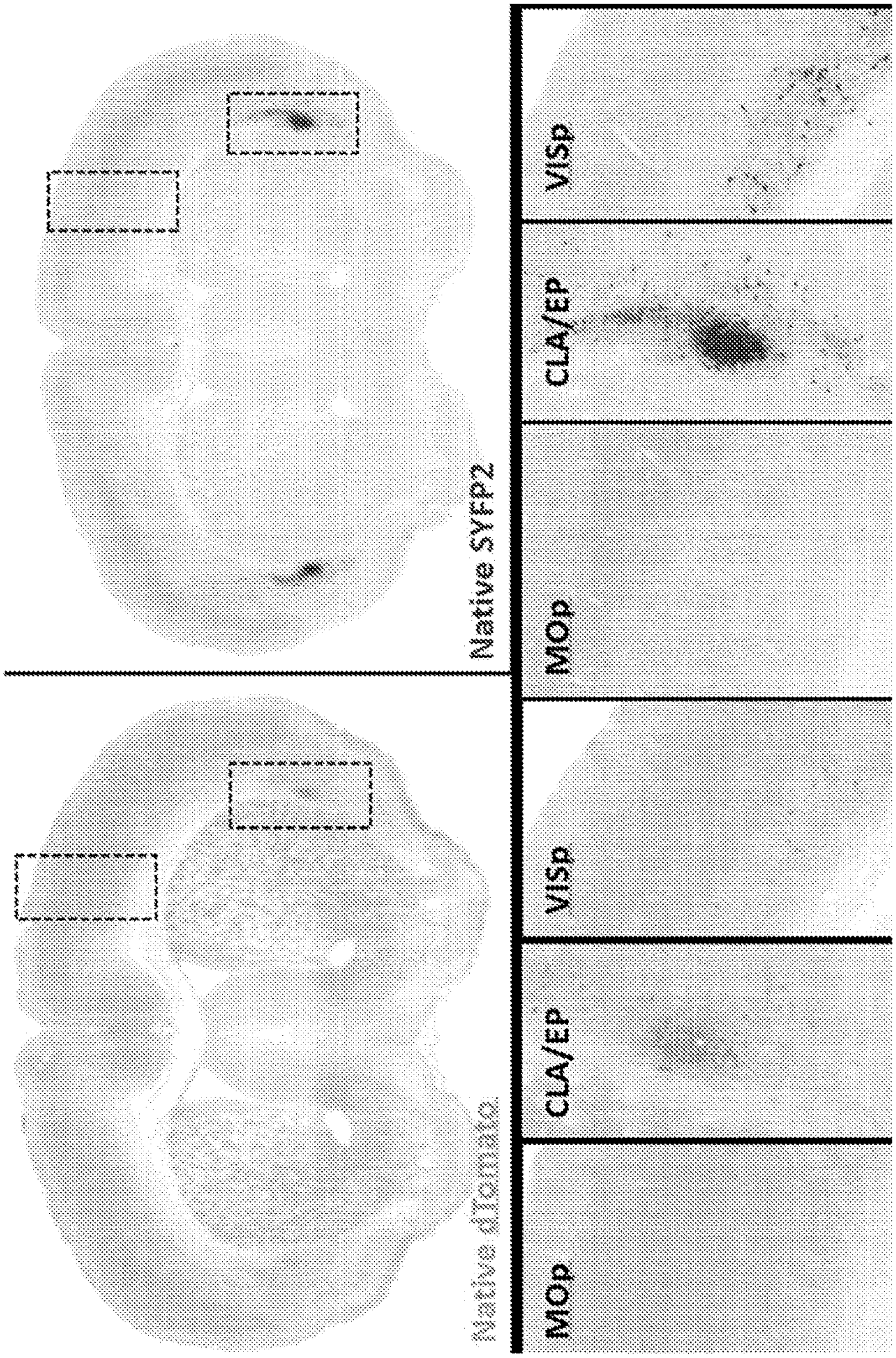
FIGS. 4A-4D: Fluorescent reporter expression in mouse brain coronal sections following retro-orbital injection of AAV vectors designated above. (4A, 4B) Native fluorescence from the virally expressed fluorescent proteins. (4C, 4D) Fluorescence is observed due to injection of Cre or Flp virus into Ai193, a Cre or Flp reporter. Relevant brain regions include claustrum (CLA), primary motor cortex (MOp) and primary visual cortex (VISp).
Figures 4C, 4D:
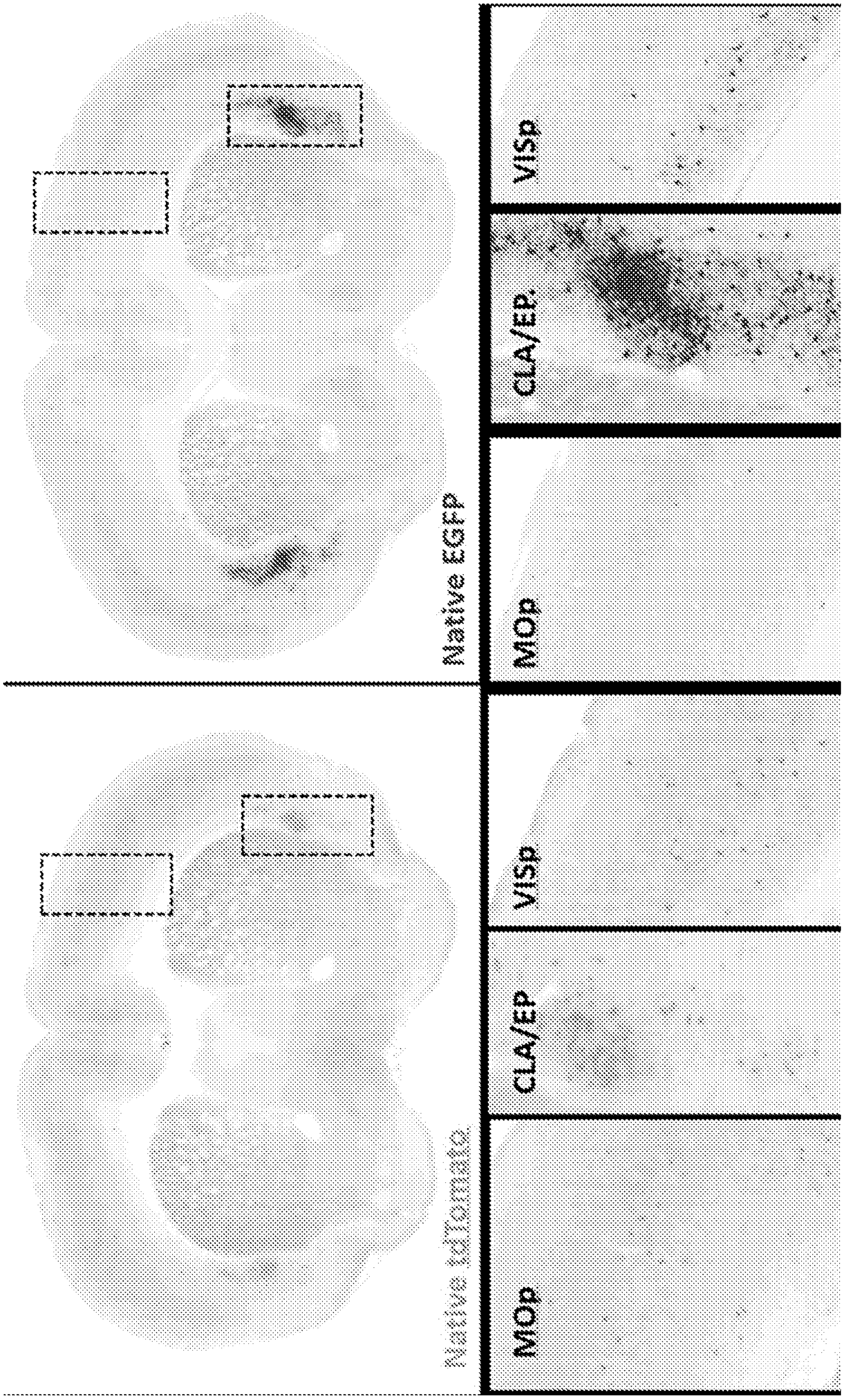
Figure 5:
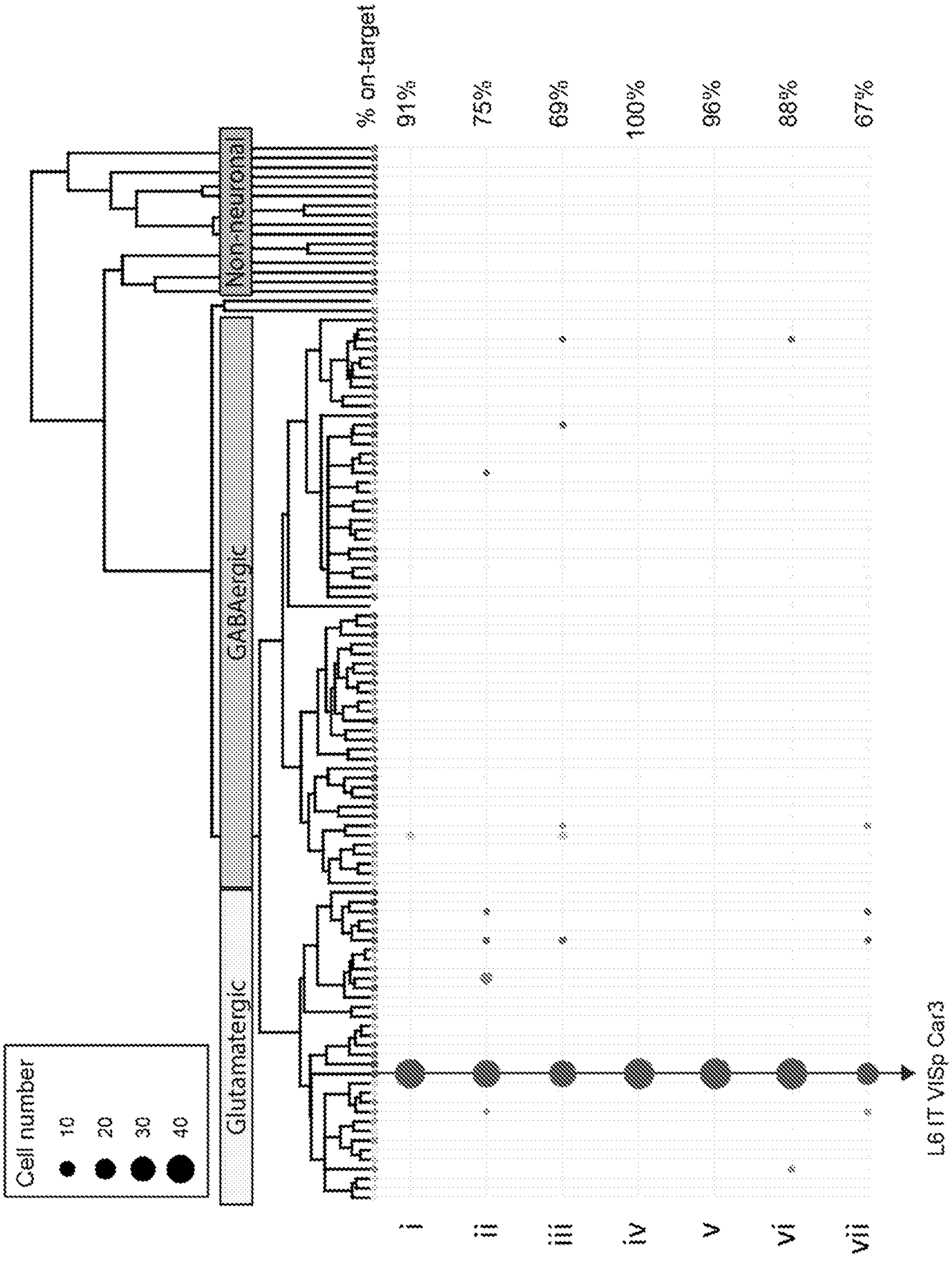
FIG. 5: Single cell RNA-sequencing of cells isolated from claustrum following retro-orbital injection of AAV vectors serotype PHPeB designated on the left. The transcriptomic identity of the cells was assessed by mapping to VISp taxonomy from Tasic et al. Nature 2018. Most cells map to a single transcriptomic type, L6 IT Car3, which represents rare neurons in VISp that are most transcriptomically related to excitatory cells from CLA (as shown in Yao et al., Cell, 2021). Labels on left are i) AiV1211 MGT_E51 FlpO CLA GFP-positive, DAPI-negative; ii) AiV1212 MGT_E52 FlpO CLA RFP-positive, DAPI-negative; iii) AiV1218 MGT_E57 FlpO CLA-RFP-positive, DAPI-negative; iv) AiV1277 MGT_E51 SYFP2 CLA GFP-positive, DAPI-negative; v) AiV1278 MGT_E52 SYFP2 CLA GFP-positive, DAPI-negative; vi) AiV1279 MGT_E57 SYFP2 CLA GFP-positive, DAPI-negative; and vii) AiV1344 MGT_E52 iCre CLA GFP-positive, DAPI-negative.
Figure 6A:
FIGS. 6A-6D. (6A) Fluorescent reporter expression in mouse brain sagittal section following retro-orbital injection of AAV vector #CN2606 serotype PHPeB. Scale bar: 1 mm. Native SYFP2 signal in the claustrum region is indicated by the black arrow. (6B) Allen Mouse Brain Atlas at matched sagittal level showing annotation of brain regions. Relevant brain regions include claustrum (CLA) and visual cortex (VIS) region of neocortex (CTX). (6C) Higher magnification view of native SYFP2 expression in the boxed VIS region of CTX from FIG. 6A. Scale bar: 200 microns. (6D) Higher magnification view of native SYFP2 expression in the boxed CLA region from FIG. 6A. Scale bar: 200 microns.
Figure 6B:
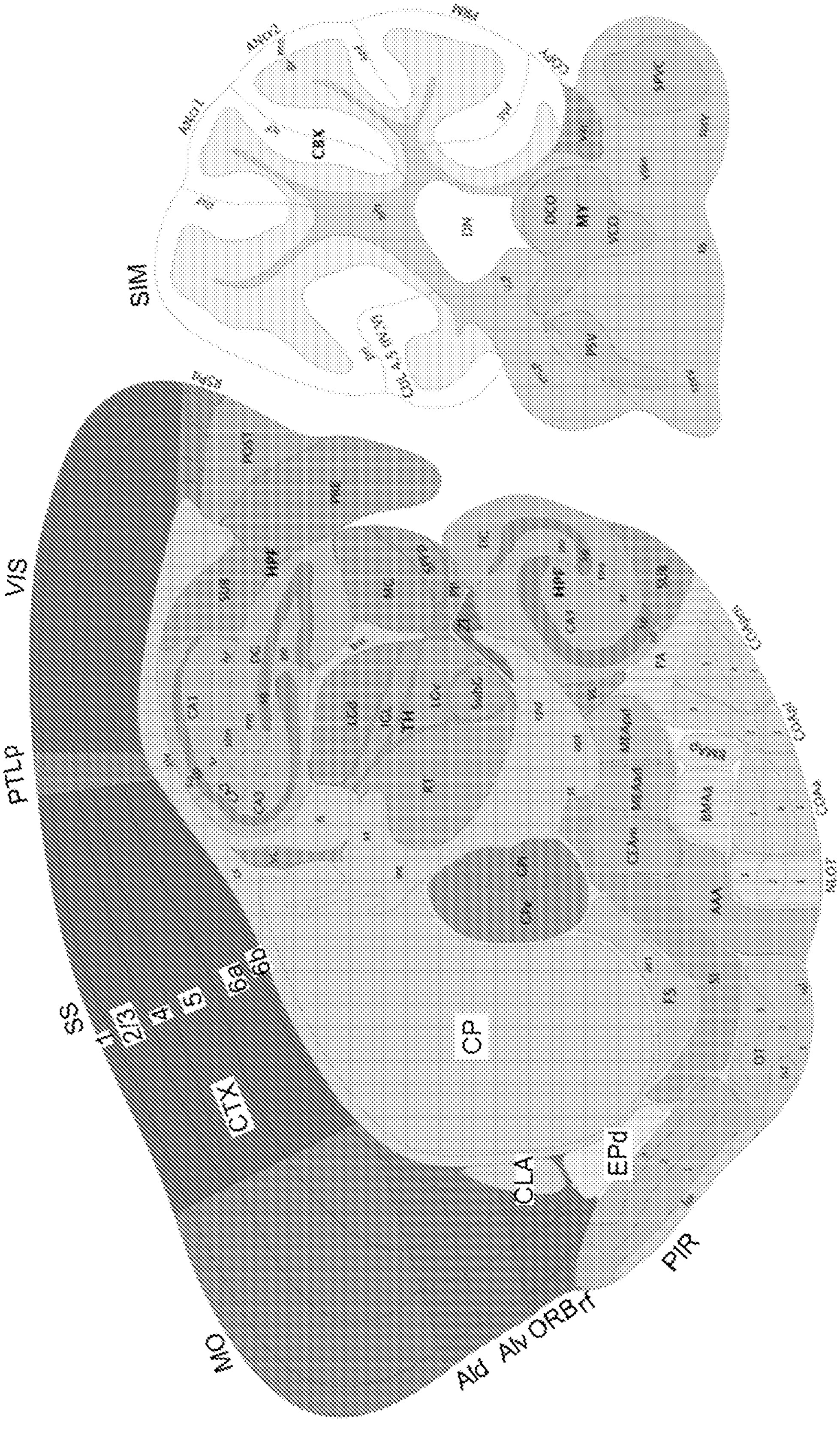
Figure 6C:
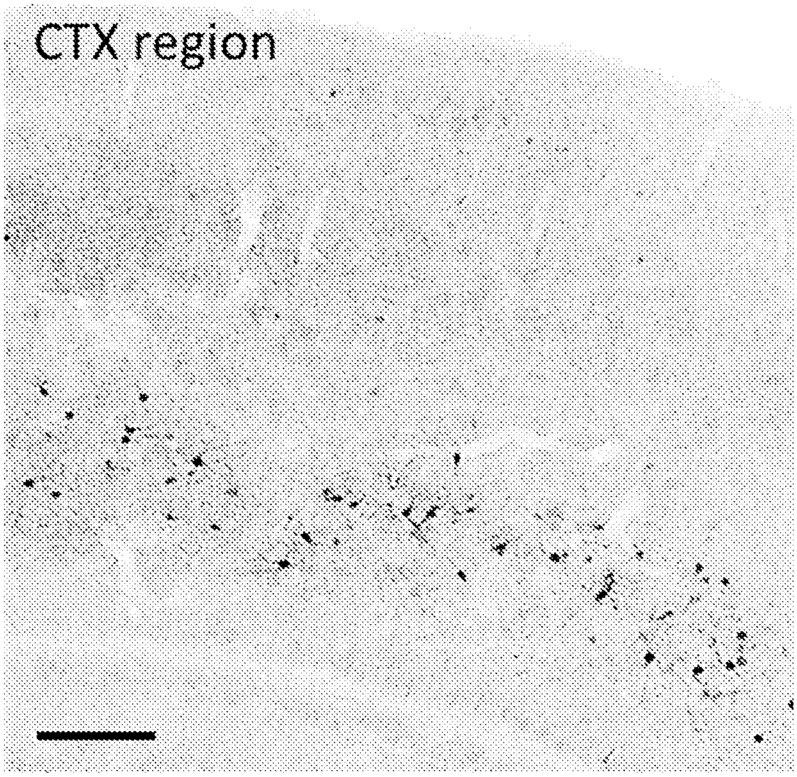
Figure 6D:
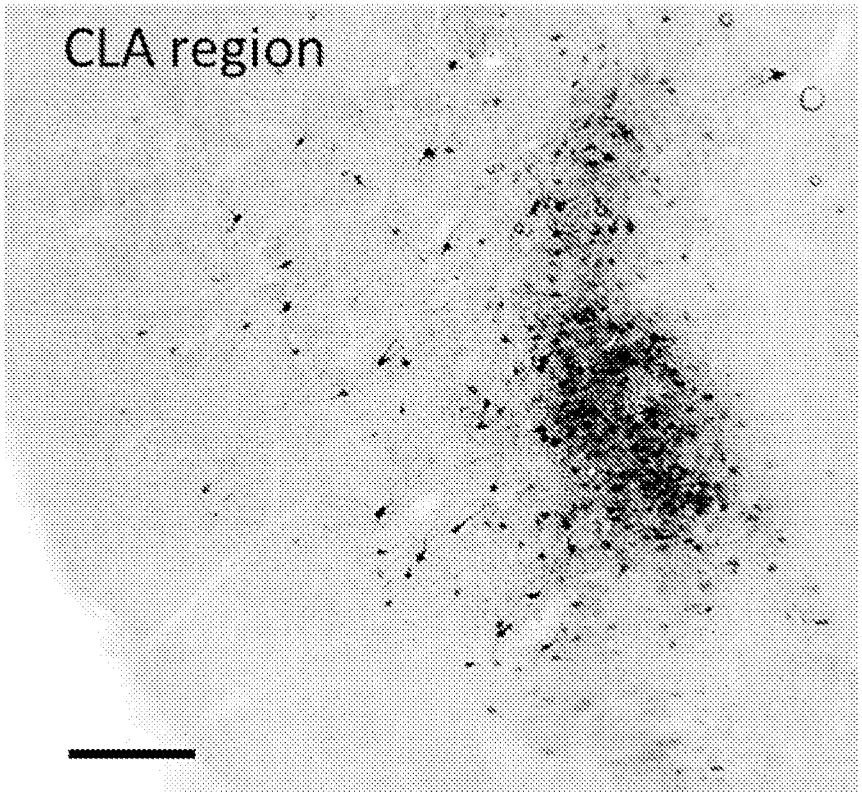
Figure 7A:
FIGS. 7A-7D. (7A) Fluorescent reporter expression in mouse brain sagittal section following retro-orbital injection of AAV vector #CN2612 serotype PHPeB. Scale bar: 1 mm. Native SYFP2 signal in the claustrum region is indicated by the black arrow. (7B) Allen Mouse Brain Atlas at matched sagittal level showing annotation of brain regions. Relevant brain regions include claustrum (CLA) and visual cortex (VIS) region of neocortex (CTX). (7C) Higher magnification view of native SYFP2 expression in the boxed VIS region of CTX from FIG. 7A. Scale bar: 200 microns. (7D) Higher magnification view of native SYFP2 expression in the boxed CLA region from FIG. 7A. Scale bar: 200 microns.
Figure 7B:
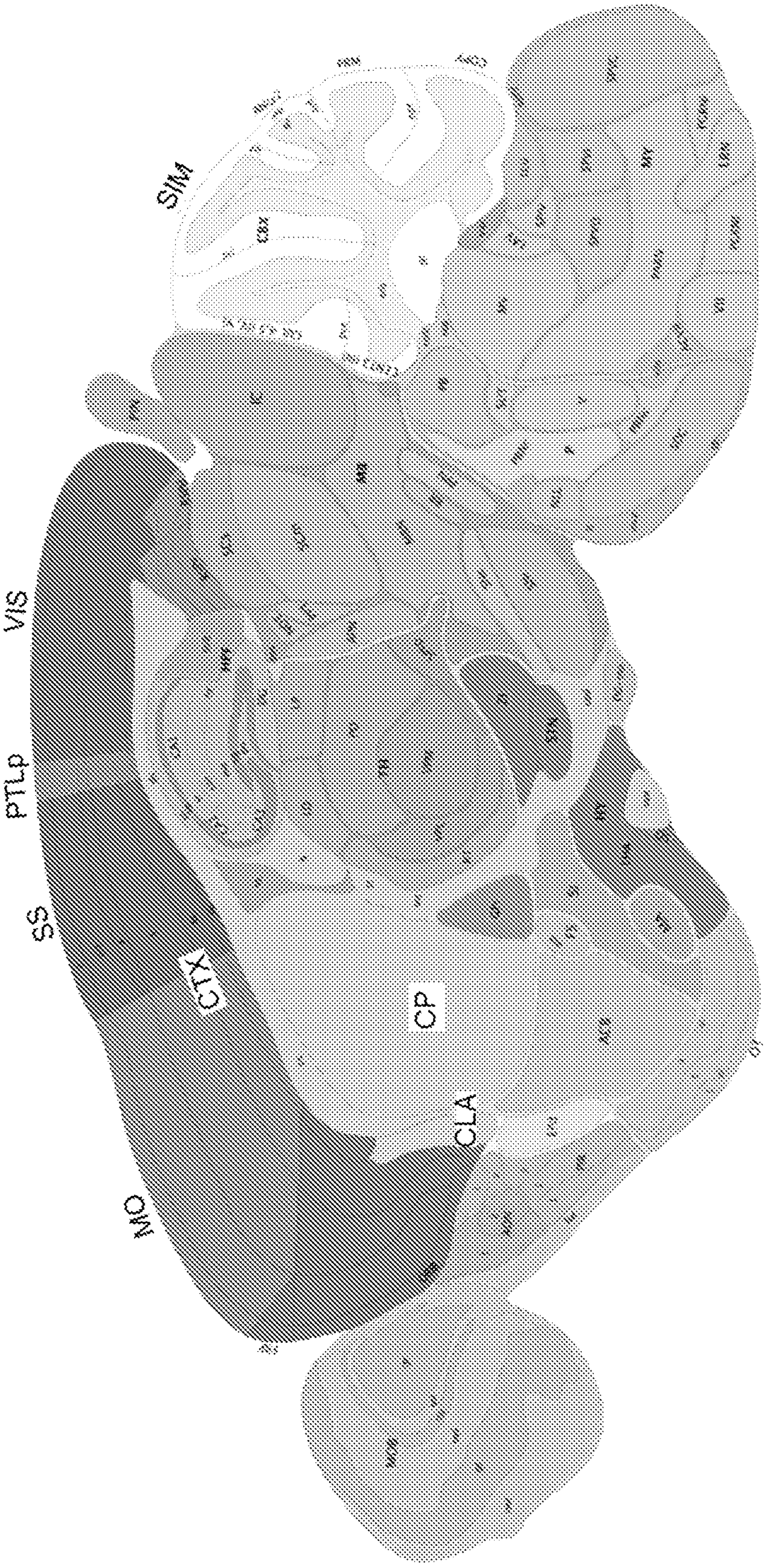
Figure 7C:
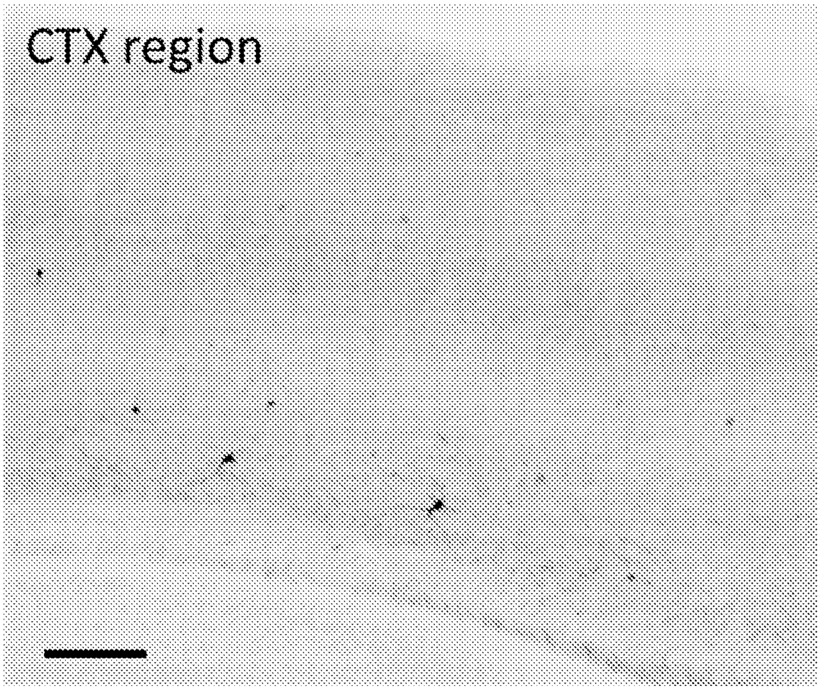
Figure 7D:
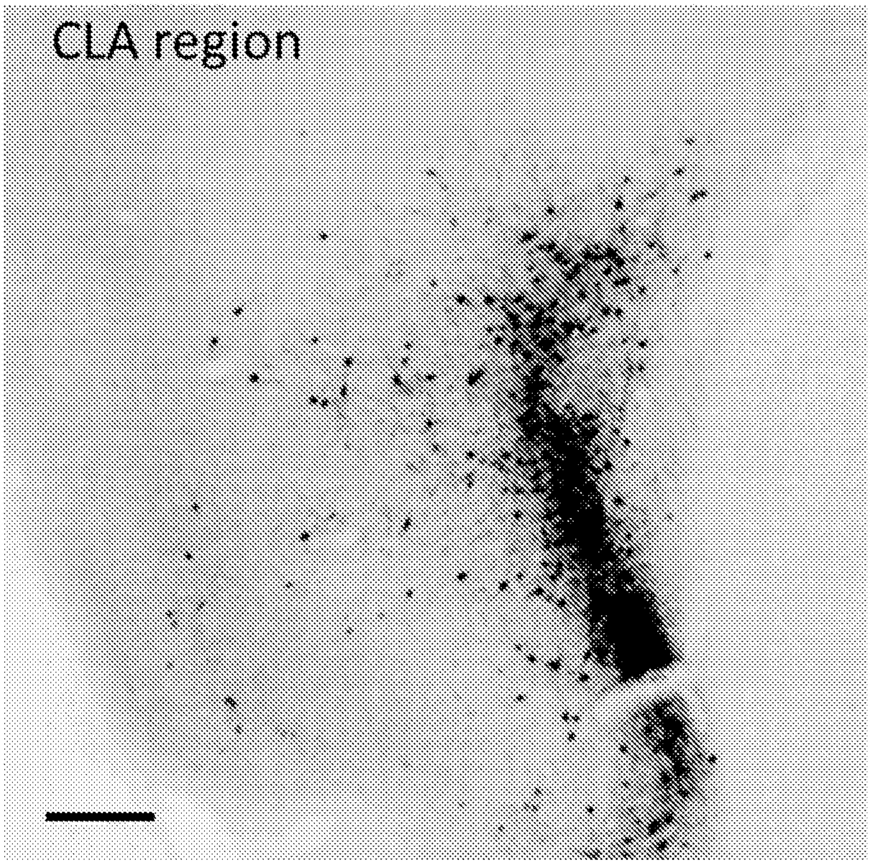
Figure 8A:
FIGS. 8A, 8B. Fluorescent reporter expression in mouse brain sagittal sections at 36 days following retro-orbital injection of AAV vector #CN2612 serotype PHP.eB (8A) and optimized 3xCore design #CN3608 (8B) at a matched dose of 5E+11vg. Scale bar: 1 mm. Native SYFP2 signal in the claustrum region is indicated by the black arrow. Imaging was performed using matched exposure times.
Figure 8B:
Figure 9:
FIG. 9. Fluorescent reporter expression in rat brain sagittal section following intracerebroventricular injection of AAV vector #CN2612 serotype PHPeB at a dose of 1.53E11 vg. Scale bar: 1 mm. Native SYFP2 signal in the claustrum region is indicated by the black arrow.

To fully understand the biology of the brain, different cell types need to be distinguished and defined and, to further study them, artificial expression constructs that can label and perturb them need to be identified (Tasic, Curr. Opin. Neurobiol. 50, 242-249 (2018); Zeng & Sanes, Nat. Rev. Neurosci. 18, 530-546 (2017)). In mouse, recombinase driver lines have been used to great effect to label cell populations that share marker gene expression (Daigle et al., Cell 174, 465-480.e22 (2018); Taniguchi, et al., Neuron 71, 995-1013 (2011); Gong et al., J. Neurosci. 27, 9817-9823 (2007)). However, the creation, maintenance, and use of such lines that label cell types with high specificity can be costly, frequently requiring triple transgenic crosses, which yield a low frequency of experimental animals. Furthermore, those tools require germline transgenic animals and thus are not applicable to humans.

The current disclosure provides artificial expression constructs that drive gene expression in claustrum neurons. Particular embodiments of the artificial expression constructs utilize the following enhancers to drive gene expression within claustrum neurons MGT_E51, MGT_E52, MGT_E57, eHGT_770m, eHGT_774m, eHGT_772m, eHGT_486m, eHGT_875m, eHGT_923m, eHGT_924m, eHGT_925m, and eHGT_926m.

In particular embodiments, the artificial enhancer elements include a concatenated core of an enhancer. Examples include a core or concatenated core of eHGT_774m, eHGT_772m, and/or eHGT486m. These artificial enhancer elements can provide higher levels and more rapid onset of transgene expression compared to a single full length original (native) enhancer.

In particular embodiments, the enhancer core includes the sequence as set forth in any one of SEQ ID NO: 54, SEQ ID NO: 56, and SEQ ID NO: 58. In particular embodiments, these cores are concatenated and have 2, 3, 4, 5, 6, 7, 8, 9, or 10 copies of the core sequence. In particular embodiments, a three-copy concatemer of the selected enhancer cores include the sequence as set forth in any one of SEQ ID NO: 55, SEQ ID NO: 57, and SEQ ID NO: 59.

Particular embodiments of the artificial expression constructs utilize 3xcore2_eHGT_774m, 3xcore2_eHGT_772m, and/or 3xCore_eHGT486m to drive gene expression within claustrum neurons.

Particular embodiments provide artificial expression constructs including the features of vectors described herein including vectors: AiP1211, AiP1212, AiP1218, CN2603, CN2606, CN2612, CN2261, AiP1279, AiP1277, AiP1278, AiP1344, CN3041, CN3608, CN2582, CN3367, CN4095, CN4096, CN3430, and CN3431.

Aspects of the disclosure are now described with the following additional options and detail: (i) Artificial Expression Constructs & Vectors for Targeted Expression of Genes in Targeted Cell Types; (ii) Compositions for Administration (iii) Cell Lines Including Artificial Expression Constructs; (iv) Transgenic Animals; (v) Methods of Use; (vi) Kits and Commercial Packages; (vii) Exemplary Embodiments; and (viii) Closing Paragraphs. These headings are provided for organization purposes only and do not limit the scope or interpretation of the disclosure.

(i) Artificial Expression Constructs & Vectors for Targeted Expression of Genes in Targeted Cell Types. Artificial expression constructs disclosed herein include (i) an enhancer sequence that leads to targeted expression of a coding sequence within a targeted central nervous system cell type, (ii) a coding sequence that is expressed, and (iii) a promoter. The artificial expression construct can also include other regulatory elements if necessary or beneficial.

In particular embodiments, an "enhancer" or an "enhancer element" is a cis-acting sequence that increases the level of transcription associated with a promoter and can function in either orientation relative to the promoter and the coding sequence that is to be transcribed and can be located upstream or downstream relative to the promoter or the coding sequence to be transcribed. There are art-recognized methods and techniques for measuring function(s) of enhancer element sequences. Particular examples of enhancer sequences utilized within artificial expression constructs disclosed herein include MGT_E51, MGT_E52, MGT_E57, eHGT_770m, eHGT_774m, eHGT_772m, eHGT_486m, eHGT_875m, eHGT_923m, eHGT_924m, eHGT_925m, and eHGT_926m and concatenated enhancer cores, such as 3xcore2_eHGT_774m, 3xcore2_eHGT_772m, and 3xCore_eHGT486m.

In particular embodiments, a targeted central nervous system cell type enhancer is an enhancer that is uniquely or predominantly utilized by the targeted central nervous system cell type. A targeted central nervous system cell type enhancer enhances expression of a gene in the targeted central nervous system. In certain embodiments, a targeted central nervous system cell type enhancer is also a targeted central nervous system type enhancer that enhances expression of a gene in the targeted central nervous system and does not substantially direct expression of genes in other non-targeted cell types, thus having cell type specific transcriptional activity.

When a heterologous coding sequence operatively linked to an enhancer disclosed herein leads to expression in a targeted cell type, it leads to expression of the administered heterologous coding sequence in the intended cell type.

When a heterologous coding sequence is selectively expressed in selected cells, it leads to expression of the administered heterologous coding sequence in the intended cell type and is not substantially expressed in other cell types, as explained din additional detail below. In particular embodiments, not substantially expressed in other cell types is less than 50% expression in a reference cell type as compared to a targeted cell type; less than 40% expression in a reference cell type as compared to a targeted cell type; less than 30% expression in a reference cell type as compared to a targeted cell type; less than 20% expression in a reference cell type as compared to a targeted cell type; or less than 10% expression in a reference cell type as compared to a targeted cell type. In particular embodiments, a reference cell type refers to non-targeted cells. The non-targeted cells can be within the same anatomical structure as the targeted cells and/or can project to a common anatomical area. In particular embodiments, a reference cell type is within an anatomical structure that is adjacent to an anatomical structure that includes the targeted cell type. In particular embodiments, a reference cell type is a non-targeted cell with a different gene expression profile than the targeted cells.

In particular embodiments, the product of the coding sequence may be expressed at low levels in non-selected cell types, for example at less than 1% or 1%, 2%, 3%, 5%, 10%, 15% or 20% of the levels at which the product is expressed in selected cells. In particular embodiments, the targeted central nervous system cell type is the only cell type that expresses the right combination of transcription factors that bind an enhancer disclosed herein to drive gene expression. Thus, in particular embodiments, expression occurs exclusively within the targeted cell type.

In particular embodiments, targeted cell types (e.g. neuronal, and/or non-neuronal) can be identified based on transcriptional profiles, such as those described in Tasic et al., Nature 563, 72-78 (2018) and Hodge et al., Nature 573, 61-68 (2019). For reference, the following description of cell types and distinguishing features is also provided:

Neocortical GABAergic neuron Subclasses:

All: Express GABA synthesis genes Gad1/GAD1 and Gad2/GAD2.

Lamp5, Sncg, Serpinf1, and Vip GABAergic neurons: Developmentally derived from neuronal progenitors from the caudal ganglionic eminence (CGE) or preoptic area (POA).

Sst and Pvalb GABAergic neurons: Developmentally derived from neuronal progenitors in the medial ganglionic eminence (MGE).

Lamp5 GABAergic neurons: Found in many neocortical layers, especially upper (L1-L2/3), and have mainly neurogliaform and single bouquet morphology.

Lamp5_Lhx6 GABAergic neurons: A subset of Lamp5 GABAergic neurons that co-express Lamp5 and Lhx6.

Sncg GABAergic neurons: Found in many neocortical layers, and have molecular overlaps with Lamp5 and Vip cells, but inconsistent expression of Lamp5 or vasoactive intestinal peptide (Vip), with more consistent expression of Sncg.

Serpinf1 GABAergic neurons: Found in many neocortical layers, and have molecular overlaps with Sncg and Vip cells, but inconsistent expression of Sncg or Vip, with more consistent expression of Serpinf1.

Vip GABAergic neurons: Found in many neocortical layers, but especially frequent in upper layers (L1-L4), and highly express the neurotransmitter Vip.

SstGABAergic neurons: Found in many neocortical layers, but especially frequent in lower layers (L5-L6). They highly express the neurotransmitter somatostatin (Sst), and frequently block dendritic inputs to postsynaptic neurons. Included in this subclass are sleep-active Sst Chodi neurons (which also express Nos1 and Tacr1) that are highly distinct from other Sst neurons but express some shared marker genes including Sst. In human, SST gene expression is often detected in layer 1 LAMP5+ GABAergic neuron subtypes.

Pvalb GABAergic neurons: Found in many neocortical layers, but especially frequent in lower layers (L5-L6). They highly express the calcium-binding protein parvalbumin (Pvalb), express neuropeptide Tac1, and frequently dampen the output of postsynaptic neurons. Most fast-spiking GABAergic neurons express Pvalb strongly. Included in this subclass are chandelier cells, which have distinct, chandelier-like morphology and express the markers Cpne5 and Vipr2 in mouse, and NOG and UNC5B in human.

Meis2: A distinct subclass defined by a single type, only neocortical GABAergic neuron type that expresses Meis2 gene, and does not express some other genes that are expressed by all other neocortical GABAergic neuron types (for example, Thy1 and Scn2b). This type is found in L6b and subcortical white matter.

Neocortical glutamatergic neuron subclasses:

All: Express glutamate transmitters Slc17a6 and/or Slc17a7. They all express Snap25 and lack expression of Gad1/Gad2.

L2/3 IT glutamatergic neurons: Primarily reside in Layer 2/3 and have mainly intratelencephalic (cortico-cortical) projections.

L4 IT glutamatergic neurons: Primarily reside in Layer 4 and mainly have either local or intratelencephalic (cortico-cortical) projections.

L5 IT glutamatergic neurons: Primarily reside in Layer 5 and have mainly intratelencephalic (cortico-cortical) projections. Also called L5a.

L5 PT glutamatergic neurons: Primarily reside in Layer 5 and have mainly cortico-subcortical (pyramidal tract or corticofugal) projections. Also called L5b or L5 CF (corticofugal) or L5 ET (extratelencephalic). This subclass includes cells that are located in the primary motor cortex and neighboring areas and are corticospinal projection neurons, which are associated with motor neuron/movement disorders, such as ALS. This subclass includes thick-tufted pyramidal neurons, including distinctive subtypes found only in specialized regions, e.g., Betz cells, Meynert cells, and von Economo cells.

L5 NP glutamatergic neurons: Primarily reside in Layer 5 and have mainly nearby projections.

L6 CT glutamatergic neurons: Primarily reside in Layer 6 and have mainly cortico-thalamic projections.

L6 IT glutamatergic neurons: Primarily reside in Layer 6 and have mainly intratelencephalic (cortico-cortical) projections.

L6 IT Car3 glutamatergic neurons: Most densely present in claustrum and endopyriform nucleus, and sparsely throughout L6 in many cortical areas including the primary visual cortex. These cells have mainly intratelencephalic (cortico-cortical) projections. Additional marker genes for claustrum enriched neurons include Gnb4 and Ntng2.

L6b glutamatergic neurons: Primarily reside in the neocortical subplate (L6b), with local (near the cell body) projections and some cortico-cortical projections from VISp to anterior cingulate, and cortico-subcortical projections to the thalamus.

CR neurons: A distinct subclass defined by a single type in L1, Cajal-Retzius cells express distinct molecular markers Lhx5 and Trp73.

Cerebellar Purkinje cells: large GABAergic neurons that are the only projection neurons and the sole output from the cerebellum. Their cell bodies form a single layer, so called 'Purkinje cell layer', and they express parvalbumin.

Deep cerebellar nucleus neurons: neurons located in the deep cerebellar nuclei structures. These include glutamatergic and GABAergic cells that express the gene Pvalb.

Non-neuronal Subclasses:

Astrocytes: Neuroectoderm-derived glial cells which express the marker Aqp4 and often GFAP, but do not express neuronal marker SNAP25. They can have a distinct star-shaped morphology and are involved in metabolic support of other cells in the brain. Multiple astrocyte morphologies are observed in mouse and human Oligodendrocytes: Neuroectoderm-derived glial cells, which express the marker Sox10. This category includes oligodendrocyte precursor cells (OPCs). Oligodendrocytes are the subclass that is primarily responsible for myelination of neurons.

VLMCs: Vascular leptomeningeal cells (VLMCs) are part of the meninges that surround the outer layer of the cortex and express the marker genes Lum and Col1a1.

Pericytes: Blood vessel-associated cells that express the marker genes Kcnj8 and Abcc9. Pericytes wrap around endothelial cells and are important for regulation of capillary blood flow and are involved in blood-brain barrier permeability.

SMCs: Specialized smooth-muscle cells which are blood vessel-associated cells that express the marker gene Acta2. SMCs cover arterioles in the brain and are involved in blood-brain barrier permeability.

Endothelial cells: Cells that line blood vessels of the brain. Endothelial cells express the markers Tek and PDGF-B.

Microglia: hematopoietic-derived immune cells, which are brain-resident macrophages, and perivascular macrophages (PVMs) that may be transitionally associated with brain tissue or included as a biproduct of brain dissection methods. Microglia are known to express Cx3cr1, Tmem119, and PTPRC (CD45).

In particular embodiments, a coding sequence is a heterologous coding sequence that encodes an effector element. An effector element is a sequence that is expressed to achieve, and that in fact achieves, an intended effect. Examples of effector elements include reporter genes/proteins and functional genes/proteins.

Exemplary reporter genes/proteins include those expressed by Addgene ID #s 83894 (pAAV-hDIx-Flex-dTomato-Fishell_7), 83895 (pAAV-hDIx-Flex-GFP-Fishell_6), 83896 (pAAV-hDIx-GiDREADD-dTomato-Fishell-5), 83898 (pAAV-mDIx-ChR2-mCherry-Fishell-3), 83899 (pAAV-mDIx-GCaMP6f-Fishell-2), 83900 (pAAV-mDIx-GFP-Fishell-1), and 89897 (pcDNA3-FLAG-mTET2 (N500)). Exemplary reporter genes particularly can include those which encode an expressible fluorescent protein, or expressible biotin; blue fluorescent proteins (e.g. eBFP, eBFP2, Azurite, mKalamal, GFPuv, Sapphire, T-sapphire); cyan fluorescent proteins (e.g. eCFP, Cerulean, CyPet, AmCyanl, Midoriishi-Cyan, mTurquoise); green fluorescent proteins (e.g. GFP, GFP-2, tagGFP, turboGFP, EGFP, Emerald, Azami Green, Monomeric Azami Green (mAzamigreen), CopGFP, AceGFP, avGFP, ZsGreenl, Oregon Green™ (Thermo Fisher Scientific)); Luciferase; orange fluorescent proteins (mOrange, mKO, Kusabira-Orange, Monomeric Kusabira-Orange, mTangerine, tdTomato, dTomato); red fluorescent proteins (mKate, mKate2, mPlum, DsRed monomer, mCherry, mRuby, mRFP1, DsRed-Express, DsRed2, DsRed-Monomer, HcRed-Tandem, HcRedl, AsRed2, eqFP611, mRaspberry, mStrawberry, Jred, Texas Red™ (Thermo Fisher Scientific)); far red fluorescent proteins (e.g., mPlum and mNeptune); yellow fluorescent proteins (e.g., YFP, eYFP, Citrine, SYFP2, Venus, YPet, PhiYFP, ZsYellowl); and tandem conjugates.

GFP is composed of 238 amino acids (26.9 kDa), originally isolated from the jellyfish *Aequorea victoria/Aequorea aequorea/Aequorea forskalea* that fluoresces green when exposed to blue light. The GFP from *A. victoria* has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostability and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted ε), also known as its optical cross section of 9.13×10-21 $m^2$/molecule, also quoted as 55,000 L/(mol·cm). Superfolder GFP, a series of mutations that allow GFP to rapidly fold and mature even when fused to poorly folding peptides, was reported in 2006.

The "yellow fluorescent protein" (YFP) is a genetic mutant of green fluorescent protein, derived from *Aequorea victoria*. Its excitation peak is 514 nm and its emission peak is 527 nm.

Exemplary functional molecules include functioning ion transporters, cellular trafficking proteins, enzymes, transcription factors, neurotransmitters, calcium reporters, channelrhodopsins, guide RNA, nucleases, microRNA, or designer receptors exclusively activated by designer drugs (DREADDs).

Ion transporters are transmembrane proteins that mediate transport of ions across cell membranes. These transporters are pervasive throughout most cell types and important for regulating cellular excitability and homeostasis. Ion transporters participate in numerous cellular processes such as action potentials, synaptic transmission, hormone secretion, and muscle contraction. Many important biological processes in living cells involve the translocation of cations, such as calcium (Ca2+), potassium (K+), and sodium (Na+) ions, through such ion channels. In particular embodiments, ion transporters include voltage gated sodium channels (e.g., SCN1A), potassium channels (e.g., KCNQ2), and calcium channels (e.g. CACNA1C)).

Exemplary enzymes, transcription factors, receptors, membrane proteins, cellular trafficking proteins, signaling molecules, and neurotransmitters include enzymes such as lactase, lipase, helicase, alpha-glucosidase, amylase; transcription factors such as SP1, AP-1, Heat shock factor protein 1, C/EBP (CCAA-T/enhancer binding protein), and Oct-1; receptors such as transforming growth factor receptor beta 1, glial cell line-derived neurotrophic factor (GDNF), platelet-derived growth factor receptor, epidermal growth factor receptor, vascular endothelial growth factor receptor, and interleukin 8 receptor alpha; membrane proteins, cellular trafficking proteins such as clathrin, dynamin, caveolin, Rab-4A, and Rab-11A; signaling molecules such as nerve growth factor (NGF), platelet-derived growth factor (PDGF), transforming growth factor β (TGFβ), epidermal growth factor (EGF), GTPase and HRas; and neurotransmitters such as cocaine and amphetamine regulated transcript, substance P, oxytocin, and somatostatin.

In particular embodiments, functional molecules include reporters of cell function and states such as calcium reporters. Intracellular calcium concentration is an important predictor of numerous cellular activities, which include neuronal activation, muscle cell contraction and second messenger signaling. A sensitive and convenient technique to monitor the intracellular calcium levels is through the genetically encoded calcium indicator (GECI). Among the GECIs, green fluorescent protein (GFP) based calcium sensors named GCaMPs are efficient and widely used tools. The GCaMPs are formed by fusion of M13 and calmodulin protein to N- and C-termini of circularly permutated GFP. Some GCaMPs yield distinct fluorescence emission spectra (Zhao et al., Science, 2011, 333(6051): 1888-1891). Exemplary GECIs with green fluorescence include GCaMP3, GCaMP5G, GCaMP6s, GCaMP6m, GCaMP6f, jGCaMP7s, jGCaMP7c, jGCaMP7b, jGCaMP7f, jGCaMP8s, jGCaMP8m, and jGCaMP8f. Furthermore, GECIs with red fluorescence include jRGECO1a and jRGECO1b. AAV products containing GECIs are commercially available. For example, Vigene Biosciences provides AAV products including AAV8-CAG-GCaMP3 (Cat. No: BS4-CX3AAV8), AAV8-Syn-FLEX-GCaMP6s-WPRE (Cat. No: BS1-NXSAAV8), AAV8-Syn-FLEX-GCaMP6s-WPRE (Cat. No: BS1-NXSAAV8), AAV9-CAG-FLEX-GCaMP6m-WPRE (Cat. No: BS2-CXMAAV9), AAV9-Syn-FLEX-jGCaMP7s-WPRE (Cat. No: BS12-NX-SAAV9), AAV9-CAG-FLEX-jGCaMP7f-WPRE (Cat. No: BS12-CXFAAV9), AAV9-Syn-FLEX-jGCaMP7b-WPRE (Cat. No: BS12-NXBAAV9), AAV9-Syn-FLEX-jGCaMP7c-WPRE (Cat. No: BS12-NXCAAV9), AAV9-Syn-FLEX-NES-jRGECO1a-WPRE (Cat. No: BS8-NXAAAV9), and AAV8-Syn-FLEX-NES-jRCaMP1b-WPRE (Cat. No: BS7-NXBAAV8).

In particular embodiments calcium reporters include the genetically encoded calcium indicators GECI, NTnC; Myosin light chain kinase, GFP, Calmodulin chimera; Calcium indicator TN-XXL; BRET-based auto-luminescent calcium indicator; and/or Calcium indicator protein OeNL(Ca2+)-18u).

In particular embodiments, functional molecules include modulators of neuronal activity like channelrhodopsins (e.g., channelrhodopsin-1, channelrhodopsin-2, and variants thereof). Channelrhodopsins are a subfamily of retinylidene proteins (rhodopsins) that function as light-gated ion channels. In addition to channelrhodopsin 1 (ChR1) and channelrhodopsin 2 (ChR2), several variants of channelrhodopsins have been developed. For example, Lin et al. (*Biophys J,* 2009, 96(5): 1803-14) describe making chimeras of the transmembrane domains of ChR1 and ChR2, combined with site-directed mutagenesis. Zhang et al. (*Nat Neurosci,* 2008, 11(6): 631-3) describe VChR1, which is a red-shifted channelrhodopsin variant. VChR1 has lower light sensitivity and poor membrane trafficking and expression. Other known channelrhodopsin variants include the ChR2 variant described in Nagel, et al., *Proc Natl Acad Sci USA,* 2003, 100(24): 13940-5), ChR2/H134R (Nagel, G., et al., *Curr Biol,* 2005, 15(24): 2279-84), and ChD/ChEF/ChIEF (Lin, J. Y., et al., *Biophys J,* 2009, 96(5): 1803-14), which are activated by blue light (470 nm) but show no sensitivity to orange/red light. Additional variants are described in Lin, Experimental Physiology, 2010, 96.1: 19-25 and Knopfel et al., *The Journal of Neuroscience,* 2010, 30(45): 14998-15004; and Mardinly et al., *Nat Neurosci.* 2018, 21(6):881-893).

In particular embodiments, functional molecules include DNA and RNA editing tools such CRISPR/CAS (e.g., guide RNA and a nuclease, such as Cas, Cas9 or cpf1). Functional molecules can also include engineered Cpf1s such as those described in US 2018/0030425, US 2016/0208243, WO/2017/184768 and Zetsche et al. (2015) *Cell* 163: 759-771; single gRNA (see e.g., Jinek et al. (2012) Science 337:816-821; Jinek et al. (2013) eLife 2:e00471; Segal (2013) eLife 2:e00563) or editase, guide RNA molecules, microRNA, or homologous recombination donor cassettes.

In particular embodiments, functional molecules include a localizing cassette. In particular embodiments, localizing cassettes are used to localize a molecule (e.g., a vector, a protein, a sensor) to a specific subcellular compartment such as the soma, axon, or dendrite(s) of a neuron. In particular embodiments, localizing cassettes include a soma tag (e.g. soma (EE-RR)) to localize at the soma; an axon tag (e.g. derived from GAP43) or synaptophysin (sy) to localize at the axon; hydrophobic tails to localize at the plasma membrane; and hydrophobicity or alkyl chain to localize at the endoplasmic reticulum. In particular embodiments, localizing cassettes are fused to a sensor molecule such as a GECI. In particular embodiments, fusion proteins of a GECI and a localizing cassette includes soma-jGCaMP8s, axon-jRGECO1a, syGCaMP5G, and soma-jGCaAMP7s.

In particular embodiments, functional molecules include tag cassettes. Tag cassettes include His tag (HHHHHH; SEQ ID NO: 80), Flag tag (DYKDDDDK; SEQ ID NO: 81), Xpress tag (DLYDDDDK; SEQ ID NO: 82), Avi tag (GLNDIFEAQKIEWHE; SEQ ID NO: 83), Calmodulin tag (KRRWKKNFIAVSAANRFKKISSSGAL; SEQ ID NO: 84), Polyglutamate tag, HA tag (YPYDVPDYA; SEQ ID NO: 85), Myctag (EQKLISEEDL; SEQ ID NO: 86), Strep tag (which refers the original STREP® tag (WRHPQFGG; SEQ ID NO: 87), STREP® tag II (WSHPQFEK SEQ ID NO: 88 (IBA Institut fur Bioanalytik, Germany); see, e.g., U.S. Pat. No. 7,981,632), Softag 1 (SLAELLNAGLGGS; SEQ ID NO: 89), Softag 3 (TQDPSRVG; SEQ ID NO: 90), and V5 tag (GKPIPNPLLGLDST; SEQ ID NO: 91). In particular embodiments, a tag cassette includes a fusion of tag cassettes such as 3XFLAG. In particular embodiments, 3XFLAG includes the sequence set forth in SEQ ID NO: 65.

Sequences are publicly-available. As examples, lactase (e.g., GenBank: EAX11622.1), lipase (e.g., GenBank: AAA60129.1), helicase (e.g., GenBank: AMD82207.1), amylase (e.g., GenBank: AAA51724.1), alpha-glucosidase (e.g., GenBank: AB153718.1), transcription factor SP1 (e.g., UniProtKB/Swiss-Prot: P08047.3), transcription factor AP-1 (e.g., NP_002219.1), heat shock factor protein 1 (e.g., UniProtKB/Swiss-Prot: Q00613.1), CCAAT/enhancer-binding protein (C/EBP) beta isoform a (e.g., NP_005185.2), Oct-1 (e.g., UniProtKB/Swiss-Prot: P14859.2), TGFβ (e.g., GenBank: CAF02096.2), glial cell line-derived neurotrophic factor (GDNF) (e.g., NP_001177397.1), platelet-derived growth factor receptor (e.g., GenBank: AAA60049.1), epidermal growth factor receptor (e.g., GenBank: CAA25240.1), vascular endothelial growth factor receptor (e.g., GenBank: AAC16449.2), interleukin 8 receptor alpha (e.g., GenBank: AAB59436.1), caveolin (e.g., GenBank: CAA79476.1), dynamin (e.g., GenBank: AAA88025.1), clathrin heavy chain 1 isoform 1 (e.g., NP_004850.1), clathrin heavy chain 2 isoform 1 (e.g., NP_009029.3), clathrin light chain A isoform a (e.g., NP_001824.1), clathrin light chain B isoform a (e.g., NP 001825.1), ras-related protein Rab-4A isoform 1 (e.g., NP_004569.2), ras-related protein Rab-11A (e.g., UniProtKB/Swiss-Prot: P62491.3), platelet-derived growth factor (e.g., GenBank: AAA60552.1), transforming growth factor-beta3 (e.g., GenBank: AAA61161.1), nerve growth factor (e.g., GenBank: CAA37703.1), EGF (e.g., GenBank: CAA34902.2), cocaine and amphetamine regulated transcript (Chain A) (e.g., PDB: 1HY9_A), protachykinin-1 (e.g., UniProtKB—P20366), oxytocin-neurophysin 1 (e.g., UniProtKB—P01178), somatostatin (e.g., GenBank: AAH32625.1), genetically-encoded green calcium indicator NTnC (chain A) [synthetic construct](e.g., PDB: 5MWC_A), calcium indicator TN-XXL [synthetic construct], (e.g., GenBank: ACF93133.1), BRET-based autoluminescent calcium indicator [synthetic construct](e.g., GenBank ADF42668.1), calcium indicator protein OeNL (Ca2+)-18u [synthetic construct], ((e.g., GenBank BBB18812.1), myosin light chain kinase, Green fluorescent protein, Calmodulin chimera (Chain A) [synthetic construct] ((e.g., PDB: 3EKJ_A), channelopsin 1 (e.g., UniProtKB—F8UVI5), channelopsin 1 (e.g., GenBank: AER58217.1), channelrhodopsin-2 ((e.g., UniProtKB-B4Y105), channel rhodopsin 2 [synthetic construct]((e.g., GenBank: AB064386.1), CRISPR-associated protein (Cas) (e.g., GenBank: AKG27598.1), Cas9 [synthetic construct](e.g., GenBank: AST09977.1), CRISPR-associated endonuclease Cpf1 (e.g., UniProtKB/Swiss-Prot: U2UMQ6.1), ribonuclease 4 or ribonuclease L (e.g., UniProtKB/Swiss-Prot: Q05823.2), deoxyribonuclease II beta (e.g., GenBank: AAF76893.1), sodium channel protein type 1 subunit alpha (e.g., UniProtKB—P35498), potassium voltage-gated channel subfamily KQT member 2 (e.g., UniProtKB—043526), and voltage-dependent L-type calcium channel subunit alpha-1C (e.g., UniProtKB—Q13936).

Additional effector elements include Cre, iCre, dgCre, FlpO, and tTA2. iCre refers to a codon-improved Cre. dgCre refers to an enhanced GFP/Cre recombinase fusion gene with an N terminal fusion of the first 159 amino acids of the *Escherichia coli* K-12 strain chromosomal dihydrofolate reductase gene (DHFR or folA) harboring a G67S mutation and modified to also include the R12Y/Y1001 destabilizing domain mutation. FlpO refers to a codon-optimized form of FLPe that greatly increases protein expression and FRT recombination efficiency in mouse cells. Like the Cre/LoxP system, the FLP/FRT system has been widely used for gene expression (and generating conditional knockout mice, mediated by the FLP/FRT system). tTA2 refers to tetracycline transactivator.

Exemplary expressible elements are expression products that do not include effector elements, for example, a non-functioning or defective protein. In particular embodiments, expressible elements can provide methods to study the effects of their functioning counterparts. In particular embodiments, expressible elements are non-functioning or defective based on an engineered mutation that renders them non-functioning. In these aspects, non-expressible elements are as similar in structure as possible to their functioning counterparts.

Exemplary self-cleaving peptides include the 2A peptides which lead to the production of two proteins from one mRNA. The 2A sequences are short (e.g., 20 amino acids), allowing more use in size-limited constructs. Particular examples include P2A, T2A, E2A, and F2A. In particular embodiments, the artificial expression constructs include an internal ribosome entry site (IRES) sequence. IRES allow ribosomes to initiate translation at a second internal site on a mRNA molecule, leading to production of two proteins from one mRNA.

Artificial expression constructs can encode nuclear localization proteins, such as Histone H1, Histone H2A, Histone H2B, Histone H3, Histone H4, histone-like protein HPhA.

Coding sequences encoding molecules (e.g., RNA, proteins) described herein can be obtained from publicly available databases and publications. Coding sequences can further include various sequence polymorphisms, mutations, and/or sequence variants wherein such alterations do not affect the function of the encoded molecule. The term "encode" or "encoding" refers to a property of sequences of nucleic acids, such as a vector, a plasmid, a gene, cDNA, mRNA, to serve as templates for synthesis of other molecules such as proteins.

The term "gene" may include not only coding sequences but also regulatory regions such as promoters, enhancers, insulators, and/or post-regulatory elements, such as termination regions. The term further can include all introns and other DNA sequences spliced from the mRNA transcript, along with variants resulting from alternative splice sites. The sequences can also include degenerate codons of a reference sequence or sequences that may be introduced to provide codon preference in a specific organism or cell type.

Promoters can include general promoters, tissue-specific promoters, cell-specific promoters, and/or promoters specific for the cytoplasm. Promoters may include strong promoters, weak promoters, constitutive expression promoters, and/or inducible promoters. Inducible promoters direct expression in response to certain conditions, signals or cellular events. For example, the promoter may be an inducible promoter that requires a particular ligand, small molecule, transcription factor or hormone protein in order to effect transcription from the promoter. Particular examples of promoters include minBglobin (also referred to as minBGprom), CMV, minCMV, minCMV* (minCMV* is minCMV with a Sac restriction site removed), minRho, minRho* (minRho* is minRho with a SacI restriction site removed), SV40 immediately early promoter, the Hsp68 minimal promoter (proHSP68), and the Rous Sarcoma Virus (RSV) long-terminal repeat (LTR) promoter. Minimal promoters have no activity to drive gene expression on their own but can be activated to drive gene expression when linked to a proximal enhancer element.

In particular embodiments, expression constructs are provided within vectors. The term vector refers to a nucleic acid molecule capable of transferring or transporting another nucleic acid molecule, such as an expression construct. The transferred nucleic acid is generally linked to, e.g., inserted into, the vector nucleic acid molecule. A vector may include sequences that direct autonomous replication in a cell or may include sequences that permit integration into host cell DNA. Useful vectors include, for example, plasmids (e.g., DNA plasmids or RNA plasmids), transposons, cosmids, bacterial artificial chromosomes, and viral vectors.

Viral vector is widely used to refer to a nucleic acid molecule that includes virus-derived components that facilitate transfer and expression of non-native nucleic acid molecules within a cell. The term adeno-associated viral vector refers to a viral vector or plasmid containing structural and functional genetic elements, or portions thereof, that are primarily derived from AAV. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, that are primarily derived from a lentivirus, and so on. The term "hybrid vector" refers to a vector including structural and/or functional genetic elements from more than one virus type.

Adenovirus vectors refer to those constructs containing adenovirus sequences sufficient to (a) support packaging of an artificial expression construct and (b) to express a coding sequence that has been cloned therein in a sense or antisense orientation. A recombinant Adenovirus vector includes a genetically engineered form of an adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range, and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut-off. The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5'-tripartite leader (TPL) sequence which makes them preferred mRNAs for translation.

Other than the requirement that an adenovirus vector be replication defective, or at least conditionally defective, the nature of the adenovirus vector is not believed to be crucial to the successful practice of particular embodiments disclosed herein. The adenovirus may be of any of the 42 different known serotypes or subgroups A-F. In particular embodiments, adenovirus type 5 of subgroup C is the preferred starting material in order to obtain a conditional replication-defective adenovirus vector for use in particular embodiments, since Adenovirus type 5 is a human adenovirus about which a great deal of biochemical and genetic information is known, and it has historically been used for most constructions employing adenovirus as a vector.

As indicated, the typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of a deleted E3 region in E3 replacement vectors or in the E4 region where a helper cell line or helper virus complements the E4 defect.

Adeno-Associated Virus (AAV) is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Various serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter.

The AAV DNA is 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three AAV viral promoters have been identified and named p5, p19, and p40, according to their map position. Transcription from p5 and p19 results in production of rep proteins, and transcription from p40 produces the capsid proteins.

AAVs stand out for use within the current disclosure because of their superb safety profile and because their capsids and genomes can be tailored to allow expression in targeted cell populations. scAAV refers to a self-complementary AAV. pAAV refers to a plasmid adeno-associated virus. rAAV refers to a recombinant adeno-associated virus.

Other viral vectors may also be employed. For example, vectors derived from viruses such as vaccinia virus, polioviruses and herpes viruses may be employed. They offer several attractive features for various mammalian cells.

Retroviruses are a common tool for gene delivery. "Retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV), Rous Sarcoma Virus (RSV), and lentivirus.

"Lentivirus" refers to a group (or genus) of complex retroviruses. Illustrative lentiviruses include: HIV (human immunodeficiency virus; including HIV type 1, and HIV type 2); visna-maedi virus (VMV); the caprine arthritis-encephalitis virus (CAEV); equine infectious anemia virus (EIAV); feline immunodeficiency virus (FIV); bovine immune deficiency virus (BIV); and simian immunodeficiency virus (SIV). In particular embodiments, HIV based vector backbones (i.e., HIV cis-acting sequence elements) can be used.

A safety enhancement for the use of some vectors can be provided by replacing the U3 region of the 5' LTR with a heterologous promoter to drive transcription of the viral genome during production of viral particles. Examples of heterologous promoters which can be used for this purpose include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In particular embodiments, the heterologous promoter has additional advantages in controlling the manner in which the viral genome is transcribed. For example, the heterologous promoter can be inducible, such that transcription of all or part of the viral genome will occur only when the induction factors are present. Induction factors include one or more chemical compounds or the physiological conditions such as temperature or pH, in which the host cells are cultured.

In particular embodiments, viral vectors include a TAR element. The term "TAR" refers to the "trans-activation response" genetic element located in the R region of lentiviral LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly(A) tract. The R region is also defined as being flanked by the U3 and U5 regions. The R region plays a role during reverse transcription in permitting the transfer of nascent DNA from one end of the genome to the other.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid. Examples include the woodchuck hepatitis virus posttranscriptional regulatory element (WPRE; Zufferey et al., 1999, J. Virol., 73:2886); the posttranscriptional regulatory element present in hepatitis B virus (HPRE) (Smith et al., Nucleic Acids Res. 26(21):4818-4827, 1998); and the like (Liu et al., 1995, Genes Dev., 9:1766). In particular embodiments, vectors include a posttranscriptional regulatory element such as a WPRE or HPRE. In particular embodiments, vectors lack or do not include a posttranscriptional regulatory element such as a WPRE or HPRE.

Elements directing the efficient termination and polyadenylation of a heterologous nucleic acid transcript can increase heterologous gene expression. Transcription termination signals are generally found downstream of the polyadenylation signal. In particular embodiments, vectors include a polyadenylation signal 3' of a polynucleotide encoding a molecule (e.g., protein) to be expressed. The term "poly(A) site" or "poly(A) sequence" denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Particular embodiments may utilize BGHpA, hGHpA, or SV40pA. In particular embodiments, a preferred embodiment of an expression construct includes a terminator element. These elements can serve to enhance transcript levels and to minimize read through from the construct into other plasmid sequences.

In particular embodiments, a viral vector further includes one or more insulator elements. Insulators elements may contribute to protecting viral vector-expressed sequences, e.g., effector elements or expressible elements, from integration site effects, which may be mediated by cis-acting elements present in genomic DNA and lead to deregulated expression of transferred sequences (i.e., position effect; see, e.g., Burgess-Beusse et al., *PNAS., USA,* 99:16433; 2002; and Zhan et al., *Hum. Genet.,* 109:471, 2001). In particular embodiments, viral transfer vectors include one or more insulator elements at the 3' LTR and upon integration of the provirus into the host genome, the provirus includes the one or more insulators at both the 5' LTR and 3' LTR, by virtue of duplicating the 3' LTR. Suitable insulators for use in particular embodiments include the chicken β-globin insulator (see Chung et al., *Cell* 74:505, 1993; Chung eta., *PNAS USA* 94:575 1997; and Bell et al, *Cell*298:387, 1999), SP10 insulator (Abhyankaretal, *JBC* 282:36143, 2007), or other small CTCF recognition sequences that function as enhancer blocking insulators (Liu et al., *Nature Biotechnology,* 33:198, 2015).

Beyond the foregoing description, a wide range of suitable expression vector types will be known to a person of ordinary skill in the art. These can include commercially available expression vectors designed for general recombinant procedures, for example plasmids that contain one or more reporter genes and regulatory elements required for expression of the reporter gene in cells. Numerous vectors are commercially available, e.g., from Invitrogen, Stratagene, Clontech, etc., and are described in numerous associated guides. In particular embodiments, suitable expression vectors include any plasmid, cosmid or phage construct that is capable of supporting expression of encoded genes in mammalian cell, such as pUC or Bluescript plasmid series.

Particular embodiments of vectors disclosed herein include:

| Expression Construct Name | Features |
|---|---|
| AiP1211 | rAAV: MGT_E51-minBglobin-FlpO-WPRE-hGHpA |
| AiP1212 | rAAV: MGT_E52-minBglobin-FlpO-WPRE-hGHpA |
| AiP1218 | rAAV: MGT_E57-minBglobin-FlpO-WPRE-hGHpA |
| CN2603 | rAAV: eHGT_770m-minBglobin-SYFP2-WPRE3-BGHpA |
| CN2606 | rAAV: eHGT_774m-minBglobin-SYFP2-WPRE3-BGHpA |
| CN2612 | rAAV: eHGT_772m-minBglobin-SYFP2-WPRE3-BGHpA |
| CN2261 | rAAV: eHGT_486m-minBglobin-SYFP2-WPRE3-BGHpA |
| AiP1279 | rAAV: MGT_E57-minBglobin-SYFP2-WPRE-hGHpA |
| AiP1277 | rAAV: MGT_E51-minBglobin-SYFP2-WPRE-hGHpA |
| AiP1278 | rAAV: MGT_E52-minBglobin-SYFP2-WPRE-hGHpA |
| AiP1344 | pAAV: MGT_E52-minBglobin-iCre-hGHpA |
| CN3041 | rAAV: 3xcore2_eHGT_774m-minBglobin-SYFP2-WPRE3-BGHpA |
| CN3608 | rAAV: 3xcore2_eHGT_772m- minBglobin -SYFP2-WPRE3-BGHpA |
| CN2582 | rAAV: eHGT_3xCore_eHGT486m-minBglobin-SYFP2-WPRE3-BGHpA |
| CN3367 | pAAV: eHGT_875m-minBglobin-SYFP2-P2A-3XFLAG-10aa-H2B-WPRE3-BGHpA |
| CN4095 | pAAV: eHGT_923m-minBglobin-SYFP2-P2A-3XFLAG-10aa-H2B-WPRE3-BGHpA |
| CN4096 | pAAV: eHGT_924m-minBglobin-SYFP2-P2A-3XFLAG-10aa-H2B-WPRE3-BGHpA |
| CN3430 | pAAV: eHGT_925m-minBglobin-SYFP2-P2A-3XFLAG-10aa-H2B-WPRE3-BGHpA |
| CN3431 | pAAV: eHGT_926m-minBglobin-SYFP2-P2A-3XFLAG-10aa-H2B-WPRE3-BGHpA |

Subcomponent sequences within the larger vector sequences can be readily identified by one of ordinary skill in the art and based on the contents of the current disclosure (see FIG. 10). Nucleotides between identifiable and enumerated subcomponents reflect restriction enzyme recognition sites used in assembly (cloning) of the constructs, and in some cases, additional nucleotides do not convey any identifiable function. These segments of complete vector sequences can be adjusted based on use of different cloning strategies and/or vectors. In general, short 6-nucleotide palindromic sequences reflect vector construction artifacts that are not important to vector function.

In particular embodiments vectors (e.g., AAV) with capsids that cross the blood-brain barrier (BBB) are selected. In particular embodiments, vectors are modified to include capsids that cross the BBB. Examples of AAV with viral capsids that cross the blood brain barrier include AAV9 (Gombash et al., Front Mol Neurosci. 2014; 7:81), AAVrh.10 (Yang, et al., Mol Ther. 2014; 22(7): 1299-1309), AAV1R6, AAV1R7 (Albright et al., Mol Ther. 2018; 26(2): 510), rAAVrh.8 (Yang, et al., supra), AAV-BR1 (Marchio et al., EMBO Mol Med. 2016; 8(6): 592), AAV-PHP.S (Chan et al., Nat Neurosci. 2017; 20(8): 1172), AAV-PHP.B (Deverman et al., *Nat Biotechnol.* 2016; 34(2): 204), AAV-PPS (Chen et al., Nat Med. 2009; 15: 1215), and PHP.eB. In particular embodiments, the PHP.eB capsid differs from AAV9 such that, using AAV9 as a reference, amino acids starting at residue 586: S-AQ-A (SEQ ID NO: 48) are changed to S-DGTLAVPFK-A (SEQ ID NO: 49). In particular embodiments, PHP.eb refers to SEQ ID NO: 32.

AAV9 is a naturally occurring AAV serotype that, unlike many other naturally occurring serotypes, can cross the BBB following intravenous injection. It transduces large sections of the central nervous system (CNS), thus permitting minimally invasive treatments (Naso et al., BioDrugs. 2017; 31(4): 317), for example, as described in relation to clinical trials for the treatment of spinal muscular atrophy (SMA) syndrome by AveXis (AVXS-101, NCT03505099) and the treatment of CLN3 gene-Related Neuronal Ceroid-Lipofuscinosis (NCT03770572).

AAVrh.10, was originally isolated from rhesus macaques and shows low seropositivity in humans when compared with other common serotypes used for gene delivery applications (Selot et al., Front Pharmacol. 2017; 8: 441) and has been evaluated in clinical trials LYS-SAF302, LYSOGENE, and NCT03612869.

AAV1R6 and AAV R7, two variants isolated from a library of chimeric AAV vectors (AAV1 capsid domains swapped into AAVrh.10), retain the ability to cross the BBB and transduce the CNS while showing significantly reduced hepatic and vascular endothelial transduction.

rAAVrh.8, also isolated from rhesus macaques, shows a global transduction of glial and neuronal cell types in regions of clinical importance following peripheral administration and also displays reduced peripheral tissue tropism compared to other vectors.

AAV-BR1 is an AAV2 variant displaying the NRGTEWD (SEQ ID NO: 50) epitope that was isolated during in vivo screening of a random AAV display peptide library. It shows high specificity accompanied by high transgene expression in the brain with minimal off-target affinity (including for the liver) (K6rbelin et al., EMBO Mol Med. 2016; 8(6): 609).

AAV-PHP.S (Addgene, Watertown, MA) is a variant of AAV9 generated with the CREATE method that encodes the 7-mer sequence QAVRTSL (SEQ ID NO: 51), transduces neurons in the enteric nervous system, and strongly transduces peripheral sensory afferents entering the spinal cord and brain stem.

AAV-PHP.B (Addgene, Watertown, MA) is a variant of AAV9 generated with the CREATE method that encodes the 7-mer sequence TLAVPFK (SEQ ID NO: 52). It transfers genes throughout the CNS with higher efficiency than AAV9 and transduces the majority of astrocytes and neurons across multiple CNS regions.

AAV-PPS, an AAV2 variant crated by insertion of the DSPAHPS (SEQ ID NO: 53) epitope into the capsid of AAV2, shows a dramatically improved brain tropism relative to AAV2.

For additional information regarding capsids that cross the blood brain barrier, see Chan et al., Nat. Neurosci. 2017 August: 20(8): 1172-1179.

(ii) Compositions for Administration. Artificial expression constructs and vectors of the present disclosure (referred to herein as physiologically active components) can be formulated with a carrier that is suitable for administration to a cell, tissue slice, animal (e.g., mouse, non-human primate), or human. Physiologically active components within compositions described herein can be prepared in neutral forms, as freebases, or as pharmacologically acceptable salts.

Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers of physiologically active components can include solvents, dispersion media, vehicles, coatings, diluents, isotonic and absorption delaying agents, buffers, solutions, suspensions, colloids, and the like. The use of such carriers for physiologically active components is well known in the art. Except insofar as any conventional media or agent is incompatible with the physiologically active components, it can be used with compositions as described herein.

The phrase "pharmaceutically-acceptable carriers" refer to carriers that do not produce an allergic or similar untoward reaction when administered to a human, and in particular embodiments, when administered intravenously (e.g., at the retro-orbital plexus).

In particular embodiments, compositions can be formulated for intravenous, intraparenchymal, intraocular, intravitreal, parenteral, subcutaneous, intracerebro-ventricular, intramuscular, intrathecal, intraspinal, intraperitoneal, oral or nasal inhalation, or by direct injection in or application to one or more cells, tissues, or organs.

Compositions may include liposomes, lipids, lipid complexes, microspheres, microparticles, nanospheres, and/or nanoparticles.

The formation and use of liposomes is generally known to those of skill in the art. Liposomes have been developed with improved serum stability and circulation half-times (see, for instance, U.S. Pat. No. 5,741,516). Further, various methods of liposome and liposome like preparations as potential drug carriers have been described (see, for instance U.S. Pat. Nos. 5,567,434; 5,552,157; 5,565,213; 5,738,868; and 5,795,587).

The disclosure also provides for pharmaceutically acceptable nanocapsule formulations of the physiologically active components. Nanocapsules can generally entrap compounds in a stable and reproducible way (Quintanar-Guerrero et al., *Drug Dev Ind Pharm* 24(12):1113-1128, 1998; Quintanar-Guerrero et al., *Pharm Res.* 15(7):1056-1062, 1998; Quintanar-Guerrero et al., *J. Microencapsul.* 15(1):107-119, 1998; Douglas et al., *Crit Rev Ther Drug Carrier Syst* 3(3):233-261, 1987). To avoid side effects due to intracellular polymeric overloading, such ultrafine particles can be designed using polymers able to be degraded in vivo. Biodegradable polyalkyl-cyanoacrylate nanoparticles that meet these requirements are contemplated for use in the present disclosure. Such particles can be easily made, as described in Couvreur et al., *J Pharm Sci* 69(2):199-202, 1980; Couvreur et al., *Crit Rev Ther Drug Carrier Syst.* 5(1)1-20, 1988; zur Muhlen et al., *Eur J Pharm Biopharm,* 45(2):149-155, 1998; Zambaux et al., *J Control Release* 50(1-3):31-40, 1998; and U.S. Pat. No. 5,145,684.

Injectable compositions can include sterile aqueous solutions or dispersions and sterile powders for the extemporaneous preparation of sterile injectable solutions or dispersions (U.S. Pat. No. 5,466,468). For delivery via injection, the form is sterile and fluid to the extent that it can be delivered by syringe. In particular embodiments, it is stable under the conditions of manufacture and storage, and optionally contains one or more preservative compounds against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and/or antifungal agents, for example, parabens, chlorobutanol, phenol, sorbic acid, thimerosal, and the like. In various embodiments, the preparation will include an isotonic agent(s), for example, sugar(s) or sodium chloride. Prolonged absorption of the injectable compositions can be accomplished by including in the compositions of agents that delay absorption, for example, aluminum monostearate and gelatin. Injectable compositions can be suitably buffered, if necessary, and the liquid diluent first rendered isotonic with sufficient saline or glucose.

Dispersions may also be prepared in glycerol, liquid polyethylene glycols, and mixtures thereof and in oils. As indicated, under ordinary conditions of storage and use, these preparations can contain a preservative to prevent the growth of microorganisms.

Sterile compositions can be prepared by incorporating the physiologically active component in an appropriate amount of a solvent with other optional ingredients (e.g., as enumerated above), followed by filtered sterilization. Generally, dispersions are prepared by incorporating the various sterilized physiologically active components into a sterile vehicle that contains the basic dispersion medium and the required other ingredients (e.g., from those enumerated above). In the case of sterile powders for the preparation of sterile injectable solutions, preferred methods of preparation can be vacuum-drying and freeze-drying techniques which yield a powder of the physiologically active components plus any additional desired ingredient from a previously sterile-filtered solution thereof.

Oral compositions may be in liquid form, for example, as solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). Tablets may be coated by methods well-known in the art.

Inhalable compositions can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Compositions can also include microchip devices (U.S. Pat. No. 5,797,898), ophthalmic formulations (Bourlais et al., *Prog Retin Eye Res,* 17(1):33-58, 1998), transdermal matrices (U.S. Pat. Nos. 5,770,219 and 5,783,208) and feedback-controlled delivery (U.S. Pat. No. 5,697,899).

Supplementary active ingredients can also be incorporated into the compositions.

Typically, compositions can include at least 0.1% of the physiologically active components or more, although the percentage of the physiologically active components may, of course, be varied and may conveniently be between 1 or 2% and 70% or 80% or more or 0.5-99% of the weight or volume of the total composition. Naturally, the amount of physiologically active components in each physiologically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of compositions and dosages may be desirable.

In particular embodiments, for administration to humans, compositions should meet sterility, pyrogenicity, and the general safety and purity standards as required by United States Food and Drug Administration (FDA) or other applicable regulatory agencies in other countries.

(iii) Cell Lines Including Artificial Expression Constructs. The present disclosure includes cells including an artificial expression construct described herein. A cell that has been transformed with an artificial expression construct can be used for many purposes, including in neuroanatomical studies, assessments of functioning and/or non-functioning proteins, and drug screens that assess the regulatory properties of enhancers.

A variety of host cell lines can be used, but in particular embodiments, the cell is a mammalian cell. In particular embodiments, the artificial express construct includes an enhancer and/or a vector sequence of MGT_E51, MGT_E52, MGT_E57, eHGT_770m, eHGT_774m, eHGT_772m, eHGT_486m, eHGT_875m, eHGT_923m, eHGT_924m, eHGT_925m, eHGT_926m, 3xcore2_eHGT_774m, 3xcore2_eHGT_772m, and/or 3xCore_eHGT486m and/or AiP1211, AiP1212, AiP1218, CN2603, CN2606, CN2612, CN2261, AiP1279, AiP1277, AiP1278, AiP1344, CN3041, CN3608, CN2582, CN3367, CN4095, CN4096, CN3430, and/or CN3431, and the cell line is a human, primate, or murine cell. Cell lines which can be utilized for transgenesis in the present disclosure also include primary cell lines derived from living tissue such as rat or mouse brains and organotypic cell cultures, including brain slices from animals such as rats, mice, non-human primates, or human neurosurgical tissue. The PC12 cell line (available from the American Type Culture Collection, ATCC, Manassas, VA) has been shown to express a number of neuronal marker proteins in response to Neuronal Growth Factor (NGF). The PC12 cell line is considered to be a neuronal cell line and is applicable for use with this disclosure. JAR cells (available from ATCC) are a platelet derived cell-line that express some neuronal genes, such as the serotonin transporter gene, and may be used with embodiments described herein.

WO 91/13150 describes a variety of cell lines, including neuronal cell lines, and methods of producing them. Similarly, WO 97/39117 describes a neuronal cell line and methods of producing such cell lines. The neuronal cell lines disclosed in these patent applications are applicable for use in the present disclosure.

In particular embodiments, "neuronal" describes something that is of, related to, or includes, neuronal cells. Neuronal cells are defined by the presence of an axon and dendrites. The term "neuronal-specific" refers to something that is found, or an activity that occurs, in neuronal cells or cells derived from neuronal cells, but is not found in or occur in, or is not found substantially in or occur substantially in, non-neuronal cells or cells not derived from neuronal cells, for example glial cells such as astrocytes or oligodendrocytes.

In particular embodiments, non-neuronal cell lines may be used, including mouse embryonic stem cells. Cultured mouse embryonic stem cells can be used to analyze expression of genetic constructs using transient transfection with plasmid constructs. Mouse embryonic stem cells are pluripotent and undifferentiated. These cells can be maintained in this undifferentiated state by Leukemia Inhibitory Factor (LIF). Withdrawal of LIF induces differentiation of the embryonic stem cells. In culture, the stem cells form a variety of differentiated cell types. Differentiation is caused by the expression of tissue specific transcription factors, allowing the function of an enhancer sequence to be evaluated. (See for example Fiskerstrand et al., *FEBS Lett* 458: 171-174, 1999).

Methods to differentiate stem cells into neuronal cells include replacing a stem cell culture media with a media including basic fibroblast growth factor (bFGF) heparin, an N2 supplement (e.g., transferrin, insulin, progesterone, putrescine, and selenite), laminin and polyornithine. A process to produce myelinating oligodendrocytes from stem cells is described in Hu, et al., 2009*, Nat. Protoc.* 4:1614-22. Bibel, et al., 2007*, Nat. Protoc.* 2:1034-43 describes a protocol to produce glutamatergic neurons from stem cells while Chatzi, et al., 2009*, Exp. Neurol.* 217:407-16 describes a procedure to produce GABAergic neurons. This procedure includes exposing stem cells to all-trans-RA for three days. After subsequent culture in serum-free neuronal induction medium including Neurobasal medium supplemented with B27, bFGF and EGF, 95% GABA neurons develop U.S. Publication No. 2012/0329714 describes use of prolactin to increase neural stem cell numbers while U.S. Publication No. 2012/0308530 describes a culture surface with amino groups that promotes neuronal differentiation into neurons, astrocytes and oligodendrocytes. Thus, the fate of neural stem cells can be controlled by a variety of extracellular factors. Commonly used factors include brain derived growth factor (BDNF; Shetty and Turner, 1998*, J. Neurobiol.* 35:395-425); fibroblast growth factor (bFGF; U.S. Pat. No. 5,766,948; FGF-1, FGF-2); Neurotrophin-3 (NT-3) and Neurotrophin-4 (NT-4); Caldwell, et al., 2001, *Nat. Biotechnol.* 1; 19:475-9); ciliary neurotrophic factor (CNTF); BMP-2 (U.S. Pat. Nos. 5,948,428 and 6,001,654); isobutyl 3-methylxanthine; leukemia inhibitory growth factor (LIF; U.S. Pat. No. 6,103,530); somatostatin; amphiregulin; neurotrophins (e.g., cyclic adenosine monophosphate; epidermal growth factor (EGF); dexamethasone (glucocorticoid hormone); forskolin; GDNF family receptor ligands; potassium; retinoic acid (U.S. Pat. No. 6,395,546); tetanus toxin; and transforming growth factor-α and TGF-β (U.S. Pat. Nos. 5,851,832 and 5,753,506).

In particular embodiments, yeast one-hybrid systems may also be used to identify compounds that inhibit specific protein/DNA interactions, such as transcription factors for MGT_E51, MGT_E52, MGT_E57, eHGT_770m, eHGT_774m, eHGT_772m, eHGT_486m, eHGT_875m, eHGT_923m, eHGT_924m, eHGT_925m, eHGT_926m, 3xcore2_eHGT_774m, 3xcore2_eHGT_772m, or 3xCore_eHGT486m.

Transgenic animals are described below. Cell lines may also be derived from such transgenic animals. For example, primary tissue culture from transgenic mice (e.g., also as described below) can provide cell lines with the artificial expression construct already integrated into the genome. (for an example see MacKenzie & Quinn, *Proc Natl Acad Sci USA* 96: 15251-15255, 1999).

(iv) Transgenic Animals. Another aspect of the disclosure includes transgenic animals, the genome of which contains an artificial expression construct including MGT_E51, MGT_E52, MGT_E57, eHGT_770m, eHGT_774m, eHGT_772m, eHGT_486m, eHGT_875m, eHGT_923m, eHGT_924m, eHGT_925m, eHGT_926m, 3xcore2_eHGT_774m, 3xcore2_eHGT_772m, and/or 3xCore_eHGT486m operatively linked to a heterologous coding sequence. In particular embodiments, the genome of a transgenic animal includes AiP1211, AiP1212, AiP1218, CN2603, CN2606, CN2612, CN2261, AiP1279, AiP1277, AiP1278, AiP1344, CN3041, CN3608, CN2582, CN3367, CN4095, CN4096, CN3430, and/or CN3431. In particular embodiments, when a non-integrating vector is utilized, a transgenic animal includes an artificial expression construct including MGT_E51, MGT_E52, MGT_E57, eHGT_770m, eHGT_774m, eHGT_772m, eHGT_486m, eHGT_875m, eHGT_923m, eHGT_924m, eHGT_925m, eHGT_926m, 3xcore2_eHGT_774m, 3xcore2_eHGT_772m, and/or 3xCore_eHGT486m and/or AiP1211, AiP1212, AiP1218, CN2603, CN2606, CN2612, CN2261, AiP1279, AiP1277, AiP1278, AiP1344, CN3041, CN3608, CN2582, CN3367, CN4095, CN4096, CN3430, and/or CN3431.

Detailed methods for producing transgenic animals are described in U.S. Pat. No. 4,736,866. Transgenic animals may be of any nonhuman species, but preferably include nonhuman primates (NHPs), sheep, horses, cattle, pigs, goats, dogs, cats, rabbits, chickens, and rodents such as guinea pigs, hamsters, gerbils, rats, mice, and ferrets.

In particular embodiments, construction of a transgenic animal results in an organism that has an engineered construct present in all cells in the same genomic integration site. Thus, cell lines derived from such transgenic animals will be consistent in as much as the engineered construct will be in the same genomic integration site in all cells and hence will suffer the same position effect variegation. In contrast, introducing genes into cell lines or primary cell cultures can give rise to heterologous expression of the construct. A disadvantage of this approach is that the expression of the introduced DNA may be affected by the specific genetic background of the host animal.

As indicated above in relation to cell lines, the artificial expression constructs of this disclosure can be used to genetically modify mouse embryonic stem cells using techniques known in the art. Typically, the artificial expression construct is introduced into cultured murine embryonic stem cells. Transformed ES cells are then injected into a blastocyst from a host mother and the host embryo re-implanted into the mother. This results in a chimeric mouse whose tissues are composed of cells derived from both the embryonic stem cells present in the cultured cell line and the embryonic stem cells present in the host embryo. Usually, the mice from which the cultured ES cells used for transgenesis are derived are chosen to have a different coat color from the host mouse into whose embryos the transformed cells are to be injected. Chimeric mice will then have a variegated coat color. As long as the germ-line tissue is derived, at least in part, from the genetically modified cells, then the chimeric mice crossed with an appropriate strain can produce offspring that will carry the transgene.

In addition to the methods of delivery described above, the following techniques are also contemplated as alternative methods of delivering artificial expression constructs to target cells or targeted tissues and organs of an animal, and in particular, to cells, organs, or tissues of a vertebrate mammal: sonophoresis (e.g., ultrasound, as described in U.S. Pat. No. 5,656,016); intraosseous injection (U.S. Pat. No. 5,779,708); microchip devices (U.S. Pat. No. 5,797,898); ophthalmic formulations (Bourlais et al., *Prog Retin Eye Res,* 17(1):33-58, 1998); transdermal matrices (U.S. Pat. Nos. 5,770,219 and 5,783,208); feedback-controlled delivery (U.S. Pat. No. 5,697,899), and any other delivery method available and/or described elsewhere in the disclosure.

(v) Methods of Use. In particular embodiments, a composition including a physiologically active component described herein is administered to a subject to result in a physiological effect.

In particular embodiments, the disclosure includes the use of the artificial expression constructs described herein to modulate expression of a heterologous gene which is either partially or wholly encoded in a location downstream to that enhancer in an engineered sequence. Thus, there are provided herein methods of use of the disclosed artificial expression constructs in the research, study, and potential development of medicaments for preventing, treating or ameliorating the symptoms of a disease, dysfunction, or disorder.

Particular embodiments include methods of administering to a subject an artificial expression construct that includes MGT_E51, MGT_E52, MGT_E57, eHGT_770m, eHGT_774m, eHGT_772m, eHGT_486m, eHGT_875m, eHGT_923m, eHGT_924m, eHGT_925m, eHGT_926m, 3xcore2_eHGT_774m, 3xcore2_eHGT_772m, and/or 3xCore_eHGT486m and/or AiP1211, AiP1212, AiP1218, CN2603, CN2606, CN2612, CN2261, AiP1279, AiP1277, AiP1278, AiP1344, CN3041, CN3608, CN2582, CN3367, CN4095, CN4096, CN3430, and/or CN3431 as described herein to drive expression of a gene in claustrum neurons. The subject can be an isolated cell, a network of cells, a tissue slice, an experimental animal, a veterinary animal, or a human.

As is well known in the medical arts, dosages for any one subject depends upon many factors, including the subject's size, surface area, age, the particular compound to be administered, sex, time and route of administration, general health, and other drugs being administered concurrently. Dosages for the compounds of the disclosure will vary, but, in particular embodiments, a dose could be from $10^5$ to $10^{100}$ copies of an artificial expression construct of the disclosure. In particular embodiments, a patient receiving intravenous, intraparenchymal, intraspinal, retro-orbital, or intrathecal administration can be infused with from $10^6$ to $10^{22}$ copies of the artificial expression construct.

An "effective amount" is the amount of a composition necessary to result in a desired physiological change in the subject. Effective amounts are often administered for research purposes. Effective amounts disclosed herein can cause a statistically-significant effect in an animal model, human study, in vivo, or in vitro assay.

Serotonergic psychedelic drugs including psilocybin have been purported to have broad therapeutic potential for a range of human disorders including anxiety, depression, OCD, addiction, etc., yet the cellular mechanisms of action in the mammalian brain remain poorly understood. A promising approach to understanding the cellular mechanisms of drug action is to use mature brain slices of the mammalian brain and assay drug effects on intrinsic and synaptic responses measured from neurons using electrophysiology and/or activity imaging.

One major target for evaluating effects of serotonergic psychedelic drugs is the claustrum, a small brain region rich in expression of the gene HTR2a, which is believed to be the main brain receptor through which these drugs act. Thus, artificial expression constructs disclosed herein for targeting the claustrum can be used to facilitate targeted analysis of serotonergic psychedelic drug action, or for screening the efficacy of new related compounds with therapeutic potential but that do not elicit a psychedelic experience. Additionally, artificial expression constructs disclosed herein that target the claustrum may be leveraged to deliver into neurons various transgenes or peptides that could be helpful in dissecting the signaling pathways activated by these drugs.

Artificial expression constructs disclosed herein can be delivered in vivo (e.g., intravenous, CSF, or brain parenchymal routes) or applied to ex vivo brain slice culture preparations. In particular embodiments, artificial expression constructs can be used in diverse mammalian species for marking claustrum neurons, including in non-human primates or with human neurosurgical tissue, which would be especially helpful to inform the development of novel therapies intended for human patients.

In particular embodiments, psychedelic drugs can be administered for experimental purposes by pipetting a psychedelic drug onto a brain slice or administering a psychedelic drug to a laboratory animal (e.g., mouse or non-human primate) or a human. The effect of the psychedelic drug can be analyzed. In particular embodiments, artificial expression constructs described herein can be used to express a transgene in the claustrum to further understand the mechanism of action of psychedelic drugs. In particular embodiments, the transgene includes any gene or encodes any peptide suspected of being involved in the signaling pathway of a drug. In particular embodiments, the transgene includes HTR2a. In particular embodiments, the transgene includes a molecule that blocks expression of HTR2a. In particular embodiments, the drug is a psychedelic drug. The effect of psychedelic drugs has been tested in laboratory animals, for example, the psychedelic-induced head-twitch response in rodents was first reported in 1956 (Keller and Umbreit. Science. 1956; 124:723-724; and Winter and Flataker. Proc Soc Exp Biol Med. 1956; 92:285-289) and validated in 1967 (Corne and Pickering. Psychopharmacologia. 1967; 11:65-78).

In particular embodiments, it may be desirable to provide multiple, or successive administrations of the psychedelic drugs, either over a relatively short, or a relatively prolonged period of time.

One or more psychedelic drugs can be administered alone or in combination with an artificial expression construct described herein to examine the effect of the presence of the artificial expression construct on the effects of the drug. When administered in vivo, measured responses can be changes in, for example, mood, alertness, or attention of the subject.

The amount of expression constructs and time of administration of such compositions will be within the purview of the skilled artisan having benefit of the present teachings. It is likely, however, that the administration of effective amounts of the disclosed compositions may be achieved by a single administration, such as for example, a single injection of sufficient numbers of infectious particles to provide an effect in the subject. Alternatively, in some circumstances, it may be desirable to provide multiple, or successive administrations of the artificial expression construct compositions or other genetic constructs, either over a relatively short, or a relatively prolonged period of time, as may be determined by the individual overseeing the administration of such compositions. For example, the number of infectious particles administered to a mammal may be $10^7$, $10^8$, $10^1$, $10^{10}$, $10^{11}$, $10^{12}$, $10^{13}$, or even higher, infectious particles/ml given either as a single dose or divided into two or more administrations as may be required to achieve an intended effect. In fact, in certain embodiments, it may be desirable to administer two or more different expression constructs in combination to achieve a desired effect.

In certain circumstances it will be desirable to deliver the artificial expression construct in suitably formulated compositions disclosed herein either by pipette, retro-orbital injection, subcutaneously, intraocularly, intravitreally, parenterally, subcutaneously, intravenously, intraparenchymally, intracerebro-ventricularly, intramuscularly, intrathecally, intraspinally, intraperitoneally, by oral or nasal inhalation, or by direct application or injection to one or more cells, tissues, or organs. The methods of administration may also include those modalities as described in U.S. Pat. Nos. 5,543,158; 5,641,515 and 5,399,363.

(vi) Kits and Commercial Packages. Kits and commercial packages contain an artificial expression construct described herein. The artificial expression construct can be isolated. In particular embodiments, the components of an expression product can be isolated from each other. In particular embodiments, the expression product can be within a vector, within a viral vector, within a cell, within a tissue slice or sample, and/or within a transgenic animal. Such kits may further include one or more reagents, restriction enzymes, peptides, therapeutics, pharmaceutical compounds, or means for delivery of the compositions such as syringes, injectables, and the like.

Embodiments of a kit or commercial package will also contain instructions regarding use of the included components, for example, in basic research, electrophysiological research, neuroanatomical research, and/or the research and/or treatment of a disorder, disease or condition.

The Exemplary Embodiments and Experimental Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(vii) Exemplary Embodiments.

1. A core of an eHGT 774m, eHGT_772m, or eHGT486m enhancer or a concatenated core of an eHGT_774m, eHGT_772m, or eHGT486m enhancer.

2. The core or concatenated core of embodiment 1, wherein the core includes the sequence as set forth in SEQ ID NO: 54, SEQ ID NO: 56, and/or SEQ ID NO: 58 or the concatenated core includes the sequence as set forth in SEQ ID NO: 54, SEQ ID NO: 56, or SEQ ID NO: 58 or a sequence having at least 90% sequence identity to the sequence as set forth in SEQ ID NO: 54, SEQ ID NO: 56, or SEQ ID NO: 58.

3. The concatenated core of embodiments 1 or 2, wherein the concatenated core includes 2, 3, 4, 5, 6, 7, 8, 9, or 10 copies of the core of eHGT_774m, core of eHGT_772m, and/or core of eHGT486m.

4. The concatenated core of any of embodiments 1-3, including 2, 3, 4, 5, 6, 7, 8, 9, or 10 copies of the sequence as set forth in SEQ ID NO: 54, SEQ ID NO: 56, and/or SEQ ID NO: 58 or a sequence having at least 90% sequence identity to the sequence as set forth in SEQ ID NO: 54, SEQ ID NO: 56, and/or SEQ ID NO: 58.

5. The concatenated core of any of embodiments 1-4, including 2, 3, 4, 5, 6, 7, 8, 9, or 10 copies of the sequence as set forth in SEQ ID NO: 54.

6. The concatenated core of any of embodiments 1-4, including 2, 3, 4, 5, 6, 7, 8, 9, or 10 copies of the sequence as set forth in SEQ ID NO: 56.

7. The concatenated core of any of embodiments 1-4, including 2, 3, 4, 5, 6, 7, 8, 9, or 10 copies of the sequence as set forth in SEQ ID NO: 58.

8. The concatenated core of embodiment 5, including 3 copies of the sequence as set forth in SEQ ID NO: 54.

9. The concatenated core of embodiment 6, including 3 copies of the sequence as set forth in SEQ ID NO: 56.

10. The concatenated core of embodiment 7, including 3 copies of the sequence as set forth in SEQ ID NO: 58.

11. The concatenated core of embodiment 8, wherein the concatenated core includes the sequence as set forth in SEQ ID NO: 55.

12. The concatenated core of embodiment 9, wherein the concatenated core includes the sequence as set forth in SEQ ID NO: 57.

13. The concatenated core of embodiment 10, wherein the concatenated core includes the sequence as set forth in SEQ ID NO: 59.

14. An artificial expression construct including (i) an enhancer selected from MGT_E51, MGT_E52, MGT_E57, eHGT_770m, eHGT_774m, eHGT_772m eHGT_486m, eHGT_875m, eHGT_923m, eHGT_924m, eHGT_925m, eHGT_926m, 3xcore2_eHGT_774m, 3xcore2_eHGT_772m, and/or 3xCore_eHGT486m; (ii) a promoter; and (iii) a heterologous coding sequence.

15. The artificial expression construct of embodiment 14, wherein the heterologous coding sequence encodes an effector element or an expressible element.

16. The artificial expression construct of embodiments 14 or 15, wherein the effector element includes a reporter protein or a functional molecule.

17. The artificial expression construct of embodiment 16, wherein the reporter protein includes a fluorescent protein.

18. The artificial expression construct of embodiment 16, wherein the functional molecule includes a functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or a designer receptor exclusively activated by designer drug (DREADD).

19. The artificial expression construct embodiment 15, wherein the expressible element includes a non-functional molecule.

20. The artificial expression construct of embodiment 19, wherein the non-functional molecule includes a non-functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or a DREADD.

21. The artificial expression construct of any of embodiments 14-20, wherein the artificial expression construct is associated with a capsid that crosses the blood brain barrier.

22. The artificial expression construct of embodiment 21, wherein the capsid includes PHP.eB, AAV-BR1, AAV-PHP.S, AAV-PHP.B, or AAV-PPS.

23. The artificial expression construct of any of embodiments 14-22, wherein the artificial expression construct includes or encodes a skipping element.

24. The artificial expression construct of embodiment 23, wherein the skipping element includes a 2A peptide and/or an internal ribosome entry site (IRES).

25. The artificial expression construct of embodiment 24, wherein the 2A peptide includes T2A, P2A, E2A, or F2A.

26. The artificial expression construct of any of embodiments 14-25, wherein the artificial expression construct includes or encodes a set of features selected from: MGT_E51, MGT_E52, MGT_E57, eHGT_770m, eHGT_774m, eHGT_772m, eHGT_486m, eHGT_875m, eHGT_923m, eHGT_924m, eHGT_925m, eHGT_926m, 3xcore2_eHGT_774m, 3xcore2_eHGT_772m, 3xCore_eHGT486m AAV, scAAV, rAAV, pAAV, minB-globin, CMV, minCMV, minRho, minRho*, fluorescent protein (e.g., EGFP, SYFP2, GFP), Cre, iCre, dgCre, 10aa, nuclear localization protein, tag cassette, FlpO, tTA2, SP10 (e.g., 3xSP10), WPRE, WPRE3, hGHpA, and/or BGHpA.

27. The artificial expression construct of any of embodiments 14-26, wherein the artificial expression construct includes or encodes a set of features selected from:

MGT_E51-[minimal promoter]-[heterologous coding sequence]-WPRE-hGHpA;
MGT_E52-[minimal promoter]-[heterologous coding sequence]-WPRE-hGHpA;
MGT-E57-[minimal promoter]-[heterologous coding sequence]-WPRE-hGHpA;
eHGT_770m-[minimal promoter]-[heterologous coding sequence]-WPRE3-BGHpA;
eHGT_774m-[minimal promoter]-[heterologous coding sequence]-WPRE3-BGHpA;
eHGT_772m-[minimal promoter]-[heterologous coding sequence]-WPRE3-BGHpA;
eHGT_486m-[minimal promoter]-[heterologous coding sequence]-WPRE3-BGHpA;
MGT_E52-[minimal promoter]-[heterologous coding sequence]-hGHpA;
eHGT_875m-[minimal promoter]-[heterologous coding sequence]-WPRE3-BGHpA;
eHGT_923m-[minimal promoter]-[heterologous coding sequence]-WPRE3-BGHpA;
eHGT_924m-[minimal promoter]-[heterologous coding sequence]-WPRE3-BGHpA;
eHGT_925m-[minimal promoter]-[heterologous coding sequence]-WPRE3-BGHpA;
eHGT_926m-[minimal promoter]-[heterologous coding sequence]-WPRE3-BGHpA;
3xCore_eHGT486m-[minimal promoter]-[heterologous coding sequence]-WPRE3-BGHpA;
3xcore2_eHGT 774m-[minimal promoter]-[heterologous coding sequence]-WPRE3-BGHpA;
3xcore2_eHGT_772m-[minimal promoter]-[heterologous coding sequence]-WPRE3-BGHpA;
MGT_E51-[minimal promoter]-[heterologous coding sequence]-[post-regulatory elements];
MGT_E52-[minimal promoter]-[heterologous coding sequence]-[post-regulatory elements];
MGT_E57-[minimal promoter]-[heterologous coding sequence]-[post-regulatory elements];
eHGT_770m-[minimal promoter]-[heterologous coding sequence]-[post-regulatory elements];
eHGT_774m-[minimal promoter]-[heterologous coding sequence]-[post-regulatory elements];
eHGT_772m-[minimal promoter]-[heterologous coding sequence]-[post-regulatory elements];
eHGT_486m-[minimal promoter]-[heterologous coding sequence]-[post-regulatory elements];
eHGT_875m-[minimal promoter]-[heterologous coding sequence]-[post-regulatory elements];
eHGT_923m-[minimal promoter]-[heterologous coding sequence]-[post-regulatory elements];
eHGT_924m-[minimal promoter]-[heterologous coding sequence]-[post-regulatory elements];
eHGT_925m-[minimal promoter]-[heterologous coding sequence]-[post-regulatory elements];
eHGT_926m-[minimal promoter]-[heterologous coding sequence]-[post-regulatory elements]; or
3xCore_eHGT486m-[minimal promoter]-[heterologous coding sequence]-[post-regulatory elements].

28. A vector including an artificial expression construct of any of embodiments 14-27.

29. The vector of embodiment 28, wherein the vector includes a viral vector.

30. The vector of embodiment 28 or 29, wherein the viral vector includes a recombinant adeno-associated viral (AAV) vector.

31. An adeno-associated viral (AAV) vector including at least one heterologous coding sequence, wherein the heterologous coding sequence is under control of a promoter and an enhancer selected from MGT_E51, MGT_E52, MGT_E57, eHGT_770m, eHGT_774m, eHGT_772m, eHGT_486m, eHGT_875m, eHGT_923m, eHGT_924m, eHGT_925m, eHGT_926m, 3xcore2_eHGT_774m, 3xcore2_eHGT_772m, and 3xCore_eHGT486m.

32. The AAV vector of embodiment 31, wherein the heterologous coding sequence encodes an effector element or an expressible element.

33. The AAV vector of embodiment 32, wherein the effector element includes a reporter protein or a functional molecule.

34. The AAV vector of embodiment 33, wherein the reporter protein includes a fluorescent protein.

35. The AAV vector of embodiment 33, wherein the functional molecule includes a functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or DREADD.

36. The AAV vector of embodiment 32, wherein the expressible element includes a non-functional molecule.

37. The AAV vector of embodiment 36, wherein the non-functional molecule includes a non-functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or DREADD.

38. A transgenic cell including an expression construct or vector of any of the preceding embodiments.

39. The transgenic cell of embodiment 38, wherein the transgenic cell is a claustrum neuron.

40. The transgenic cell of embodiment 39, wherein the transgenic cell is an L6 IT Car3 neuron.

41. The transgenic cell of embodiment 38, wherein the transgenic cell is murine, human, or non-human primate.

42. A non-human transgenic animal including an artificial expression construct, vector, or transgenic cell of any of the preceding embodiments.

43. The non-human transgenic animal of embodiment 42, wherein the non-human transgenic animal is a mouse or a non-human primate.

44. An administrable composition including an expression construct, vector, or transgenic cell of any of the preceding embodiments.

45. A kit including an artificial expression construct, vector, transgenic cell, transgenic animal, and/or administrable compositions of any of the preceding embodiments.

46. A method for expressing a heterologous gene within a population of cells in vivo or in vitro, the method including providing the administrable composition of embodiment 44 in a sufficient dosage and for a sufficient time to a sample or subject including the population of cells thereby expressing the gene within the population of cells.

47. The method of embodiment 46, wherein the heterologous gene encodes an effector element or an expressible element.

48. The method of embodiment 47, wherein the effector element includes a reporter protein or a functional molecule.

49. The method of embodiment 48, wherein the reporter protein includes a fluorescent protein.

50. The method of embodiment 48, wherein the functional molecule includes a functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or a DREADD.

51. The method of embodiment 50, wherein the receptor is a serotonin receptor.

52. The method of embodiment 51, wherein the serotonin receptor is an HTR2a receptor.

53. The method of embodiment 47, wherein the expressible element includes a non-functional molecule.

54. The method of embodiment 53, wherein the non-functional molecule includes a non-functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or DREADD.

55. The method of embodiment 54, wherein the non-functional receptor is a non-functional serotonin receptor.

56. The method of embodiment 55, wherein the non-functional serotonin receptor is a non-functional HTR2a receptor.

57. The method of any of embodiments 46-56, wherein the gene includes or encodes a molecule that reduces HTR2a expression.

58. The method of any of embodiments 46-57, further including administering a psychedelic drug.

59. The method of embodiment 58, wherein the psychedelic drug includes psilocybin; psilocin; lysergic acid diethylamide (LSD; N,N-dimethyltryptamine (DMT); mescaline; 5-MeO-DMT; 5-Methoxy-diisopropyltryptamine (5-MeO-DIPT); dipropyltryptamine (DPT), 2C-T-7, 2,5-dimethoxy-4-methylamphetamine (DOM), 2,5-dimethoxy-4-bromoamphetamine (DOB), 2,5-Dimethoxy-4-iodoamphetamine (DOI), or 2C-I 60. The method of any of embodiments 46-59, wherein the providing includes pipetting.

61. The method of embodiment 60, wherein the pipetting is to a brain slice.

62. The method of embodiment 61, wherein the brain slice includes a claustrum neuron.

63. The method of embodiment 62, wherein the brain slice includes an L6 IT Car3 neuron.

64. The method of any of embodiments 61-63, wherein the brain slice is murine, human, or non-human primate.

65. The method of any of embodiments 46-64, wherein the providing includes administering to a living subject.

66. The method of embodiment 65, wherein the living subject is a human, non-human primate, or a mouse.

67. The method of embodiments 65 or 66, further including evaluating the living subject for an effect of the psychedelic drug.

68. The method of embodiment 67, wherein the effect of the psychedelic drug is a change in mood, alertness, or attention.

69. The method of any of embodiments 65-68, wherein the administering to a living subject is through injection.

70. The method of embodiment 69, wherein the injection includes intravenous injection, intraparenchymal injection into brain tissue, intracerebroventricular (ICV) injection, intra-cisterna magna (ICM) injection, or intrathecal injection.

71. An artificial expression construct including a sequence as set forth in SEQ ID NO: 41, SEQ ID NO: 69, SEQ ID NO: 42, SEQ ID NO:43, SEQ ID NO: 44, SEQ ID NO: 45, SEQ ID NO: 46, SEQ ID NO: 47, SEQ ID NO: 68, SEQ ID NO:70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, or SEQ ID NO: 79 or a sequence having at least 90% sequence identity to a sequence as set forth in SEQ ID NO: 41, SEQ ID NO: 69, SEQ ID NO: 42, SEQ ID NO:43, SEQ ID NO: 44, SEQ ID NO: 45, SEQ ID NO: 46, SEQ ID NO: 47, SEQ ID NO: 68, SEQ ID NO:70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, or SEQ ID NO: 79.

(viii) Closing Paragraphs. Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in nonessential regions of a polypeptide do not substantially alter biological activity (see, e.g., Watson et al. *Molecular Biology of the Gene,* 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Iie), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, lie, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, *J. Mol. Biol.* 157(1), 105-32). Each amino acid has been assigned a hydropathic index on the basis of its hydrophobicity and charge characteristics (Kyte and Doolittle, 1982). These values are: lie (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gin (+0.2); Gly (0); Thr (−0.4); Pro (−0.5±1); Ala (−0.5); His (−0.5); Cys (−1.0); Met (−1.3); Val (−1.5); Leu (−1.8); lie (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.](1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g., 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The term concatenate is broadly used to describe linking together into a chain or series. It is used to describe the linking together of nucleotide or amino acid sequences into a single nucleotide or amino acid sequence, respectively. The term "concatamerize" should be interpreted to recite: "concatenate."

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in expression in claustrum neurons using enhancer MGT_E51, MGT_E52, MGT_E57, eHGT_770m, eHGT_774m, eHGT_772m, eHGT_486m, eHGT_875m, eHGT_923m, eHGT_924m, eHGT_925m, eHGT_926m, 3xcore2_eHGT_774m, 3xcore2_eHGT_772m, and/or 3xCore_eHGT486m.

In particular embodiments, artificial means not naturally occurring.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; +16% of the stated value; ±15% of the stated value; ±14% of the stated value; ±13% of the stated value; ±12% of the stated value; ±11% of the stated value; ±10% of the stated value; ±9% of the stated value; +8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. An artificial expression construct comprising (i) an enhancer selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 60, SEQ ID NO: 61, SEQ ID NO: 62, SEQ ID NO: 63, SEQ ID NO: 64, SEQ ID NO: 55, SEQ ID NO: 57, SEQ ID NO: 59, SEQ ID NO: 54, SEQ ID NO: 56, and/or SEQ ID NO: 58; (ii) a promoter; and (iii) a coding sequence.

2. The artificial expression construct of claim 1, wherein the coding sequence encodes a fluorescent protein, a receptor, or a neurotransmitter.

3. The artificial expression construct of claim 1, wherein the artificial expression construct is associated with a capsid that crosses the blood brain barrier.

4. The artificial expression construct of claim 3, wherein the capsid comprises PHP.eB, AAV-BR1, AAV9, AAVrh.10, AAV-PHP.S, AAV-PHP.B, or AAV-PPS.

5. The artificial expression construct of claim 1, wherein the artificial expression construct comprises or encodes a skipping element.

6. The artificial expression construct of claim 5, wherein the skipping element comprises a T2A peptide, P2A peptide, E2A peptide, F2A peptide, and/or an internal ribosome entry site (IRES).

7. The artificial expression construct of claim 1, wherein the artificial expression construct is within a viral vector.

8. An artificial enhancer having a sequence as set forth in SEQ ID NO: 54, SEQ ID NO: 56, or SEQ ID NO: 58.

9. The artificial enhancer of claim 8, having:

2, 3, 4, 5, 6, 7, 8, 9, or 10 copies of the sequence as set forth in SEQ ID NO: 54;

2, 3, 4, 5, 6, 7, 8, 9, or 10 copies of the sequence as set forth in SEQ ID NO: 56; or 2, 3, 4, 5, 6, 7, 8, 9, or 10 copies of the sequence as set forth in SEQ ID NO: 58.

10. The artificial enhancer of claim 8, wherein the artificial enhancer has the sequence as set forth in SEQ ID NO: 55, SEQ ID NO: 57, or SEQ ID NO: 59.

11. A method for expressing a gene within a population of cells in vivo or in vitro, the method comprising providing an administrable composition comprising an artificial expression construct comprising: (i) an enhancer selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 60, SEQ ID NO: 61, SEQ ID NO: 62, SEQ ID NO: 63, SEQ ID NO: 64, SEQ ID NO: 55, SEQ ID NO: 57, SEQ ID NO: 59, SEQ ID NO: 54, SEQ ID NO: 56, and/or SEQ ID NO: 58; (ii) a promoter; and (iii) a coding sequence;

in a sufficient dosage and for a sufficient time to a sample or subject comprising the population of cells thereby expressing the coding sequence within the population of cells.

12. The method of claim 11, wherein the coding sequence encodes a fluorescent protein, a receptor, or a neurotransmitter.

13. The method of claim 12, wherein the receptor is a serotonin receptor.

14. The method of claim 13, wherein the serotonin receptor is a HTR2a receptor.

15. The method of claim 11, wherein the coding sequence comprises or encodes a molecule that reduces HTR2a expression.

16. The method of claim 11, further comprising administering a psychedelic drug.

17. The method of claim 16, wherein the psychedelic drug comprises psilocybin; psilocin; lysergic acid diethylamide (LSD); N,N-dimethyltryptamine (DMT); mescaline; 5-MeO-DMT; 5-Methoxy-diisopropyltryptamine (5-MeO-DIPT); dipropyltryptamine (DPT), 2C-T-7, 2,5-dimethoxy-4-methylamphetamine (DOM), 2,5-dimethoxy-4-bromoamphetamine (DOB), 2,5-Dimethoxy-4-iodoamphetamine (DOI), or 2C-I.

18. The method of claim 11, wherein the providing comprises pipetting to a brain slice or administering to a living subject.

19. The method of claim 18, wherein the brain slice comprises a claustrum neuron.

20. The method of claim 18, wherein the brain slice comprises an L6 IT Car3 neuron.

* * * * *